(12) United States Patent
Shin et al.

(10) Patent No.: US 11,107,552 B2
(45) Date of Patent: Aug. 31, 2021

(54) DATA PROCESSING, ANALYSIS METHOD OF GENE EXPRESSION DATA TO IDENTIFY ENDOGENOUS REFERENCE GENES

(71) Applicants: ABION, INC., Seoul (KR); GENCURIX INC., Seoul (KR)

(72) Inventors: Young Kee Shin, Seoul (KR); Mi Jeong Kwon, Seoul (KR); En Sel Oh, Seoul (KR); Yong Ho In, Yongsin-Si (KR); Sang Seok Koh, Daejeon (KR)

(73) Assignees: ABION, INC., Seoul (KR); GENCURIX INC., Seoul (KR)

( * ) Notice: Subject to any disclaimer, the term of this patent is extended or adjusted under 35 U.S.C. 154(b) by 105 days.

(21) Appl. No.: 16/129,206

(22) Filed: Sep. 12, 2018

(65) Prior Publication Data

US 2019/0012429 A1    Jan. 10, 2019

Related U.S. Application Data

(63) Continuation of application No. 15/582,330, filed on Apr. 28, 2017, now Pat. No. 10,304,561, which is a continuation of application No. 13/631,279, filed on Sep. 28, 2012, now Pat. No. 9,639,660, which is a continuation of application No. 12/521,498, filed as application No. PCT/KR2007/006890 on Dec. 27, 2007, now abandoned.

(30) Foreign Application Priority Data

Dec. 27, 2006    (KR) .......................... 10-2006-0134883

(51) Int. Cl.
*C12Q 1/6851*    (2018.01)
*G16B 25/00*    (2019.01)
*C12Q 1/6813*    (2018.01)

(52) U.S. Cl.
CPC ........... *G16B 25/00* (2019.02); *C12Q 1/6813* (2013.01); *C12Q 1/6851* (2013.01); *C12Q 2600/166* (2013.01)

(58) Field of Classification Search
None
See application file for complete search history.

(56) References Cited

U.S. PATENT DOCUMENTS

2006/0234270 A1    10/2006    Houts

FOREIGN PATENT DOCUMENTS

WO    WO-2006/010150 A2    1/2006
WO    WO-2006/119439 A2    11/2006

OTHER PUBLICATIONS

De Jonge, et al. Evidence Based Selection of Housekeeping Genes. PLoS One 2(9): e898. (Year: 2007).*

Sgarlato, et al. Panel of Genes Transcriptionally Up-regulated in Squamous Cell Carcinoma of the Cervix Identified by Representational Difference Analysis, Confirmed by Macroarray, and Validated by Real-Time Quantitative Reverse Transcription-PCR. Clinical Chemistry 51:1, 27-34. (Year: 2005).*

Pagedar, N. A., et al.; "Gene expression analysis of distinct populations of cells isolated from mouse and human inner ear FFPE tissue using laser capture microdissection—a Technical report based on a preliminary findings", Brain Research, 2006, vol. 1091, pp. 289-299.

Kim, S., et al.; "Selection of optimal internal controls for gene expression profiling of liver disease", BioTechniques, 2003, vol. 35, No. 3, pp. 456-460.

Khimani, A. H., et al.; "Housekeeping genes in cancer: normalization of array data", BioTechniques, 2005, vol. 38, No. 5, pp. 739-745.

Pahl, P. M. B., et al., "ZNF207, a Ubiquitously Expressed Zinc Finger Gene on Chromosome 6p21.3", Genomics, 1998, vol. 53, pp. 410-412.

Radonic, A., et al.; "Guideline to reference gene selection for quantitative real-time PCR", BBRC, 2004, vol. 313, pp. 410-412.

Jin, P., et al.; "Selection of and validation of endogenous reference genes using a high throughput approach", BMC Genomics, 2004, vol. 5:55, pp. 1-17.

Vandesompele, J., et al; "Accurate normalization of real-time quantitative PT-PCR data by geometric averaging of multiple internal control genes", Genome Biology, 2002, vol. 3(7), pp. 0034.1-0034.12.

Notice of Allowance from corresponding Japanese Patent Application No. 2015-248677, dated Jun. 22, 2017.

Andersen, C. L., et al.; "Normalization of Real-Time Quantitative Reverse Transcription-PCR Data: A Model-Based Variance Estimation Approach to Identify Genes Suited for Normalization, Applied to Bladder and Colon Cancer Data Sets", Cancer Research, vol. 64 (15), pp. 5245-5250, Aug. 1, 2004.

Pfaffl, M. W., et al.; "Determination of stable housekeeping genes, differentially regulated target genes and sample integrity: BestKeeper—Excel-based tool using pair-wise correlations", Biotechnology Letters, 26, pp. 509-515, Mar. 2004.

(Continued)

*Primary Examiner* — Samuel C Woolwine
(74) *Attorney, Agent, or Firm* — Harness, Dickey & Pierce, P.L.C.

(57) ABSTRACT

Disclosed are data processing and analysis methods for gene expression data for identifying endogenous reference genes and a composition for the quantitative analysis of gene expression, comprising a pair of primers and/or probes useful in amplifying the identified endogenous reference genes. Introduced with the concepts of "Zero's proportion" and CV, the method allows different datasets to be integrally analyzed, thereby searching for novel reference genes. By the method, 2,087 genes are first found as housekeeping genes which are expressed in most tissues, and the usefulness thereof in the relative quantification of different target genes is determined by analyzing their expression stability. Of the 2,087 genes, 13 genes show higher expression stability with lower expression levels across a wide range of samples than traditional reference genes such as GAPDH and ACTS, and therefore are suitable for the normalization of universal genes having relatively low expression levels.

2 Claims, 9 Drawing Sheets

Specification includes a Sequence Listing.

(56) References Cited

OTHER PUBLICATIONS

Vandesompele, J., et al.; "Accurate normalization of real-time quantitative RT-PCR data by geometric averaging of multiple internal control genes", Genome Biology, vol. 3 No. 7, Jun. 2002, pp. 1-12.
Selvey, S., et al.; "ß-Actin—an unsuitable internal control for RT-PCR", Molecular and Cellular Probes (2001) 15, pp. 307-311.
Lee, P. D., et al.; "Control Genes and Variability: Absence of Ubiquitous Reference Transcripts in Diverse Mammalian Expression Studies", Genome Research, 12: pp. 292-297, 2001.
Zhong H., et al.; "Direct Comparison of GAPDH, ß-Actin, Cyclophilin, and 28S rRNA as Internal Standards for Quantifying RNA Levels under Hypoxia", Biochemical and Biophysical Research Communications 259, pp. 523-526 (1999).
Schmittgen, T. D.; et al.; "Effect of experimental treatment on housekeeping gene expression: validation by real-time, quantitative RT-PCR", J. Biochem. Biophys. Methods 46 (2000) 69-81.
Haller F., et al.; "Equivalence test in quantitative reverse transcription polymerase chain reaction: confirmation of reference genes suitable for normalization", Analytical Biochemistry 335 (2004) pp. 1-9.
Van Ruissen, F., et al.; "Evaluation of the similarity of gene expression data estimated with SAGE and Affymetrix GeneChips", BMC Genomics, Jun. 14, 2005, 6:91.
Ohl, F., et al.; "Gene expression studies in prostate cancer tissue: which reference gene should be selected for normalization?", J Mol Med (2005) 83: 1014-1024.
Czechowski, T., et al.; "Genome-Wide Identification and Testing of Superior Reference Genes for Transcript Normalization in Arabidopsis[1][w]", Plant Physiology, Sep. 2005, vol. 139, pp. 5-17.
Rubie, C., et al.; "Housekeeping gene variability in normal and cancerous colorectal, pancreatic, esophageal, gastric and hepatic tissues", Molecular and Cellular Probes 19 (2005) 101-109.
Thellin, O., et al.; "Housekeeping genes as internal standards: use and limits", Journal of Biotechnology 75 (1999) 291-295.
Hamalainen, H. K., et al.; "Identification and Validation of Endogenous Reference Genes for Expression Profiling of T Helper Cell Differentiation by Quantitative Real-Time RT-PCR[1]", Analytical Biochemistry 299, 63-70 (2001).
Haverty, P. M., et al.; "Limited agreement among three global gene expression methods highlights the requirement for non-global validation", vol. 20 No. 18 2004, pp. 3431-3441.
De Kok, J. B., et al.; "Normalization of gene expression measurements in tumor tissues: comparison of 13 endogenous control genes", Laboratory Investigation (2005) 85, 154-159.
Tricarico, C., et al.; "Quantitative real-time reverse transcription polymerase chain reaction: normalization to rRNA or single housekeeping genes is inappropriate for human tissue biopsies", Analytical Biochemistry 309 (2002) 293-300.
Huggett, J., et al.; "Real-time RT-PCR normalisation; strategies and considerations", Genes and Immunity (2005), 1-6.
Hoerndli, F. J., et al.; "Reference genes identiWed in SH-SY5Y cells using custom-made gene arrays with validation by quantitative polymerase chain reaction", Analytical Biochemistry 335 (2004) 30-41.
Goidin, D., et al.; "Ribosomal 18S RNA Prevails over Glyceraldehyde-3-Phosphate Dehydrogenase and ß-Actin Genes as Internal Standard for Quantitative Comparison of mRNA Levels in Invasive and Noninvasive Human Melanoma Cell Subpopulations", Analytical Biochemistry 295, 17-21 (2001).
Sun, M., et al.; "SAGE is far more sensitive than EST for detecting low-abundance transcripts", BMC Genomics, Jan. 5, 2004, 5:1, pp. 1-4.
Kobayashi, M. S., et al.; "Screening for Control Genes in Rat Global Cerebral Ischemia Using High-Density Oligonucleotide Array", Journal of Neuroscience Research 76:512-518 (2004).
Shulzhenko, N., et al.; "Selection of control genes for quantitative RT-PCR based on microarray data", Biochemical and Biophysical Research Communications 337 (2005) 306-312.
Bereta, J., et al.; "Stimulation of Glyceralydehyde-3-Phosphate Dehydrogenase mRNA Levels By Endogenous Nitric Oxide In Cytokine-Activated Endothelium", Biochemical and Biophysical Research Communications, pp. 363-369, vol. 217, No. 1, Dec. 5, 1995.
Dheda, K., et al.; "The implications of using an inappropriate reference gene for real-time reverse transcription PCR data normalization", Analytical Biochemistry 344 (2005) 141-143.
Brunner, A. M., et al.; "Validating internal controls for quantitative plant gene expression studies", BMC Plant Biology 2004, 4:14, pp. 1-7.
Hsiao, L., et al.; "A compendium of gene expression in normal human tissues", Physiol Genomics 7: 97-104, 2001.
Wang, Y., et al.; "An evaluation of new criteria for CpG islands in the human genome as gene markers", Bioinformatics, vol. 20 No. 7 2004, pp. 1170-1177.
Pfaffl, M. W.; "A new mathematical model for relative quantification in real-time RT-PCR", Nucleic Acids Research, 2001, vol. 29, No. 9, pp. 2003-2007.
Ramakers, C., et al.; Assumption-free analysis of quantitative real-time polymerase chain reaction (PCR) data:, Neuroscience Letters 339 (2003) 62-66.
Warrington, J. A., et al.; Comparison of human adult and fetal expression andidentification of 535 housekeeping/maintenance genes, Physiol Genomics, 2: 143-147, 2000.
Ponger, L., et al.; "Determinants of CpG Islands: Expression in Early Embryo and Isochore Structure", Genome Research, 11:1854-1860, 2001.
Eisenberg, E., et al.; "Human housekeeping genes are compact", TRENDS in Genetics vol. 19 No. 7 Jul. 2003.
Szabo, A., et al.; "Statistical modeling for selecting housekeeper genes", Genome Biology 2004, vol. 5, Issue 8, Article R59, pp. 1-10.
Ruepp, A., et al.; "The FunCat, a functional annotation scheme for systematic classification of proteins from whole genomes", Nucleic Acids Research, 2004, vol. 32, No. 18, p. 5539-5545.
Office Action from corresponding European Patent Application No. 17194976.1, dated Mar. 20, 2019.
Ping Jin, et al.; "Selection and validation of endogenous reference genes using a high throughput approach", BMC Genomics 2004, 5:55, Aug. 13, 2004.
Aleksandar Radonic, et al.; "Guideline to reference gene selection for quantitative real-time PCR", Biochemical and Biophysical Research Communications 313 (2004) 856-862.

* cited by examiner

DATA PROCESSING, ANALYSIS METHOD OF GENE EXPRESSION DATA TO IDENTIFY ENDOGENOUS REFERENCE GENES

CROSS-REFERENCE TO RELATED APPLICATIONS

This application is a continuation application of U.S. application Ser. No. 15/582,330, filed on 28 Apr. 2017, which is a continuation application of U.S. application Ser. No. 13/631,279, filed on 28 Sep. 2012, now U.S. Pat. No. 9,639,660, issued on 2 May 2017, which is a continuation application of U.S. application Ser. No. 12/521,498, filed on 26 Jun. 2009, which is a National phase application of PCT Application No. PCT/KR07/06890, filed on 27 Dec. 2007, which claims priority to Korean Patent Application No. 10-2006-0134883, filed on 27 Dec. 2006. The entire disclosures of the applications identified in this paragraph are incorporated herein by reference.

SEQUENCE LISTING

The instant application contains a Sequence Listing which has been submitted in ASCII format via EFS-Web and is hereby incorporated by reference in its entirety. Said ASCII copy, created on May 24, 2013, is named 84346-CON-301519_ST25.txt and is 8,058 bytes in size.

TECHNICAL FIELD

The present invention relates to a data processing and analysis method of gene expression data for identifying endogenous reference genes and a composition for the quantitative analysis of gene expression, comprising a pair of primers and/or probes useful in the amplification of the identified endogenous reference genes. More particularly, the present invention relates to a data processing and analysis method for identifying novel endogenous reference genes using gene expression data from EST, SAGE and microarray datasets with zero's proportion and coefficient of variation, and a composition for the quantitative analysis of gene expression, comprising a pair of primers and/or probes useful in the amplification of the identified endogenous reference genes.

BACKGROUND ART

As many as 50,000-100,000 genes can be found in each human cell, but are selectively used in each cell. Of them, a significant number of genes are involved in basic functions and routine cellular metabolic processes required for the sustenance of the cell. Such genes are called housekeeping genes (hereinafter referred to as "HKG"). In various gene expression analysis methods utilizing the quantification of messenger RNA (hereinafter referred to as "mRNA") to determine expression levels of specific or multiple genes with the aim of identifying the functions of specific genes, searching for genes directed to specific functions, profiling the gene expression of organisms under specific conditions, and describing other biological purposes, endogenous reference genes mean housekeeping genes useful in the normalization of the mRNA level for the relative quantification of genes of interest.

Endogenous reference genes are most widely used to normalize mRNA level for accurate comparison of gene expression between different samples (Vandesompele J et al., Genome Biol 3(7), p. RESEARCH0034, 2002). Endogenous reference genes are usually used in gene expression analysis techniques ranging from conventional reverse transcriptase polymerase chain reaction (hereinafter referred to as "RT-PCR") to recently developed quantitative real time PCR (hereinafter referred to as "qRT-PCT"), serial analysis of gene expression (hereinafter referred to as "SAGE") and microarray. Traditional reference genes such as glyceraldehyde-3-phosphate dehydrogenase (hereinafter referred to as "GAPDH") and β-actin (hereinafter referred to as "ACTB") have been used without proper validation, assuming that they are expressed at constant levels across different samples, irrespectively cell or tissue type and are not regulated by experimental treatment.

However, it is well known that the expression of traditional reference genes may vary among different tissues and cell types and can be regulated by experimental conditions, including sample treatment, developmental stage and pathological states (Bereta J and Bereta M, Biochem Biophys Res Commun 217(1)363-369, 1995; Tricarico C et al., Anal Biochem 309(2):293-300, 2002; Thellin O et al., J Biotechnol 75(2-3):291-295, 1999; Rubie C et al., Mol Cell Probes 19(2):101-109, 2005; Schmittgen T D and Zakrajsek B A, J Biochem Biophys Methods 46(1-2):69-81, 2000; Zhong H and JSimons W, Biochem Biophys Res Commun 259(3): 523-526, 1999; Selvey S et al., Mol Cell Probes 15(5):307-311, 2001; Wu Y Y and LRees J, Acta Derm Venereol 80(1):2-3, 2000; Lee P D et al., Genome Res 12(2):292-297, 2002; Hamalainen H K et al., Anal Biochem 299(1):63-70, 2001). The use of inappropriate reference genes in the relative quantification of gene expression may result in biased expression profiles. This concern has already been raised by many researchers (Tricarico C et al., Anal Biochem 309(2):293-300 2002; Dheda K et al., Anal Biochem 344 (1):141-143, 2005; de Kok J B et al., Lab Invest 85( ):154-159, 2005; Brunner A M et al., BMC Plant Biol 4:14, 2004). Particularly, the selection of proper endogenous reference genes is essential for accurate measurement in qRT-PCR, which is a reliable method for detecting gene expression with high sensitivity and accuracy though accurate normalization, and may not be required in qualitative analysis such as northern blot or conventional RT-PCR (Huggett J et al., Genes Immun 6(4):279-284, 2005).

With the acknowledgement of the importance of the proper validation of traditional reference genes and the identification of more suitable reference genes, a number of studies have been undertaken to select the most suitable genes among commonly used reference genes in specific experimental conditions, or to identify novel genes, which are superior to the traditional genes that are universally used for mRNA quantification. However, most of the previous studies have been focused on the selection (validation) of the most stable genes among commonly used reference genes in specific experimental systems or a given set of limited tissue samples (Goidin D et al., Anal Biochem 295(1):17-21, 2001; Haller F et al., Anal Biochem 335(1):1-9, 2004; Ohl F et al., J Mol Med 83(12):1014-1024, 2005; Radonic A et al., Biochem Biophys Res Comnun 313(4):856-862, 2004). Some programs are now available for identifying the most appropriate genes among multiple reference genes using qRT-PCR results (Vandesompele J et al., Genome Biol 3(7), p. RESEARCH0034, 2002; Pfaffl M W et al., Biotechnol Lett 26(6):509-15, 2004; Andersen C L et al., Cancer Res 64(15):5245-5250, 2004).

In addition, novel endogenous reference genes have been found mostly on the basis of microarray data (Hamalainen H K et al., Anal Biochem 299(1):63-70, 2001; Hoerndli F J et al., Anal Biochem 335(1):30-41, 2004; Czechowski T et al., Plant Physiol 139(1):5-17, 2005; Jin P et al., BMC Genomics, 5(1):55, 2004; Kobayashi M S et al., J. Neurosci Res 76(4):512-518, 2004; Shulzhenko N et al., Biochem Biophys Res Commun 337(1):306-12, 2005). As is well-known, the microarray technique has some problems and limitations (errors) due to the potential for inaccurate cross hybridization between probes and unintended transcripts, the potential for differences in hybridization efficiency between probe sets, and the potential for the incorrect annotation of transcripts (Haverty P M et al., Bioinformatics 20(18):3431-3441, 2004; van Ruissen F et al., BMC Genomics 6:91, 2005). The microarray technique also allows the detection of expression of genes only on the chip, in contrast to expressed sequence tag (hereinafter referred to as "EST") and SAGE, in which the expression profiles of whole transcripts in samples (cDNA libraries) can be measured (van Ruissen F et al., BMC Genomics 6:91, 2005). The use of gene expression data from different platforms together is expected to complement the limitation of individual platforms. For example, SAGE is far more sensitive than EST for detecting low-abundance transcripts (Sun M et al., BMC Genomics 5(1):1-4, 2004).

Even if an ideal endogenous reference gene does not exist, it is possible to find a more ideal endogenous reference gene applicable to most experimental conditions than traditional reference genes through various, large gene expression data.

Leading to the present invention, intensive and thorough research on accurate comparison of gene expression among different samples, conducted by the present inventors, resulted in the finding that gene expression datasets constructed from microarray data, in addition to EST and SAGE data, are useful in searching for endogenous reference genes, and that novel reference genes identified using the datasets are superior to previously used genes and show more stable expression across a wide range of samples, thus being universally useful for the normalization of gene expression, rather than being limited for use on specific tissue samples or in specific studies.

DISCLOSURE

Technical Problem

Therefore, it is an object of the present invention to provide a method of processing and analyzing gene expression data, with a statistical concept introduced thereinto, to identify endogenous reference genes which are superior to traditional reference genes in terms of expression stability across a wide range of samples, thus being universally useful for the normalization of gene expression, and a composition for the quantitative analysis of gene expression, comprising a pair of primers and/or probes useful in the amplification of the identified endogenous reference genes.

Technical Solution

In order to accomplish the above objects, the present invention provides a method for selecting candidate endogenous reference genes (ERG), comprising: 1) computing expression levels of genes from EST, SAGE and microarray datasets; and 2) identifying genes which are constitutively expressed across a wide range of tissues using the computed gene expression levels of step 1) and zero(0)'s proportions thereof.

Also, the present invention provides a composition for detecting at least one candidate endogenous reference gene selected according to the present invention, comprising a detection reagent applicable to amplification of the candidate endogenous reference gene.

Also, there is provided a method for quantifying an expression level of a gene of interest, comprising: 1) performing real-time PCR to amplify the gene of interest with a pair of primers and/or probes and then performing real-time PCR to amplify the a candidate endogenous reference gene with the composition; and 2) normalizing the expression level of the gene of interest relative to that of the candidate endogenous reference gene.

Furthermore, there is provided a method for selecting guide genes, comprising: measuring the candidate endogenous reference genes selected using the method for coefficient of variation (CV); and ranking the endogenous reference genes in an ascending order of CV. Also, the present invention provides a composition for detecting at least one guide reference gene identified according to the present invention, comprising a detection reagent applicable to amplification of the guide gene.

There is provided a method for quantifying an expression level of a target gene, comprising: 1) synthesizing cDNA from RNA of a subject; 2) performing real-time PCR to amplify the target gene using a pair of primers and/or probes, with the cDNA serving as a template and then performing real-time PCR to amplify the candidate endogenous reference gene using the composition; and 3) normalizing an expression level of the target gene to that of the candidate endogenous reference gene of step 2).

Moreover, there is provided a method for identifying the amplification of a target gene in genomic DNA, comprising: 1) amplifying the target gene with a pair of primers or probes through real-time PCR, with a genomic DNA of a subject serving as a template and then performing real-time PCR to amplify the candidate endogenous reference gene with the composition; and 2) normalizing an expression level of the target gene to that of the candidate endogenous reference gene.

Advantageous Effects

Introduced with the concepts of 'Zero's proportion' and CV, the method of the present invention allows different datasets to be integrally analyzed, thereby searching for novel reference genes. By the method, 2,087 genes were first found as housekeeping genes which are expressed in most tissues, and the usefulness thereof in the relative quantification of different target genes was determined by analyzing their expression stability. Out of the 2,087 genes, 13 genes were found to show higher expression stability with lower expression levels across a wide range of samples than traditional reference genes such as GAPDH and ACTB, and therefore are suitable for the normalization of universal genes having relatively low expression levels.

Numeral: numbers of genes

A: protein fate (folding, modification, destination); B: cellular transport, transport facilitation and transport route; C: transcription; D: cellular communication/signal transduction mechanism; E: cell cycle and DNA processing; F: protein synthesis; G: metabolism; H: energy; I: cell fate; J:

interaction with cellular environment; K: interaction with environment(systemic); L: organ differentiation; M: development (systemic); N: protein activity regulation; O: tissue differentiation; P: Biogenesis of cellular components; Q: cell rescue, defense and virulence; and R: cell type differentiation.

Figure 3:
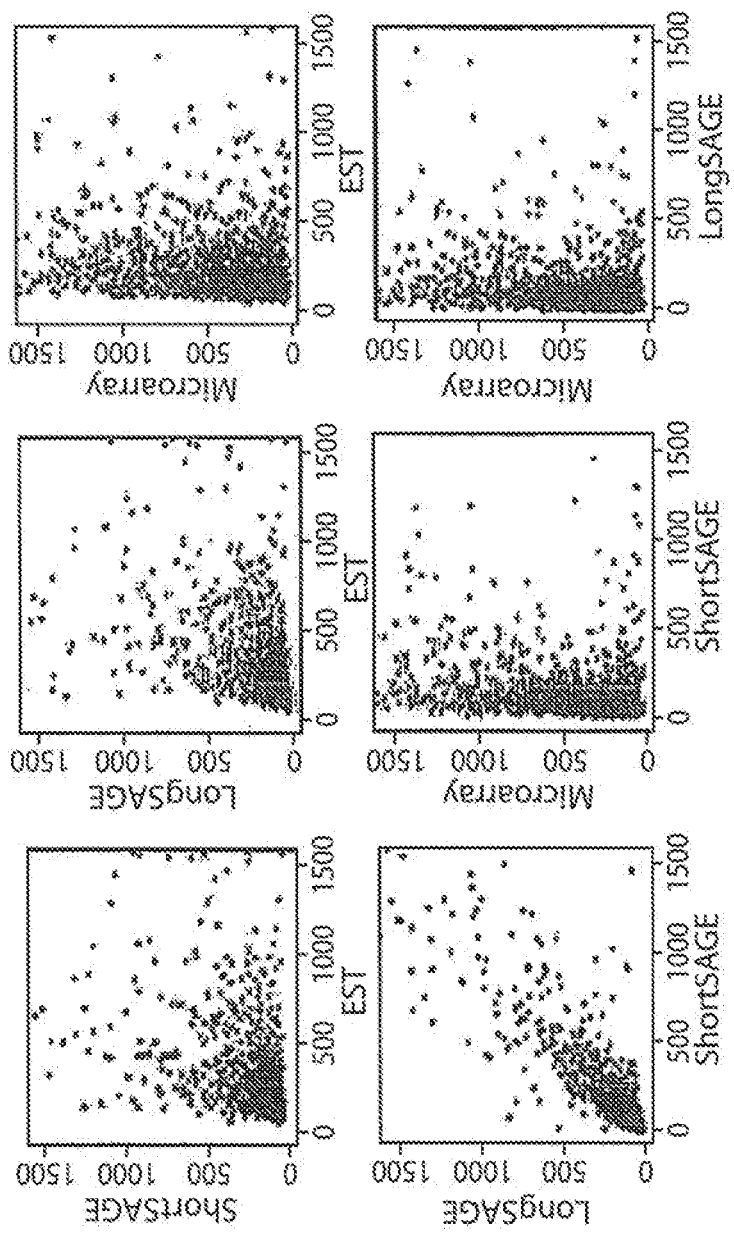

FIG. 3 shows correlations of gene expression of 2,087 candidates ERG among four datasets [EST (expressed sequence tag), ShortSAGE, LongSAGE and microarray datasets].

Figure 4:
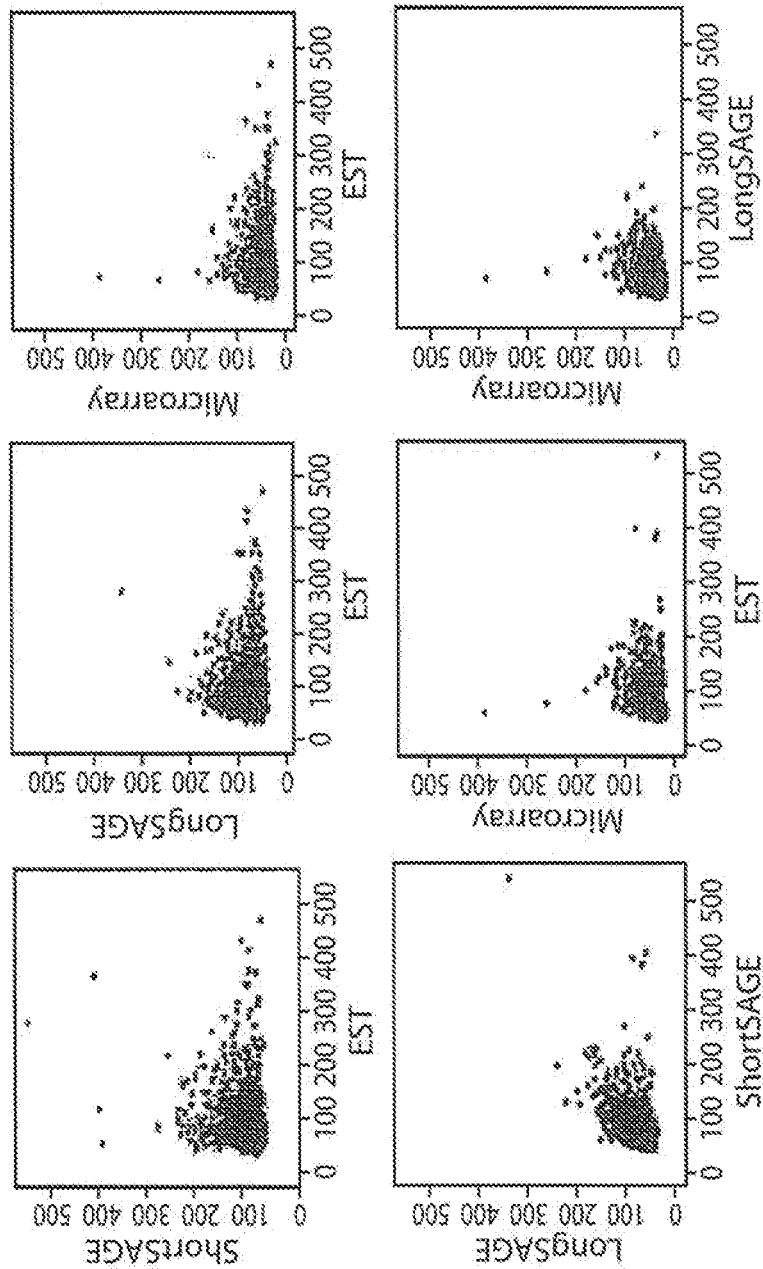

FIG. 4 shows correlations of CV (coefficient of variation %) of 2,087 candidates ERGs among four datasets (EST, ShortSAGE, LongSAGE and microarray datasets).

Figure 5:
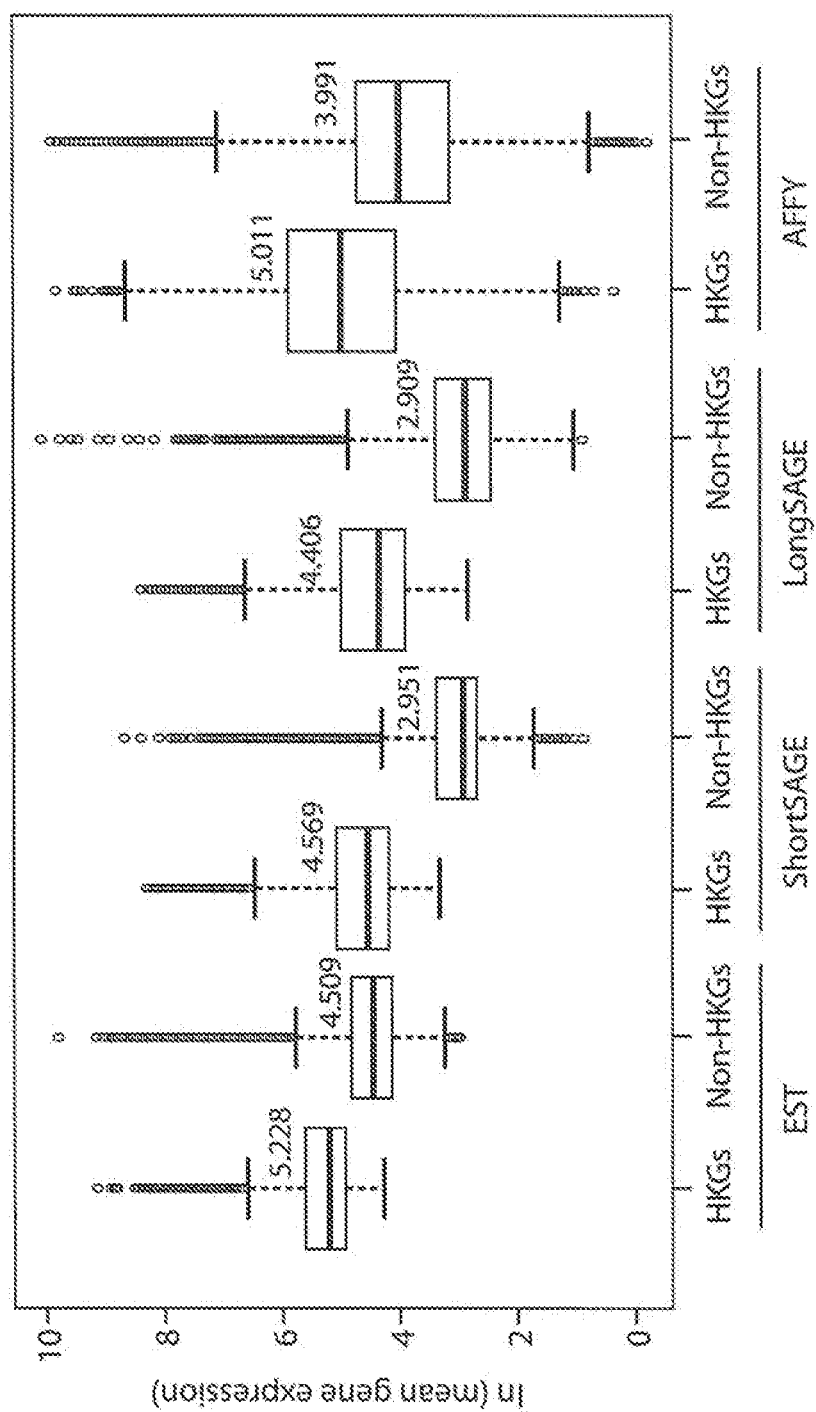

FIG. 5 is a graph showing the comparison of gene expression between the candidate ERGs, selected according to the present invention, and non-candidate ERGs among each dataset:

Box and Whisker plots: expression distribution expressed as natural log value (ln);

Bottom surface of box: corresponding to 25% of the total expression levels in ascending order; and Top surface of box: corresponding to 75% of the total expression levels in ascending order.

Figure 6:
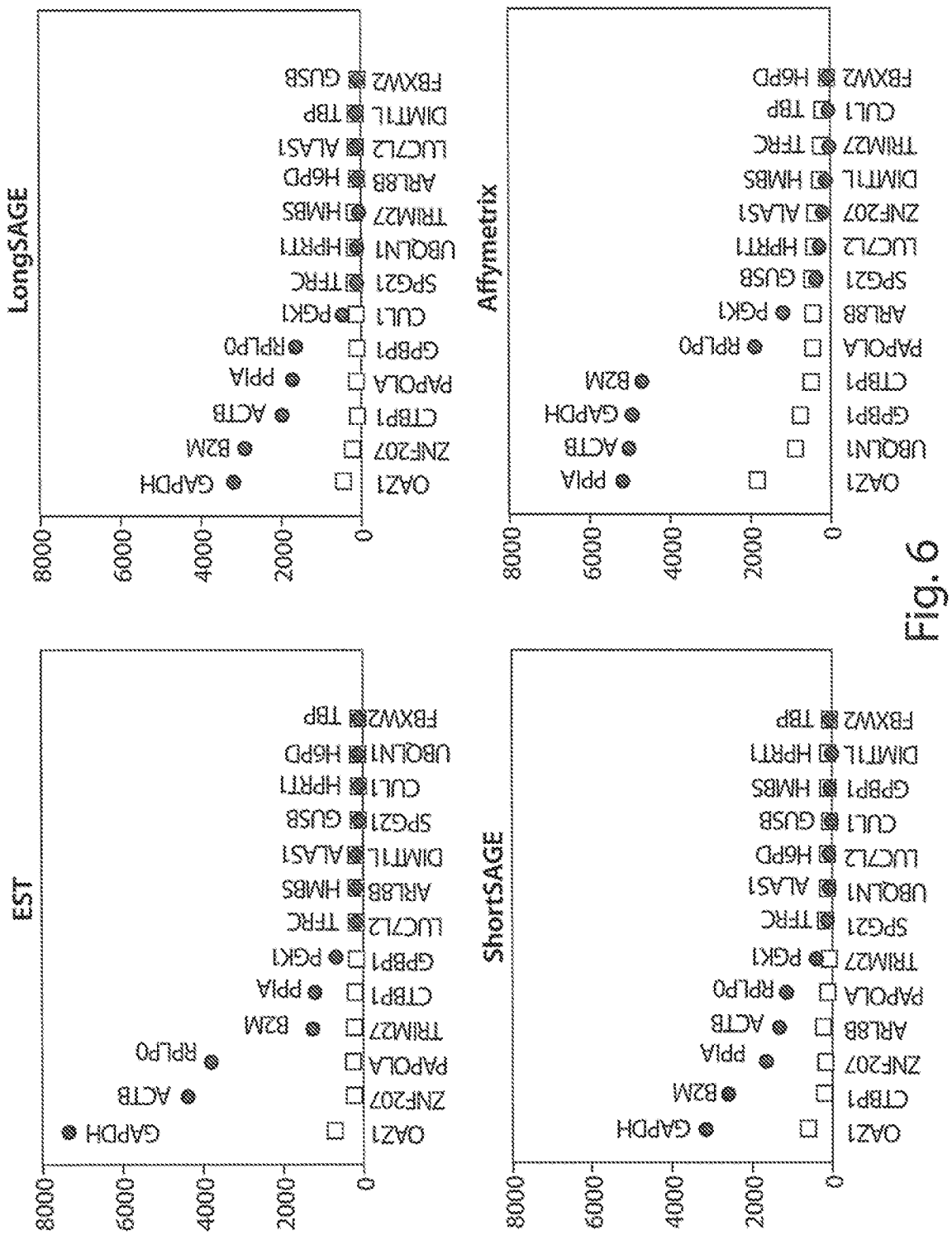

FIG. 6 shows the comparison of gene expression between the 13 ERGs of the present invention and 13 arbitrarily selected traditional ERGs.

Figure 7:
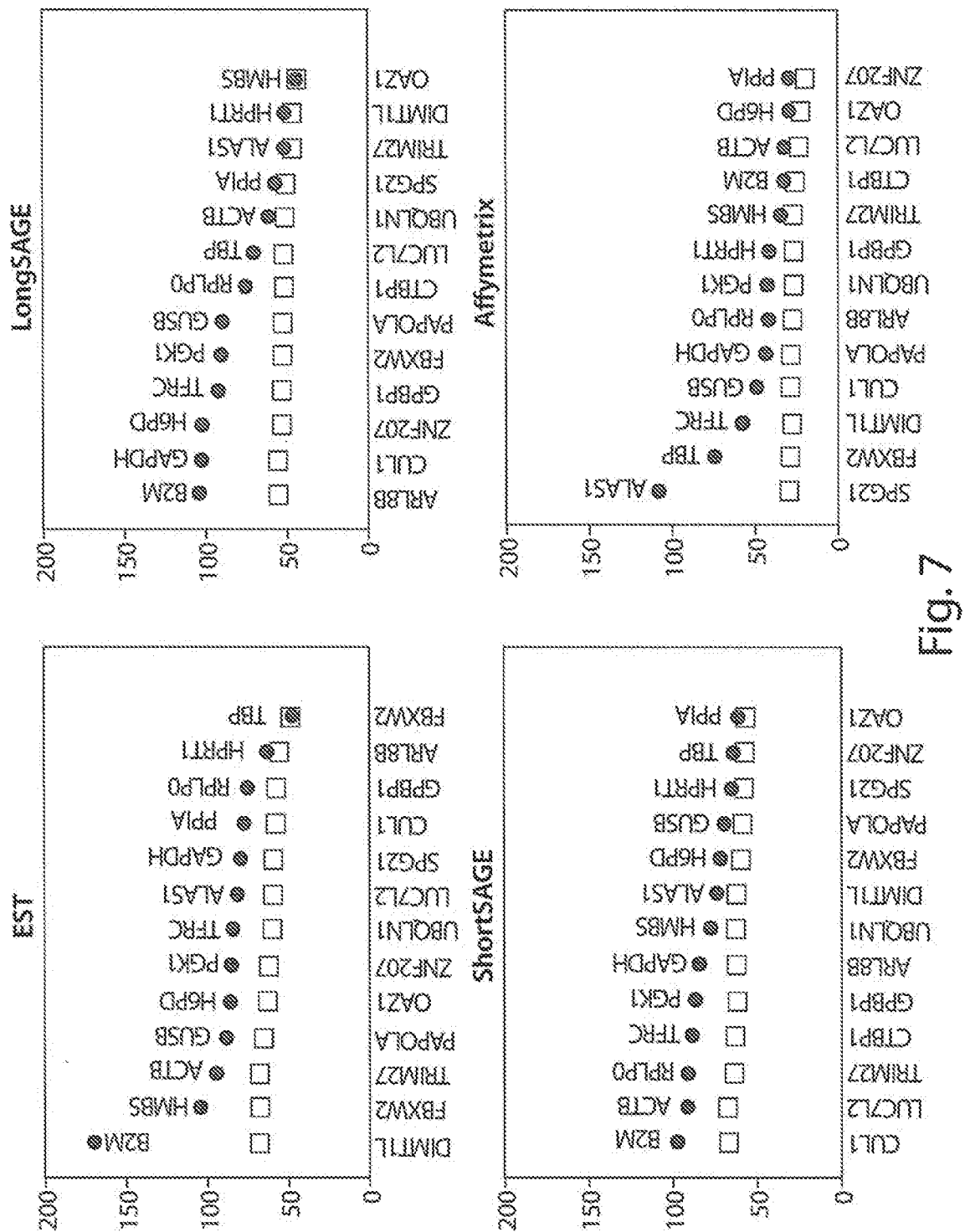

FIG. 7 shows the comparison of CV (%) between the 13 ERGs of the present invention and 13 arbitrarily selected traditional ERGs.

Figure 8:
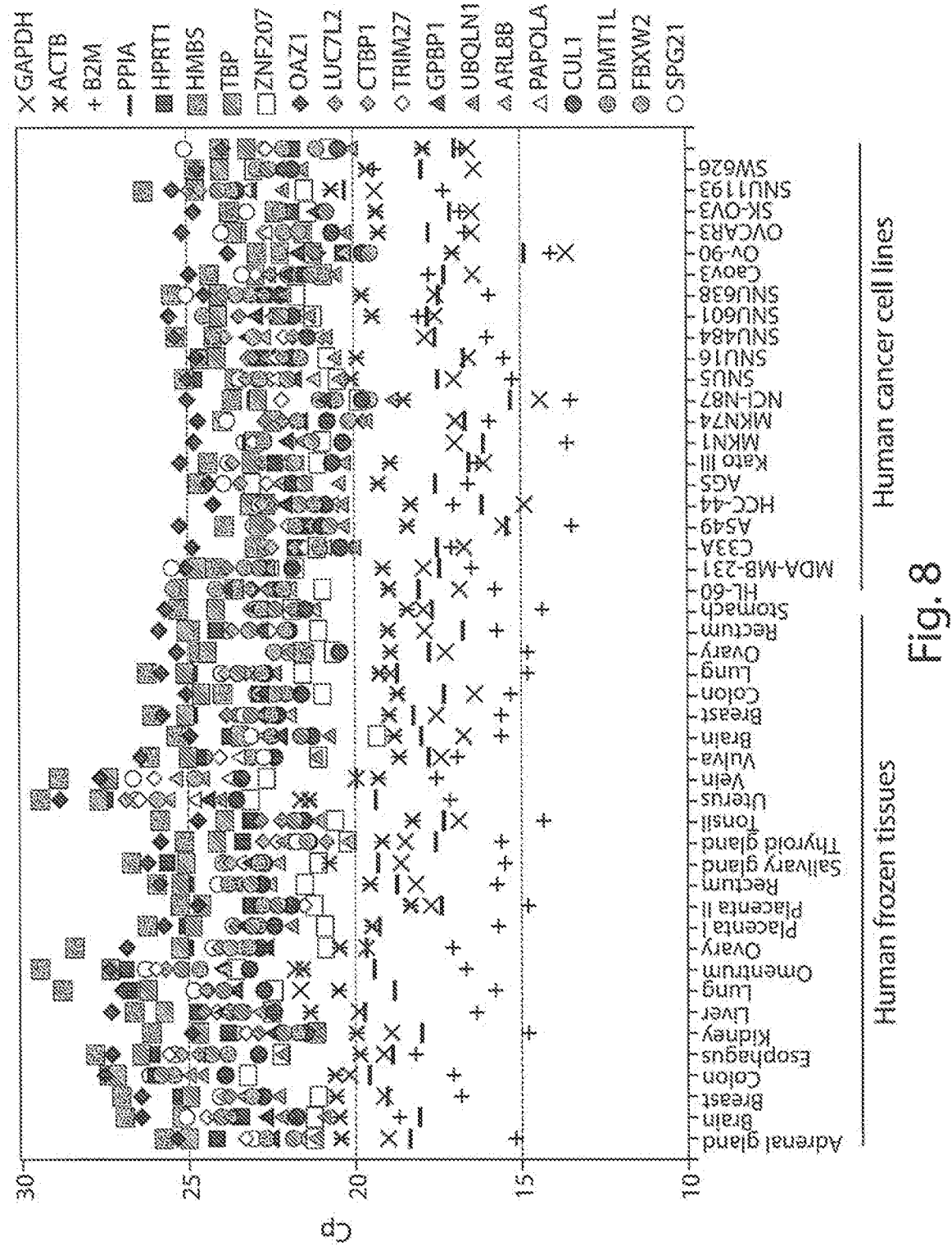

FIG. 8 is a graph showing mRNA level distributions of the novel and traditional ERGs, determined by real-time PCR, in 48 samples including frozen human tissues and cancer cell lines.

Figure 9:
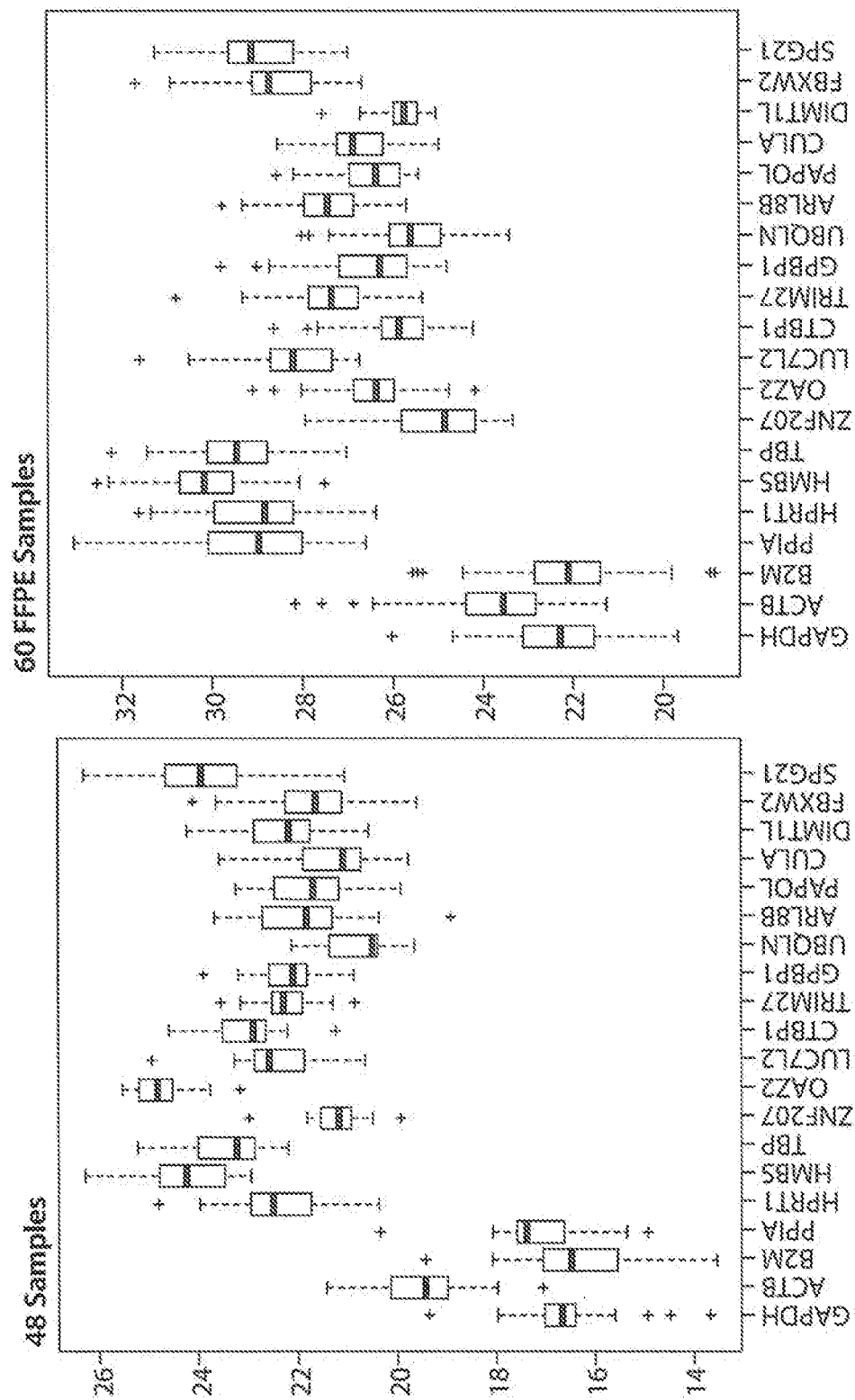

FIG. 9 shows mRNA level distributions, expressed as Cp values determined using real-time PCR, of the novel and traditional ERGs in 48 samples (including frozen human tissues and cancer cell lines) and 60 FFPE (formalin-fixed paraffin-embedded) tissues. In the boxes, the middle lines represent median values of Cp, and the bottom and the top surfaces correspond to 25% and 75% of the total Cp values in ascending order, respectively.

BEST MODE

The terms used herein are defined before embodiments of the present invention are described in detail.

The term "candidate reference gene", as used herein, is intended to refer to a gene, selected using the method of the present invention, which shows a housekeeping gene (HKG)'s properties of being constitutively expressed across a wide range of tissues.

The term "guide gene", as used herein, is intended to refer to a gene, selected from among candidate reference genes, which shows as low an expression level and variation in expression level as most transcripts within cells, which is also expressed as "reference gene" or "endogenous reference gene".

In accordance with an aspect thereof, the present invention provides a method for selecting candidate endogenous reference genes (ERG), comprising:

1) computing expression levels of genes from EST, SAGE and microarray datasets; and 2) identifying genes which are constitutively expressed across a wide range of tissues using the computed gene expression levels of step 1) and zero(0)'s proportions thereof.

Endogenous reference genes (ERG) are most widely used to normalize mRNA levels for an accurate comparison of gene expression between different samples. ERG is usually applied to gene expression analysis, such as RT-PCR (reverse transcriptase polymerase chain reaction), qRT-PCR (quantitative real time PCR), SAGE (serial analysis of gene expression) and microarray. Traditional reference genes, such as glyceraldehyde-3-phosphate dehydrogenase (GAPDH) and R-actin (ACTB), have been used without proper validation, assuming that they are expressed at constant levels across different samples irrespectively the various origins thereof, and are not regulated according to experimental conditions. However, it is well known that the expression of traditional reference genes may differ from one tissue or cell type to another and can be regulated by experimental conditions, including sample treatment, developmental stage and pathological states.

In order to search for candidate housekeeping genes (HKG) whose expression is maintained on similar levels in most tissues, first, datasets were constructed using EST and SAGE human gene expression data collected from the publicly available CGAP site (The Cancer Genome Project, http://cgap.nci.nih.gov/) and microarray gene expression data obtained from the GeneExpress Oncology Datasuite™ of Gene Logic Inc., based on the Affymetrix Human Genome U133 array set. Although the above-mentioned databases were combined to construct new datasets, it should be noted that availability is not limited to the databases. Using the expression data from the datasets, the expression level of a given gene is determined according to the following Mathematical Formulas 1 and 2. The EST (expressed sequence tag) expression levels and the SAGE expression levels of a gene in a given library can be calculated according to Mathematical Formulas 1 and 2, respectively ⟨Mathematical Formula 1⟩

$$ETS \text{ gene expression} = \frac{\text{No of } EST \text{ of a Given Gene in Library}}{\text{Total No. of } ESTs \text{ in } Libaray} \times 1{,}000{,}000$$

⟨Mathematical Formula 2⟩

$$Sage \text{ gene expression} = \frac{\text{No of Tags of a Given Gene in Library}}{\text{Total No. of Tags in } Libaray} \times 1{,}000{,}000$$

In accordance with the present invention, data from the different databases were analyzed to determine their integrity and to identify commonality therebetween. In this regard, the concept of zero (0)'s proportion is introduced to determine the possibility that a given gene might be a housekeeping gene (HKG), which is ubiquitously expressed across most tissues.

⟨Mathematical Formula 3⟩

$$0\text{'s Proportion} = \frac{\text{No. of Tissues with No Expression of a Given Gene}}{\text{Total No. of Tissues}}$$

As expressed by Mathematical Formula 3, zero(0)'s proportion is defined as the ratio of the number of the tissues with no expression of a given gene to the total number of tissues. The lower the 0's proportion is, the higher is the possibility that the given gene might be an HKG. Utilizing the concept of 0's proportion, genes which have low 0's proportions in EST, ShortSAGE, and LongSAGE datasets were sorted. 2,087 genes common to the 3 datasets were selected and categorized as "candidate reference genes" or "candidate ERGs". The genes which have low 0's proportions refer to genes with 0's proportions less than 0.4 for EST, 0.1 for ShortSAGE, and 0.3 for LongSAGE. The mean gene expression values and CV (%) of the 2,087 candidate reference genes were calculated using another dataset, Affymetrix HG-U133, as well as in EST and SAGE datasets. The expression data of 1,990 UniGene clusters (gene expression data for 5,238 different probe sets, 5317 fragments) corresponding to 2,087 ERGs were obtained.

As a result, a significant correlation of the mean expression values is observed among all of the four datasets (EST (expressed sequence tag), ShortSAGE, LongSAGE and microarray dataset)) (see FIG. 3). Correlation analysis on CV showed lower agreement between datasets than on the mean gene expression levels, although a significant correlation was detected (see FIG. 4).

In addition, the candidate ERGs were compared with non-ERGs with regard to gene expression in each dataset. As we expected, the mean gene expression level of the candidate ERGs was significantly higher than that of non-ERGs in all of the four datasets ($p<0.0001$) (see FIG. 5).

In accordance with another aspect thereof, the present invention provides a composition for detecting at least one candidate endogenous reference gene selected according to the present invention, comprising a detection reagent applicable to amplification of the candidate endogenous reference gene.

The candidate endogenous reference gene useful in the present invention is one or more genes selected from a group consisting of Accession No. Hs 120(PRDX6), Accession No. Hs 142(SULT1A1), Accession No. Hs 202(BZRP), Accession No. Hs 429(ATP5G3), Accession No. Hs 695 (CSTB), Accession No. Hs 808 (HNRPF), Accession No. Hs 861 (MAPK3), Accession No. Hs 1063(SNRPC), Accession No. Hs 1103(TGFB1), Accession No. Hs 2430(TCFL1), Accession No. Hs 2533(ALDH9A1), Accession No. Hs 2795(LDHA), Accession No. Hs 2853(PCBP1), Accession No. Hs 3100(KARS), Accession No. Hs 3254(MRPL23), Accession No. Hs 3353(G3BP), Accession No. Hs 3416 (ADFP), Accession No. Hs 439(STOML2), Accession No. Hs 3530(FUSIP1), Accession No. Hs 3989(PLXNB2), Accession No. Hs 4055(KLF6), Accession No. Hs 4742 (GPAA1), Accession No. Hs 4747(DKC1), Accession No. Hs 4766(FAM32A), Accession No. Hs 4859(CCNL1), Accession No. Hs 4997(RBM23), Accession No. Hs 4998 (TMOD3), Accession No. Hs 5062(TM4SF8), Accession No. Hs 5086(MGC10433), Accession No. Hs 5120 (DNCL1), Accession No. Hs 5158(ILK), Accession No. Hs 5245(FLJ20643), Accession No. Hs 5258(MAGED1), Accession No. Hs 5268(ZDHHC4), Accession No. Hs 5298 (ADIPOR1), Accession No. Hs 5308(UBA52), Accession No. Hs 5324(C2orf25), Accession No. Hs 5345(RNPEPL1), Accession No. Hs 5662(GNB2L1), Accession No. Hs 5710 (CREG1), Accession No. Hs 5719(CNAP1), Accession No. Hs 5912(FBX07), Accession No. Hs 5947(RAB8A), Accession No. Hs 6396(JTB), Accession No. Hs 6454 (RGS19IP1), Accession No. Hs 6459(GPR172A), Accession No. Hs 6551(ATP6AP1), Accession No. Hs 6891 (SFRS6), Accession No. Hs 7101(ANAPC5), Accession No. Hs 7236(NOSIP), Accession No. Hs 7476(ATP6VOB), Accession No. Hs 7527(DKFZP566E144), Accession No. Hs 7744(NDUFV1), Accession No. Hs 7753(CALU), Accession No. Hs 7768(FIBP), Accession No. Hs 7862 (PNRC2), Accession No. Hs 7910(RYBP), Accession No. Hs 7917(HIG1), Accession No. Hs 8102(RPS20), Accession No. Hs 8372(UQCR), Accession No. Hs 8737(WDR6), Accession No. Hs 8752(TMEM4), Accession No. Hs 8765 (DDX42), Accession No. Hs 8859(CANT1), Accession No. Hs 8867(CYR61), Accession No. Hs 9003(FLJ13868), Accession No. Hs 9015(MGC52000), Accession No. Hs 9043(C14orf120), Accession No. Hs 9234(NIFIE14), Accession No. Hs 9235(NME4), Accession No. Hs 9527 (C2orf28), Accession No. Hs 9534(SEC11L1), Accession No. Hs 9573(ABCF1), Accession No. Hs 9589(UBQLN1), Accession No. Hs 9788(NDFIP1), Accession No. Hs 9825 (CGI-128), Accession No. Hs 9857(DCXR), Accession No. Hs 10326(COPE), Accession No. Hs 10842(RAN), Accession No. Hs 10848(BMS1L), Accession No. Hs 11125 (SPCS1), Accession No. Hs 11184(UBE2R2), Accession No. Hs 11223(IDH1), Accession No. Hs 11355(TMPO), Accession No. Hs 11463(UMP-CMPK), Accession No. Hs 12013(ABCE1), Accession No. Hs 12084(TUFM), Accession No. Hs 12102(SNX3), Accession No. Hs 12107(BC-2), Accession No. Hs 12109(WDR39), Accession No. Hs 12144 (KIAA1033), Accession No. Hs 12152(SRPRB), Accession No. Hs 12272(BECN1), Accession No. Hs 12341(ADAR), Accession No. Hs 12457(NUP133), Accession No. Hs 12865(NSFL1C), Accession No. Hs 13662(MGC5508), Accession No. Hs 14317(NOLA3), Accession No. Hs 14333 (FLJ10349), Accession No. Hs 14745(C10orf9), Accession No. Hs 14839(POLR2G), Accession No. Hs 14846 (SLC7A1), Accession No. Hs 14894(TGOLN2), Accession No. Hs 15277(C16orf33), Accession No. Hs 15591 (COPS6), Accession No. Hs 15738(RAB7), Accession No. Hs 16059(HSPC009), Accession No. Hs 16130(E2-230K), Accession No. Hs 16349(KIAA0431), Accession No. Hs 17118(FLJ11730), Accession No. Hs 17250(MGC4767), Accession No. Hs 17680(FUCA2), Accession No. Hs 17731 (FLJ12892), Accession No. Hs 17883 (PPM1G), Accession No. Hs 18069(LGMN), Accession No. Hs 18128 (C20orf44), Accession No. Hs 18349(MRPL15), Accession No. Hs 19673(MAF1), Accession No. Hs 20013(P29), Accession No. Hs 20107(KNS2), Accession No. Hs 20157 (CDK5RAP3), Accession No. Hs 20521(HRMT1L2), Accession No. Hs 20529(LOC127262), Accession No. Hs 20573(IGF1R), Accession No. Hs 20716(TIMM17A), Accession No. Hs 22393(DENR), Accession No. Hs 22543 (UBE3A), Accession No. Hs 22546(CYBASC3), Accession No. Hs 22616(KIAA0664), Accession No. Hs 23033 (LOC92912), Accession No. Hs 23111(FARSLA), Accession No. Hs 23978(SAFB), Accession No. Hs 24301 (POLR2E), Accession No. Hs 24379(TRAPPC1), Accession No. Hs 24601(FBLN1), Accession No. Hs 24950(RGS5), Accession No. Hs 25155(NET1), Accession No. Hs 25450 (SLC29A1), Accession No. Hs 25723(MTVR1), Accession No. Hs 26010(PFKP), Accession No. Hs 26023(FOXJ3), Accession No. Hs 26136(MGC14156), Accession No. Hs 26232(MAN2C1), Accession No. Hs 26403(GSTZ1), Accession No. Hs 26518(TM4SF7), Accession No. Hs 27222(NOLA2), Accession No. Hs 28491(SAT), Accession No. Hs 28914(APRT), Accession No. Hs 29203(GBL), Accession No. Hs 29665(CLSTN1), Accession No. Hs 30011(MGC2963), Accession No. Hs 30026(HSPC182), Accession No. Hs 30345(TRAP1), Accession No. Hs 30954 (PMVK), Accession No. Hs 31053(CKAP1), Accession No. Hs 31334(C20orf14), Accession No. Hs 31387 (DKFZP564J0123), Accession No. Hs 34045(CDCA4), Accession No. Hs 34576(TAX1BP1), Accession No. Hs 34906(BLOC1S2), Accession No. Hs 35052(TEGT), Accession No. Hs 35828(MARK3), Accession No. Hs 36587 (PPP1R7), Accession No. Hs 36927(HSPH1), Accession No. Hs 37616(STRA13), Accession No. Hs 37916(DPP7), Accession No. Hs 42806(Cab45), Accession No. Hs 43297 (MTPN), Accession No. Hs 47062(POLR2I), Accession No. Hs 50098 (NDUFA4), Accession No. Hs 50308(HIP2), Accession No. Hs 50425(TEBP), Accession No. Hs 53066 (HSPBP1), Accession No. Hs 54277(FAM50A), Accession No. Hs 54457(CD81), Accession No. Hs 54642(MAT2B), Accession No. Hs 54649(RY1), Accession No. Hs 55682 (EIF3S7), Accession No. Hs 55847(MRPL51), Accession No. Hs 58488(CTNNAL1), Accession No. Hs 58992 (SMC4L1), Accession No. Hs 59486(HSDL2), Accession No. Hs 61812(PTPN12), Accession No. Hs 65234(DDX27), Accession No. Hs 65238(RNF40), Accession No. Hs 66048 (BPY2IP1), Accession No. Hs 66915(C22orf16), Accession No. Hs 68714(SFRS1), Accession No. Hs 9293(HEXB), Accession No. Hs 69554(RNF126), Accession No. Hs 69855(UNR), Accession No. Hs 71465(SQLE), Accession No. Hs 71787(MRPS7), Accession No. Hs 73527 (CSNK2B), Accession No. Hs 73722(APEX1), Accession No. Hs 73799(GNAI3), Accession No. Hs 73965 (SFRS2), Accession No. Hs 74047(ETFB), Accession No. Hs 74050 (FVT1), Accession No. Hs 74137(TMP21), Accession No. Hs 74375(DVL1), Accession No. Hs 74405(YWHAQ), Accession No. Hs 74471(GJA1), Accession No. Hs 74563 (OAZ2), Accession No. Hs 74564(SSR2), Accession No. Hs 74576(GDI1), Accession No. Hs 75056(TIMM13), Accession No. Hs 75061(MARCKSL1), Accession No. Hs 75066 (TSN), Accession No. Hs 75087(FASTK), Accession No. Hs 75117(ILF2), Accession No. Hs 75133(TFAM), Accession No. Hs 75139(ARFIP2), Accession No. Hs 75189(DAP), Accession No. Hs 75227(NDUFA9), Accession No. Hs 75243(BRD2), Accession No. Hs 75249(ARL6IP), Accession No. Hs 75254(IRF3), Accession No. Hs 75318 (TUBA1), Accession No. Hs 75348(PSME1), Accession No. Hs 75438(QDPR), Accession No. Hs 75527(ADSL), Accession No. Hs 75724(COPB2), Accession No. Hs 75798 (C20orf111), Accession No. Hs 75841(C12orf8), Accession No. Hs 75890(MBTPS1), Accession No. Hs 75914(RNP24), Accession No. Hs 76111(DAG1), Accession No. Hs 76394 (ECHS1), Accession No. Hs 76480(UBL4), Accession No. Hs 76662(ZDHHC16), Accession No. Hs 76686(GPX1), Accession No. Hs 76847(GANAB), Accession No. Hs 77060(PSMB6), Accession No. Hs 77269(GNAI2), Accession No. Hs 77313(CDK10), Accession No. Hs 77422 (PLP2), Accession No. Hs 77558(HMGN3), Accession No. Hs 77578(USP9X), Accession No. Hs 77793(CSK), Accession No. Hs 77897(SF3A3), Accession No. Hs 77961(HLA-B), Accession No. Hs 77978(DKFZp761I2123), Accession No. Hs 78466(PSMD8), Accession No. Hs 78601(UROD), Accession No. Hs 78771(PGK1), Accession No. Hs 78880 (ILVBL), Accession No. Hs 78888(DBI), Accession No. Hs 78989(ADH5), Accession No. Hs 79064(DHPS), Accession No. Hs 79081(PPP1CC), Accession No. Hs 79088(RCN2), Accession No. Hs 79101(CCNG1), Accession No. Hs 79110 (NCL), Accession No. Hs 79322(QARS), Accession No. Hs 79335(SMARCD1), Accession No. Hs 79387(PSMC5), Accession No. Hs 79402(POLR2C), Accession No. Hs 79411(RPA2), Accession No. Hs 79625(C20orf149), Accession No. Hs 80545(RPL37), Accession No. Hs 80919 (SYPL), Accession No. Hs 80986(ATP5G1), Accession No. Hs 81328(NFKBIA), Accession No. Hs 81424(SUMO1), Accession No. Hs 81848(RAD21), Accession No. Hs 81964 (SEC24C), Accession No. Hs 82201(CSNK2A2), Accession No. Hs 82327(GSS), Accession No. Hs 82719(MGC21416), Accession No. Hs 82793(PSMB3), Accession No. Hs 82887 (PPP1R11), Accession No. Hs 82890(DAD1), Accession No. Hs 82916(CCT6A), Accession No. Hs 82927(AMPD2), Accession No. Hs 83190(FASN), Accession No. Hs 83347 (AAMP), Accession No. Hs 83383(PRDX4), Accession No. Hs 83734(STX4A), Accession No. Hs 83753(SNRPB), Accession No. Hs 83765(DHFR), Accession No. Hs 83916 (NDUFA5), Accession No. Hs 84359(GABARAP), Accession No. Hs 84753(FLJ12442), Accession No. Hs 85155 (ZFP36L1), Accession No. Hs 85769(ERBP), Accession No. Hs 85962(DERPC), Accession No. Hs 86131(FADD), Accession No. Hs 87752(MSN), Accession No. Hs 89545 (PSMB4), Accession No. Hs 89643(TKT), Accession No. Hs 89649(EPHX1), Accession No. Hs 89781(UBTF), Accession No. Hs 89864(SKIV2L), Accession No. Hs 90061(PGRMC1), Accession No. Hs 90093(HSPA4), Accession No. Hs 90107(ADRM1), Accession No. Hs 90443(NDUFS8), Accession No. Hs 91142(KHSRP), Accession No. Hs 91531(MLLT6), Accession No. Hs 93659 (ERP70), Accession No. Hs 93832(LOC54499), Accession No. Hs 95577(CDK4), Accession No. Hs 96530(COX11), Accession No. Hs 96852(FLJ21128), Accession No. Hs 96996(HNRPA0), Accession No. Hs 97616(SH3GL1), Accession No. Hs 97887(RCN1), Accession No. Hs 98751 (FUBP3), Accession No. Hs 98791(ACTR1B), Accession No. Hs 102696(MCTS1), Accession No. Hs 102798 (PSMA1), Accession No. Hs 103561(ARL6IP4), Accession No. Hs 103834(MGC5576), Accession No. Hs 104839 (TIMP2), Accession No. Hs 105547(NPDC1), Accession No. Hs 106185(RALGDS), Accession No. Hs 106876 (ATP6VOD1), Accession No. Hs 106909(ANAPC13), Accession No. Hs 107003(CCNB1IP1), Accession No. Hs 107101(FLJ31031), Accession No. Hs 107387(C7orf20), Accession No. Hs 107393(C3orf4), Accession No. Hs 108029(SH3BGRL), Accession No. Hs 108080(CSRP1), Accession No. Hs 108371(E2F4), Accession No. Hs 108408 (APH-1A), Accession No. Hs 108957(RPS27L), Accession No. Hs 108969(PTD008), Accession No. Hs 109051 (SH3BGRL3), Accession No. Hs 109052(C14orf2), Accession No. Hs 109672(SIAT7F), Accession No. Hs 109798 (C6orf48), Accession No. Hs 110695(SF3B5), Accession No. Hs 110849(ESRRA), Accession No. Hs 111286 (MRPS11), Accession No. Hs 111577(ITM2C), Accession No. Hs 111801(ARS2), Accession No. Hs 112058(SIVA), Accession No. Hs 112318(TOMM7), Accession No. Hs 112955(NUDT5), Accession No. Hs 114033(SSR1), Accession No. Hs 114286(CD9), Accession No. Hs 114412 (TXNL1), Accession No. Hs 115474(RFC3), Accession No. Hs 115792(EXOSC7), Accession No. Hs 116448(GLS), Accession No. Hs 117176(PABPN1), Accession No. Hs 117715(ST5), Accession No. Hs 118110(BST2), Accession No. Hs 118400(FSCN1), Accession No. Hs 118463(PN-PLA2), Accession No. Hs 118638(NME1), Accession No. Hs 118722(FUT8), Accession No. Hs 118964(p66alpha), Accession No. Hs 118983(GSDMDC1), Accession No. Hs 19177(ARF3), Accession No. Hs 119192(H2AFZ), Accession No. Hs 119251(UQCRC1), Accession No. Hs 119591 (AP2S1), Accession No. Hs 119598(RPL3), Accession No. Hs 120323(DNAPTP6), Accession No. Hs 121088 (NUP153), Accession No. Hs 121549(CDIPT), Accession No. Hs 122363(WIPI-2), Accession No. Hs 122523(SND1), Accession No. Hs 124126(ARPC1A), Accession No. Hs 124147(FBXL11), Accession No. Hs 124246(C10orf119), Accession No. Hs 124366(BBX), Accession No. Hs 125113 (CCT8), Accession No. Hs 125867(EVL), Accession No. Hs 125898(GNAS), Accession No. Hs 126497(AEBP2), Accession No. Hs 126774(RAMP), Accession No. Hs 126938 (NAPA), Accession No. Hs 127092(DHX38), Accession No.

Hs 127249(EAP30), Accession No. Hs 127386(MAMDC2), Accession No. Hs 127764(RAB5C), Accession No. Hs 128065(CTSC), Accession No. Hs 128199(SEPT11), Accession No. Hs 128548(WDR1), Accession No. Hs 129634 (CINP), Accession No. Hs 129673(EIF4A1), Accession No. Hs 130031(TRIO), Accession No. Hs 130098(DDX23), Accession No. Hs 130293(CROP), Accession No. Hs 130413(TM9SF2), Accession No. Hs 131226(BNIP3L), Accession No. Hs 132497(PRNPIP), Accession No. Hs 132513 HSD17B12), Accession No. Hs 133892(TPM1), Accession No. Hs 134074(SLC35E1), Accession No. Hs 134688(PSMD13), Accession No. Hs 135406(CEBPZ), Accession No. Hs 136905(UREB1), Accession No. Hs 136947(RALY), Accession No. Hs 137510(NCOR2), Accession No. Hs 138860(ARHGAP1), Accession No. Hs 139896(MAEA), Accession No. Hs 140452(M6PRBP1), Accession No. Hs 142442(HP1-BP74), Accession No. Hs 143187(DDX49), Accession No. Hs 143766(DRPLA), Accession No. Hs 143873(S100A10), Accession No. Hs 144058(EBSP), Accession No. Hs 144468(MGC3234), Accession No. Hs 144835(EEF1G), Accession No. Hs 144868(VTI1B), Accession No. Hs 144941(MUF1), Accession No. Hs 144949(ZNF313), Accession No. Hs 144980 (SCAMP4), Accession No. Hs 145049(PLEKHM2), Accession No. Hs 145442(MAP2K1), Accession No. Hs 145575 (UBL3), Accession No. Hs 146070(TPM3), Accession No. Hs 146393(HERPUD1), Accession No. Hs 146602(QP-C), Accession No. Hs 146804(SPIN), Accession No. Hs 146806 (CUL1), Accession No. Hs 147433(PCNA), Accession No. Hs 148078(RBAF600), Accession No. Hs 148272(CCM2), Accession No. Hs 148330(ARF4), Accession No. Hs 148340(PTPRG), Accession No. Hs 148670(RHOBTB1), Accession No. Hs 149004(FBX031), Accession No. Hs 149957(RPS6KA1), Accession No. Hs 149983(PEX14), Accession No. Hs 150107(BIRC6), Accession No. Hs 150540(BC002942), Accession No. Hs 150580(SUI1), Accession No. Hs 150837(TXNDC5), Accession No. Hs 151134(OXA1L), Accession No. Hs 151220(KIAA0992), Accession No. Hs 151413(GMFB), Accession No. Hs 151787(U5-116KD), Accession No. Hs$^1$52536($p^{44}$S10), Accession No. Hs 153177(RPS28), Accession No. Hs 154023(TXNDC4), Accession No. Hs 154073(SLC35B1), Accession No. Hs 155165(ZFPL1), Accession No. Hs 155218(HNRPUL1), Accession No. Hs 155396(NFE2L2), Accession No. Hs 155829(KIAA0676), Accession No. Hs 156171(PSMC6), Accession No. Hs 156367(RPS29), Accession No. Hs 156667(KIAA1536), Accession No. Hs 157160(MRPS34), Accession No. Hs 157351(PTD004), Accession No. Hs 157379(H2AFV), Accession No. Hs 157394(HAGH), Accession No. Hs 159014(PRPF4B), Accession No. Hs 159118(AMD1), Accession No. Hs 159130(RAF1), Accession No. Hs 159161(ARHGDIA), Accession No. Hs 159699(FBXO21), Accession No. Hs 159799(THRAP2), Accession No. Hs 160958(CDC37), Accession No. Hs 161357(PDHB), Accession No. Hs 162032(HBP1), Accession No. Hs 162233(CHD4), Accession No. Hs 162877(PACSIN2), Accession No. Hs 163645 (MOCS2), Accession No. Hs 163776(UBE2J1), Accession No. Hs 163893(PICALM), Accession No. Hs 165195 (VAPA), Accession No. Hs 166011(CTNND1), Accession No. Hs 166204(PHF1), Accession No. Hs 166463(HNRPU), Accession No. Hs 166924(SEC13L1), Accession No. Hs 166975(SFRS5), Accession No. Hs 167535(SRP54), Accession No. Hs 168073(TRPC4AP), Accession No. Hs 168799 (METTL3), Accession No. Hs 169611(DIABLO), Accession No. Hs 169718(CNN2), Accession No. Hs 170107 (UQCRFS1), Accession No. Hs 170131(NFIC), Accession No. Hs 170553(CNOT7), Accession No. Hs 170622(CFL1), Accession No. Hs 171626(SKP1A), Accession No. Hs 172550(PTBP1), Accession No. Hs 172755(BRP44L), Accession No. Hs 172928(COL1A1), Accession No. Hs 173024(NYREN18), Accession No. Hs 173162(NOC4), Accession No. Hs 173381(DPYSL2), Accession No. Hs 173464(FKBP8), Accession No. Hs 173611(NDUFS2), Accession No. Hs 173705(LOC401152), Accession No. Hs 173724(CKB), Accession No. Hs 174050(EDF1), Accession No. Hs 174195(IFITM2), Accession No. Hs 175473(AK1), Accession No. Hs 175955(YT521), Accession No. Hs 177530(ATP5E), Accession No. Hs 177766(PARP1), Accession No. Hs 178551(RPL8), Accession No. Hs 178728 (MBD3), Accession No. Hs 179986(FLOT1), Accession No. Hs 180141(CFL2), Accession No. Hs 180312(MRPS16), Accession No. Hs 180414(HSPA8), Accession No. Hs 180877(H3F3B), Accession No. Hs 180903(384D8-2), Accession No. Hs 180909(PRDX1), Accession No. Hs 180933(CXXC1), Accession No. Hs 181046(DUSP3), Accession No. Hs 181112(MED4), Accession No. Hs 181163(HMGN2), Accession No. Hs 181244(HLA-A), Accession No. Hs 181368(PRPF8), Accession No. Hs 181444(TMEM9), Accession No. Hs 182255(NHP2L1), Accession No. Hs 182626(C22orf5), Accession No. Hs 182885(SLC35B2), Accession No. Hs 183684(EIF4G2), Accession No. Hs 183706(ADD1), Accession No. Hs 183800(RANGAP1), Accession No. Hs 183850(DCTD), Accession No. Hs 183994(PPP1CA), Accession No. Hs 184062(C20orf24), Accession No. Hs 184211(PMPCB), Accession No. Hs 184233(HSPA9B), Accession No. Hs 184492(ELAVL1), Accession No. Hs 185172(GNB2), Accession No. Hs 185597(SPG7), Accession No. Hs 187199 (MALAT1), Accession No. Hs 187635(RPS15A), Accession No. Hs 187763(BRD4), Accession No. Hs 187866(SDFR1), Accession No. Hs 187946(SLC20A1), Accession No. Hs 188501(PAFAH1B2), Accession No. Hs 188614 (PLEKHA5), Accession No. Hs 188879(RBM6), Accession No. Hs 188882(NUDT3), Accession No. Hs 189075(PTK9), Accession No. Hs 189119(CXXC5), Accession No. Hs 189329(SMURF1), Accession No. Hs 189716(NDUFAB1), Accession No. Hs 189772(CCT2), Accession No. Hs 190028(GSTO1), Accession No. Hs 190086(MRCL3), Accession No. Hs 190334(RAP1A), Accession No. Hs 190384(COPS4), Accession No. Hs 190722(HSPC142), Accession No. Hs 190904(STRN4), Accession No. Hs 191186(TTC17), Accession No. Hs 191346(SEPT7), Accession No. Hs 191518(DHX9), Accession No. Hs 191987 (UBE2J2), Accession No. Hs 192316(CDCl$_2$L1), Accession No. Hs 192374(TRA1), Accession No. Hs 192425(EIF3S8), Accession No. Hs 193118(RAI17), Accession No. Hs 193163(BIN1), Accession No. Hs 193491(TUBB6), Accession No. Hs 194329(TCEAL4), Accession No. Hs 194718 (ZNF265), Accession No. Hs 195464(FLNA), Accession No. Hs 195642(C17orf27), Accession No. Hs 196983 (SSFA2), Accession No. Hs 198281(PKM2), Accession No. Hs 199561(RANBP2), Accession No. Hs 199625(HAX1), Accession No. Hs 200063(HDAC7A), Accession No. Hs 200600(SCAMP3), Accession No. Hs 200804(SDCBP), Accession No. Hs 201253(ch-TOG), Accession No. Hs 201390(WDR45L), Accession No. Hs 201712(GLG1), Accession No. Hs 202011(GK001), Accession No. Hs 202085(VDAC1), Accession No. Hs 202166(HNRPH1), Accession No. Hs 202179(SMN2), Accession No. Hs 203099(KIAA0261), Accession No. Hs 203910(SGTA), Accession No. Hs 204041(AHSA1), Accession No. Hs 204773(MEP50), Accession No. Hs 205163(MRPL3), Accession No. Hs 206500(CTTN), Accession No. Hs 206824(MGC71993), Accession No. Hs 208597(CTBP1), Accession No. Hs 209983(STMN1), Accession No. Hs 210469(EIM02), Accession No. Hs 210532(KIAA0141), Accession No. Hs 211463(DNM2), Accession No. Hs 211594(PSMC4), Accession No. Hs 211914(NDUFS7), Accession No. Hs 212102(TXNDC7), Accession No. Hs 212395(CIZ1), Accession No. Hs 213061(NUCKS), Accession No. Hs 213470(PSMB7), Accession No. Hs 213541, Accession No. Hs 213666(KIAA0460), Accession No. Hs 213724(SUPT16H), Accession No. Hs 216653(FBX09), Accession No. Hs 220950(FOXO3A), Accession No. Hs 221847(SLC38A2), Accession No. Hs 222510(DAZAP1), Accession No. Hs 223141(DDX21), Accession No. Hs 224607(SDC1), Accession No. Hs 226007(RDH11), Accession No. Hs 226117(H1F0), Accession No. Hs 226755 (YWHAH), Accession No. Hs 227067(ATAD3A), Accession No. Hs 227253(TOMM70A), Accession No. Hs 227777(PTP4A1), Accession No. Hs 229641(PC4), Accession No. Hs 231295(PITPNC1), Accession No. Hs 231616 (HSPC023), Accession No. Hs 232194(KIAA0174), Accession No. Hs 232543(PDCD4), Accession No. Hs 233458 (NFYC), Accession No. Hs 233552(CDCl$_2$L5), Accession No. Hs 233952(PSMA7), Accession No. Hs 234521 (MAPKAPK3), Accession No. Hs 236030(SMARCC2), Accession No. Hs 237536(MGC20781), Accession No. Hs 237971(XTP3TPA), Accession No. Hs 238839(SCYL1), Accession No. Hs 240170(MGC2731), Accession No. Hs 241336(ATPIF1), Accession No. Hs 241543(POLDIP2), Accession No. Hs 241558(ARIH2), Accession No. Hs 241575(GNPTG), Accession No. Hs 241576(DERL1), Accession No. Hs 241579(SERPINH1), Accession No. Hs 242458(SPG21), Accession No. Hs 242947(DGKI), Accession No. Hs 246112(ASCC3L1), Accession No. Hs 246310 (ATP5J), Accession No. Hs 246413(CPNE1), Accession No. Hs 246781(FBX011), Accession No. Hs 247077(RHOA), Accession No. Hs 247186(FBS1), Accession No. Hs 247975 (HSPD1), Accession No. Hs 248267(MPST), Accession No. Hs 248941(TAF9), Accession No. Hs 49600(DLGAP4), Accession No. Hs 250009(ARL10C), Accession No. Hs 250429(SUPT6H), Accession No. Hs 250758(PSMC3), Accession No. Hs 250899(HSBP1), Accession No. Hs 250905(LOC51234), Accession No. Hs 251531(PSMA4), Accession No. Hs 252457(MVD), Accession No. Hs 252713 (TTC15), Accession No. Hs 252967 DKFZp566C0424), Accession No. Hs 253726(PAPOLA), Accession No. Hs 253903(STOM), Accession No. Hs 254042(BAT1), Accession No. Hs 255015(VPS24), Accession No. Hs 255093 (PFKL), Accession No. Hs 255932(XRN2), Accession No. Hs 255935(BTG1), Accession No. Hs 255973(CRI1), Accession No. Hs 256301(MGC13170), Accession No. Hs 256549(NUBP2), Accession No. Hs 257008(PLD3), Accession No. Hs 257341(SAV1), Accession No. Hs 57761 (SH3BP5), Accession No. Hs 258551(DNPEP), Accession No. Hs 258563(FEZ2), Accession No. Hs 258798 C10orf86), Accession No. Hs 259461(PALM2-AKAP2), Accession No. Hs 260603(PIP5K2B), Accession No. Hs 262823(FLJ10326), Accession No. Hs 265829(ITGA3), Accession No. Hs 268488(KIAA1185), Accession No. Hs 268530(GPS1), Accession No. Hs 268742(C13orf12), Accession No. Hs 268849(GLO1), Accession No. Hs 268939(MATR3), Accession No. Hs 269528(MAK3), Accession No. Hs 269577(PTPRA), Accession No. Hs 269782(GNAQ), Accession No. Hs 269944(MTCH2), Accession No. Hs 270291(ACTN4), Accession No. Hs 270428(SUCLG1), Accession No. Hs 270525(LASS5), Accession No. Hs 270869(ZNF410), Accession No. Hs 271135(ATP5C1), Accession No. Hs 271695(NOB1P), Accession No. Hs 272062(PTPRF), Accession No. Hs 272168(TDE1), Accession No. Hs 272630(ATP6V1D), Accession No. Hs 272927(SEC23A), Accession No. Hs 273077(TMEM14B), Accession No. Hs 274184(TFE3), Accession No. Hs 274772(C15orf15), Accession No. Hs 274873(CARS), Accession No. Hs 275243(S100A6), Accession No. Hs 275775(SEPP1), Accession No. Hs 275865(PCNP), Accession No. Hs 276878(NUP93), Accession No. Hs 277035(MGLL), Accession No. Hs 277517 (C11orf2), Accession No. Hs 278186(ARHGEF1), Accession No. Hs 278362(MEA), Accession No. Hs 278426 (PDAP1), Accession No. Hs 278429(C9orf78), Accession No. Hs 278500(GNPDA1), Accession No. Hs 278569 (SNX17), Accession No. Hs 278573(CD59), Accession No. Hs 278721(SLC39A7), Accession No. Hs 279061 (C17orf25), Accession No. Hs 279245(TACC1), Accession No. Hs 279257(PCMT1), Accession No. Hs 279413 (POLD1), Accession No. Hs 279529(PX19), Accession No. Hs 279583(DREV1), Accession No. Hs 279623(SEPX1), Accession No. Hs 279640(TPR), Accession No. Hs 279652 (MRPL4), Accession No. Hs 279669(TUBG1), Accession No. Hs 279696(SUMF2), Accession No. Hs 279806 (DDX5), Accession No. Hs 79836(COMMD9), Accession No. Hs 279920(YWHAB), Accession No. Hs 279929 (TMED9), Accession No. Hs 80202(SBF1), Accession No. Hs 280342(PRKAR1A), Accession No. Hs 280378 (SNRPB2), Accession No. Hs 282410(CALM1), Accession No. Hs 282700(SPCS2), Accession No. Hs 282901 (RNPC2), Accession No. Hs 282998(RBM9), Accession No. Hs 283111(C14orf124), Accession No. Hs 283454 (BNIP2), Accession No. Hs 283521(RHEB), Accession No. Hs 283610(APG4B), Accession No. Hs 283652(IDI1), Accession No. Hs 283739(UBQLN4), Accession No. Hs 284208(ANKRD25), Accession No. Hs 284279(HMOX2), Accession No. Hs 284286(MRPS24), Accession No. Hs 284491(PDXK), Accession No. Hs 285354(MAX), Accession No. Hs 285976(LASS2), Accession No. Hs 286221 (ARF1), Accession No. Hs 286226(MYO1C), Accession No. Hs 288193(KPNA4), Accession No. Hs 288856 (PFDN5), Accession No. Hs 288969(HSCARG), Accession No. Hs 289008(C6orf68), Accession No. Hs 289092 (COTL1), Accession No. Hs 289123(DCTN2), Accession No. Hs 289271(CYC1), Accession No. Hs 290243(GBF1), Accession No. Hs 290404(SLC25A3), Accession No. Hs 290758(DDB1), Accession No. Hs 291587(ARID1B), Accession No. Hs 292026(EIF4E2), Accession No. Hs 292063(EIF4B), Accession No. Hs 292078(LARP), Accession No. Hs 292265(ZMYND11), Accession No. Hs 292457, Accession No. Hs 292493(G22P1), Accession No. Hs 292524(CCNH), Accession No. Hs 292579(PTDSS1), Accession No. Hs 293563(FLJ12666), Accession No. Hs 295917(ATP6V1B2), Accession No. Hs 297324(TIMP3), Accession No. Hs 298198(CKLFSF3), Accession No. Hs 298280(ATP5A1), Accession No. Hs 298654(DUSP6), Accession No. Hs 299002(FBL), Accession No. Hs 299055 (GDI2), Accession No. Hs 300141(RPL39), Accession No. Hs 300684(RCP9), Accession No. Hs 300772(TPM2), Accession No. Hs 300816 RAB1B), Accession No. Hs 300834(GALNT2), Accession No. Hs 301404(RBM3), Accession No. Hs 301412(Ufc1), Accession No. Hs 302742 (MRPS6), Accession No. Hs 302903(UBE2I), Accession No. Hs 303676(G3BP2), Accession No. Hs 304192(DSTN), Accession No. Hs 304682(CST3), Accession No. Hs 306123 (MAGEF1), Accession No. Hs 306242(RANBP9), Accession No. Hs 306329(ZA20D3), Accession No. Hs 306425 (IBTK), Accession No. Hs 308122(ITPK1), Accession No. Hs 308340(NUP188), Accession No. Hs 308709(GRP58), Accession No. Hs 309090(SFRS7), Accession No. Hs 309231(C6orf153), Accession No. Hs 309641(RNF11), Accession No. Hs 309753(STARD3NL), Accession No. Hs 309849(C14orf159), Accession No. Hs 310542(TOMM40), Accession No. Hs 310645(RAB1A), Accession No. Hs 311072(MRPS35), Accession No. Hs 311346(CMAS), Accession No. Hs 311609(DDX39), Accession No. Hs 311640(RPS27A), Accession No. Hs 312098(ADAM15), Accession No. Hs 313847(TXNDC11), Accession No. Hs 314263(BAZ2A), Accession No. Hs 314359(EIF3S12), Accession No. Hs 315177(IFRD2), Accession No. Hs 315230(GC20), Accession No. Hs 319334(NASP), Accession No. Hs 321391(MGC4549), Accession No. Hs 321541 (RAB11A), Accession No. Hs 323363(APG9L1), Accession No. Hs 323489(FLJ20758), Accession No. Hs 324250 (NDUFB2), Accession No. Hs 324844(VKORC1), Accession No. Hs 325650(EHD2), Accession No. Hs 326387 (MORF4L2), Accession No. Hs 330384(CORO1C), Accession No. Hs 331431(SCC-112), Accession No. Hs 333388(EEF1D), Accession No. Hs 333579(HSPC152), Accession No. Hs 333786(PSMA2), Accession No. Hs 333823(MRPL13), Accession No. Hs 334017(K-ALPHA-1), Accession No. Hs 334479(TRAF7), Accession No. Hs 334534(GNS), Accession No. Hs 334587(RBPMS), Accession No. Hs 334713(BMSC-UbP), Accession No. Hs 334851(LASP1), Accession No. Hs 334868(PPP2R5E), Accession No. Hs 335003(ANKRD11), Accession No. Hs 335057(SEPT2), Accession No. Hs 335163(KIAA1102), Accession No. Hs 335918(FDPS), Accession No. Hs 337295(STIP1), Accession No. Hs 337766(TXNRD1), Accession No. Hs 339278(COPB), Accession No. Hs 339639(COX7A2L), Accession No. Hs 339697(GRINA), Accession No. Hs 343911(EI24), Accession No. Hs 345694 (KCMF1), Accession No. Hs 346868(EBNA1BP2), Accession No. Hs 348418(DR1), Accession No. Hs 349656 (SCARB2), Accession No. Hs 350194(ZMAT2), Accession No. Hs 350229(CASC3), Accession No. Hs 350268 (IRF2BP2), Accession No. Hs 350364(C9orf10OS), Accession No. Hs 350927(SLC25A6), Accession No. Hs 351099 (FLJ10241), Accession No. Hs 351296(LOC51035), Accession No. Hs 351316(TM4SF1), Accession No. Hs 351474(PAQR4), Accession No. Hs 351680, Accession No. Hs 351875(COX6C), Accession No. Hs 352341(STCH), Accession No. Hs 352656(GHITM), Accession No. Hs 352768(PSMB1), Accession No. Hs 354056(POR), Accession No. Hs 355141(TNIP1), Accession No. Hs 355606 (MGC23909), Accession No. Hs 355643(RNPS1), Accession No. Hs 355708(FLJ20507), Accession No. Hs 355750 (MGC5306), Accession No. Hs 355753 (DKFZp586M1819), Accession No. Hs 355867(MARS), Accession No. Hs 355927(VDAC2), Accession No. Hs 355934(SFPQ), Accession No. Hs 355983(BZW1), Accession No. Hs 356061(MAP1LC3B), Accession No. Hs 356096(FLJ10350), Accession No. Hs 356190(UBB), Accession No. Hs 356270(SDHD), Accession No. Hs 356285(HMGN1), Accession No. Hs 356331(PPIA), Accession No. Hs 356366(RPS2), Accession No. Hs 356371 (RPL28), Accession No. Hs 356377(LOC149603), Accession No. Hs 356467(MGC2747), Accession No. Hs 356501 (PHF6), Accession No. Hs 356502(RPLP1), Accession No. Hs 356549(SNRPD3), Accession No. Hs 356630(NUTF2), Accession No. Hs 356647(SNX6), Accession No. Hs 356654(PSMC1), Accession No. Hs 56766( ), Accession No. Hs 356769(MAN2B1), Accession No. Hs 356799, Accession No. Hs 357901(SOX4), Accession No. Hs 362728(SEP15), Accession No. Hs 365116(U2AF1), Accession No. Hs 368084(LRPPRC), Accession No. Hs 368149 (CCT7), Accession No. Hs 368157(PYGB), Accession No. Hs 368240(DYRK1A), Accession No. Hs 68264 (PPP2R5C), Accession No. Hs 368376(SRPR), Accession No. Hs 368402(LOC51337), Accession No. Hs 368404 (EXT2), Accession No. Hs 368525(PDLIM1), Accession No. Hs 368598(LEREPO4), Accession No. Hs 368934 (MGC40157), Accession No. Hs 368985(TRIP12), Accession No. Hs 369017(RAB2), Accession No. Hs 369052 (SELT), Accession No. Hs 369068(DNCLI2), Accession No. Hs 369125(PSMD14), Accession No. Hs 369285 (DKFZP434B168), Accession No. Hs 369356(MLL5), Accession No. Hs 369606(CPSF6), Accession No. Hs 369607(GAK), Accession No. Hs 369614(COPS2), Accession No. Hs 369615(FLJ20551), Accession No. Hs 369761 (DAZAP2), Accession No. Hs 369785(MGC2749), Accession No. Hs 369920(RAP1B), Accession No. Hs 370024 (SEC31L1), Accession No. Hs 370247(APLP2), Accession No. Hs 370292(BCCIP), Accession No. Hs 370312(FNTA), Accession No. Hs 370408(COMT), Accession No. Hs 370581(CAPl), Accession No. Hs 370770(XPO1), Accession No. Hs 370771(CDKN1A), Accession No. Hs 370895 (RPN2), Accession No. Hs 370927(PRO1855), Accession No. Hs 370937(TAPBP), Accession No. Hs 371001 (EIF3S9), Accession No. Hs 371416(CARM1), Accession No. Hs 371563(RAB14), Accession No. Hs 371788 (DKFZP547E1010), Accession No. Hs 371889(ATP1A1), Accession No. Hs 372003(C9orf10), Accession No. Hs 372050(SMAP-5), Accession No. Hs 372286(CUL3), Accession No. Hs 372331(SPTAN1), Accession No. Hs 372541(KBTBD2), Accession No. Hs 372616(ARL1), Accession No. Hs 372914(NDRG1), Accession No. Hs 373550(TGIF), Accession No. Hs 373741(HM13), Accession No. Hs 373763(HNRPR), Accession No. Hs 373952 (CAMTA2), Accession No. Hs 373959(VGLL4), Accession No. Hs 374043(ASXL1), Accession No. Hs 374257 (SIAT4A), Accession No. Hs 374378(CKS1B), Accession No. Hs 374477(EWSR1), Accession No. Hs 374503 (MORF4L1), Accession No. Hs 374588(RPL17), Accession No. Hs 374596(TPT1), Accession No. Hs 374650(IFITM3), Accession No. Hs 374973(PRPF4), Accession No. Hs 375001(TLN1), Accession No. Hs 375108(CD24), Accession No. Hs 375217(RNF31), Accession No. Hs 376046 (BTN3A2), Accession No. Hs 376933(GUK1), Accession No. Hs 377155(LYRIC), Accession No. Hs 378103(RPS5), Accession No. Hs 378532(HBS1L), Accession No. Hs 378808(eIF2A), Accession No. Hs 380403(PCGF4), Accession No. Hs 380774(DDX3X), Accession No. Hs 380953 (RPL38), Accession No. Hs 380973(SUMO2), Accession No. Hs 381008(HLA-E), Accession No. Hs 381058 (KIAA0146), Accession No. Hs 381072(PPIF), Accession No. Hs 381123(RPL21), Accession No. Hs 381126(RPS14), Accession No. Hs 381189(CBX3), Accession No. Hs 381219, Accession No. Hs 381256(GLTP), Accession No. Hs 382044(MRPS2), Accession No. Hs 382168(NCOA3), Accession No. Hs 385913(ANP32E), Accession No. Hs 385986(UBE2B), Accession No. Hs 386434(ANXA7), Accession No. Hs 386465(CHERP), Accession No. Hs 386939(USP7), Accession No. Hs 387208(FAU), Accession No. Hs 387804(PABPC1), Accession No. Hs 388034 (RXRB), Accession No. Hs 388654(ATP6V1G1), Accession No. Hs 388664(RPL11), Accession No. Hs 388739 (XRCC5), Accession No. Hs 388927(YY1), Accession No. Hs 388956(C19orf22), Accession No. Hs 389037 (MCM3APAS), Accession No. Hs 389107(ATP6VOC), Accession No. Hs 389171(PINK1), Accession No. Hs 389649(DDX48), Accession No. Hs 389734(TCEAL8), Accession No. Hs 389996(CHCHD2), Accession No. Hs 390667(GSTK1), Accession No. Hs 393201(ACTR2), Accession No. Hs 395482(PTK2), Accession No. Hs 396644(PAIP2), Accession No. Hs 396740(NIP30), Accession No. Hs 396783(SLC9A3R1), Accession No. Hs 397609 (RPS16), Accession No. Hs 399800(AKAP8L), Accession No. Hs 400295(RPL30), Accession No. Hs 401509 (RBM10), Accession No. Hs 401903(COX5A), Accession No. Hs 401929(RPL10), Accession No. Hs 403917(STK24), Accession No. Hs 404056(EIF3S1), Accession No. Hs 404321(GARS), Accession No. Hs 405144(SFRS3), Accession No. Hs 405410(OGT), Accession No. Hs 405514 (LOC284058), Accession No. Hs 405590(EIF3S6), Accession No. Hs 405880(MRPS21), Accession No. Hs 405942 (LOC339229), Accession No. Hs 406062(NDUFA11), Accession No. Hs 406068(UBE2M), Accession No. Hs 406096(ZA20D2), Accession No. Hs 406277(SF3A1), Accession No. Hs 406300(RPL23), Accession No. Hs 406423(SF3B2), Accession No. Hs 406510(ATP5B), Accession No. Hs 406520(LOC389541), Accession No. Hs 406534(HMG20B), Accession No. Hs 406590(PGR1), Accession No. Hs 406620(RPS10), Accession No. Hs 406683(RPS15), Accession No. Hs 406799(RAB18), Accession No. Hs 406840(SLC35A4), Accession No. Hs 407368(C19orf13), Accession No. Hs 407580(PKP4), Accession No. Hs 407995(MIF), Accession No. Hs 408018 (RPL36), Accession No. Hs 408073(RPS6), Accession No. Hs 408236(TXNL5), Accession No. Hs 408257(NDUFS6), Accession No. Hs 408293(KAB), Accession No. Hs 408324 (FLJ10769), Accession No. Hs 408428(CHES1), Accession No. Hs 408581(SVIL), Accession No. Hs 408909 (GOLPH3), Accession No. Hs 409140(ATP5O), Accession No. Hs 409223(SSR4), Accession No. Hs 409230 (AGPAT1), Accession No. Hs 409834(PHPT1), Accession No. Hs 410197(IDH3G), Accession No. Hs 410596 (HAN11), Accession No. Hs 410817(RPL13), Accession No. Hs 411480(AUP1), Accession No. Hs 411641 (EIF4EBP1), Accession No. Hs 411847(MAPK6), Accession No. Hs 412103(EFHA1), Accession No. Hs 412117 (ANXA6), Accession No. Hs 412196(ESRRBL1), Accession No. Hs 412433(AIP), Accession No. Hs 412468 (KLHDC3), Accession No. Hs 412842(C10orf7), Accession No. Hs 413036(WBSCR22), Accession No. Hs 413482 (C21orf33), Accession No. Hs 414579(SCOTIN), Accession No. Hs 415342(KIAA1049), Accession No. Hs 416049 (TNPO2), Accession No. Hs 416436(TRIM50A), Accession No. Hs 417004(S100A11), Accession No. Hs 417029 (DERP6), Accession No. Hs 418123(CTSL), Accession No. Hs 418175(VPS28), Accession No. Hs 418233(MRPL24), Accession No. Hs 418450(MRPL11), Accession No. Hs 418533(BUB3), Accession No. Hs 418668(ATP5D), Accession No. Hs 419640(PARK7), Accession No. Hs 420269 (COL6A2), Accession No. Hs 420272(H2AFY), Accession No. Hs 421257(RPL7), Accession No. Hs 421509(CCT4), Accession No. Hs 422113(ZNF511), Accession No. Hs 423935(RDBP), Accession No. Hs 423968(TTC11), Accession No. Hs 424126(SERF2), Accession No. Hs 424908 (LSM5), Accession No. Hs 425777(UBE2L6), Accession No. Hs 426296(C10orf104), Accession No. Hs 426359 (DKFZp564J157), Accession No. Hs 429052(ITGB1), Accession No. Hs 429353(SEPN1), Accession No. Hs 429581(RTN4), Accession No. Hs 429819(PITPNA), Accession No. Hs 429839(MGC23908), Accession No. Hs 430425(GNB1), Accession No. Hs 430551(IQGAP1), Accession No. Hs 430606(CS), Accession No. Hs 430657 (ARF5), Accession No. Hs 430733(CLNS1A), Accession No. Hs 431101(GNG12), Accession No. Hs 431367 (C6orf55), Accession No. Hs 431498(FOXP1), Accession No. Hs 431550(MAP4K4), Accession No. Hs 431668 (COX6B1), Accession No. Hs 431850(MAPK1), Accession No. Hs 431861(PPP5C), Accession No. Hs 431926 NFKB1), Accession No. Hs 432121(PRDX2), Accession No. Hs 432438(EML4), Accession No. Hs 432491(ESD), Accession No. Hs 432690(SLC39A9), Accession No. Hs 432760(CAPZB), Accession No. Hs 432898(RPL4), Accession No. Hs 432976(NR1H2), Accession No. Hs 433154 (PLSCR3), Accession No. Hs 433201(CDK2AP1), Accession No. Hs 433222(NPC2), Accession No. Hs 433291 (ARD1), Accession No. Hs 433307(BCKDHA), Accession No. Hs 433343(SRRM2), Accession No. Hs 433345, Accession No. Hs 433419(COX4I1), Accession No. Hs 433512 (ACTR3), Accession No. Hs 433529(RPS11), Accession No. Hs 433540(DNAJC8), Accession No. Hs 433573 (Bles03), Accession No. Hs 433615(TUBB2), Accession No. Hs 433701(RPL37A), Accession No. Hs 433722 (KIAA1967), Accession No. Hs 33732(CLK1), Accession No. Hs 433750(EIF4G1), Accession No. Hs 433759 (BANF1), Accession No. Hs 433795(SHC1), Accession No. Hs 433863(PBP), Accession No. Hs 433901(COX8A), Accession No. Hs 433951(GPX4), Accession No. Hs 434102(HMGB1), Accession No. Hs 434207(HARS2), Accession No. Hs 434219(ANKHD1), Accession No. Hs 434401(ZNF638), Accession No. Hs 434937(PPIB), Accession No. Hs 434953(HMGB2), Accession No. Hs 434980 (APP), Accession No. Hs 435044(TBC1D22A), Accession No. Hs 435064(KIAA1608), Accession No. Hs 435120 (KIF1C), Accession No. Hs 435136(TXN), Accession No. Hs 435166(LBR), Accession No. Hs 435231(ZFR), Accession No. Hs 435255(UBXD1), Accession No. Hs 435326 (ACTL6A), Accession No. Hs 435512(PPP3CA), Accession No. Hs 435535(ZNF395), Accession No. Hs 435610(WAC), Accession No. Hs 435741(GCSH), Accession No. Hs 435759(THAP4), Accession No. Hs 435771(API5), Accession No. Hs 435841(TNRC15), Accession No. Hs 435850 (LYPLA1), Accession No. Hs 435933(PHF10), Accession No. Hs 435948(ATAD1), Accession No. Hs 435952 (CDK5RAP1), Accession No. Hs 435974(MTHFD1), Accession No. Hs 436035(TUBA6), Accession No. Hs 436093(BAT2), Accession No. Hs 436204(ZNF289), Accession No. Hs 436298(EMP1), Accession No. Hs 436405 (IDH3B), Accession No. Hs 436437(ALDH2), Accession No. Hs 436446(ARMET), Accession No. Hs 436500 (DBNL), Accession No. Hs 436568(CD74), Accession No. Hs 436578(POLR2F), Accession No. Hs 436657(CLU), Accession No. Hs 436687(SET), Accession No. Hs 436803 (VBP1), Accession No. Hs 437056(SUPT5H), Accession No. Hs 437060(CYCS), Accession No. Hs 437110 (ANXA2), Accession No. Hs 437178(ACADVL), Accession No. Hs 437256(GRINL1A), Accession No. Hs 437277 (MGAT4B), Accession No. Hs 437367(GBAS), Accession No. Hs 437388(PIGT), Accession No. Hs 437403(PP), Accession No. Hs 437594(RPLP2), Accession No. Hs 437638(XBP1), Accession No. Hs 437779(C11orf10), Accession No. Hs 437831(C14orf32), Accession No. Hs 438072(UNC84A), Accession No. Hs 438219(GPS2), Accession No. Hs 438429(RPS19), Accession No. Hs 438678(TALDO1), Accession No. Hs 438720(MCM7), Accession No. Hs 438970(TBL1XR1), Accession No. Hs 438974(CUTL1), Accession No. Hs 439480(RBM5), Accession No. Hs 439481(SUPT4H1), Accession No. Hs 439548(FLJ22875), Accession No. Hs 439552, Accession No. Hs 439815(HBXIP), Accession No. Hs 440382(RFP), Accession No. Hs 440544(CLIC4), Accession No. Hs 440599(DDX1), Accession No. Hs 440604(PSMD7), Accession No. Hs 440899(TTYH3), Accession No. Hs 440932(SEPT9), Accession No. Hs 440960(RAD23A), Accession No. Hs 440961(CAST), Accession No. Hs 441072(POLR2L), Accession No. Hs 441550(C20orf22), Accession No. Hs 442344(IRS2), Accession No. Hs 442798 (RNF10), Accession No. Hs 443134(GBA2), Accession No. Hs 443379(PSMD11), Accession No. Hs 443837(NPEPPS), Accession No. Hs 443914(SOD1), Accession No. Hs 444279(DKFZp761C169), Accession No. Hs 444356 (GRB2), Accession No. Hs 444468(CTDSP1), Accession No. Hs 444472(SDHC), Accession No. Hs 444569(VMP1), Accession No. Hs 444673(CRR9), Accession No. Hs 444724(AZI2), Accession No. Hs 444818(CGGBP1), Accession No. Hs 444931(CRSP6), Accession No. Hs 444969(C2orf4), Accession No. Hs 444986(METAP2), Accession No. Hs 445081(NS5ATP13TP2), Accession No. Hs 445351(LGALS1), Accession No. Hs 445394(VPS29), Accession No. Hs 445498(SKIIP), Accession No. Hs 445511(RIOK3), Accession No. Hs 445570(CD63), Accession No. Hs 445803(DC2), Accession No. Hs 445893 (KHDRBS1), Accession No. Hs 445977(GTF3A), Accession No. Hs 446017(WSB1), Accession No. Hs 446091 (WTAP), Accession No. Hs 446123(CAPZA2), Accession No. Hs 446149(LDHB), Accession No. Hs 446260 (PSMA6), Accession No. Hs 446336(PXN), Accession No. Hs 446345(FTH1), Accession No. Hs 446414(CD47), Accession No. Hs 446427(OAZ1), Accession No. Hs 446445(YIF1), Accession No. Hs 446450(ITM2B), Accession No. Hs 446574(TMSB10), Accession No. Hs 446588 (RPS13), Accession No. Hs 446623(HNRPL), Accession No. Hs 446628(RPS4X), Accession No. Hs 446641 (ARAF), Accession No. Hs 446852(EIF3S6IP), Accession No. Hs 447477(ST13), Accession No. Hs 447492(PGAM1), Accession No. Hs 447547(VPS35), Accession No. Hs 48226 (RPLP0), Accession No. Hs 448588(NGFRAP1), Accession No. Hs 448646(RPL27A), Accession No. Hs 448879, Accession No. Hs 449114(HNRPC), Accession No. Hs 449171(HNRPK), Accession No. Hs 454534(USF2), Accession No. Hs 454699(IL6ST), Accession No. Hs 456507 (PKD1-like), Accession No. Hs 456557(FLJ10597), Accession No. Hs 458320(DC12), Accession No. Hs 458358 (TSPYL1), Accession No. Hs 458414(IFITM1), Accession No. Hs 458458(C19orf27), Accession No. Hs 458747 (ANP32A), Accession No. Hs 459106(OAZIN), Accession No. Hs 459149(BTBD1), Accession No. Hs 459174 (FLJ23790), Accession No. Hs 459211(AKAP13), Accession No. Hs 459596(MPG), Accession No. Hs 459649 (CLCN7), Accession No. Hs 459927(PTMA), Accession No. Hs 459940(LITAF), Accession No. Hs 460238 (SH3GLB2), Accession No. Hs 460317(ALS4), Accession No. Hs 460336(GGA2), Accession No. Hs 460468(XP06), Accession No. Hs 460499(ATXN2L), Accession No. Hs 460574(LOC124446), Accession No. Hs 460923(CNOT1), Accession No. Hs 460929(GOT2), Accession No. Hs 460978(APPBP1), Accession No. Hs 461047(G6PD), Accession No. Hs 461131(CYB5-M), Accession No. Hs 461361(CFDP1), Accession No. Hs 461379(GABARAPL2), Accession No. Hs 461722(HSPC176), Accession No. Hs 461777(PCOLN3), Accession No. Hs 461896 (CRK), Accession No. Hs 461925(RPA1), Accession No. Hs 462035(UBE2G1), Accession No. Hs 462086(RIP), Accession No. Hs 462306(UBE2S), Accession No. Hs 462316 (TTC19), Accession No. Hs 462492(USP22), Accession No. Hs 462550(PIGS), Accession No. Hs 462956(PPARBP), Accession No. Hs 462998(IGFBP4), Accession No. Hs 463010(SMARCE1), Accession No. Hs 463035(FKBP10), Accession No. Hs 463041(RERE), Accession No. Hs 463059(STAT3), Accession No. Hs 463295(CDC127), Accession No. Hs 463506(AKAP1), Accession No. Hs 463702(BCAS3), Accession No. Hs 463797(C1orf33), Accession No. Hs 464071(PGD), Accession No. Hs 464137 (ACOX1), Accession No. Hs 464210(SYNGR2), Accession No. Hs 464336(P4HB), Accession No. Hs 464438 (AGTRAP), Accession No. Hs 464472(MRLC2), Accession No. Hs 464595(PPP4R1), Accession No. Hs 464652 (TNFSF5IP1), Accession No. Hs 464912(P15RS), Accession No. Hs 465224(NARS), Accession No. Hs 465374 (EFHD2), Accession No. Hs 465498(TXNL4A), Accession No. Hs 465529(MIDN), Accession No. Hs 465543 (BTBD2), Accession No. Hs 465627(MAP2K2), Accession No. Hs 465645(C19orf10), Accession No. Hs 465808 (HNRPM), Accession No. Hs 465849(PIN1), Accession No. Hs 465924(SDHB), Accession No. Hs 466044(PKN1), Accession No. Hs 466088(TPM4), Accession No. Hs 466148(NR2F6), Accession No. Hs 466471(GPI), Accession No. Hs 466693(SIRT2), Accession No. Hs 466766 (LTBP4), Accession No. Hs 466775(SNRPA), Accession No. Hs 467084(EIF4G3), Accession No. Hs 467097 (SNRP70), Accession No. Hs 467192(PPP2R1A), Accession No. Hs 467279(LENG4), Accession No. Hs 467284 (RPS9), Accession No. Hs 467408(TRIM28), Accession No. Hs 467637(CDC142), Accession No. Hs 467696(HPCAL1), Accession No. Hs 467701(ODC1), Accession No. Hs 467807(LAPTM4A), Accession No. Hs 467824(PUM2), Accession No. Hs 467960(RAB10), Accession No. Hs 468018(PPP1CB), Accession No. Hs 468415(PIGF), Accession No. Hs 468442(CALM2), Accession No. Hs 468760 (AFTIPHILIN), Accession No. Hs 469022(DGUOK), Accession No. Hs 469171(DKFZP564D0478), Accession No. Hs 469331(STARD7), Accession No. Hs 469820 (RALB), Accession No. Hs 469863(YWHAZ), Accession No. Hs 469925(FLJ14346), Accession No. Hs 469970 (SFRS4), Accession No. Hs 470091(YWHAE), Accession No. Hs 470233(ARL5), Accession No. Hs 470417, Accession No. Hs 470477(PTP4A2), Accession No. Hs 470577 (EIF2S2), Accession No. Hs 470588(KPNA6), Accession No. Hs 470943(STAT1), Accession No. Hs 471011(SF3B1), Accession No. Hs 471104(NOP5/NOP58), Accession No. Hs 471207(NDUFS1), Accession No. s 471441(PSMB2), Accession No. Hs 471461(ACSL3), Accession No. Hs 471593(CAB39), Accession No. Hs 471768(MGC4796), Accession No. Hs 471818(M11S1), Accession No. Hs 471851(HDLBP), Accession No. Hs 471873(DTYMK), Accession No. Hs 471933(FKBP1A), Accession No. Hs 471975(C20orf116), Accession No. Hs 472010(PRNP), Accession No. Hs 472024(C20orf30), Accession No. Hs 472031(UBE2D3), Accession No. Hs 472038(CGI-94), Accession No. Hs 472056(SYNCRIP), Accession No. Hs 472119(MKKS), Accession No. Hs 472185(NDUFS5), Accession No. Hs 472213(RRBP1), Accession No. Hs 472330(C20orf3), Accession No. Hs 472475(MACF1), Accession No. Hs 472535(AKIP), Accession No. Hs 472558 (SDBCAG84), Accession No. Hs 472651(BLCAP), Accession No. Hs 472737(TOP1), Accession No. Hs 473296 (TPD52L2), Accession No. Hs 473583(NSEP1), Accession No. Hs 473648(GART), Accession No. Hs 473721 (SLC2A1), Accession No. Hs 473761(RTN3), Accession No. Hs 473788(OTUB1), Accession No. Hs 474005 (SUM03), Accession No. Hs 474010(PTTG1IP), Accession No. Hs 474053(COL6A1), Accession No. Hs 474083 (B4GALT2), Accession No. Hs 474213(UFD1L), Accession No. Hs 474584(AKR1A1), Accession No. Hs 474643 (HSPC117), Accession No. Hs 474751(MYH9), Accession No. Hs 474833(CSNK1E), Accession No. Hs 474914 (RUTBC3), Accession No. Hs 474938(SLC25A17), Accession No. Hs 474949(RBX1), Accession No. Hs 474982 (ACO2), Accession No. Hs 475125(ATXN10), Accession No. Hs 475319(LRRFIP2), Accession No. Hs 475382 (FLJ22405), Accession No. Hs 475392(LOC55831), Accession No. Hs 475663(RAB5A), Accession No. Hs 475733 (TOP2B), Accession No. Hs 475812(SIMP), Accession No. Hs 476018(CTNNB1), Accession No. Hs 476033(TLP19), Accession No. Hs 476179(SMARCC1), Accession No. Hs 476221(IHPK2), Accession No. Hs 76231(IMPDH2), Accession No. Hs 476308(ALAS1), Accession No. Hs 476365(SCP2), Accession No. Hs 476448(FLNB), Accession No. Hs 476706(MRPL37), Accession No. Hs 476930 (DKFZP5640123), Accession No. Hs 477157(DULLARD), Accession No. Hs 477789(ATP1B3), Accession No. Hs 477892(GYG), Accession No. Hs 478000(MBNL1), Accession No. Hs 478044(PA2G4), Accession No. Hs 478553 (EIF4A2), Accession No. Hs 479208(FBXL5), Accession No. Hs 479264(LAP3), Accession No. Hs 479634 (SLC30A9), Accession No. Hs 479693(SFRS11), Accession No. Hs 479728(GAPD), Accession No. Hs 479747 (BCAR1), Accession No. Hs 479814(POLR2B), Accession No. Hs 480073(HNRPD), Accession No. Hs 480311 (PDLIM5), Accession No. Hs 480465(SCYE1), Accession No. Hs 80653(ANXA5), Accession No. Hs 481571 (UQCRH), Accession No. Hs 481720(MYO10), Accession No. Hs 481898(KAT3), Accession No. Hs 482144(RPL26), Accession No. Hs 482363(SLC30A5), Accession No. Hs 482526(TINP1), Accession No. Hs 482868(KIAA0372), Accession No. Hs 483036(PJA2), Accession No. Hs 483067 (C5orf13), Accession No. Hs 483305(HINT1), Accession No. Hs 483408(PPP2CA), Accession No. Hs 483454 (CNN3), Accession No. Hs 483486(JMJD1B), Accession No. Hs 484138(FBXW11), Accession No. Hs 484188 (ATP6VOE), Accession No. 484242(ETEA), Accession No. Hs 484288(DDX41), Accession No. Hs 484363(RNF130), Accession No. Hs 484551(CPM), Accession No. Hs 484813 (DEK), Accession No. Hs 485155(RPL35), Accession No. Hs 485195(SORT1), Accession No. Hs 485246(PSMA5), Accession No. Hs 485262(MTCH1), Accession No. Hs 485365(AHCYL1), Accession No. Hs 485616(DST), Accession No. Hs 486542(BCLAF1), Accession No. Hs 487027(VIL2), Accession No. Hs 487054(TCP1), Accession No. Hs 487635(BZW2), Accession No. Hs 487774 (HNRPA2B1), Accession No. Hs 488171(KIAA1068), Accession No. Hs 488181(OGDH), Accession No. Hs 488307(DKFZP564K0822), Accession No. Hs 488478 (FLJ10099), Accession No. Hs 488671(BAZ1B), Accession No. Hs 489207(ASNS), Accession No. Hs 489284 (ARPC1B), Accession No. Hs 489287(CPSF4), Accession No. Hs 489336(SYAP1), Accession No. Hs 489615 (PBEF1), Accession No. Hs 490203(CALD1), Accession No. Hs 490394(SSBP1), Accession No. Hs 490415(ZYX), Accession No. Hs 490745(DNAJB6), Accession No. Hs 490795(CHR2SYT), Accession No. Hs 490874(MTX1), Accession No. Hs 491336(ELP3), Accession No. Hs 491359 (LMNA), Accession No. Hs 491440(PPP2CB), Accession No. Hs 491494(CCT3), Accession No. Hs 491597 (VDAC3), Accession No. Hs 491695(UBE2V2), Accession No. Hs 491745(TCEA1), Accession No. Hs 491988 (TRAM1), Accession No. Hs 492236(WDR42A), Accession No. Hs 492314(LAPTM4B), Accession No. Hs 492445 (EDD), Accession No. Hs 492599(EIF3S3), Accession No. Hs 492805(CGI-07), Accession No. Hs 493362(AK3L1), Accession No. Hs 493750(WDR40A), Accession No. Hs 494173(ANXA1), Accession No. Hs 494419(LAMP1), Accession No. Hs 494457(NINJ1), Accession No. Hs 494604(ANP32B), Accession No. Hs 494614(XTP2), Accession No. Hs 494691(PFN1), Accession No. Hs 494700 (CDW92), Accession No. Hs 494985(FBXW2), Accession No. Hs 495039(NDUFA8), Accession No. Hs 495349 (KIAA0515), Accession No. Hs 495471(PMPCA), Accession No. Hs 495605(CD99), Accession No. Hs 495851 (MGC4825), Accession No. Hs 495960(ATP6AP2), Accession No. Hs 496068(PCTK1), Accession No. Hs 496098(DKFZp761A052), Accession No. Hs 496271, Accession No. Hs 496487(ATF4), Accession No. Hs 496646 (IL13RA1), Accession No. Hs 496684(LAMP2), Accession No. Hs 497183(IVNS1ABP), Accession No. Hs 497599 (WARS), Accession No. Hs 497692(C1orf48), Accession No. Hs 497893(ENAH), Accession No. Hs 498239(FH), Accession No. Hs 498313(ADSS), Accession No. Hs 498317(PNAS-4), Accession No. Hs 498455(KIAA0217), Accession No. Hs 498548(RBM17), Accession No. Hs 498727(DHCR24), Accession No. Hs 499145(YME1L1), Accession No. Hs 499158(GGA1), Accession No. Hs 499594(TIMM23), Accession No. Hs 499833(C10orf74), Accession No. Hs 499891(HNRPH3), Accession No. Hs 499925(VPS26), Accession No. Hs 499960(SARA1), Accession No. Hs 500067(PPP3CB), Accession No. Hs 500101(VCL), Accession No. Hs 500375(ENTPD6), Accession No. Hs 500409(GLUD1), Accession No. Hs 500546 (IDE), Accession No. Hs 500674(SMBP), Accession No. Hs 500775(ZNF207), Accession No. Hs 500842(MGEA5), Accession No. Hs 500874(CUEDC2), Accession No. Hs 501012(ADD3), Accession No. Hs 501023(MXI1), Accession No. Hs 501203(TIAL1), Accession No. Hs 501293 (BSG), Accession No. Hs 501309(CIRBP), Accession No. Hs 501353(PLEKHJ1), Accession No. Hs 501376(UROS), Accession No. Hs 501420(NCLN), Accession No. Hs 501629(IER2), Accession No. Hs 501684(NAP1L4), Accession No. Hs 501735(STIM1), Accession No. Hs 501853 (C11orf15), Accession No. Hs 501924(USP47), Accession No. Hs 501991(MLSTD2), Accession No. Hs 502302 (CAT), Accession No. Hs 502328(CD44), Accession No. Hs 502461(DGKZ), Accession No. Hs 502528(NDUFS3), Accession No. Hs 502630(C11orf31), Accession No. Hs 502659(RHOC), Accession No. Hs 502705(PRP19), Accession No. Hs 502745(FADS2), Accession No. Hs 502769 (SLC3A2), Accession No. Hs 502773(MTCBP-1), Accession No. Hs 502823(PRDX5), Accession No. Hs 502829 (SF1), Accession No. Hs 502836(ARL2), Accession No. Hs 502842(CAPN1), Accession No. Hs 502872(MAP3K11), Accession No. Hs 502876(RHOB), Accession No. Hs 503093(ZFP36L2), Accession No. Hs 503222(RAB6A), Accession No. Hs 503251(PME-1), Accession No. Hs 503597(HSPC148), Accession No. Hs 503709(PORIMIN), Accession No. Hs 503716(MGC2714), Accession No. Hs 503787(DARS), Accession No. Hs 504237(ITM1), Accession No. Hs 504517(RPS27), Accession No. Hs 504613 (PTMS), Accession No. Hs 504620(REA), Accession No. Hs 504687(MYL9), Accession No. Hs 504828(DDX47), Accession No. Hs 504895(STRAP), Accession No. Hs 505033(KRAS2), Accession No. Hs 505059(PSMD4), Accession No. Hs 505625(C12orf10), Accession No. Hs 505652(COPZ1), Accession No. Hs 505676(CIP29), Accession No. Hs 505705(MYL6), Accession No. Hs 505806 (PBXIP1), Accession No. Hs 505824(CGI-51), Accession No. Hs 506215(RARS), Accession No. Hs 506325 (NUDT4), Accession No. Hs 06759(ATP2A2), Accession No. Hs 506861(DDX54), Accession No. Hs 507074 (KIAA0152), Accession No. Hs 507162(FLJ12750), Accession No. Hs 507584(MGC9850), Accession No. Hs 507680 (PFAAP5), Accession No. Hs 507910(PGRMC2), Accession No. Hs 507916(TGFB1I4), Accession No. Hs 508010(FNDC3A), Accession No. Hs 508644(FLJ10154), Accession No. Hs 509163(KIAA1181), Accession No. Hs 509226(FKBP3), Accession No. Hs 509264(KLHDC2), Accession No. Hs 509414(KTN1), Accession No. Hs 509622(RGL2), Accession No. Hs 509736(HSPCB), Accession No. Hs 509791(ERH), Accession No. Hs 509909 (NUMB), Accession No. Hs 510087(ENSA), Accession No. Hs 510328(DDX24), Accession No. Hs 510402(MCP), Accession No. Hs 511067(FLJ10579), Accession No. Hs 511138(DKFZP564G2022), Accession No. Hs 511149 (SNAP23), Accession No. Hs 511425(SRP9), Accession No. Hs 511504(TCF12), Accession No. Hs 511862, Accession No. Hs 511952(CBX6), Accession No. Hs 512005(ARPC3), Accession No. Hs 512465(SURF4), Accession No. Hs 512525(RPS17), Accession No. Hs 512607(MIR16), Accession No. Hs 512640 (PRKCSH), Accession No. Hs 512661 (KIAA1160), Accession No. Hs 512676, Accession No. Hs 512693(FLJ20859), Accession No. Hs 512756(THAP7), Accession No. Hs 512815(AP3D1), Accession No. Hs 512857(CD151), Accession No. Hs 512867(H63), Accession No. Hs 512908(ARPP-19), Accession No. Hs 513043 (C15orf12), Accession No. Hs 513055(REC14), Accession No. Hs 513057(RANBP5), Accession No. Hs 513058 (TMED3), Accession No. Hs 513071(MESDC1), Accession No. Hs 513083(RPL9), Accession No. Hs 513141(IDH2), Accession No. Hs 513145(NEUGRIN), Accession No. Hs 513153(FURIN), Accession No. Hs 513230(MRPL28), Accession No. Hs 513242(RHOT2), Accession No. Hs 513261(C16orf34), Accession No. Hs 513266(NDUFB10), Accession No. Hs 513470(NFATC2IP), Accession No. Hs 513488(MVP), Accession No. Hs 513490(ALDOA), Accession No. Hs 513520(BCKDK), Accession No. Hs 513522 (FUS), Accession No. Hs 513631(ARL2BP), Accession No. Hs 513856(DPH2L1), Accession No. Hs 513984(FLII), Accession No. Hs 514012(MAP2K3), Accession No. Hs 514036(SDF2), Accession No. Hs 514038(FLOT2), Accession No. Hs 514174(JUP), Accession No. Hs 514196 (RPL27), Accession No. Hs 514211(MGC4251), Accession No. Hs 514216(CGI-69), Accession No. Hs 514220(GRN), Accession No. Hs 514297(FLJ13855), Accession No. Hs 514303(PHB), Accession No. Hs 514435(SF3B3), Accession No. Hs 514489(WBP2), Accession No. Hs 514535 (LGALS3BP), Accession No. Hs 514581(ACTG1), Accession No. Hs 514590(HGS), Accession No. Hs 514819 (AP2B1), Accession No. Hs 514870(ATP5F1), Accession No. Hs 514920(NDP52), Accession No. Hs 514934 (CAPZA1), Accession No. Hs 515003(C19orf6), Accession No. Hs 515005(STK11), Accession No. Hs 515018 (GNA13), Accession No. Hs 515053(AES), Accession No. Hs 515070(EEF2), Accession No. Hs 515092(CLPP), Accession No. Hs 515155(MGC2803), Accession No. Hs 515162(CALR), Accession No. Hs 515164(GADD45GIP1), Accession No. Hs 515210(DNAJB1), Accession No. Hs 515255(LSM4), Accession No. Hs 515266(RENT1), Accession No. Hs 515271(SFRS14), Accession No. Hs 515329 (RPL22), Accession No. Hs 515371(CAPNS1), Accession No. Hs 515406(AKT2), Accession No. Hs 515417(EGLN2), Accession No. Hs 515432(DEDD2), Accession No. Hs 515472(SNRPD2), Accession No. Hs 515475(SYMPK), Accession No. Hs 515487(CALM3), Accession No. Hs 515494(SLC1A5), Accession No. Hs 515500(SAE1), Accession No. Hs 515515(KDELR1), Accession No. Hs 515517(RPL18), Accession No. Hs 515524(NUCB1), Accession No. Hs 515540(PTOV1), Accession No. Hs 515550(LOC284361), Accession No. Hs 515598(PRPF31), Accession No. Hs 515607(PPP1R12C), Accession No. Hs 515642(GPSN2), Accession No. Hs 515785(BLVRB), Accession No. Hs 515846(RUVBL2), Accession No. Hs 515848(HADHB), Accession No. Hs 515890(YPEL5), Accession No. Hs 516075(TIA1), Accession No. Hs 516077 (FLJ14668), Accession No. Hs 516087(TEX261), Accession No. Hs 516111(DCTN1), Accession No. Hs 516114 (WBP1), Accession No. Hs 516157(MAT2A), Accession No. Hs 516450(FLJ20297), Accession No. Hs 516522 (FLJ21919), Accession No. Hs 516539(HNRPA3), Accession No. Hs 516587(UBE2Q), Accession No. Hs 516633 (NCKAP1), Accession No. Hs 516711(CHPF), Accession No. Hs 516790(ARHGEF2), Accession No. Hs 516807 (STK25), Accession No. Hs 516826(TRIB3), Accession No. Hs 516855(CENPB), Accession No. Hs 517080(SLC35C2), Accession No. Hs 517106(CEBPB), Accession No. Hs 517134(C20orf43), Accession No. Hs 517145(ENO1), Accession No. Hs 517168(TAGLN2), Accession No. Hs 517216(PEA15), Accession No. Hs 517232(PEX19), Accession No. Hs 517240(IFNGR2), Accession No. Hs 517262 (SON), Accession No. Hs 517293(F11R), Accession No. Hs 517338(ATP6V1E1), Accession No. Hs 17342(DEDD), Accession No. Hs 517356(COL18A1), Accession No. Hs 517357(DGCR2), Accession No. Hs 517421(PCQAP), Accession No. Hs 517438(ASCC2), Accession No. Hs 517517(EP300), Accession No. Hs 517543(PES1), Accession No. Hs 517582(MCM5), Accession No. Hs 517622 (UNC84B), Accession No. Hs 517641(L3MBTL2), Accession No. Hs 517666(DIA1), Accession No. Hs 517731 (PP2447), Accession No. Hs 517768(DKFZP564B167), Accession No. Hs 517792(C3orf10), Accession No. Hs 517817(MGC3222), Accession No. Hs 517821, Accession No. Hs 517888(CRTAP), Accession No. Hs 517948 (DHX30), Accession No. Hs 517949(MAP4), Accession No. Hs 517969(APEH), Accession No. Hs 517981(TUSC2), Accession No. Hs 518060(ARL6IP5), Accession No. Hs 518123(TFG), Accession No. Hs 518236(SEC61A1), Accession No. Hs 518244(RPN1), Accession No. Hs 518249(ZNF9), Accession No. Hs 518250(COPG), Accession No. Hs 518265(H41), Accession No. Hs 518326 (SERP1), Accession No. Hs 518346(SSR3), Accession No. Hs 518374(QSCN6), Accession No. Hs 518424(NDUFB5), Accession No. Hs 518460(AP2M1), Accession No. Hs 518464(PSMD2), Accession No. Hs 518525(GLUL), Accession No. Hs 518551(RPL31), Accession No. Hs 518608(PP784), Accession No. Hs 518609(ARPC5), Accession No. Hs 518750(OCIAD1), Accession No. Hs 18805 (HMGA1), Accession No. Hs 518827(CCNI), Accession No. Hs 519276(MAPKAPK2), Accession No. Hs 519304 (PELO), Accession No. Hs 519346(ERBB2IP), Accession No. Hs 519347(SFRS12), Accession No. Hs 519520 (RPS25), Accession No. Hs 519523(SERPINB6), Accession No. Hs 519557(TMEM14C), Accession No. Hs 519718 (TTC1), Accession No. Hs 519756(STK10), Accession No. Hs 519818(MGAT1), Accession No. Hs 519909 (MARCKS), Accession No. Hs 519930(C6orf62), Accession No. Hs 520026(VARS2), Accession No. Hs 520028 (HSPA1A), Accession No. Hs 520037(NEU1), Accession No. Hs 520070(C6orf82), Accession No. Hs 520140(SRF), Accession No. Hs 520189(ELOVL5), Accession No. Hs 520205(EIF2AK1), Accession No. Hs 520210(KDELR2), Accession No. Hs 520287(C6orf111), Accession No. Hs 520313(CD164), Accession No. Hs 520383(STX7), Accession No. Hs 520421(PERP), Accession No. Hs 520459 (GTF2I), Accession No. Hs 520623(C7orf27), Accession No. Hs 520640(ACTB), Accession No. Hs 520740 (SCRN1), Accession No. Hs 520794(YKT6), Accession No. Hs 520898(CTSB), Accession No. Hs 520943(WBSCR1), Accession No. Hs 520967(MDH2), Accession No. Hs 520973(HSPB1), Accession No. Hs 520974(YWHAG), Accession No. Hs 521064(ZNF655), Accession No. Hs 521151(FLJ22301), Accession No. Hs 521289(REPIN1), Accession No. Hs 521487(MGC8721), Accession No. Hs 521640(RAD23B), Accession No. Hs 521809(COBRA1), Accession No. Hs 521903(LY6E), Accession No. Hs 521924 (SIAHBP1), Accession No. Hs 521969(NDUFB11), Accession No. Hs 521973(WDR13), Accession No. Hs 522074 (DSIPI), Accession No. Hs 522110(CREB3), Accession No. Hs 522114(CLTA), Accession No. Hs 522310(NANS), Accession No. Hs 522373(GSN), Accession No. Hs 522394 (HSPA5), Accession No. Hs 522463(EEF1A1), Accession No. Hs 522507(FBXW5), Accession No. Hs 522584 (TMSB4X), Accession No. Hs 522590(EIF1AX), Accession No. Hs 522632(TIMP1), Accession No. Hs 522665 (MAGED2), Accession No. Hs 522675(FLJ12525), Accession No. Hs 522752(PSMD10), Accession No. Hs 522817 (BCAP31), Accession No. Hs 522819(IRAK1), Accession No. Hs 522823(EMD), Accession No. Hs 522932(NCOA4), Accession No. Hs 522995(EIF4EBP2), Accession No. Hs 523004(PSAP), Accession No. Hs 523012(DDIT4), Accession No. Hs 523054(SMP1), Accession No. Hs 523131 (TRAPPC3), Accession No. Hs 523145(DDOST), Accession No. Hs 523215(NDUFB8), Accession No. Hs 523238 (NOLC1), Accession No. Hs 523262(C1orf8), Accession No. Hs 523299(EIF3S10), Accession No. Hs 523302 (PRDX3), Accession No. Hs 523560(HSPCA), Accession No. Hs 523680(SSRP1), Accession No. Hs 523789(TncRNA), Accession No. Hs 523829(POLD4), Accession No. Hs 523836(GSTP1), Accession No. Hs 523852(CCND1), Accession No. Hs 523875(INPPL1), Accession No. Hs 524009(AASDHPPT), Accession No. Hs 524081 (DPAGT1), Accession No. Hs 524084(RNF26), Accession No. Hs 524161(RSU1), Accession No. Hs 524171(RAD52), Accession No. Hs 524183(FKBP4), Accession No. Hs 524195(ARHGAP21), Accession No. Hs 524214(MLF2), Accession No. Hs 524219(TPI1), Accession No. Hs 524271 (PHC2), Accession No. Hs 524367(CBARA1), Accession No. Hs 524395(TUBA3), Accession No. Hs 524464 (ATP5G2), Accession No. Hs 524502(RNF41), Accession No. Hs 524530(CTDSP2), Accession No. Hs 524590 (RAB21), Accession No. Hs 524599(NAP1L1), Accession No. Hs 524690(PPIE), Accession No. Hs 524788(RAB35), Accession No. Hs 524809(RSN), Accession No. Hs 524899 (SAP18), Accession No. Hs 524920(ZFP91), Accession No. Hs 524969(Ufm1), Accession No. Hs 525134(FLJ20277), Accession No. Hs 525163(ANKRD10), Accession No. Hs 525232(LRP10), Accession No. Hs 525238(C14orf119), Accession No. Hs 525330(ARF6), Accession No. Hs 525391(FLJ20580), Accession No. Hs 525527(RER1), Accession No. Hs 525626(PACS1L), Accession No. Hs 525899(C6orf49), Accession No. Hs 526464(PML), Accession No. Hs 526521(MDH1), Accession No. Hs 527105 (HNRPDL), Accession No. Hs 527193(RPS23), Accession No. Hs 527348(AKAP9), Accession No. Hs 527412 (ASAH1), Accession No. Hs 527861(OS-9), Accession No. Hs 527862(PKD1), Accession No. Hs 527980(DUT), Accession No. Hs 528050(HARS), Accession No. Hs 528222(NDUFS4), Accession No. Hs 528300(PITRM1), Accession No. Hs 528305(DDX17), Accession No. Hs 528572(SCAM-1), Accession No. Hs 528668(RPL6), Accession No. Hs 528780(GSPT1), Accession No. Hs 528803(UQCRC2), Accession No. Hs 529059(EIF3S4), Accession No. Hs 529132(SEPW1), Accession No. Hs 529244(NCK2), Accession No. Hs 529280(ANAPC7), Accession No. Hs 529303(ARPC2), Accession No. Hs 529369(AFAP), Accession No. Hs 529400(IFNAR1), Accession No. Hs 529420(UBE2G2), Accession No. Hs 529591(TLOC1), Accession No. Hs 529618(TFRC), Accession No. Hs 529631(RPL35A), Accession No. Hs 529782 (VCP), Accession No. Hs 529798(BTF3), Accession No. Hs 529862(CSNK1A1), Accession No. Hs 529890(CANX), Accession No. Hs 529892(SQSTM1), Accession No. Hs 529957(SEC63), Accession No. Hs 530096(EIF3S2), Accession No. Hs 530118(LUC7L2), Accession No. Hs 530291(ANXA11), Accession No. Hs 530314(SSNA1), Accession No. Hs 530331(PDHA1), Accession No. Hs 530381(PIM3), Accession No. Hs 530412(PAI-RBP1), Accession No. Hs 530436(STXBP3), Accession No. Hs 530479(PMF1), Accession No. Hs 530687(RNH), Accession No. Hs 530734(MRPL16), Accession No. Hs 530753 (FLJ20625), Accession No. Hs 530823(COPS7A), Accession No. Hs 530862(PRKAG1), Accession No. Hs 531081 (LGALS3), Accession No. Hs 531089(PSMA3), Accession No. Hs 531176(SARS), Accession No. Hs 531330 (CBWD1), Accession No. Hs 531614(BTBD14B), Accession No. Hs 531752(RANBP3), Accession No. Hs 531856 (GAS5), Accession No. Hs 531876(DNCL2A), Accession No. Hs 531879(RAD1), Accession No. Hs 532359(RPL5), Accession No. Hs 532399(KIAA0663), Accession No. Hs 532755(GTL3), Accession No. Hs 532790(NMT1), Accession No. Hs 532793(KPNB1), Accession No. Hs 532803 (HN1), Accession No. Hs 532826(MCL1), Accession No. Hs 532853(NDUFB7), Accession No. Hs 533030 (HRIHFB2122), Accession No. Hs 533059(TUBB), Accession No. Hs 533122(SFRS10), Accession No. Hs 533136 (LRPAP1), Accession No. Hs 533192(TOMM20), Accession No. Hs 533222(HSA9761), Accession No. Hs 533245(DDX46), Accession No. Hs 533282(NONO), Accession No. Hs 533308(PPP2R5D), Accession No. Hs 533317(VIM), Accession No. Hs 533437(TCEB1), Accession No. Hs 533440(WWP1), Accession No. Hs 533474 (PPP1R8), Accession No. Hs 533479(LYPLA2), Accession No. Hs 533526(ATRX), Accession No. Hs 533624(H3F3A), Accession No. Hs 533712(RBM4), Accession No. Hs 533732(SRP14), Accession No. Hs 533771(STUB1), Accession No. Hs 533782(KRT8), Accession No. Hs 533977(TXNIP), Accession No. Hs 533985(EXOC7), Accession No. Hs 533986(ZNF258), Accession No. Hs 534125(HLA-C), Accession No. Hs 534168(NDUFA1), Accession No. Hs 534212(SEC22L1), Accession No. Hs 534255(B2M), Accession No. Hs 534307(CCND3), Accession No. Hs 534314(EIF5A), Accession No. Hs 534326 (ITGB4BP), Accession No. Hs 534338(PPP4C), Accession No. Hs 534346(RPS7), Accession No. Hs 534350 (SMARCB1), Accession No. Hs 534453(GRIM19), Accession No. Hs 534456(ANAPC11), Accession No. Hs 534457 (C14orf166), Accession No. Hs 534473(TOMM22), Accession No. Hs 534483(MGC2941), Accession No. Hs 536275(PACS1), Accession No. Hs 541269(NDUFB9), Accession No. Hs 546248(CTSD), Accession No. Hs 546250(DNCI2), Accession No. Hs 546253(FDFT1), Accession No. Hs 546261(HNRPA1), Accession No. Hs 546269(RPL10A), Accession No. Hs 546271(PCBP2), Accession No. Hs 546286(RPS3), Accession No. Hs 546289 (RPS12), Accession No. Hs 546290(RPS18), Accession No. Hs 546291(NET-5), Accession No. Hs 546339(SMAP), Accession No. Hs 546356(RPL13A), Accession No. Hs 546394(HSPC016), Accession No. Hs 547759(SSBP3), Accession No. Hs 549178(C9orf86), Accession No. Hs 552590(HTF9C), Accession No. Hs 553496(PGM3), Accession No. Hs 553512(C3F), Accession No. Hs 554767 (NUP88), Accession No. Hs 554776(SREBF1), Accession No. Hs 554894(FLJ12953), Accession No. Hs 554896

(MGC11257), Accession No. Hs 555194(FAM36A), Accession No. Hs 555866(C1QBP), Accession No. Hs 555873 (HNRPAB), Accession No. Hs 555875(IDH3A), Accession No. Hs 555889(PSMC2), Accession No. Hs 555890 (RBBP4), Accession No. Hs 555911(RBM8A), Accession No. Hs 555969(RIC8), Accession No. Hs 555971(PP1201), Accession No. Hs 555973(MRPS25), Accession No. Hs 555994(LONP), Accession No. Hs 556267(FBXL10), Accession No. Hs 556461(NDUFV2), Accession No. Hs 556795(PAICS), Accession No. Hs 557550(NPM1), Accession No. Hs 558296(ACP1), Accession No. Hs 558313 (COX6A1), Accession No. Hs 558322(EEF1B2), Accession No. Hs 558325(EIF5), Accession No. Hs 558328(FKBP5), Accession No. Hs 558330(FTL), Accession No. Hs 558338 (HSPE1), Accession No. Hs 558345(IK), Accession No. Hs 558354(LAMR1), Accession No. Hs 558360(NDUFB4), Accession No. Hs 558361(NME2), Accession No. Hs 558362(NUMA1), Accession No. Hs 558376(RAC1), Accession No. Hs 558381(RNU65), Accession No. Hs 558382(RPL15), Accession No. Hs 558383(RPL18A), Accession No. Hs 558384(RPL19), Accession No. Hs 558385(RPL23A), Accession No. Hs 558386(RPL34), Accession No. Hs 558388(RPS3A), Accession No. Hs 558389(RPS8), Accession No. Hs 558390(RPS24), Accession No. Hs 558391(RPS26), Accession No. Hs 558396 (SCD), Accession No. Hs 558424(CSDA), Accession No. Hs 558426(EIF3S5), Accession No. Hs 558429(G10), Accession No. Hs 558431(RPL14), Accession No. Hs 558442(PDCD6IP), Accession No. Hs 558448(TXNL2), Accession No. Hs 558453(ATP5L), Accession No. Hs 558454(NUDC), Accession No. Hs 558458(COPS8), Accession No. Hs 558473(C18orf10), Accession No. Hs 558499(8D6A), Accession No. Hs 558511(PSARL), Accession No. Hs 558521(C2orf33), Accession No. Hs 558591 (ORMDL1), Accession No. Hs 558825(PDE4DIP), Accession No. Hs 558995, Accession No. Hs 567260(CD2BP2), Accession No. Hs 567263(C1orf43), Accession No. Hs 567267(ATP2C1) and Accession No. Hs 567279(HCNGP). According to the present invention, the detection reagent is a pair of primers and/or probes applicable to the amplification of the candidate reference gene.

Suitable for use in the composition of the present invention is a pair of a sense primer and an antisense primer, both ranging in length from 10 to 50 bp, corresponding to a sense or antisense sequence of the selected candidate reference gene, respectively. The sense primer is preferably 12-30 bp, more preferably 15-26 bp, and most preferably 17-22 bp in length. This is also true of the antisense primer. However, as long as they are useful in the amplification of the gene, the primers used in the present invention can be any length. The primers may be designed using a well-known primer design program. Additionally, the primers are not limited as to their position on the gene, as long as they can be used in the amplification of the gene.

In contrast to previously reported traditional HKGs, in which genes encoding metabolism and ribosome proteins are contained in high proportions (Eisenberg E & Levanon E Y, Trends Genet 19:362-5, 2003; Hsiao L L et al., Physiol Genomics 7:97-104, 2001), genes encoding proteins involved in protein fate (23%, 308/1318) and cellular transport (21%, 273/1318) are found at a high proportion within the candidate ERGs when they are classified by FunCat (Functional Classification Catalogue, Version 2.0, Ruepp A et al., Nucleic Acids Res 32:5539-45, 2004) (see FIG. 2). Further, analysis on the 2,087 genes shows a high frequency of CpG islands, which is in line with the results of previous reports (Larsen F et al., Genomics 13:1095-107, 1992; Ponger L et al., Genome Res 11:1854-60, 2001) (see TABLE 1).

Moreover, the genes can be detected using microarray, SAGE (Serial Analysis of Gene Expression) or qRT-PCR (quantitative real time PCR). Out of the genes, the most abundant transcript was found to come from EEF1A1 in EST and LongSAGE, from DGK1 in ShortSAGE, and from RPL10A in HG-U133 microarray (see Table 2).

In addition, the reference genes selected and identified according to the present invention are adopted as candidate reference genes which may be useful in the analysis of the genes of interest through the validation of expression stability.

In accordance with a further aspect thereof, the present invention provides a method for quantifying an expression level of a gene of interest, comprising:

1) performing real-time PCR to amplify the gene of interest with a pair of primers and/or probes and then performing real-time PCR to amplify the candidate endogenous reference gene with the composition; and 2) normalizing the expression level of the gene of interest relative to that of the candidate endogenous reference gene.

In accordance with still a further aspect thereof, the present invention provides a method for selecting guide genes, comprising measuring the selected candidate endogenous reference genes for coefficient of variation (CV) and ranking the endogenous reference genes in an ascending order of CV.

In an embodiment, the guide genes are expressed in most human body tissues. The guide genes can be used to normalize expression levels for relative quantification of gene expression between different samples. The higher the coefficient of variation (CV) is, the more greatly the gene expression varies from one tissue to another.

Figure 1:
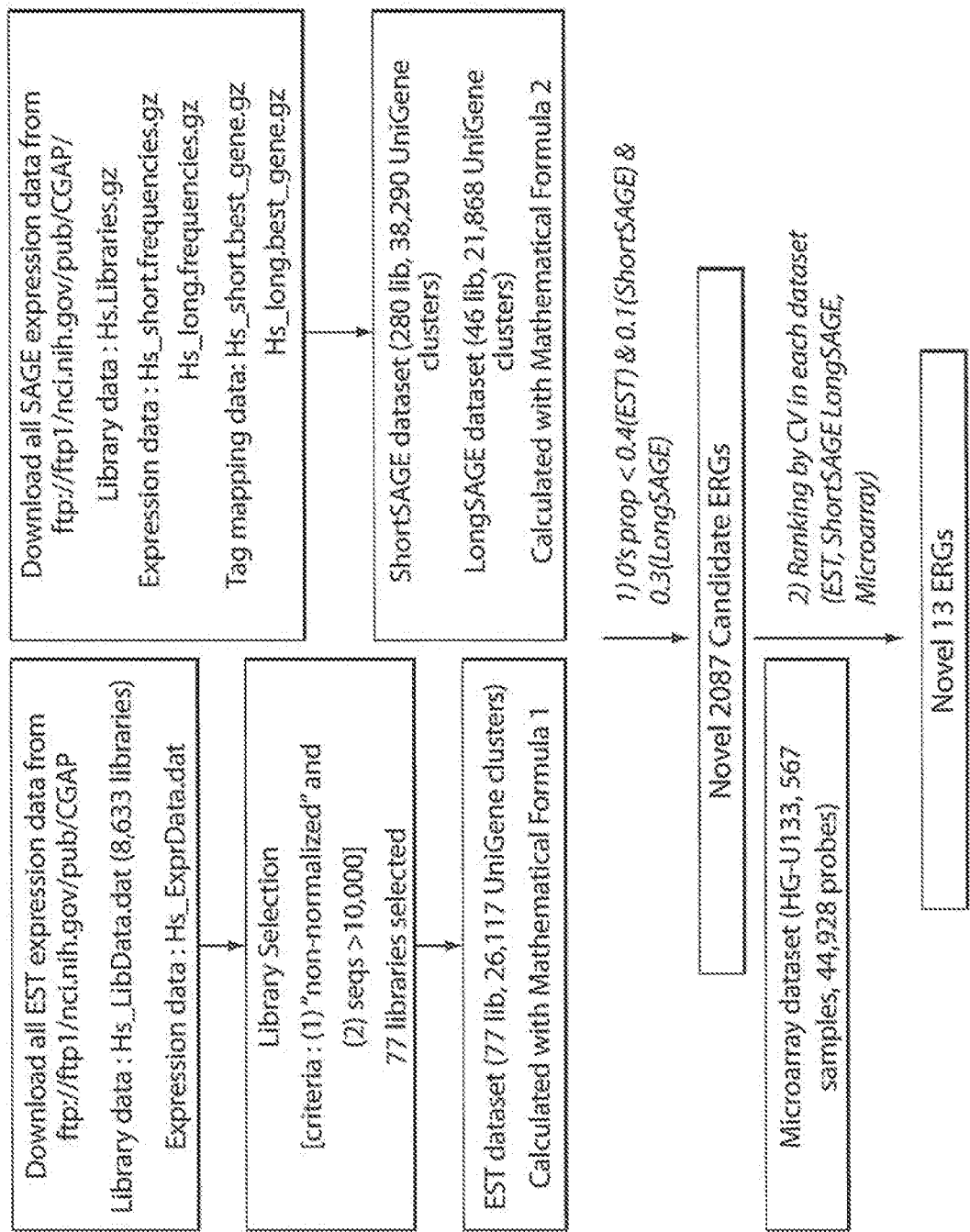
FIG. 1 is a schematic view showing a process of identifying endogenous reference genes (ERGs).

CVs of the candidate reference genes, selected using the selection method of the present invention, were calculated for each UniGene cluster in the datasets including EST, ShortSAGE, LongSAGE and microarray, and the genes were arranged in ascending order of CV. From the candidate ERG were selected the reference genes which were found to be stably expressed across a wide range of tissues. Out of the 400 genes (corresponding to about 20% of the candidate ERG) which were preferentially ranked in ascending order of CV from each dataset, 13 ERGs common to all four datasets were selected (see FIG. 1 and Table 3). The 13 reference genes are identified as Accession No. Hs 500775 (ZNF207), Accession No. Hs 446427(OAZ1), Accession No. Hs 530118(LUC7L2), Accession No. Hs 208597 (CTBP1), Accession No. Hs 440382(TRIM27), Accession No. Hs 444279(GPBP1), Accession No. Hs 250009 (ARL8B), Accession No. Hs 9589(UBQLN1), Accession No. Hs 253726(PAPOLA), Accession No. Hs 146806 (CUL1), Accession No. Hs 533222(DIMT1L), Accession No. Hs 494985(FBXW2) and Accession No. Hs 242458 (SPG21).

In other words, the reference genes are genes that show lower expression variations than do the other genes among the 2,087 genes expressed in most tissues. The reference genes identified according to the present invention are expressed in a manner similar to that in which the majority of the intracellular transcripts are expressed at low abundance.

In an aspect of gene expression level and CV, the 13 reference genes identified according to the present invention were compared with 13 traditional reference genes (see Table 4). In all datasets, six of the 13 traditional reference genes showed relatively high mean expression levels, while the other traditional reference genes indicated expression levels similar to or lower than those of the reference genes of the present invention. In terms of both expression level and CV, the traditional reference genes are generally greater than the endogenous reference genes of the present invention (see FIGS. 6 and 7).

In order to validate the suitability of the 13 genes for reference genes, they were examined for gene copy number variation with reference to the Database of Genomic Variants(//projects.tcag.ca/variation/)(see Table 5). As a result, only OAZ1 and DIMT1L, among the 13 genes of the present invention, were found on chromosome regions known for gene copy variation, whereas many (ACTB, GAPDH, PGK1, B2M, TBP, TFRC, ALAS1) of the traditional reference genes were located in such chromosome regions.

Furthermore, the quantitative real-time RT-PCR (qRT-PCR) analysis (see Table 7) of ERG on human tissue samples and cancer cell lines (see Table 6) indicated that the 13 novel ERGs were expressed in all 48 samples, including frozen human tissues and cancer cell lines (see FIG. 8). The novel 13 ERGs ranged from 19 to 29 in Cp (Crossing Point, the cycle number at which fluorescence crosses the background signal upon qRT-PCR) (see FIG. 9). In addition, using geNorm v3.4 software (Vandesompele J et al., Genome Biol 3:RESEARCH0034, 2002) and NormFinder software (Andersen C L et al., Cancer Res 64:5245-50, 2004), ERGs were analyzed for expression stability according to the following Mathematical Formula 4 in consideration of the efficiency of the PCR performed above (see Table 8). All of the 13 novel ERGs according to the present invention were found to show higher expression stability than were the traditional ERGs as calculated by the geNorm and NormFinder programs (see Table 9). In Table 9, lower expression stability values (M by geNorm, S by NormFinder) mean more stable expression.

Relative Expression=$(1+E)^{\Delta Cp}$     <Mathematical Formula 4>

$\Delta Cp$=Minimum Cp−Sample Cp;
Minimum Cp=lowest Cp value; and
E=PCR Efficiency There was no significant correlation between the M values, which were calculated with geNorm (M) and CV in microarray and LongSAGE datasets, but significance was found in EST and ShortSAGE datasets. Likewise, as for the stability values(S), calculated with NormFinder, significant correlation was found in EST, ShortSAGE and LongSAGE, but not in microarray. Both the M and the S values showed highest agreement with CV in ShortSAGE (see Table 10).

These results indicate that the reference genes identified according to the present invention are more stably expressed than are the traditional reference genes.

In consideration of the fact that the majority of intracellular transcripts are expressed in low abundance (Warrington J A et al., Physiol Genomics 2(3):143-147, 2000), traditional reference genes, having high expression levels, may not be suitable for use in normalization. A reference gene with an expression level similar to that of a target gene is recommended, so that the measurement can be done on the same linear scale (Szabo A et al., Genome Biol 5(8):R59, 2004; RocheAppliedScience Technical Note No. LC 15/2005). Therefore, the endogenous reference genes identified according to the present invention are believed to be more suitable and widely used because they show relatively lower expression and lower variability than do the traditional reference genes (Czechowski T et al., Plant Physiol 139(1): 5-17, 2005).

In accordance with still another aspect thereof, the present invention provides a composition for detecting at least one of the guide genes identified according to the present invention, comprising a detection reagent applicable to amplification of the guide gene.

In an embodiment of this aspect, the guide genes feature low expression levels, like most low-abundance intracellular transcripts. The guide gene useful in the present invention is one or more genes selected from a group consisting of Accession No. Hs 500775(ZNF207), Accession No. Hs 446427(OAZ1), Accession No. Hs 530118(LUC7L2), Accession No. Hs 208597(CTBP1), Accession No. Hs 440382(TRIM27), Accession No. Hs 444279(GPBP1), Accession No. Hs 250009(ARL8B), Accession No. Hs 9589(UBQLN1), Accession No. Hs 253726(PAPOLA), Accession No. Hs 146806(CUL1), Accession No. Hs 533222(DIMT1L), Accession No. Hs 494985(FBXW2) and Accession No. Hs 242458(SPG21). According to the present invention, the detection reagent is a pair of primers and/or probes applicable to the amplification of the guide gene.

Suitable for use in the composition of the present invention is a pair of a sense primer and an antisense primer, both ranging in length from 10 to 50 bp corresponding to sense or antisense sequence of the identified guide genes, respectively. The sense primer is preferably 12-30 bp, more preferably 15-26 bp, and most preferably 17-22 bp in length. This is also true of the antisense primer. However, as long as they are useful in the amplification of the gene, any length of primers can be used in the present invention. The primers may be designed using a well-known primer design program. Additionally, the primers are not limited by the position on the gene as long as they can be used in the amplification of the gene.

In addition, the detection method is preferably conducted using microarray, SAGE (Serial Analysis of Gene Expression) or qRT-PCR (quantitative real time PCR).

In accordance with yet a further aspect thereof, the present invention provides a method for quantifying an expression level of a target gene, comprising:

1) synthesizing cDNA from RNA of a subject;
2) performing real-time PCR to amplify the target gene using a pair of primers and/or probes, with the cDNA serving as a template and then performing real-time PCR to amplify the candidate endogenous reference gene using the composition; and
2) normalizing the expression level of the target gene to that of the candidate endogenous reference gene.

In accordance with yet another aspect thereof, the present invention provides a method for identifying the amplification of a target gene in genomic DNA, comprising:

1) amplifying the target gene with a pair of primers or probes through real-time PCR, with a genomic DNA of a subject serving as a template and than performing real-time PCR to amplify the candidate endogenous reference gene with the composition; and
2) normalizing the expression level of the target gene to that of the candidate endogenous reference gene.

[Mode for Invention]

A better understanding of the present invention may be obtained through the following examples which are set forth to illustrate, but are not to be construed as the limit of the present invention.

Example 1: Gene Expression Dataset Construction

EST (expressed sequence tag) and SAGE (serial analysis of gene expression) human gene expression data were collected from the publicly available CGAP site (The Cancer Genome Project, http://cgap.nci.nih.gov/). Microarray gene expression data were obtained from the GeneExpress Oncology Datasuitem of Gene Logic Inc., based on the Affymetrix Human Genome U133 array set.

Out of a total of 8,633 libraries in Hs_LibData.dat (31, Oct. 2005) file, 77 libraries meeting the requirements: 1) non-normalized and 2) >10,000 sequences, were included in the EST dataset constructed from the CGAP site. EST frequency in each library was obtained from Hs_ExprData.dat (31, Oct. 2005) file. 29 different tissues, including normal and tumor samples, and 26,117 UniGene clusters were included in these libraries.

SAGE short data for all 280 libraries (Hs_short.frequencies.gz, 5, Dec. 2006), representing 38,290 UniGene clusters, and SAGE long data (Hs_long.frequencies.gz, 5, Dec. 2006) for 46 libraries, representing 21,868 UniGene clusters, were used in creating the dataset for SAGE short (ShortSAGE) and long (LongSAGE), respectively. Also, SAGE tags were mapped to UniGene clusters using the files Hs_short.best_gene.gz (5, Dec. 2006) and Hs_long.best_gene.gz (5, Dec. 2006). ShortSAGE and LongSAGE contained information on SAGE expression in 28 and 9 different tissues, including normal and tumor samples, respectively.

Affymetrix GeneChips gene expression data from 567 different samples representing 13 different tissues including the brain, the breast, the colon, the esophagus, the kidney, the liver, the lung, the lymph node, the ovary, the pancreas, the prostate, the rectum and the stomach were also analyzed (Table 11). Affymetrix (CA) HG-U133 and 44,760 different probe sets (total 44,928 probe sets) were included in the microarray dataset.

Example 2: Selection of Candidate ERG

Using the datasets constructed in Example 1, expression level was calculated for UniGene clusters so as to search for housekeeping genes which are constitutively expressed in most human tissues.

Gene expression levels of EST dataset for each gene were calculated as the number of ESTs of a gene in a given library, divided by the total number of ESTs in all genes in a given library and then multiplied by 1,000,000, as expressed by Mathematical Formula 1.

Likewise, Gene expression levels of SAGE dataset for each gene were calculated as the number of tags (sum of tag frequency) of a gene in a given library, divided by the total number of tags and then 1640 multiplied by 1,000,000, as expressed by Mathematical Formula 2.

⟨Mathematical Formula 1⟩

$$ETS \text{ gene expression} = \frac{\text{No of } EST \text{ of a Given Gene in Library}}{\text{Total No. of } ESTs \text{ in } Libaray} \times 1{,}000{,}000$$

⟨Mathematical Formula 2⟩

$$SAGE \text{ gene expression} = \frac{\text{No of Tags of a Given Gene in Library}}{\text{Total No. of Tags in } Libaray} \times 1{,}000{,}000$$

Expression levels in Microarray dataset were represented by the signal intensity calculated for each transcript by the analysis algorithm of Affymetrix Microarray Suite 5.0. Mean gene expression was defined as the average of gene expression level of a given gene in all libraries.

HKGs for use in identifying endogenous reference genes, which are expressed in most human tissues, were investigated using EST and SAGE datasets. In order to examine whether a given gene might be an HKG which is constitutively expressed across a wide range of tissues, the proportion of the tissues not expressing the given gene to the total tissues of the EST and SAGE datasets was calculated. If gene expression frequency is found in any one library of multiple libraries corresponding to one tissue, that gene was considered to be expressed in that tissue. For this, the 0's proportion, which is defined as the ratio of the number of the tissues in which a given gene was not expressed to the total number of tissues, was introduced. In the 0's proportion, "0" indicates that the gene is expressed in all tissues, and conversely, "1" means that the gene is not expressed in any tissue.

⟨Mathematical Formula 3⟩

$$0's \text{ Proportion} = \frac{\text{No. of Tissues with No Expression of a Given Gene}}{\text{Total No. of Tissues}}$$

In a study of 101 samples obtained from 47 different human tissues and cell lines, cutoff values for the 0's proportion were determined in each of EST and SAGE datasets so as to include most of the 575 housekeeping genes identified from previous microarray data using the Affymetrix U95A chip (CA), containing 2,600 probes (Eisenberg E and Levanon E Y, Trends Genet, 19(7), 362-365, 2003). Genes with 0's proportion <0.4 for EST (EST, 4,027 UniGene clusters), 0.1 for ShortSAGE (4,758 UniGene clusters) and 0.3 for LongSAGE (4,569 UniGene clusters) were sorted. 2,087 genes common to the three datasets were selected Out of the 575 genes obtained by U95A, 451(78.43%) in EST, 432(75.13%) in ShortSAGE, and 446(77.57%) in LongSAGE were included in the selected housekeeping genes, respectively. A majority of the 575 HKGs was found to have low 0's proportion in the constructed datasets, EST, ShortSAGE and LongSAGE even though some genes showed the 0's proportion greater than 0.5 unexpectedly. Traditional reference genes like RPLP0, ACTB, PPIA, GAPDH, PGK1, B2M and were TFRC also found in the 2,087 genes.

The mean gene expression value and CV (%) of the housekeeping genes selected from the EST and SAGE datasets were calculated in the microarray dataset (Affymetrix HG-U133, CA). The microarray expression data of 5,238 different probe sets (gene expression data for 5,317 fragments, 1,990 UniGene clusters) corresponding to the selected HKGs were obtained.

UniGene clusters were used to allow respective gene probes to correspond thereto in the datasets. On the chip set HG-U133 were found cases where multiple probe sets, which show various expression intensities, correspond to one gene or UniGene cluster. In such cases, one probe set for one UniGene cluster, showing the lowest CV 1700 among several probe sets, was selected.

The 2,087 HKGs obtained above were categorized as "candidate ERGs" or "candidate reference genes" in accordance with the present invention.

Experimental Example 1: Analysis of Candidate ERG

<1-1> Functional Classification of Candidate ZRG

Using FunCat (Functional Classification Catalogue, Version 2.0, Ruepp, A., et al. Nucleic Acids Res, 32, 5539-45, 2004), the 2,087 genes obtained above were classified.

Figure 2:
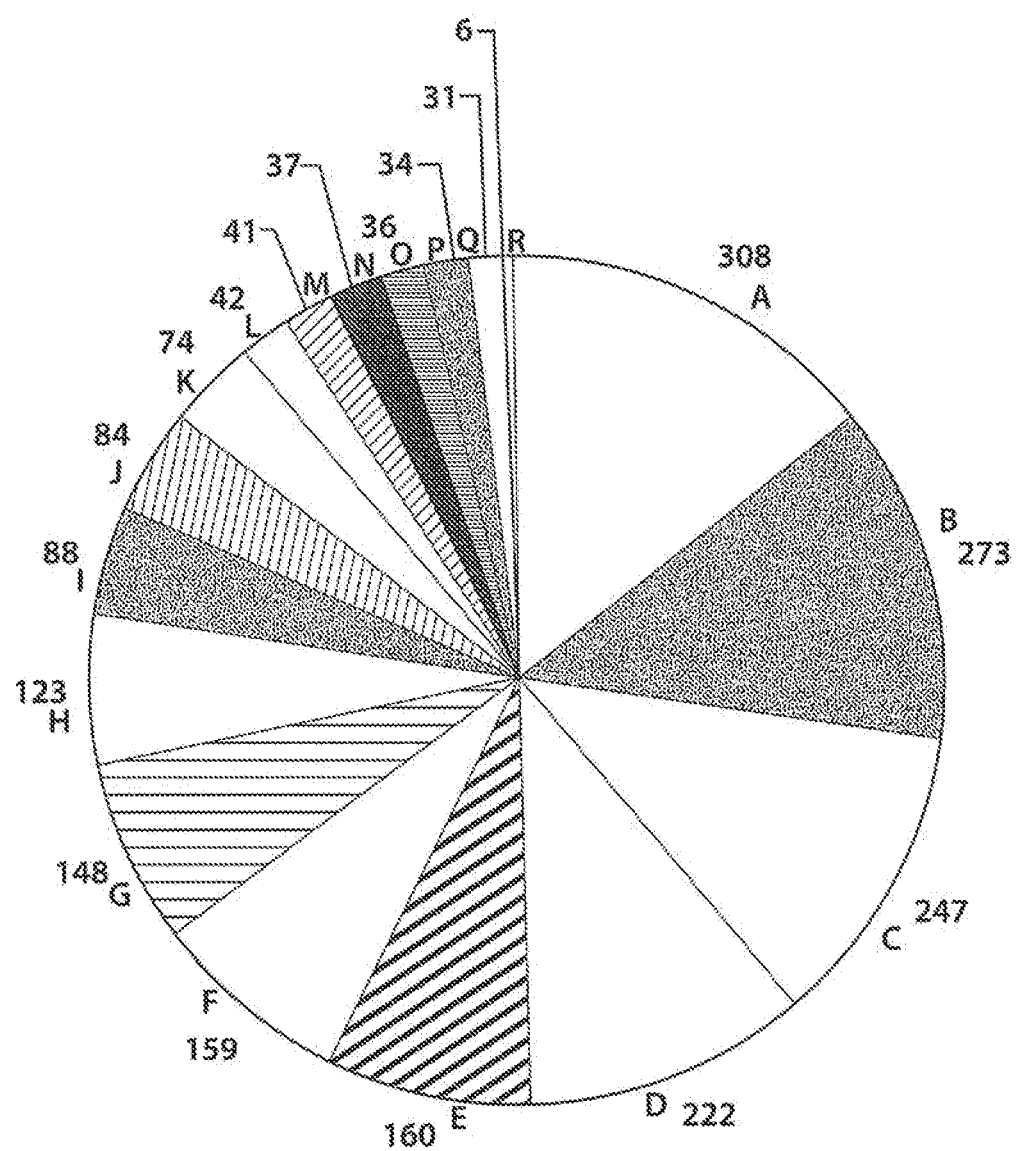
FIG. 2 is a graph showing a functional distribution of candidate ERGs classified according to FunCat (Functional Classification Catalogue)

Out of the 2,087 candidate ERGs, 1,689 UniGene clusters were associated with GO terms allocated to MIPS (Munich Information Center for Protein Sequences) FunCat (Functional Catalogue). Among the 1,689 UniGene clusters, 1,318 UniGene clusters were functionally classified to be associated with GO terms corresponding to biological processes. These 1,318 genes were identified to be involved in various basic cellular functions. While a high proportion of the previously reported traditional HKGs encode metabolism and ribosome proteins (Eisenberg E & Levanon E Y, Trends Genet 19:362-5, 2003; Hsiao L L et al., Physiol Genomics 7:97-104, 2001), genes encoding proteins involved in protein fate (23%, 308/1318) and cellular transport (21%, 273/1318) are found in large amounts in the candidate ERGs (FIG. 2).

<1-2> Analysis of Candidate ERGs for CpG Island

Sequences upstream of the annotated transcription start site of the ERGs according to the present invention were obtained from the UCSC site (//hgdownload.cse.ucsc.edu/goldenPath/hgl8/bigZips/). CpG islands located 1,000, 2,000 and 5,000 bp upstream of the transcription start points on the basis of a DNA sequence longer than 500 bp, and having a G+C content of 55% and a CpG observed/expected ratio of 0.65 (Takai D & Jones P A Proc Natl Acad Sci USA, 99, 3740-5, 2002), were searched for using CpGIE software (Wang, Y & Leung, F C Bioinformatics, 20, 1170-7, 2004).

The Z-test (R program, //www.R-project.org) was applied to assess whether there was a statistical significance of differences in the frequency of genes with CpG island between the candidate ERGs and non-candidate ERGs. P<0.05 was considered to be significant.

In line with the previous reports (Larsen, F., et al., Genomics, 13, 1095-107. 1992; Ponger, L., et al., Genome Res, 11, 1854-60. 42, 2001), most candidate ERGs were found to show high frequencies of CpG islands in upstream sequences (1000 bp; 70%, 2000 bp; 73%, 5000 bp; 76%). In contrast, CpG islands were found at low frequencies in the upstream sequences of non-candidate ERGs (p<0.001, Table 1).

TABLE 1

Comparison of the Proportion of Genes with CpG Islands in Upstream Sequences of the transcription start site in Candidate ERG and Non-Candidate ERG

| | Candidate ERG (No. = 2002) | | Non-Candidate ERG (No. = 14848) | | |
|---|---|---|---|---|---|
| Upstream Bp | No. of Genes | Ratios of Genes with CpG Islands | No. of Genes | Ratios of Genes with CpG Islands | p-values |
| 5000 | 1516 | 76% | 8036 | 54% | <0.001 |
| 2000 | 1456 | 73% | 7410 | 50% | <0.001 |
| 1000 | 1410 | 70% | 7048 | 47% | <0.001 |

Experimental Example 2: Correlation Analysis

Correlation analysis was performed using a correlation coefficient, which indicates linear association between two groups, with a significance level of p<0.05. All calculations and scatter plots were produced with the statistical analysis program R-Package (//www.r-project.org).

First, Pearson and Spearman's rank correlation analysis were performed to compare the candidate ERGs selected from the four datasets in terms of gene expression and CV. FIG. 3 is a scatter plot of gene expression for the four datasets of the candidate ERGs.

It was observed that there was a significant correlation of expression values between all four datasets. ShortSAGE versus LongSAGE showed the highest Spearman correlation coefficient of 0.853 (p<0.0001) and the lowest Spearman correlation of 0.339 between EST and Microarray (p<0.0001).

Next, the coefficient of variation (CV, %) was computed to investigate the consistency of the expression level of the candidate ERGs across various libraries in each dataset. Pearson and Spearman's rank correlation analyses were performed on the CV thus obtained, indicating that the CV was less similar between datasets (Spearman correlation coefficient<0.5) than was the gene expression level although a significant correlation was still found (p≤0.001) (FIG. 4).

These results may be attributed to the difference in the kind and number of samples between datasets because expression levels may vary depending on the kind and number of the samples.

Experimental Example 3: Comparison Between Candidate ERG and Non-Candidate ERG A t-test was conducted to examine whether there was a significant difference in mean gene expression between candidate ERG and non-candidate ERG. FIG. 5 shows the distribution of the gene expressions of candidate ERG and non-candidate ERG for each dataset. As was expected, the mean gene expression level of the candidate ERGs was significantly higher than that of non-candidate ERGs in all four datasets (p<0.0001). These results are in line with previous reports (Eisenberg E and Levanon E Y, Trends Genet, 19(7), 362-365, 2003).

Gene expression levels were found to range from 73.83 to 9324.87 in EST, from 28.58 to 4086.25 in ShortSAGE, from 17.47 to 4621.60 in LongSAGE, and from 1.47 to 18598.26 in HG-U133 microarray. A significant number of genes encoding ribosomal proteins showed the highest expression levels in all four datasets. The most abundant transcript was found to come from EEF1A1 in EST and LongSAGE, from DGK1 in ShortSAGE, and from RPL10A in HG-U133 microarray (Table 2)

TABLE 2

A list of 2087 candidate endogenous reference genes

| UniGene cluster | Symbol | Gene Names | EST Mean | EST CV | EST 0's P | SHORT SAGE Mean |
|---|---|---|---|---|---|---|
| 120 | PRDX6 | Peroxiredoxin 6 | 458.61 | 113.71 | 0.034 | 222.30 |
| 142 | SULT1A1 | Sulfotransferase family, cytosolic. 1A, phenol-preferring, member 1 | 248.16 | 105.30 | 0.241 | 177.46 |
| 202 | TSPO | translocator protein | 198.55 | 80.83 | 0.207 | 233.57 |
| 429 | ATP5G3 | ATP synthase. H+ transporting, mitochondrial F0 complex, subunit c (subunit 9) isoform 3 | 211.73 | 76.87 | 0.103 | 522.98 |
| 695 | CSTB | Cystatin B (stefin B) | 138.20 | 109.45 | 0.345 | 151.39 |
| 808 | HNRPF | Heterogeneous nuclear ribonucleoprotein F | 340.14 | 74.87 | 0.034 | 137.03 |
| 861 | MAPK3 | Mitogen-activated protein kinase 3 | 145.68 | 106.68 | 0.241 | 68.60 |
| 1063 | SNRPC | Small nuclear ribonucleoprotein polypeptide C | 171.26 | 77.26 | 0.276 | 96.52 |
| 1103 | TGFB1 | Transforming growth factor, beta 1 (Camurati-Engelmann disease) | 197.32 | 110.45 | 0.345 | 106.49 |
| 2430 | VPS72 | Vacuolar protein sorting 72 homolog (*S. cerevisiae*) | 117.28 | 76.90 | 0.241 | 41.98 |
| 2533 | ALDH9A1 | Aldehyde dehydrogenase 9 family. member A1 | 119.81 | 68.68 | 0.207 | 60.36 |
| 2795 | LDHA | Lactate dehydrogenase A | 723.58 | 109.92 | 0.034 | 334.22 |
| 2853 | PCBP1 | Poly(rC) binding protein 1 | 203.55 | 81.02 | 0.103 | 154.67 |
| 3100 | KARS | Lysyl-tRNA synthetase | 242.90 | 76.66 | 0.138 | 67.12 |
| 3254 | MRPL23 | Mitochondrial ribosomal protein L23 | 105.59 | 58.85 | 0.379 | 97.41 |
| 3353 | G3BP1 | GTPase activating protein (SH3 domain) binding protein 1 | 221.63 | 105.29 | 0.138 | 78.09 |
| 3416 | ADFP | Adipose differentiation-related protein | 250.88 | 167.90 | 0.241 | 109.67 |
| 3439 | STOML2 | Stomatin (EPB72)-like 2 | 303.44 | 78.37 | 0.069 | 70.64 |
| 3530 | FUSIP1 | FUS interacting protein (serine/arginine-rich) 1 | 188.96 | 77.05 | 0.138 | 79.35 |
| 3989 | PLXNB2 | Plexin B2 | 365.44 | 108.04 | 0.138 | 98.71 |
| 4055 | KLF6 | Kruppel-like factor 6 | 258.77 | 121.39 | 0.276 | 257.29 |
| 4742 | GPAA1 | GPAA1P anchor attachment protein 1 homolog (yeast) | 334.17 | 107.33 | 0.207 | 107.98 |
| 4747 | DKC1 | Dyskeratosis congenita 1, dyskerin | 232.08 | 109.39 | 0.138 | 62.19 |
| 4766 | FAM32A | Family with sequence similarity 32, member A | 182.68 | 72.56 | 0.138 | 55.17 |
| 4859 | CCNL1 | Cyclin L1 | 117.20 | 67.94 | 0.379 | 101.90 |
| 4997 | RBM23 | RNA binding motif protein 23 | 151.36 | 66.00 | 0.345 | 65.10 |
| 4998 | TMOD3 | Tropomodulin 3 (ubiquitous) | 117.77 | 105.21 | 0.345 | 60.81 |
| 5062 | TSPAN3 | Tetraspanin 3 | 230.30 | 90.95 | 0.069 | 333.07 |
| 5086 | RBM42 | RNA binding motif protein 42 | 232.32 | 80.47 | 0.172 | 62.72 |
| 5120 | DYNLL1 | Dynein, light chain, LC8-type 1 | 202.21 | 103.08 | 0.103 | 212.71 |
| 5158 | ILK | Integrin-linked kinase-2 | 154.41 | 64.84 | 0.138 | 163.14 |
| 5245 | PIH1D1 | PIH1 domain containing 1 | 300.56 | 124.75 | 0.207 | 64.41 |
| 5258 | MAGED1 | Melanoma antigen family D. 1 | 605.46 | 103.33 | 0.138 | 122.13 |
| 5268 | ZDHHC4 | Zinc finger. DHHC-type containing 4 | 105.02 | 62.27 | 0.345 | 71.67 |
| 5298 | ADIPOR1 | Adiponectin receptor 1 | 175.47 | 95.76 | 0.138 | 78.91 |
| 5308 | UBA52 | Ubiquitin A-52 residue ribosomal protein fusion product 1 | 482.46 | 229.44 | 0.103 | 354.49 |
| 5324 | C2orf25 | Chromosome 2 open reading frame 25 | 665.12 | 222.84 | 0.138 | 73.70 |
| 5345 | RNPEPL1 | Arginyl aminopeptidase (aminopeptidase B)-like 1 | 174.04 | 85.31 | 0.310 | 69.83 |
| 5662 | GNB2L1 | Guanine nucleotide binding protein (G protein), beta polypeptide 2 like 1 | 2888.02 | 78.73 | 0.000 | 632.04 |
| 5710 | CREG1 | Cellular repressor of E1A-stimulated genes 1 | 186.09 | 125.07 | 0.241 | 58.67 |
| 5719 | NCAPD2 | Non-SMC condensin I complex. subunit D2 | 285.44 | 132.20 | 0.241 | 289.65 |
| 5912 | FBXO7 | F-box protein 7 | 203.36 | 91.84 | 0.207 | 53.23 |
| 5947 | RAB8A | RAB8A, member RAS oncogene family | 195.76 | 70.42 | 0.138 | 44.57 |
| 6396 | JTB | Jumping translocation breakpoint | 264.77 | 96.40 | 0.172 | 138.04 |
| 6454 | GIPC1 | GIPC PDZ domain containing family. member 1 | 283.16 | 100.25 | 0.069 | 233.69 |
| 6459 | GPR172A | G protein-coupled receptor 172A | 180.95 | 83.98 | 0.276 | 117.70 |
| 6551 | ATP6AP1 | ATPase. H+ transporting, lysosomal accessory protein 1 | 238.13 | 103.93 | 0.207 | 113.84 |
| 6891 | SFRS6 | Splicing factor, arginine/serine-rich 6 | 131.50 | 89.49 | 0.241 | 113.93 |
| 7101 | ANAPC5 | Anaphase promoting complex subunit 5 | 248.20 | 68.36 | 0.103 | 57.03 |
| 7236 | NOSIP | Nitric oxide synthase interacting protein | 160.80 | 86.71 | 0.310 | 73.56 |
| 7476 | ATP6V0B | ATPase, H+ transporting. lysosomal 21 kDa, V0 subunit c" | 179.43 | 84.77 | 0.241 | 134.42 |
| 7527 | REXO2 | REX2, RNA exonuclease 2 homolog (*S. cerevisiae*) | 137.24 | 85.72 | 0.379 | 91.89 |
| 7744 | NDUFV1 | NADH dehydrogenase (ubiquinone) flavoprotein 1, 51 kDa | 373.45 | 70.69 | 0.069 | 253.95 |
| 7753 | CALU | Calumenin | 251.14 | 83.95 | 0.069 | 200.10 |
| 7768 | FIBP | Fibroblast growth factor (acidic) intracellular binding protein | 149.44 | 71.07 | 0.138 | 81.86 |
| 7862 | PNRC2 | Proline-rich nuclear receptor coactivator 2 | 165.82 | 66.37 | 0.241 | 93.55 |
| 7910 | RYBP | RING1 and YY1 binding protein | 148.78 | 147.82 | 0.310 | 165.96 |
| 7917 | HIGD1A | HIG1 family, member 1A | 1039.59 | 201.55 | 0.103 | 249.49 |
| 8102 | RPS20 | Ribosomal protein S20 | 808.74 | 200.51 | 0.000 | 918.89 |
| 8372 | UQCR | Ubiquinol-cytochrome c reductase, 6.4 kDa subunit | 171.69 | 131.04 | 0.172 | 357.79 |
| 8737 | WDR6 | WD repeat domain 6 | 214.98 | 113.65 | 0.172 | 102.30 |
| 8752 | TMEM4 | Transmembrane protein 4 | 133.39 | 83.23 | 0.345 | 56.83 |
| 8765 | DDX42 | DEAD (Asp-Glu-Ala-Asp) box polypeptide 42 | 139.51 | 72.23 | 0.310 | 48.25 |
| 8859 | CANT1 | Calcium activated nucleotidase 1 | 195.72 | 80.27 | 0.310 | 74.83 |
| 8867 | CYR61 | Cysteine-rich, angiogenic inducer. 61 | 267.57 | 79.91 | 0.379 | 187.29 |
| 9003 | C16orf58 | Chromosome 16 open reading frame 58 | 148.64 | 68.89 | 0.207 | 73.69 |
| 9015 | LOC57255 | Hypothetical locus LOC572558 | 130.09 | 98.43 | 0.276 | 184.94 |
| 9043 | NGDN | Neuroguidin, EIF4E binding protein | 117.81 | 54.04 | 0.379 | 56.29 |
| 9234 | TMEM147 | Transmembrane protein 147 | 129.58 | 83.82 | 0.207 | 68.85 |
| 9235 | NME4 | Protein expressed in non-metastatic cells 4 | 148.59 | 103.05 | 0.379 | 93.18 |
| 9527 | C2orf28 | Chromosome 2 open reading frame 28 | 184.04 | 88.83 | 0.207 | 81.51 |

TABLE 2-continued

A list of 2087 candidate endogenous reference genes

| | | | | | | |
|---|---|---|---|---|---|---|
| 9534 | SEC11A | SEC11 homolog A (*S. cerevisiae*) | 146.99 | 82.65 | 0.069 | 98.58 |
| 9573 | ABCF1 | ATP-binding cassette. sub-family F (GCN20). member 1 | 173.73 | 124.13 | 0.276 | 46.97 |
| 9589 | UBQLN1 | Ubiquilin 1 | 111.34 | 60.19 | 0.310 | 75.93 |
| 9788 | NDFIP1 | Nedd4 family interacting protein 1 | 167.04 | 73.62 | 0.172 | 82.06 |
| 9825 | FAM96B | Family with sequence similarity 96. member B | 139.95 | 94.16 | 0.345 | 76.79 |
| 9857 | DCXR | Dicarbonyl/L-xylulose reductase | 170.77 | 74.16 | 0.379 | 194.06 |
| 10326 | COPE | Coatomer protein complex, subunit epsilon | 383.31 | 95.38 | 0.103 | 164.06 |
| 10842 | RAN | RAN. member RAS oncogene family | 825.56 | 82.38 | 0.000 | 182.70 |
| 10848 | BMS1 | BMS1 homolog, ribosome assembly protein (yeast) | 121.69 | 60.27 | 0.345 | 38.94 |
| 11125 | SPCS1 | Signal peptidase complex subunit 1 homolog (*S. cerevisiae*) | 151.97 | 92.91 | 0.276 | 94.29 |
| 11184 | UBE2R2 | Ubiquitin-conjugating enzyme E2R 2 | 379.09 | 474.01 | 0.172 | 129.52 |
| 11223 | IDH1 | Isocitrate dehydrogenase 1 (NADP+), soluble | 199.04 | 77.27 | 0.103 | 52.37 |
| 11355 | TMPO | Thymopoietin | 213.98 | 130.12 | 0.172 | 63.16 |
| 11463 | CMPK | Cytidylate kinase | 180.54 | 86.53 | 0.172 | 123.53 |
| 12013 | ABCE1 | ATP-binding cassette, sub-family E (OABP), member 1 | 179.59 | 72.05 | 0.241 | 47.30 |
| 12084 | TUFM | Tu translation elongation factor, mitochondrial | 518.02 | 95.08 | 0.207 | 235.78 |
| 12102 | SNX3 | Sorting nexin 3 | 280.04 | 91.18 | 0.207 | 131.08 |
| 12107 | CHMP2A | Chromatin modifying protein 2A | 108.77 | 44.44 | 0.207 | 76.75 |
| 12109 | CIAO1 | Cytosolic iron-sulfur protein assembly 1 homolog (*S. cerevisiae*) | 127.53 | 69.27 | 0.207 | 66.06 |
| 12144 | KIAA1033 | KIAA1033 | 109.38 | 59.10 | 0.345 | 39.29 |
| 12152 | SRPRB | Signal recognition particle receptor, B subunit | 197.29 | 199.04 | 0.310 | 64.91 |
| 12272 | BECN1 | Beclin 1 (coiled-coil, myosin-like BCL2 interacting protein) | 135.99 | 56.22 | 0.310 | 50.41 |
| 12341 | ADAR | Adenosine deaminase. RNA-specific | 272.66 | 83.29 | 0.103 | 99.54 |
| 12457 | NUP133 | Nucleoporin 133 kDa | 134.39 | 100.25 | 0.310 | 69.13 |
| 12865 | NSFL1C | NSFL1 (p97) cofactor (p47) | 137.86 | 79.36 | 0.276 | 48.09 |
| 13662 | TMEM109 | Transmembrane protein 109 | 180.15 | 110.32 | 0.276 | 52.31 |
| 14317 | NOLA3 | Nucleolar protein family A, member 3 (H/ACA small nucleolar RNPs) | 205.32 | 119.91 | 0.310 | 169.22 |
| 14333 | ATPBD1B | ATP binding domain 1 family, member B | 159.24 | 82.57 | 0.379 | 150.04 |
| 14745 | CCNY | Cyclin Y | 133.37 | 75.66 | 0.276 | 86.24 |
| 14839 | POLR2G | Polymerase (RNA) II (DNA directed) polypeptide G | 141.30 | 66.30 | 0.207 | 89.01 |
| 14846 | SLC7A1 | Solute carrier family 7 (cationic amino acid transporter, y+ system member 1 | 139.07 | 71.59 | 0.310 | 60.63 |
| 14894 | TGOLN2 | Trans-golgi network protein 2 | 157.54 | 69.37 | 0.241 | 121.24 |
| 15277 | C16orf33 | Chromosome 16 open reading frame 33 | 120.09 | 75.30 | 0.310 | 84.56 |
| 15591 | COPS6 | COP9 constitutive photomorphogenic homolog subunit 6 (*Arabidopsis*) | 217.83 | 90.78 | 0.172 | 83.92 |
| 15738 | RAB7A | RAB7A, member RAS oncogene family | 400.18 | 95.67 | 0.069 | 120.91 |
| 16059 | CCDC56 | Coiled-coil domain containing 56 | 143.39 | 86.29 | 0.345 | 96.29 |
| 16130 | UBE2O | Ubiquitin-conjugating enzyme E2O | 157.52 | 114.59 | 0.241 | 63.36 |
| 16349 | ASCIZ | ATM/ATR-Substrate Chk2-Interacting Zn2+-finger protein | 122.72 | 69.67 | 0.310 | 39.01 |
| 17118 | C1orf149 | Chromosome 1 open reading frame 149 | 139.92 | 85.35 | 0.310 | 67.64 |
| 17250 | COQ5 | Coenzyme Q5 homolog, methyltransferase (*S. cerevisiae*) | 91.88 | 50.52 | 0.345 | 105.68 |
| 17680 | FUCA2 | Fucosidase, alpha-L-2. plasma | 157.91 | 93.28 | 0.276 | 55.65 |
| 17731 | CCDC14 | Coiled-coil domain containing 14 | 84.79 | 48.78 | 0.379 | 64.78 |
| 17883 | PPM1G | Protein phosphatase 1G (formerly 2C). magnesium-dependent. gamma isoform | 381.13 | 94.17 | 0.103 | 159.30 |
| 18069 | LGMN | Legumain | 189.38 | 150.90 | 0.310 | 74.08 |
| 18128 | C20orf44 | Chromosome 20 open reading frame 44 | 120.34 | 63.49 | 0.276 | 50.49 |
| 18349 | MRPL15 | Mitochondrial ribosomal protein L15 | 126.02 | 62.29 | 0.310 | 42.98 |
| 19673 | MAF1 | MAF1 homolog (*S. cerevisiae*) | 208.66 | 72.97 | 0.069 | 71.97 |
| 20013 | SYF2 | SYF2 homolog. RNA splicing factor (*S. cerevisiae*) | 109.39 | 47.58 | 0.310 | 80.86 |
| 20107 | KLC1 | Kinesin light chain 1 | 158.65 | 81.31 | 0.241 | 78.88 |
| 20157 | CDK5RAP3 | CDK5 regulatory subunit associated protein 3 | 186.17 | 71.88 | 0.276 | 79.43 |
| 20521 | PRMT1 | Protein arginine methyltransferase 1 | 270.96 | 72.70 | 0.103 | 131.53 |
| 20529 | FAM79A | Family with sequence similarity 79, member A | 101.33 | 68.50 | 0.379 | 50.65 |
| 20573 | IGF1R | Insulin-like growth factor 1 receptor | 133.12 | 72.84 | 0.379 | 106.46 |
| 20716 | TIMM17A | Translocase of inner mitochondrial membrane 17 homolog A (yeast) | 378.20 | 138.09 | 0.241 | 84.45 |
| 22393 | DENR | Density-regulated protein | 147.59 | 60.97 | 0.138 | 66.26 |
| 22543 | UBE3A | Ubiquitin protein ligase E3A (human papilloma virus E6-associated protein, Angelman syndrome) | 180.41 | 98.42 | 0.276 | 92.47 |
| 22546 | CYBASC3 | Cytochrome b, ascorbate dependent 3 | 271.22 | 114.11 | 0.276 | 52.24 |
| 22616 | KIAA0664 | KIAA0664 protein | 126.85 | 69.83 | 0.276 | 39.21 |
| 23033 | UBE2Q2 | Ubiquitin-conjugating enzyme E2Q (putative) 2 | 127.34 | 80.73 | 0.379 | 38.86 |
| 23111 | FARSA | Phenylalanyl-tRNA synthetase, alpha subunit | 239.95 | 79.63 | 0.241 | 48.89 |
| 23978 | SAFB | Scaffold attachment factor B | 195.91 | 87.35 | 0.207 | 63.83 |
| 24301 | POLR2E | Polymerase (RNA) II (DNA directed) polypeptide E, 25 kDa | 345.43 | 77.04 | 0.207 | 85.97 |
| 24379 | TRAPPC1 | Trafficking protein particle complex 1 | 155.30 | 123.38 | 0.172 | 110.66 |
| 24601 | FBLN1 | Fibulin 1 | 492.05 | 242.68 | 0.345 | 156.54 |
| 24950 | RGS5 | Regulator of G-protein signalling 5 | 561.58 | 225.25 | 0.345 | 142.46 |
| 25155 | NET1 | Neuroepithelial cell transforming gene 1 | 114.28 | 95.82 | 0.207 | 72.57 |
| 25450 | SLC29A1 | Solute carrier family 29 (nucleoside transporters). member 1 | 201.64 | 68.32 | 0.379 | 64.55 |
| 25723 | FAM89B | Family with sequence similarity 89, member B | 140.19 | 148.04 | 0.345 | 67.63 |
| 26010 | PFKP | Phosphofructokinase. platelet | 268.83 | 113.15 | 0.103 | 141.32 |
| 26023 | FOXJ3 | Forkhead box J3 | 73.83 | 44.60 | 0.379 | 59.94 |
| 26136 | PIGY | Phosphatidylinositol glycan anchor biosynthesis. class Y | 150.82 | 96.10 | 0.345 | 217.48 |
| 26232 | MAN2C1 | Mannosidase. alpha, class 2C. member 1 | 117.43 | 87.14 | 0.379 | 35.17 |

TABLE 2-continued

A list of 2087 candidate endogenous reference genes

| 26403 | GSTZ1 | Glutathione transferase zeta 1 (maleylacetoacetate isomerase) | 139.46 | 92.67 | 0.345 | 50.70 |
|---|---|---|---|---|---|---|
| 26518 | TSPAN4 | Tetraspanin 4 | 164.19 | 75.89 | 0.310 | 86.39 |
| 27222 | NOLA2 | Nucleolar protein family A. member 2 (H/ACA small nucleolar RNPs) | 172.83 | 107.54 | 0.276 | 108.00 |
| 28491 | SAT1 | Spermidine/spermine N1-acetyltransferase 1 | 578.08 | 192.92 | 0.276 | 378.42 |
| 28914 | APRT | Adenine phosphoribosyltransferase | 160.48 | 119.31 | 0.345 | 95.10 |
| 29203 | GBL | G protein beta subunit-like | 172.86 | 96.17 | 0.310 | 80.31 |
| 29665 | CLSTN1 | Calsyntenin 1 | 223.34 | 109.23 | 0.103 | 167.80 |
| 30011 | TMEM93 | Transmembrane protein 93 | 122.56 | 80.02 | 0.379 | 65.81 |
| 30026 | SSU72 | SSU72 RNA polymerase II CTD phosphatase homolog (*S. cerevisiae*) | 122.96 | 77.31 | 0.138 | 99.27 |
| 30345 | TRAP1 | TNF receptor-associated protein 1 | 433.73 | 106.66 | 0.103 | 96.17 |
| 30954 | PMVK | Phosphomevalonate kinase | 168.78 | 141.42 | 0.379 | 53.56 |
| 31053 | TBCB | Tubulin folding cofactor B | 267.45 | 128.93 | 0.276 | 115.61 |
| 31334 | PRPF6 | PRP6 pre-mRNA processing factor 6 homolog (*S. cerevisiae*) | 278.00 | 95.93 | 0.103 | 96.19 |
| 31387 | C3orf60 | Chromosome 3 open reading frame 60 | 194.85 | 96.83 | 0.276 | 72.05 |
| 34045 | CDCA4 | Cell division cycle associated 4 | 142.01 | 95.48 | 0.379 | 33.71 |
| 34576 | TAX1BP1 | Tax1 (human T-cell leukemia virus type I) binding protein 1 | 166.29 | 86.39 | 0.138 | 127.07 |
| 34906 | BLOC1S2 | Biogenesis of lysosome-related organelles complex-1, subunit 2 | 110.24 | 106.36 | 0.345 | 62.63 |
| 35052 | TEGT | Testis enhanced gene transcript (BAX inhibitor 1) | 601.46 | 76.56 | 0.000 | 357.59 |
| 35828 | MARK3 | MAP/microtubule affinity-regulating kinase 3 | 181.74 | 68.97 | 0.207 | 74.00 |
| 36587 | PPP1R7 | Protein phosphatase 1. regulatory subunit 7 | 147.34 | 89.65 | 0.207 | 55.81 |
| 36927 | HSPH1 | Heat shock 105 kDa/110 kDa protein 1 | 142.61 | 62.36 | 0.241 | 178.86 |
| 37616 | STRA13 | Stimulated by retinoic acid 13 homolog (mouse) | 132.28 | 87.28 | 0.310 | 103.87 |
| 37916 | DPP7 | Dipeptidylpeptidase 7 | 189.05 | 126.98 | 0.207 | 134.29 |
| 42806 | SDF4 | Stromal cell derived factor 4 | 395.61 | 110.02 | 0.138 | 55.59 |
| 43297 | MTPN | Myotrophin | 224.31 | 82.09 | 0.172 | 192.32 |
| 47062 | POLR2I | Polymerase (RNA) II (DNA directed) polypeptide I, 14.5 kDa | 136.77 | 76.60 | 0.310 | 77.76 |
| 50098 | NDUFA4 | NADH dehydrogenase (ubiquinone) 1 alpha subcomplex, 4, 9 kDa | 444.09 | 142.87 | 0.310 | 773.46 |
| 50308 | HIP2 | Huntingtin interacting protein 2 | 145.77 | 68.04 | 0.207 | 85.98 |
| 50425 | PTGES3 | Prostaglandin E synthase 3 (cytosolic) | 411.83 | 77.96 | 0.103 | 332.11 |
| 53066 | HSPBP1 | Hsp70-interacting protein | 202.07 | 92.49 | 0.138 | 68.61 |
| 54277 | FAM50A | Family with sequence similarity 50, member A | 145.83 | 129.34 | 0.345 | 100.96 |
| 54457 | CD81 | CD81 antigen (target of antiproliferative antibody 1) | 303.19 | 99.16 | 0.069 | 141.89 |
| 54642 | MAT2B | Methionine adenosyltransferase II, beta | 133.55 | 71.29 | 0.207 | 61.78 |
| 54649 | RY1 | Putative nucleic acid binding protein RY-1 | 203.85 | 97.67 | 0.241 | 75.69 |
| 55682 | EIF3S7 | Eukaryotic translation initiation factor 3. subunit 7 zeta. 66/67 kDa | 455.77 | 153.84 | 0.034 | 89.94 |
| 55847 | MRPL51 | Mitochondrial ribosomal protein L51 | 122.64 | 99.22 | 0.241 | 154.55 |
| 58488 | CTNNAL1 | Catenin (cadherin-associated protein), alpha-like 1 | 126.66 | 70.42 | 0.379 | 68.29 |
| 58992 | SMC4 | Structural maintenance of chromosomes 4 | 228.66 | 99.66 | 0.207 | 72.95 |
| 59486 | HSDL2 | Hydroxysteroid dehydrogenase like 2 | 129.48 | 73.68 | 0.345 | 63.64 |
| 61812 | PTPN12 | Protein tyrosine phosphatase. non-receptor type 12 | 108.62 | 74.97 | 0.345 | 108.97 |
| 65234 | DDX27 | DEAD (Asp-Glu-Ala-Asp) box polypeptide 27 | 199.19 | 91.01 | 0.241 | 62.30 |
| 65238 | RNF40 | Ring finger protein 40 | 193.26 | 81.38 | 0.172 | 54.91 |
| 66048 | MAP1S | Microtubule-associated protein 1S | 131.74 | 79.04 | 0.276 | 47.23 |
| 66915 | C22orf16 | Chromosome 22 open reading frame 16 | 135.11 | 102.77 | 0.379 | 60.49 |
| 68714 | SFRS1 | Splicing factor, arginine/serine-rich 1 (splicing factor 2. alternate splicing factor) | 249.07 | 79.18 | 0.103 | 98.30 |
| 69293 | HEXB | Hexosaminidase B (beta polypeptide) | 198.57 | 153.59 | 0.276 | 71.52 |
| 69554 | RNF126 | Ring finger protein 126 | 161.03 | 83.35 | 0.241 | 55.88 |
| 69855 | UNR | Cold shock domain containing E1, RNA-binding | 657.29 | 110.51 | 0.103 | 304.45 |
| 71465 | SQLE | Squalene epoxidase | 105.27 | 62.62 | 0.276 | 77.51 |
| 71787 | MRPS7 | Mitochondrial ribosomal protein S7 | 159.90 | 59.92 | 0.310 | 86.87 |
| 73527 | CSNK2B | Casein kinase 2. beta polypeptide | 202.65 | 73.01 | 0.207 | 101.19 |
| 73722 | APEX1 | APEX nuclease (multifunctional DNA repair enzyme) 1 | 339.50 | 85.30 | 0.103 | 230.38 |
| 73799 | GNAI3 | Guanine nucleotide binding protein (G protein). alpha inhibiting activity polypeptide 3 | 150.46 | 62.95 | 0.207 | 56.56 |
| 73965 | SFRS2 | Hypothetical protein ET | 280.26 | 73.78 | 0.000 | 222.54 |
| 74047 | ETFB | Electron-transfer-flavoprotein, beta polypeptide | 168.06 | 80.53 | 0.138 | 68.32 |
| 74050 | FVT1 | Follicular lymphoma variant translocation 1 | 98.29 | 70.32 | 0.379 | 59.60 |
| 74137 | TMED10 | Transmembrane emp24-like trafficking protein 10 (yeast) | 237.09 | 91.81 | 0.138 | 150.00 |
| 74375 | DVL1 | Dishevelled, dsh homolog 1 (*Drosophila*) | 133.54 | 77.04 | 0.276 | 79.92 |
| 74405 | YWHAQ | Tyrosine 3-monooxygenase/tryptophan 5-monooxygenase activation protein. theta polypeptide | 413.13 | 88.00 | 0.034 | 420.70 |
| 74471 | GJA1 | Gap junction protein, alpha 1. 43 kDa (connexin 43) | 183.35 | 62.77 | 0.379 | 500.49 |
| 74563 | OAZ2 | Ornithine decarboxylase antizyme 2 | 193.33 | 73.23 | 0.103 | 86.41 |
| 74564 | SSR2 | Signal sequence receptor. beta (translocon-associated protein beta) | 312.91 | 86.38 | 0.034 | 107.44 |
| 74576 | GDI1 | GDP dissociation inhibitor 1 | 230.50 | 117.59 | 0.138 | 161.01 |
| 75056 | TIMM13 | Translocase of inner mitochondrial membrane 13 homolog (yeast) | 225.25 | 76.11 | 0.345 | 109.02 |
| 75061 | MARCKSL | MARCKS-like 1 | 449.23 | 89.23 | 0.103 | 136.56 |
| 75066 | TSN | Translin | 128.46 | 75.98 | 0.345 | 72.68 |
| 75087 | FASTK | Fas-activated serine/threonine kinase | 179.06 | 68.42 | 0.345 | 123.07 |
| 75117 | ILF2 | Interleukin enhancer binding factor 2. 45 kDa | 349.26 | 76.78 | 0.034 | 86.61 |
| 75133 | TFAM | Transcription factor A, mitochondrial | 111.21 | 68.59 | 0.310 | 47.20 |
| 75139 | ARFIP2 | ADP-ribosylation factor interacting protein 2 (arfaptin 2) | 178.80 | 116.43 | 0.345 | 37.76 |
| 75189 | DAP | Death-associated protein | 217.73 | 94.24 | 0.103 | 143.76 |
| 75227 | NDUFA9 | NADH dehydrogenase (ubiquinone) 1 alpha subcomplex, 9, 39 | 290.29 | 122.15 | 0.138 | 97.37 |

TABLE 2-continued

A list of 2087 candidate endogenous reference genes

| 75243 | BRD2 | Bromodomain containing 2 | 301.76 | 102.55 | 0.069 | 150.65 |
|---|---|---|---|---|---|---|
| 75249 | ARL6IP1 | ADP-ribosylation factor-like 6 interacting protein 1 | 269.13 | 69.42 | 0.172 | 141.78 |
| 75254 | IRF3 | Interferon regulatory factor 3 | 131.45 | 93.03 | 0.345 | 57.56 |
| 75318 | TUBA4A | Tubulin, alpha 4a | 346.93 | 95.88 | 0.276 | 72.41 |
| 75348 | PSME1 | Proteasome (prosome, macropain) activator subunit 1 (PA28 alpha) | 196.67 | 85.95 | 0.138 | 139.00 |
| 75438 | QDPR | Quinoid dihydropteridine reductase | 239.93 | 101.27 | 0.345 | 88.56 |
| 75527 | ADSL | Adenylosuccinate lyase | 187.36 | 79.69 | 0.000 | 46.87 |
| 75724 | COPB2 | Coatomer protein complex, subunit beta 2 (beta prime) | 169.19 | 70.94 | 0.172 | 144.95 |
| 75798 | C20orf111 | Chromosome 20 open reading frame 111 | 138.12 | 60.97 | 0.379 | 52.53 |
| 75841 | ERP29 | Endoplasmic reticulum protein 29 | 170.38 | 80.11 | 0.276 | 109.13 |
| 75890 | MBTPS1 | Membrane-bound transcription factor peptidase, site 1 | 143.96 | 76.79 | 0.241 | 59.34 |
| 75914 | TMED2 | Transmembrane emp24 domain trafficking protein 2 | 257.34 | 78.55 | 0.103 | 201.28 |
| 76111 | DAG1 | Dystroglycan 1 (dystrophin-associated glycoprotein 1) | 185.89 | 66.32 | 0.310 | 97.04 |
| 76394 | ECHS1 | Enoyl Coenzyme A hydratase. short chain. 1. mitochondrial | 296.18 | 99.29 | 0.207 | 101.19 |
| 76480 | UBL4A | Ubiquitin-like 4A | 177.47 | 73.71 | 0.379 | 41.09 |
| 76662 | ZDHHC16 | Zinc finger. DHHC-type containing 16 | 138.92 | 90.05 | 0.276 | 57.18 |
| 76686 | GPX1 | Glutathione peroxidase 1 | 154.93 | 84.27 | 0.276 | 234.43 |
| 76847 | GANAB | Glucosidase. alpha; neutral AB | 371.62 | 103.22 | 0.138 | 252.72 |
| 77060 | PSMB6 | Proteasome (prosome, macropain) subunit. beta type. 6 | 258.61 | 103.69 | 0.172 | 150.18 |
| 77269 | GNAI2 | Guanine nucleotide binding protein (G protein), alpha inhibiting activity polypeptide 2 | 454.86 | 93.08 | 0.103 | 370.28 |
| 77313 | CDK10 | Cyclin-dependent kinase (CDC2-like) 10 | 98.89 | 72.87 | 0.345 | 69.26 |
| 77422 | PLP2 | Proteolipid protein 2 (colonic epithelium-enriched) | 189.36 | 121.71 | 0.310 | 104.42 |
| 77558 | HMGN3 | High mobility group nucleosomal binding domain 3 | 161.44 | 94.74 | 0.207 | 171.44 |
| 77578 | USP9X | Ubiquitin specific peptidase 9, X-linked (fat facets-like, *Drosophila*) | 143.39 | 67.26 | 0.310 | 52.03 |
| 77793 | CSK | C-src tyrosine kinase | 222.19 | 95.17 | 0.310 | 68.74 |
| 77897 | SF3A3 | Splicing factor 3a, subunit 3, 60 kDa | 169.65 | 127.16 | 0.276 | 81.46 |
| 77961 | HLA-B | Major histocompatibility complex, class I, B | 851.44 | 157.10 | 0.103 | 105.86 |
| 77978 | | Hypothetical protein DKFZp761I2123 | 115.47 | 65.78 | 0.345 | 70.16 |
| 78466 | PSMD8 | Proteasome (prosome, macropain) 26S subunit, non-ATPase, 8 | 274.96 | 128.74 | 0.241 | 119.08 |
| 78601 | UROD | Uroporphyrinogen decarboxylase | 187.65 | 84.63 | 0.103 | 96.65 |
| 78771 | PGK1 | Phosphoglycerate kinase 1 | 681.19 | 86.72 | 0.034 | 423.67 |
| 78880 | ILVBL | IlvB (bacterial acetolactate synthase)-like | 185.37 | 153.08 | 0.379 | 101.11 |
| 78888 | DBI | Diazepam binding inhibitor (GABA receptor modulator, acyl-Coenzyme A binding protein) | 220.96 | 127.35 | 0.241 | 166.57 |
| 78989 | ADH5 | Alcohol dehydrogenase 5 (class III), chi polypeptide | 179.39 | 72.64 | 0.034 | 89.94 |
| 79064 | DHPS | Deoxyhypusine synthase | 164.95 | 100.52 | 0.241 | 47.03 |
| 79081 | PPP1CC | Protein phosphatase 1, catalytic subunit. gamma isoform | 318.25 | 84.70 | 0.103 | 100.43 |
| 79088 | RCN2 | Reticulocalbin 2, EF-hand calcium binding domain | 150.90 | 75.39 | 0.207 | 99.10 |
| 79101 | CCNG1 | Cyclin G1 | 240.04 | 67.65 | 0.069 | 82.44 |
| 79110 | NCL | Nucleolin | 293.04 | 63.35 | 0.034 | 210.54 |
| 79322 | QARS | Glutaminyl-tRNA synthetase | 402.46 | 67.92 | 0.138 | 149.07 |
| 79335 | SMARCD1 | SWI/SNF related. matrix associated. actin dependent regulator of chromatin, subfamily d, member 1 | 146.36 | 68.95 | 0.241 | 54.24 |
| 79387 | PSMC5 | Proteasome (prosome, macropain) 26S subunit, ATPase. 5 | 243.74 | 74.96 | 0.138 | 158.29 |
| 79402 | POLR2C | Polymerase (RNA) Il (DNA directed) polypeptide C, 33 kDa | 146.42 | 65.99 | 0.241 | 62.49 |
| 79411 | RPA2 | Replication protein A2. 32 kDa | 179.33 | 111.72 | 0.345 | 81.59 |
| 79625 | C20orf149 | Chromosome 20 open reading frame 149 | 361.43 | 94.87 | 0.310 | 218.44 |
| 80545 | RPL37 | Ribosomal protein L37 | 755.77 | 355.66 | 0.103 | 2167.23 |
| 80919 | SYPL1 | Synaptophysin-like 1 | 215.72 | 101.08 | 0.207 | 132.20 |
| 80986 | ATP5G1 | ATP synthase, H+ transporting, mitochondrial F0 complex, subuni c (subunit 9), isoform 1 | 209.65 | 91.99 | 0.276 | 223.23 |
| 81328 | NFKBIA | Nuclear factor of kappa light polypeptide gene enhancer in B-cells inhibitor, alpha | 186.76 | 120.33 | 0.345 | 367.44 |
| 81424 | SUMO1 | SMT3 suppressor of mif two 3 homolog 1 (yeast) | 313.72 | 89.00 | 0.034 | 338.47 |
| 81848 | RAD21 | RAD21 homolog (*S. pombe*) | 368.76 | 164.73 | 0.103 | 102.70 |
| 81964 | SEC24C | SEC24 related gene family, member C (*S. cerevisiae*) | 186.43 | 96.07 | 0.241 | 56.08 |
| 82201 | CSNK2A2 | Casein kinase 2, alpha prime polypeptide | 123.76 | 72.38 | 0.310 | 77.63 |
| 82327 | GSS | Glutathione synthetase | 184.39 | 77.08 | 0.138 | 47.74 |
| 82719 | YIPF6 | Yip1 domain family, member 6 | 123.85 | 72.31 | 0.379 | 40.25 |
| 82793 | PSMB3 | Proteasome (prosome. macropain) subunit, beta type, 3 | 158.41 | 64.83 | 0.138 | 168.49 |
| 82887 | PPP1R11 | Protein phosphatase 1, regulatory (inhibitor) subunit 11 | 190.42 | 75.63 | 0.241 | 36.52 |
| 82890 | DAD1 | Defender against cell death 1 | 202.51 | 132.00 | 0.310 | 176.07 |
| 82916 | CCT6A | Chaperonin containing TCP1, subunit 6A (zeta 1) | 407.59 | 75.69 | 0.034 | 155.89 |
| 82927 | AMPD2 | Adenosine monophosphate deaminase 2 (isoform L) | 148.16 | 149.07 | 0.345 | 62.69 |
| 83190 | FASN | Fatty acid synthase | 562.35 | 101.57 | 0.241 | 249.20 |
| 83347 | AAMP | Angio-associated, migratory cell protein | 224.46 | 80.95 | 0.138 | 75.73 |
| 83383 | PRDX4 | Peroxiredoxin 4 | 152.24 | 74.89 | 0.379 | 62.85 |
| 83734 | STX4 | Syntaxin 4 | 117.13 | 61.41 | 0.276 | 65.02 |
| 83753 | SNRPB | Small nuclear ribonucleoprotein polypeptides B and B1 | 874.09 | 87.85 | 0.138 | 206.87 |
| 83765 | DHFR | Dihydrofolate reductase | 111.62 | 78.02 | 0.310 | 60.49 |
| 83916 | NDUFA5 | NADH dehydrogenase (ubiquinone) 1 alpha subcomplex, 5, 13 | 455.20 | 149.11 | 0.207 | 146.78 |
| 84359 | GABARAP | GABA(A) receptor-associated protein | 190.65 | 77.34 | 0.138 | 153.83 |
| 84753 | NT5DC2 | 5'-nucleotidase domain containing 2 | 158.64 | 96.33 | 0.310 | 142.25 |
| 85155 | ZFP36L1 | Zinc finger protein 36, C3H type-like 1 | 196.81 | 98.76 | 0.207 | 254.51 |
| 85769 | DNTTIP2 | Deoxynucleotidyltransferase, terminal. interacting protein 2 | 105.55 | 51.70 | 0.379 | 54.58 |
| 85962 | CTF8 | Chromosome transmission fidelity factor 8 homolog (*S. cerevisiae*) | 170.29 | 139.62 | 0.276 | 49.58 |

TABLE 2-continued

A list of 2087 candidate endogenous reference genes

| | | | | | | |
|---|---|---|---|---|---|---|
| 86131 | FADD | Fas (TNFRSF6)-associated via death domain | 158.82 | 101.13 | 0.172 | 69.23 |
| 87752 | MSN | Moesin | 275.46 | 95.27 | 0.103 | 181.99 |
| 89545 | PSMB4 | Proteasome (prosome, macropain) subunit, beta type. 4 | 463.81 | 87.69 | 0.034 | 224.28 |
| 89643 | TKT | Transketolase (Wernicke-Korsakoff syndrome) | 588.97 | 97.80 | 0.103 | 201.22 |
| 89649 | EPHX1 | Epoxide hydrolase 1, microsomal (xenobiotic) | 238.26 | 88.30 | 0.345 | 128.11 |
| 89781 | UBTF | Upstream binding transcription factor. RNA polymerase I | 121.71 | 54.79 | 0.241 | 117.56 |
| 89864 | SKIV2L | Superkiller viralicidic activity 2-like (*S. cerevisiae*) | 132.50 | 66.99 | 0.379 | 46.22 |
| 90061 | PGRMC1 | Progesterone receptor membrane component 1 | 194.16 | 93.36 | 0.172 | 99.80 |
| 90093 | HSPA4 | Heat shock 70 kDa protein 4 | 149.59 | 74.25 | 0.172 | 62.89 |
| 90107 | ADRM1 | Adhesion regulating molecule 1 | 246.89 | 81.18 | 0.172 | 107.95 |
| 90443 | NDUFS8 | NADH dehydrogenase (ubiquinone) Fe—S protein 8, 23 kDa (NADH-coenzyme Q reductase) | 153.66 | 106.13 | 0.207 | 151.21 |
| 91142 | KHSRP | KH-type splicing regulatory protein (FUSE binding protein 2) | 237.57 | 80.25 | 0.241 | 191.59 |
| 91531 | MLLT6 | Myeloid/lymphoid or mixed-lineage leukemia (trithorax homolog, *Drosophila*); translocated to, 6 | 163.44 | 99.71 | 0.207 | 48.01 |
| 93659 | PDIA4 | Protein disulfide isomerase family A. member 4 | 221.64 | 92.23 | 0.207 | 119.28 |
| 93832 | TMCO1 | Transmembrane and coiled-coil domains 1 | 215.75 | 94.44 | 0.138 | 138.95 |
| 95577 | CDK4 | Cyclin-dependent kinase 4 | 512.67 | 181.54 | 0.103 | 70.34 |
| 96530 | COX11 | COX11 homolog, cytochrome c oxidase assembly protein (yeast) | 133.50 | 61.61 | 0.241 | 44.09 |
| 96852 | EDC3 | Enhancer of mRNA decapping 3 homolog (*S. cerevisiae*) | 315.49 | 327.98 | 0.345 | 49.12 |
| 96996 | HNRPA0 | Heterogeneous nuclear ribonucleoprotein A0 | 203.93 | 87.67 | 0.172 | 175.06 |
| 97616 | SH3GL1 | SH3-domain GRB2-like 1 | 271.66 | 106.70 | 0.069 | 109.70 |
| 97887 | RCN1 | Reticulocalbin 1, EF-hand calcium binding domain | 176.05 | 78.51 | 0.207 | 128.29 |
| 98751 | FUBP3 | Far upstream element (FUSE) binding protein 3 | 115.91 | 57.99 | 0.276 | 79.69 |
| 98791 | ACTR1B | ARP1 actin-related protein 1 homolog B, centractin beta (yeast) | 154.61 | 74.84 | 0.276 | 46.33 |
| 102696 | MCTS1 | Malignant T cell amplified sequence 1 | 182.20 | 108.79 | 0.379 | 89.54 |
| 102798 | PSMA1 | Proteasome (prosome, macropain) subunit, alpha type. 1 | 222.80 | 73.98 | 0.069 | 117.56 |
| 103561 | ARL6IP4 | ADP-ribosylation-like factor 6 interacting protein 4 | 177.34 | 82.48 | 0.172 | 125.24 |
| 103834 | TMEM106C | Transmembrane protein 106C | 164.57 | 88.83 | 0.138 | 88.84 |
| 104839 | TIMP2 | TIMP metallopeptidase inhibitor 2 | 266.07 | 83.65 | 0.172 | 326.45 |
| 105547 | NPDC1 | Neural proliferation, differentiation and control, 1 | 184.55 | 89.27 | 0.345 | 240.66 |
| 106185 | RALGDS | Ral guanine nucleotide dissociation stimulator | 113.28 | 56.31 | 0.379 | 94.40 |
| 106876 | ATP6V0D1 | ATPase. H+ transporting. lysosomal 38 kDa. V0 subunit d isoform 1 | 157.31 | 76.54 | 0.207 | 90.28 |
| 106909 | ANAPC13 | Anaphase promoting complex subunit 13 | 409.28 | 124.92 | 0.310 | 82.82 |
| 107003 | CCNB1IP1 | Cyclin B1 interacting protein 1 | 198.64 | 135.06 | 0.207 | 2470.25 |
| 107101 | C1orf86 | Chromosome 1 open reading frame 86 | 132.02 | 90.12 | 0.310 | 102.36 |
| 107387 | C7orf20 | Chromosome 7 open reading frame 20 | 158.14 | 146.65 | 0.379 | 85.47 |
| 107393 | CLDND1 | Claudin domain containing 1 | 182.62 | 98.17 | 0.276 | 55.41 |
| 108029 | SH3BGRL | SH3 domain binding glutamic acid-rich protein like | 217.90 | 129.37 | 0.138 | 173.06 |
| 108080 | CSRP1 | Cysteine and glycine-rich protein 1 | 226.87 | 81.65 | 0.172 | 326.55 |
| 108371 | E2F4 | E2F transcription factor 4. p107/p130-binding | 124.23 | 53.45 | 0.207 | 64.69 |
| 108408 | APH1A | Anterior pharynx defective 1 homolog A (*C. elegans*) | 214.52 | 73.54 | 0.276 | 115.29 |
| 108957 | RPS27L | Ribosomal protein S27-like | 214.43 | 105.97 | 0.345 | 197.20 |
| 108969 | C19orf56 | Chromosome 19 open reading frame 56 | 165.48 | 98.67 | 0.207 | 145.21 |
| 109051 | SH3BGRL3 | SH3 domain binding glutamic acid-rich protein like 3 | 190.53 | 95.77 | 0.207 | 158.45 |
| 109052 | C14orf2 | Chromosome 14 open reading frame 2 | 254.93 | 147.67 | 0.310 | 191.48 |
| 109672 | ST6GALNAC6 | ST6 (alpha-N-acetyl-neuraminyl-2,3-beta-galactosyl-1,3)-N-acetylgalactosaminide alpha-2,6-sialyltransferase 6 | 113.89 | 58.27 | 0.379 | 67.37 |
| 109798 | C6orf48 | Chromosome 6 open reading frame 48 | 221.40 | 98.21 | 0.207 | 94.17 |
| 110695 | SF3B5 | Splicing factor 3b, subunit 5, 10 kDa | 161.11 | 93.81 | 0.310 | 280.95 |
| 110849 | ESRRA | Estrogen-related receptor alpha | 243.72 | 107.89 | 0.310 | 78.88 |
| 111286 | MRPS11 | Mitochondrial ribosomal protein S11 | 118.62 | 52.84 | 0.207 | 53.04 |
| 111577 | ITM2C | Integral membrane protein 2C | 293.83 | 115.98 | 0.138 | 172.80 |
| 111801 | ARS2 | ARS2 protein | 213.16 | 99.08 | 0.276 | 50.72 |
| 112058 | SIVA1 | SIVA1, apoptosis-inducing factor | 161.23 | 58.99 | 0.345 | 75.36 |
| 112318 | TOMM7 | Translocase of outer mitochondrial membrane 7 homolog (yeast) | 406.79 | 253.67 | 0.276 | 376.30 |
| 112955 | NUDT5 | Nudix (nucleoside diphosphate linked moiety X)-type motif 5 | 197.68 | 94.29 | 0.276 | 63.30 |
| 114033 | SSR1 | Signal sequence receptor, alpha (translocon-associated protein alpha) | 161.00 | 68.79 | 0.207 | 55.66 |
| 114286 | CD9 | CD9 antigen (p24) | 239.20 | 130.06 | 0.172 | 227.35 |
| 114412 | TXNL1 | Thioredoxin-like 1 | 117.31 | 93.59 | 0.207 | 120.38 |
| 115474 | RFC3 | Replication factor C (activator 1) 3, 38 kDa | 175.70 | 158.89 | 0.345 | 40.56 |
| 115792 | EXOSC7 | Exosome component 7 | 134.25 | 74.20 | 0.207 | 51.01 |
| 116448 | GLS | Glutaminase | 192.13 | 67.06 | 0.379 | 38.83 |
| 117176 | PABPN1 | Poly(A) binding protein, nuclear 1 | 124.05 | 80.27 | 0.276 | 277.14 |
| 117715 | ST5 | Suppression of tumorigenicity 5 | 101.33 | 55.39 | 0.379 | 68.40 |
| 118110 | BST2 | Bone marrow stromal cell antigen 2 | 216.68 | 84.28 | 0.241 | 177.54 |
| 118400 | FSCN1 | Fascin homolog 1, actin-bundling protein (*Strongylocentrotus purpuratus*) | 684.83 | 91.57 | 0.241 | 277.47 |
| 118463 | PNPLA2 | Patatin-like phospholipase domain containing 2 | 162.21 | 88.10 | 0.345 | 139.17 |
| 118638 | NME1 | Non-metastatic cells 1, protein (NM23A) expressed in | 290.12 | 103.60 | 0.172 | 202.48 |
| 118722 | FUT8 | Fucosyltransferase 8 (alpha (1,6) fucosyltransferase) | 118.38 | 149.55 | 0.379 | 65.86 |
| 118964 | GATAD2A | GATA zinc finger domain containing 2A | 124.22 | 85.19 | 0.310 | 40.82 |
| 118983 | GSDMDC1 | Gasdermin domain containing 1 | 184.87 | 95.75 | 0.379 | 147.97 |
| 119177 | ARF3 | ADP-ribosylation factor 3 | 239.68 | 76.49 | 0.138 | 139.61 |
| 119192 | H2AFZ | H2A histone family, member Z | 453.31 | 159.40 | 0.103 | 221.14 |
| 119251 | UQCRC1 | Ubiquinol-cytochrome c reductase core protein I | 442.99 | 74.48 | 0.103 | 152.44 |

TABLE 2-continued

A list of 2087 candidate endogenous reference genes

| 119591 | AP2S1 | Adaptor-related protein complex 2. sigma 1 subunit | 177.74 | 82.21 | 0.241 | 121.28 |
|---|---|---|---|---|---|---|
| 119598 | RPL3 | Ribosomal protein L3 | 3807.92 | 79.61 | 0.000 | 1976.38 |
| 120323 | LOC26010 | Viral DNA polymerase-transactivated protein 6 | 128.35 | 69.74 | 0.310 | 119.93 |
| 121088 | NUP153 | Nucleoporin 153 kDa | 123.13 | 79.84 | 0.310 | 76.28 |
| 121549 | CDIPT | CDP-diacylglycerol-inositol 3-phosphatidyltransferase (phosphatidylinositol synthase) | 177.98 | 81.88 | 0.241 | 115.81 |
| 122363 | WIPI2 | WD repeat domain, phosphoinositide interacting 2 | 186.76 | 89.61 | 0.138 | 78.30 |
| 122523 | SND1 | Staphylococcal nuclease domain containing 1 | 355.50 | 74.36 | 0.034 | 106.76 |
| 124126 | ARPC1A | Actin related protein 2/3 complex. subunit 1 A. 41 kDa | 206.46 | 81.13 | 0.103 | 122.85 |
| 124147 | FBXL11 | PRO1880 protein | 144.07 | 78.43 | 0.207 | 52.87 |
| 124246 | C10orf119 | Chromosome 10 open reading frame 119 | 144.50 | 66.52 | 0.172 | 76.17 |
| 124366 | BBX | Bobby sox homolog (*Drosophila*) | 147.83 | 66.94 | 0.345 | 56.68 |
| 125113 | CCT8 | Chaperonin containing TCP1, subunit 8 (theta) | 187.53 | 84.03 | 0.034 | 136.62 |
| 125867 | EVL | Enah/Vasp-like | 170.08 | 84.54 | 0.276 | 196.70 |
| 125898 | GNAS | GNAS complex locus | 669.01 | 93.40 | 0.069 | 471.82 |
| 126497 | AEBP2 | AE binding protein 2 | 102.85 | 77.77 | 0.379 | 126.95 |
| 126774 | DTL | Denticleless homolog (*Drosophila*) | 160.79 | 71.32 | 0.379 | 58.18 |
| 126938 | NAPA | N-ethylmaleimide-sensitive factor attachment protein, alpha | 196.92 | 84.26 | 0.069 | 106.30 |
| 127092 | DHX38 | DEAH (Asp-Glu-Ala-His) box polypeptide 38 | 168.85 | 103.87 | 0.379 | 51.60 |
| 127249 | SNF8 | SNF8, ESCRT-II complex subunit. homolog (*S. cerevisiae*) | 134.67 | 80.08 | 0.310 | 125.84 |
| 127386 | MAMDC2 | MAM domain containing 2 | 147.47 | 78.47 | 0.241 | 343.27 |
| 127764 | RAB5C | RAB5C, member RAS oncogene family | 242.33 | 112.45 | 0.276 | 245.24 |
| 128065 | CTSC | Cathepsin C | 238.81 | 102.05 | 0.207 | 76.06 |
| 128199 | SEPT11 | Septin 11 | 159.83 | 63.97 | 0.241 | 90.00 |
| 128548 | WDR1 | WD repeat domain 1 | 267.90 | 69.81 | 0.069 | 103.72 |
| 129634 | CINP | Cyclin-dependent kinase 2-interacting protein | 104.53 | 70.89 | 0.345 | 34.81 |
| 129673 | EIF4A1 | Eukaryotic translation initiation factor 4A. isoform 1 | 1492.15 | 82.19 | 0.000 | 380.49 |
| 130031 | TRIO | Triple functional domain (PTPRF interacting) | 142.59 | 75.94 | 0.310 | 334.92 |
| 130098 | DDX23 | DEAD (Asp-Glu-Ala-Asp) box polypeptide 23 | 188.55 | 94.45 | 0.172 | 50.98 |
| 130293 | CROP | Cisplatin resistance-associated overexpressed protein | 152.55 | 84.06 | 0.207 | 191.28 |
| 130413 | TM9SF2 | Transmembrane 9 superfamily member 2 | 210.83 | 99.09 | 0.103 | 49.93 |
| 131226 | BNIP3L | BCL2/adenovirus E1B 19 kDa interacting protein 3-like | 192.67 | 70.38 | 0.241 | 50.95 |
| 132497 | PRNPIP | Prion protein interacting protein | 168.32 | 67.74 | 0.310 | 103.21 |
| 132513 | HSD17B12 | Hydroxysteroid (17-beta) dehydrogenase 12 | 137.10 | 95.65 | 0.207 | 48.15 |
| 133892 | TPM1 | Tropomyosin 1 (alpha) | 606.98 | 169.48 | 0.207 | 189.30 |
| 134074 | SLC35E1 | Solute carrier family 35, member E1 | 110.83 | 70.67 | 0.345 | 72.41 |
| 134688 | PSMD13 | Proteasome (prosome, macropain) 26S subunit, non-ATPase, 13 | 304.05 | 104.85 | 0.207 | 57.48 |
| 135406 | CEBPZ | CCAAT/enhancer binding protein zeta | 126.72 | 64.41 | 0.207 | 51.10 |
| 136905 | HUWE1 | HECT, UBA and WWE domain containing 1 | 196.13 | 66.09 | 0.138 | 75.28 |
| 136947 | RALY | RNA binding protein. autoantigenic (hnRNP-associated with lethal yellow homolog (mouse)) | 339.69 | 92.28 | 0.069 | 169.57 |
| 137510 | NCOR2 | Nuclear receptor co-repressor 2 | 243.82 | 126.40 | 0.207 | 47.10 |
| 138860 | ARHGAP1 | Rho GTPase activating protein 1 | 106.56 | 50.87 | 0.310 | 92.98 |
| 139896 | MAEA | Macrophage erythroblast attacher | 203.45 | 84.45 | 0.276 | 56.94 |
| 140452 | M6PRBP1 | Mannose-6-phosphate receptor binding protein 1 | 381.09 | 119.04 | 0.138 | 119.07 |
| 142442 | HP1BP3 | Heterochromatin protein 1. binding protein 3 | 161.28 | 66.57 | 0.207 | 72.01 |
| 143187 | DDX49 | DEAD (Asp-Glu-Ala-Asp) box polypeptide 49 | 144.35 | 67.10 | 0.241 | 59.63 |
| 143766 | ATN1 | Atrophin 1 | 184.56 | 86.85 | 0.207 | 76.29 |
| 143873 | S100A10 | S100 calcium binding protein A10 (annexin II ligand, calpactin I, light polypeptide (p11)) | 255.56 | 111.88 | 0.172 | 675.77 |
| 144058 | NAT9 | N-acetyltransferase 9 | 99.56 | 67.02 | 0.345 | 45.72 |
| 144468 | CHID1 | Chitinase domain containing 1 | 179.03 | 105.35 | 0.241 | 103.94 |
| 144835 | EEF1G | Eukaryotic translation elongation factor 1 gamma | 4056.39 | 76.55 | 0.000 | 1929.11 |
| 144868 | VTI1B | Vesicle transport through interaction with t-SNAREs homolog 1B (yeast) | 103.57 | 54.85 | 0.310 | 47.28 |
| 144941 | LRRC41 | Leucine rich repeat containing 41 | 152.40 | 71.74 | 0.172 | 45.67 |
| 144949 | ZNF313 | Zinc finger protein 313 | 145.79 | 62.78 | 0.138 | 63.37 |
| 144980 | SCAMP4 | Secretory carrier membrane protein 4 | 127.39 | 96.37 | 0.345 | 60.46 |
| 145049 | PLEKHM2 | Pleckstrin homology domain containing. family M (with RUN domain) member 2 | 205.68 | 86.88 | 0.138 | 45.61 |
| 145442 | MAP2K1 | Mitogen-activated protein kinase kinase 1 | 101.59 | 55.16 | 0.241 | 57.21 |
| 145575 | UBL3 | Ubiquitin-like 3 | 157.68 | 79.65 | 0.345 | 90.10 |
| 146070 | TPM3 | Tropomyosin 3 | 695.80 | 102.33 | 0.000 | 175.65 |
| 146393 | HERPUD1 | Homocysteine-inducible, endoplasmic reticulum stress-inducible. ubiquitin-like domain member 1 | 226.44 | 86.29 | 0.172 | 101.04 |
| 146602 | UQCRQ | Ubiquinol-cytochrome c reductase. complex III subunit VII. 9.5 kDa | 193.38 | 169.43 | 0.276 | 312.78 |
| 146804 | SPIN1 | Spindlin 1 | 127.00 | 68.69 | 0.345 | 46.25 |
| 146806 | CUL1 | Cullin 1 | 120.27 | 57.50 | 0.207 | 69.33 |
| 147433 | PCNA | Proliferating cell nuclear antigen | 258.31 | 133.96 | 0.172 | 92.79 |
| 148078 | UBR4 | Ubiquitin protein ligase E3 component n-recognin 4 | 144.18 | 73.44 | 0.138 | 81.01 |
| 148272 | CCM2 | Cerebral cavernous malformation 2 | 199.79 | 94.01 | 0.207 | 76.34 |
| 148330 | ARF4 | ADP-ribosylation factor 4 | 385.93 | 105.50 | 0.138 | 153.40 |
| 148340 | PTPRG | Protein tyrosine phosphatase, receptor type, G | 1592.61 | 150.52 | 0.069 | 252.27 |
| 148670 | RHOBTB1 | Rho-related BTB domain containing 1 | 116.95 | 99.14 | 0.345 | 47.31 |
| 149004 | FBXO31 | F-box protein 31 | 141.63 | 81.88 | 0.379 | 71.24 |
| 149957 | RPS6KA1 | Ribosomal protein S6 kinase, 90 kDa, polypeptide 1 | 146.89 | 140.85 | 0.310 | 62.80 |
| 149983 | PEX14 | Peroxisomal biogenesis factor 14 | 132.69 | 140.50 | 0.241 | 43.40 |
| 150107 | BIRC6 | Baculoviral IAP repeat-containing 6 (apollon) | 149.90 | 66.77 | 0.345 | 78.67 |

TABLE 2-continued

A list of 2087 candidate endogenous reference genes

| 150540 | TMEM112B | Transmembrane protein 112B | 180.63 | 177.93 | 0.379 | 53.76 |
| 150580 | EIF1 | Eukaryotic translation initiation factor 1 | 458.80 | 84.42 | 0.034 | 865.15 |
| 150837 | TXNDC5 | Thioredoxin domain containing 5 | 483.23 | 126.33 | 0.034 | 99.46 |
| 151134 | OXA1L | Oxidase (cytochrome c) assembly 1-like | 238.54 | 70.29 | 0.103 | 62.00 |
| 151220 | PALLD | Palladin, cytoskeletal associated protein | 198.94 | 75.04 | 0.345 | 113.44 |
| 151413 | GMFB | Glia maturation factor beta | 190.53 | 95.31 | 0.379 | 113.32 |
| 151787 | EFTUD2 | Elongation factor Tu GTP binding domain containing 2 | 326.78 | 81.27 | 0.069 | 105.28 |
| 152536 | PSMD6 | Proteasome (prosome, macropain) 26S subunit, non-ATPase. 6 | 134.14 | 63.78 | 0.241 | 75.62 |
| 153177 | RPS28 | Ribosomal protein S28 | 437.53 | 297.35 | 0.241 | 1095.00 |
| 154023 | TXNDC4 | Thioredoxin domain containing 4 (endoplasmic reticulum) | 133.74 | 72.55 | 0.345 | 51.92 |
| 154073 | SLC35B1 | Solute carrier family 35. member B1 | 99.61 | 61.75 | 0.379 | 52.53 |
| 155165 | ZFPL1 | Zinc finger protein-like 1 | 156.23 | 92.72 | 0.310 | 64.84 |
| 155218 | HNRPUL1 | Heterogeneous nuclear ribonucleoprotein U-like 1 | 474.38 | 82.52 | 0.000 | 175.01 |
| 155396 | NFE2L2 | Nuclear factor (erythroid-derived 2)-like 2 | 182.54 | 63.38 | 0.172 | 76.81 |
| 155829 | TBC1D9B | TBC1 domain family, member 9B (with GRAM domain) | 189.13 | 67.14 | 0.241 | 61.75 |
| 156171 | PSMC6 | Proteasome (prosome, macropain) 26S subunit, ATPase. 6 | 202.42 | 86.99 | 0.172 | 72.51 |
| 156367 | RPS29 | Ribosomal protein S29 | 735.43 | 357.07 | 0.241 | 2469.70 |
| 156667 | CALCOCO | Calcium binding and coiled-coil domain 1 | 150.95 | 83.49 | 0.276 | 48.15 |
| 157160 | MRPS34 | Mitochondrial ribosomal protein S34 | 163.79 | 79.67 | 0.276 | 94.71 |
| 157351 | GTPBP9 | GTP-binding protein 9 (putative) | 256.77 | 85.59 | 0.207 | 86.88 |
| 157379 | H2AFV | H2A histone family. member V | 212.94 | 72.40 | 0.138 | 196.03 |
| 157394 | HAGH | Hydroxyacylglutathione hydrolase | 110.09 | 79.63 | 0.345 | 58.25 |
| 159014 | PRPF4B | PRP4 pre-mRNA processing factor 4 homolog B (yeast) | 101.54 | 63.09 | 0.379 | 87.15 |
| 159118 | AMD1 | Adenosylmethionine decarboxylase 1 | 179.16 | 87.63 | 0.241 | 87.60 |
| 159130 | RAF1 | V-raf-1 murine leukemia viral oncogene homolog 1 | 148.50 | 123.34 | 0.138 | 75.30 |
| 159161 | ARHGDIA | Rho GDP dissociation inhibitor (GDI) alpha | 781.87 | 98.28 | 0.138 | 124.37 |
| 159699 | FBXO21 | F-box protein 21 | 112.15 | 59.46 | 0.345 | 78.43 |
| 159799 | THRAP2 | Thyroid hormone receptor associated protein 2 | 135.37 | 68.96 | 0.345 | 57.41 |
| 160958 | CDC37 | CDC37 cell division cycle 37 homolog (S. cerevisiae) | 297.55 | 114.77 | 0.069 | 93.25 |
| 161357 | PDHB | Pyruvate dehydrogenase (lipoamide) beta | 188.51 | 80.70 | 0.172 | 57.45 |
| 162032 | HBP1 | HMG-box transcription factor 1 | 119.42 | 40.70 | 0.345 | 76.14 |
| 162233 | CHD4 | Chromodomain helicase DNA binding protein 4 | 294.77 | 95.15 | 0.207 | 209.93 |
| 162877 | PACSIN2 | Protein kinase C and casein kinase substrate in neurons 2 | 181.10 | 101.47 | 0.207 | 88.79 |
| 163645 | MOCS2 | Molybdenum cofactor synthesis 2 | 123.58 | 91.10 | 0.276 | 59.81 |
| 163776 | UBE2J1 | Ubiquitin-conjugating enzyme E2. J1 (UBC6 homolog. yeast) | 229.95 | 250.60 | 0.310 | 47.01 |
| 163893 | PICALM | Phosphatidylinositol binding clathrin assembly protein | 153.29 | 84.25 | 0.310 | 98.35 |
| 165195 | VAPA | VAMP (vesicle-associated membrane protein)-associated protein A. 33 kDa | 170.73 | 76.58 | 0.069 | 115.35 |
| 166011 | CTNND1 | Catenin (cadherin-associated protein), delta 1 | 181.39 | 76.07 | 0.138 | 75.94 |
| 166204 | PHF1 | PHD finger protein 1 | 128.96 | 77.28 | 0.345 | 43.53 |
| 166463 | HNRPU | Heterogeneous nuclear ribonucleoprotein U (scaffold attachment factor A) | 279.34 | 89.13 | 0.034 | 185.87 |
| 166924 | SEC13 | SEC13 homolog (S. cerevisiae) | 164.56 | 70.57 | 0.207 | 99.75 |
| 166975 | SFRS5 | Splicing factor, arginine/serine-rich 5 | 241.85 | 95.20 | 0.138 | 153.47 |
| 167535 | SRP54 | Signal recognition particle 54 kDa | 132.08 | 105.35 | 0.241 | 43.01 |
| 168073 | TRPC4AP | Transient receptor potential cation channel, subfamily C, member 4 associated protein | 174.32 | 67.74 | 0.241 | 95.49 |
| 168799 | METTL3 | Methyltransferase like 3 | 133.88 | 65.22 | 0.172 | 71.62 |
| 169611 | DIABLO | Diablo homolog (Drosophila) | 167.55 | 69.66 | 0.276 | 41.81 |
| 169718 | CNN2 | Calponin 2 | 263.90 | 111.61 | 0.138 | 133.00 |
| 170107 | UQCRFS1 | Ubiquinol-cytochrome c reductase, Rieske iron-sulfur polypeptide | 112.20 | 75.09 | 0.241 | 76.06 |
| 170131 | NFIC | Nuclear factor I/C (CCAAT-binding transcription factor) | 128.62 | 75.64 | 0.379 | 73.22 |
| 170553 | CNOT7 | CCR4-NOT transcription complex, subunit 7 | 119.98 | 77.62 | 0.276 | 62.09 |
| 170622 | CFL1 | Cofilin 1 (non-muscle) | 1372.26 | 96.41 | 0.034 | 1717.53 |
| 171626 | SKP1A | S-phase kinase-associated protein 1A (p19A) | 457.12 | 128.78 | 0.138 | 403.46 |
| 172550 | PTBP1 | Polypyrimidine tract binding protein 1 | 554.08 | 85.76 | 0.103 | 138.65 |
| 172755 | BRP44L | Brain protein 44-like | 150.10 | 97.09 | 0.379 | 90.49 |
| 172928 | COL1A1 | Collagen, type I, alpha 1 | 657.85 | 170.49 | 0.276 | 1790.49 |
| 173024 | NUB1 | Negative regulator of ubiquitin-like proteins 1 | 102.38 | 55.09 | 0.276 | 49.89 |
| 173162 | COX4NB | COX4 neighbor | 259.86 | 100.34 | 0.310 | 48.81 |
| 173381 | DPYSL2 | Dihydropyrimidinase-like 2 | 213.62 | 76.62 | 0.310 | 337.96 |
| 173464 | FKBP8 | FK506 binding protein 8, 38 kDa | 446.43 | 105.38 | 0.103 | 241.30 |
| 173611 | NDUFS2 | NADH dehydrogenase (ubiquinone) Fe—S protein 2, 49 kDa (NADH-coenzyme Q reductase) | 308.98 | 100.60 | 0.069 | 103.79 |
| 173705 | LOC40115 | HCV F-transactivated protein 1 | 155.92 | 91.92 | 0.207 | 105.45 |
| 173724 | CKB | Creatine kinase, brain | 395.40 | 117.54 | 0.310 | 500.02 |
| 174050 | EDF1 | Endothelial differentiation-related factor 1 | 163.11 | 77.20 | 0.345 | 295.84 |
| 174195 | IFITM2 | Interferon induced transmembrane protein 2 (1-8D) | 439.92 | 224.90 | 0.276 | 123.33 |
| 175473 | AK1 | Adenylate kinase 1 | 115.05 | 96.67 | 0.345 | 154.31 |
| 175955 | YTHDC1 | YTH domain containing 1 | 114.99 | 56.92 | 0.310 | 51.24 |
| 177530 | ATP5E | ATP synthase, H+ transporting, mitochondrial F1 complex, epsilon subunit | 343.57 | 172.81 | 0.207 | 738.25 |
| 177766 | PARP1 | Poly (ADP-ribose) polymerase family, member 1 | 260.77 | 114.80 | 0.103 | 88.33 |
| 178551 | RPL8 | Ribosomal protein L8 | 1600.62 | 93.63 | 0.034 | 951.00 |
| 178728 | MBD3 | Methyl-CpG binding domain protein 3 | 226.33 | 93.86 | 0.241 | 150.69 |
| 179986 | FLOT1 | Flotillin 1 | 239.64 | 133.66 | 0.241 | 173.68 |
| 180141 | CFL2 | Cofilin 2 (muscle) | 236.22 | 198.55 | 0.345 | 58.91 |
| 180312 | MRPS16 | Mitochondrial ribosomal protein S16 | 148.32 | 71.61 | 0.276 | 43.03 |

TABLE 2-continued

A list of 2087 candidate endogenous reference genes

| | | | | | | |
|---|---|---|---|---|---|---|
| 180414 | HSPA8 | Heat shock 70 kDa protein 8 | 1204.20 | 99.10 | 0.000 | 543.94 |
| 180877 | H3F3B | H3 histone, family 3B (H3.3B) | 701.35 | 71.33 | 0.000 | 322.18 |
| 180903 | NCAPH2 | Non-SMC condensin II complex, subunit H2 | 273.31 | 91.43 | 0.310 | 66.01 |
| 180909 | PRDX1 | Peroxiredoxin 1 | 973.56 | 146.34 | 0.138 | 346.95 |
| 180933 | CXXC1 | CXXC finger 1 (PHD domain) | 127.97 | 58.18 | 0.345 | 51.48 |
| 181046 | DUSP3 | Dual specificity phosphatase 3 (vaccinia virus phosphatase VH1-related) | 168.09 | 115.04 | 0.207 | 74.49 |
| 181112 | MED4 | Mediator of RNA polymerase II transcription, subunit 4 homolog (yeast) | 208.67 | 152.66 | 0.276 | 52.19 |
| 181163 | HMGN2 | High-mobility group nucleosomal binding domain 2 | 798.73 | 84.12 | 0.000 | 504.02 |
| 181244 | HLA-A | Major histocompatibility complex, class I. A | 874.95 | 96.35 | 0.138 | 945.29 |
| 181368 | PRPF8 | PRP8 pre-mRNA processing factor 8 homolog (yeast) | 308.98 | 76.46 | 0.138 | 57.52 |
| 181444 | TMEM9 | Transmembrane protein 9 | 210.70 | 80.44 | 0.172 | 99.45 |
| 182255 | NHP2L1 | NHP2 non-histone chromosome protein 2-like 1 (*S. cerevisiae*) | 236.95 | 69.85 | 0.069 | 216.97 |
| 182626 | C22orf5 | Chromosome 22 open reading frame 5 | 189.45 | 87.32 | 0.310 | 85.24 |
| 182885 | SLC35B2 | Solute carrier family 35, member B2 | 197.27 | 131.49 | 0.241 | 71.21 |
| 183684 | EIF4G2 | Eukaryotic translation initiation factor 4 gamma, 2 | 571.05 | 99.96 | 0.069 | 244.19 |
| 183706 | ADD1 | Adducin 1 (alpha) | 210.75 | 70.37 | 0.138 | 124.62 |
| 183800 | RANGAP1 | Ran GTPase activating protein 1 | 330.34 | 92.47 | 0.172 | 82.36 |
| 183850 | DCTD | DCMP deaminase | 140.58 | 59.00 | 0.345 | 50.00 |
| 183994 | PPP1CA | Protein phosphatase 1, catalytic subunit, alpha isoform | 374.52 | 71.55 | 0.103 | 122.79 |
| 184062 | C20orf24 | Chromosome 20 open reading frame 24 | 161.95 | 77.22 | 0.310 | 106.44 |
| 184211 | PMPCB | Peptidase (mitochondrial processing) beta | 177.15 | 64.50 | 0.138 | 44.05 |
| 184233 | HSPA9 | Heat shock 70 kDa protein 9 (mortalin) | 311.24 | 80.92 | 0.034 | 155.04 |
| 184492 | ELAVL1 | ELAV (embryonic lethal, abnormal vision, *Drosophila*)-like 1 (Hu antigen R) | 130.66 | 66.07 | 0.207 | 61.10 |
| 185172 | GNB2 | Guanine nucleotide binding protein (G protein), beta polypeptide 2 | 420.89 | 178.43 | 0.172 | 146.97 |
| 185597 | SPG7 | Spastic paraplegia 7. paraplegin (pure and complicated autosomal recessive) | 167.10 | 102.17 | 0.207 | 85.24 |
| 187199 | MALAT1 | Metastasis associated lung adenocarcinoma transcript 1 (non-coding RNA) | 3984.95 | 243.42 | 0.241 | 982.17 |
| 187635 | RPS15A | Chromosome 20 open reading frame 19 | 705.06 | 435.58 | 0.138 | 584.60 |
| 187763 | BRD4 | Bromodomain containing 4 | 226.90 | 138.89 | 0.241 | 92.81 |
| 187866 | NPTN | Neuroplastin | 120.12 | 53.64 | 0.379 | 127.00 |
| 187946 | SLC20A1 | Solute carrier family 20 (phosphate transporter). member 1 | 141.36 | 96.84 | 0.207 | 79.95 |
| 188501 | PAFAH1B2 | Platelet-activating factor acetylhydrolase. isoform Ib. beta subunit 30 kDa | 149.54 | 78.69 | 0.138 | 75.71 |
| 188614 | PLEKHA5 | Pleckstrin homology domain containing. family A member 5 | 115.79 | 66.94 | 0.379 | 53.09 |
| 188879 | RBM6 | RNA binding motif protein 6 | 100.43 | 54.89 | 0.379 | 79.10 |
| 188882 | NUDT3 | Nudix (nucleoside diphosphate linked moiety X)-type motif 3 | 129.54 | 63.13 | 0.276 | 41.12 |
| 189075 | TWF1 | Twinfilin. actin-binding protein. homolog 1 (*Drosophila*) | 164.98 | 70.22 | 0.310 | 103.18 |
| 189119 | CXXC5 | CXXC finger 5 | 97.63 | 45.99 | 0.345 | 191.46 |
| 189329 | SMURF1 | SMAD specific E3 ubiquitin protein ligase 1 | 126.19 | 77.52 | 0.379 | 46.81 |
| 189716 | NDUFAB1 | NADH dehydrogenase (ubiquinone) 1. alpha/beta subcomplex, 1. 8 kDa | 224.85 | 87.06 | 0.276 | 59.73 |
| 189772 | CCT2 | Chaperonin containing TCP1, subunit 2 (beta) | 269.61 | 95.66 | 0.069 | 124.53 |
| 190028 | GSTO1 | Glutathione S-transferase omega 1 | 178.51 | 92.79 | 0.241 | 87.26 |
| 190086 | MRCL3 | Myosin regulatory light chain MRCL3 | 469.83 | 322.83 | 0.172 | 204.74 |
| 190334 | RAP1A | RAP1A, member of RAS oncogene family | 130.79 | 76.47 | 0.310 | 49.76 |
| 190384 | COPS4 | COP9 constitutive photomorphogenic homolog subunit 4 (*Arabidopsis*) | 163.76 | 100.38 | 0.138 | 59.12 |
| 190722 | C19orf62 | Chromosome 19 open reading frame 62 | 218.33 | 85.79 | 0.207 | 75.54 |
| 190904 | STRN4 | Striatin. calmodulin binding protein 4 | 183.13 | 100.67 | 0.241 | 74.69 |
| 191186 | TTC17 | Tetratricopeptide repeat domain 17 | 125.42 | 63.68 | 0.310 | 43.91 |
| 191346 | SEPT7 | Septin 7 | 318.59 | 80.82 | 0.103 | 196.34 |
| 191518 | DHX9 | DEAH (Asp-Glu-Ala-His) box polypeptide 9 | 239.90 | 67.53 | 0.241 | 61.56 |
| 191987 | UBE2J2 | Ubiquitin-conjugating enzyme E2. J2 (UBC6 homolog. yeast) | 125.95 | 71.90 | 0.207 | 35.20 |
| 192316 | CDC2L1 | Cell division cycle 2-like 1 (PITSLRE proteins) | 102.48 | 85.83 | 0.379 | 83.41 |
| 192374 | HSP90B1 | Heat shock protein 90 kDa beta (Grp94), member 1 | 388.12 | 88.21 | 0.034 | 487.07 |
| 192425 | EIF3S8 | Eukaryotic translation initiation factor 3, subunit 8, 110 kDa | 1001.22 | 91.36 | 0.103 | 382.10 |
| 193118 | ZMIZ1 | Zinc finger. MIZ-type containing 1 | 125.42 | 71.59 | 0.345 | 103.91 |
| 193163 | BIN1 | Bridging integrator 1 | 216.65 | 88.45 | 0.241 | 86.88 |
| 193491 | TUBB6 | Tubulin. beta 6 | 255.15 | 94.70 | 0.241 | 85.60 |
| 194329 | TCEAL4 | Transcription elongation factor A (SII)-like 4 | 110.76 | 60.41 | 0.207 | 98.50 |
| 194718 | ZRANB2 | Zinc finger. RAN-binding domain containing 2 | 170.63 | 70.34 | 0.207 | 60.86 |
| 195464 | FLNA | Filamin A, alpha (actin binding protein 280) | 554.90 | 92.75 | 0.172 | 45.29 |
| 195642 | RNF213 | Ring finger protein 213 | 146.02 | 74.10 | 0.379 | 49.42 |
| 196983 | SSFA2 | Sperm specific antigen 2 | 238.74 | 197.56 | 0.241 | 41.49 |
| 198281 | PKM2 | Pyruvate kinase, muscle | 3044.33 | 101.80 | 0.000 | 562.77 |
| 199561 | RANBP2 | RAN binding protein 2 | 134.09 | 59.13 | 0.379 | 78.36 |
| 199625 | HAX1 | HCLS1 associated protein X-1 | 243.58 | 94.74 | 0.138 | 231.23 |
| 200063 | HDAC7A | Histone deacetylase 7A | 252.27 | 159.81 | 0.241 | 66.57 |
| 200600 | SCAMP3 | Secretory carrier membrane protein 3 | 165.58 | 75.71 | 0.207 | 82.26 |
| 200804 | SDCBP | Syndecan binding protein (syntenin) | 355.16 | 73.99 | 0.172 | 100.60 |
| 201253 | CKAP5 | Cytoskeleton associated protein 5 | 157.71 | 77.53 | 0.069 | 51.67 |
| 201390 | WDR45L | WDR45-like | 115.15 | 53.09 | 0.138 | 66.73 |
| 201712 | GLG1 | Golgi apparatus protein 1 | 128.23 | 88.99 | 0.310 | 62.32 |
| 202011 | CCDC47 | Coiled-coil domain containing 47 | 108.62 | 67.48 | 0.172 | 152.06 |

TABLE 2-continued

A list of 2087 candidate endogenous reference genes

| 202085 | VDAC1 | Voltage-dependent anion channel 1 | 179.22 | 70.07 | 0.276 | 154.71 |
|---|---|---|---|---|---|---|
| 202166 | HNRPH1 | Heterogeneous nuclear ribonucleoprotein H1 (H) | 199.33 | 74.31 | 0.069 | 183.12 |
| 202179 | SMN2 | Survival of motor neuron 1. telomeric | 103.17 | 55.27 | 0.379 | 77.19 |
| 203099 | WAPAL | Wings apart-like homolog (*Drosophila*) | 162.13 | 143.02 | 0.345 | 56.63 |
| 203910 | SGTA | Small glutamine-rich tetratricopeptide repeat (TPR)-containing. alpha | 213.58 | 79.65 | 0.138 | 124.15 |
| 204041 | AHSA1 | AHA1. activator of heat shock 90 kDa protein ATPase homolog 1 (yeast) | 263.29 | 112.20 | 0.207 | 131.33 |
| 204773 | WDR77 | WD repeat domain 77 | 185.81 | 74.28 | 0.172 | 65.95 |
| 205163 | MRPL3 | Mitochondrial ribosomal protein L3 | 176.93 | 58.08 | 0.069 | 129.59 |
| 206500 | CTTN | Cortactin | 148.63 | 96.70 | 0.310 | 85.71 |
| 206824 | MGC71993 | Similar to DNA segment, Chr 11, Brigham & Womens Genetics 0434 expressed | 143.54 | 88.77 | 0.345 | 218.52 |
| 208597 | CTBP1 | Hypothetical protein LOC285463 | 136.74 | 48.53 | 0.138 | 213.99 |
| 209983 | STMN1 | Stathmin 1/oncoprotein 18 | 619.09 | 139.81 | 0.034 | 198.15 |
| 210469 | ELMO2 | Engulfment and cell motility 2 (ced-12 homolog. *C. elegans*) | 96.39 | 71.43 | 0.379 | 57.31 |
| 210532 | KIAA0141 | KIAA0141 | 138.36 | 72.99 | 0.241 | 62.91 |
| 211463 | DNM2 | Dynamin 2 | 195.67 | 87.32 | 0.241 | 81.50 |
| 211594 | PSMC4 | Proteasome (prosome, macropain) 26S subunit, ATPase. 4 | 469.59 | 192.26 | 0.138 | 67.56 |
| 211914 | NDUFS7 | NADH dehydrogenase (ubiquinone) Fe—S protein 7, 20 kDa (NADH-coenzyme Q reductase) | 159.44 | 73.80 | 0.379 | 86.83 |
| 212102 | PDIA6 | Protein disulfide isomerase family A. member 6 | 274.17 | 97.91 | 0.103 | 160.42 |
| 212395 | CIZ1 | CDKN1A interacting zinc finger protein 1 | 272.61 | 88.59 | 0.138 | 50.78 |
| 213061 | NUCKS1 | Nuclear casein kinase and cyclin-dependent kinase substrate 1 | 304.71 | 64.96 | 0.138 | 231.69 |
| 213470 | PSMB7 | Proteasome (prosome, macropain) subunit. beta type. 7 | 247.81 | 65.94 | 0.034 | 222.67 |
| 213541 | LOC55288 | Hypothetical LOC552889 | 136.06 | 60.14 | 0.345 | 67.95 |
| 213666 | K1AA0460 | KIAA0460 | 96.71 | 78.04 | 0.241 | 68.88 |
| 213724 | SUPT16H | Suppressor of Ty 16 homolog (*S. cerevisiae*) | 149.27 | 79.71 | 0.207 | 52.16 |
| 216653 | FBXO9 | F-box protein 9 | 92.77 | 49.72 | 0.310 | 50.09 |
| 220950 | FOXO3 | Forkhead box O3 | 196.88 | 112.74 | 0.276 | 91.70 |
| 221847 | SLC38A2 | Solute carrier family 38, member 2 | 204.23 | 78.33 | 0.207 | 281.04 |
| 222510 | DAZAP1 | DAZ associated protein 1 | 126.05 | 97.18 | 0.276 | 67.85 |
| 223141 | DDX21 | DEAD (Asp-Glu-Ala-Asp) box polypeptide 21 | 255.54 | 70.08 | 0.069 | 103.03 |
| 224607 | SDC1 | Syndecan 1 | 241.65 | 87.87 | 0.276 | 119.67 |
| 226007 | RDH11 | Retinol dehydrogenase 11 (all-trans and 9-cis) | 340.36 | 135.94 | 0.172 | 92.30 |
| 226117 | H1F0 | H1 histone family, member 0 | 326.85 | 160.18 | 0.310 | 127.49 |
| 226755 | YWHAH | Tyrosine 3-monooxygenase/tryptophan 5-monooxygenase activation protein. eta polypeptide | 199.21 | 161.02 | 0.207 | 191.85 |
| 227067 | ATAD3A | ATPase family, AAA domain containing 3A | 254.68 | 105.30 | 0.172 | 57.56 |
| 227253 | TOMM70A | Translocase of outer mitochondrial membrane 70 homolog A (yeast) | 130.67 | 67.31 | 0.172 | 87.82 |
| 227777 | PTP4A1 | Protein tyrosine phosphatase type IVA, member 1 | 219.08 | 115.20 | 0.138 | 131.83 |
| 229641 | SUB1 | SUB1 homolog (*S. cerevisiae*) | 300.51 | 103.71 | 0.138 | 147.72 |
| 231295 | PITPNC1 | Phosphatidylinositol transfer protein, cytoplasmic 1 | 171.09 | 127.31 | 0.345 | 63.03 |
| 231616 | C19orf53 | Chromosome 19 open reading frame 53 | 162.05 | 104.55 | 0.345 | 102.58 |
| 232194 | KIAA0174 | KIAA0174 | 204.24 | 73.78 | 0.138 | 84.98 |
| 232543 | PDCD4 | Programmed cell death 4 (neoplastic transformation inhibitor) | 126.25 | 61.41 | 0.310 | 189.22 |
| 233458 | NFYC | Nuclear transcription factor Y, gamma | 92.20 | 51.11 | 0.345 | 89.24 |
| 233552 | CDC2L5 | Cell division cycle 2-like 5 (cholinesterase-related cell division controller) | 139.27 | 109.94 | 0.379 | 29.61 |
| 233952 | PSMA7 | Proteasome (prosome, macropain) subunit, alpha type, 7 | 358.81 | 133.21 | 0.069 | 431.24 |
| 234521 | MAPKAPK3 | Mitogen-activated protein kinase-activated protein kinase 3 | 185.75 | 77.03 | 0.379 | 59.41 |
| 236030 | SMARCC2 | SWI/SNF related, matrix associated, actin dependent regulator of chromatin. subfamily c. member 2 | 198.07 | 83.50 | 0.207 | 34.66 |
| 237536 | NT5C3L | 5'-nucleotidase, cytosolic III-like | 160.67 | 84.27 | 0.276 | 95.40 |
| 237971 | XTP3TPA | XTP3-transactivated protein A | 122.34 | 67.16 | 0.276 | 58.94 |
| 238839 | SCYL1 | SCY1-like 1 (*S. cerevisiae*) | 173.16 | 113.72 | 0.310 | 144.41 |
| 240170 | OBFC2B | Oligonucleotide/oligosaccharide-binding fold containing 2B | 136.42 | 69.86 | 0.345 | 96.25 |
| 241336 | ATPIF1 | ATPase inhibitory factor 1 | 227.40 | 125.29 | 0.172 | 224.03 |
| 241543 | POLDIP2 | Polymerase (DNA-directed), delta interacting protein 2 | 217.98 | 81.62 | 0.138 | 66.91 |
| 241558 | ARIH2 | Ariadne homolog 2 (*Drosophila*) | 178.45 | 77.54 | 0.172 | 65.16 |
| 241575 | GNPTG | N-acetylglucosamine-1-phosphate transferase, gamma subunit | 117.17 | 100.69 | 0.345 | 73.29 |
| 241576 | DERL1 | Der1-like domain family. member 1 | 111.58 | 87.37 | 0.310 | 72.57 |
| 241579 | SERPINH1 | Serpin peptidase inhibitor. clade H (heat shock protein 47), member 1. (collagen binding protein 1) | 380.44 | 115.76 | 0.172 | 198.12 |
| 242458 | SPG21 | Spastic paraplegia 21 (autosomal recessive, Mast syndrome) | 120.35 | 59.44 | 0.310 | 76.41 |
| 242947 | DGKI | Diacylglycerol kinase, iota | 131.75 | 120.70 | 0.379 | 4086.25 |
| 246112 | ASCC3L1 | Activating signal cointegrator 1 complex subunit 3-like 1 | 278.46 | 81.24 | 0.172 | 160.68 |
| 246310 | ATP5J | ATP synthase, H+ transporting, mitochondrial F0 complex. subunit F6 | 220.45 | 113.90 | 0.276 | 232.33 |
| 246413 | CPNE1 | RNA binding motif protein 12 | 392.42 | 88.16 | 0.069 | 93.63 |
| 246781 | FBXO11 | F-box protein 11 | 141.20 | 92.55 | 0.379 | 48.14 |
| 247077 | RHOA | Ras homolog gene family, member A | 553.79 | 77.72 | 0.034 | 545.41 |
| 247186 | FBRS | Fibrosin | 145.20 | 107.50 | 0.379 | 70.03 |
| 247975 | HSPD1 | Pro-melanin-concentrating hormone-like 1 | 241.69 | 85.58 | 0.207 | 238.18 |
| 248267 | MPST | Mercaptopyruvate sulfurtransferase | 167.67 | 112.86 | 0.276 | 80.10 |
| 248941 | TAF9 | TAF9 RNA polymerase II. TATA box binding protein (TBP)-associated factor, 32 kDa | 148.14 | 65.92 | 0.276 | 54.96 |

TABLE 2-continued

A list of 2087 candidate endogenous reference genes

| | | | | | | |
|---|---|---|---|---|---|---|
| 249600 | DLGAP4 | Discs, large (*Drosophila*) homolog-associated protein 4 | 233.49 | 169.10 | 0.276 | 98.90 |
| 250009 | ARL8B | ADP-ribosylation factor-like 8B | 132.27 | 55.79 | 0.379 | 134.21 |
| 250429 | SUPT6H | Suppressor of Ty 6 homolog (*S. cerevisiae*) | 162.25 | 82.76 | 0.379 | 44.11 |
| 250758 | PSMC3 | Proteasome (prosome, macropain) 26S subunit, ATPase, 3 | 391.11 | 115.64 | 0.138 | 111.57 |
| 250899 | HSBP1 | Heat shock factor binding protein 1 | 214.94 | 105.83 | 0.069 | 141.99 |
| 250905 | TMEM85 | Transmembrane protein 85 | 156.08 | 143.74 | 0.241 | 77.54 |
| 251531 | PSMA4 | Proteasome (prosome, macropain) subunit, alpha type, 4 | 739.81 | 217.34 | 0.138 | 172.42 |
| 252457 | MVD | Mevalonate (diphospho) decarboxylase | 170.93 | 117.34 | 0.379 | 65.93 |
| 252713 | TTC15 | Tetratricopeptide repeat domain 15 | 105.62 | 56.20 | 0.345 | 75.68 |
| 252967 | C1orf144 | Chromosome 1 open reading frame 144 | 240.90 | 109.65 | 0.207 | 105.98 |
| 253726 | PAPOLA | Poly(A) polymerase alpha | 216.15 | 65.36 | 0.172 | 118.24 |
| 253903 | STOM | Stomatin | 199.17 | 100.65 | 0.276 | 100.22 |
| 254042 | BAT1 | HLA-B associated transcript 1 | 351.44 | 89.43 | 0.069 | 144.69 |
| 255015 | VPS24 | Vacuolar protein sorting 24 (yeast) | 126.82 | 67.80 | 0.069 | 79.90 |
| 255093 | PFKL | Phosphofructokinase, liver | 342.69 | 81.83 | 0.207 | 167.85 |
| 255932 | XRN2 | 5'-3' exoribonuclease 2 | 166.16 | 57.70 | 0.069 | 53.31 |
| 255935 | BTG1 | B-cell translocation gene 1. anti-proliferative | 272.14 | 115.44 | 0.138 | 264.18 |
| 255973 | EID1 | EP300 interacting inhibitor of differentiation 1 | 227.90 | 86.79 | 0.138 | 174.44 |
| 256301 | C19orf48 | Chromosome 19 open reading frame 48 | 337.67 | 84.54 | 0.207 | 158.37 |
| 256549 | NUBP2 | Nucleotide binding protein 2 (MinD homolog. *E. coli*) | 200.75 | 98.94 | 0.241 | 76.00 |
| 257008 | PLD3 | Phospholipase D family, member 3 | 349.21 | 100.00 | 0.276 | 203.69 |
| 257341 | SAV1 | Salvador homolog 1 (*Drosophila*) | 91.57 | 65.55 | 0.276 | 34.40 |
| 257761 | SH3BP5 | SH3-domain binding protein 5 (BTK-associated) | 170.93 | 92.54 | 0.345 | 70.17 |
| 258551 | DNPEP | Aspartyl aminopeptidase | 168.16 | 84.05 | 0.138 | 38.05 |
| 258563 | FEZ2 | Fasciculation and elongation protein zeta 2 (zygin II) | 190.19 | 204.72 | 0.345 | 67.33 |
| 258798 | NSMCE4A | Non-SMC element 4 homolog A (*S. cerevisiae*) | 79.52 | 52.34 | 0.345 | 366.69 |
| 259461 | PALM2-AKAP2 | PALM2-AKAP2 protein | 171.91 | 79.41 | 0.310 | 128.63 |
| 260603 | PIP5K2B | Phosphatidylinositol-4-phosphate 5-kinase. type II, beta | 132.75 | 67.00 | 0.276 | 94.30 |
| 262823 | IARS2 | Isoleucyl-tRNA synthetase 2, mitochondrial | 139.24 | 59.53 | 0.345 | 118.15 |
| 265829 | ITGA3 | Integrin. alpha 3 (antigen CD49C, alpha 3 subunit of VLA-3 receptor) | 404.31 | 148.83 | 0.379 | 109.76 |
| 268488 | LRRC47 | Leucine rich repeat containing 47 | 115.89 | 116.32 | 0.379 | 54.76 |
| 268530 | GPS1 | Radical fringe homolog (*Drosophila*) | 263.51 | 64.58 | 0.138 | 107.13 |
| 268742 | POMP | Proteasome maturation protein | 213.22 | 98.49 | 0.276 | 212.21 |
| 268849 | GLO1 | Glyoxalase I | 293.88 | 85.24 | 0.138 | 179.31 |
| 268939 | MATR3 | Matrin 3 | 292.73 | 68.23 | 0.034 | 241.08 |
| 269528 | NAT13 | N-acetyltransferase 13 | 237.37 | 198.20 | 0.172 | 110.90 |
| 269577 | PTPRA | Protein tyrosine phosphatase, receptor type, A | 183.68 | 82.75 | 0.207 | 168.07 |
| 269782 | GNAQ | Guanine nucleotide binding protein (G protein). q polypeptide | 174.12 | 105.06 | 0.241 | 52.13 |
| 269944 | MTCH2 | Mitochondrial carrier homolog 2 (*C. elegans*) | 158.42 | 74.35 | 0.103 | 70.20 |
| 270291 | ACTN4 | Actinin, alpha 4 | 341.13 | 108.40 | 0.172 | 419.64 |
| 270428 | SUCLG1 | Succinate-CoA ligase, GDP-forming, alpha subunit | 242.34 | 241.99 | 0.241 | 106.33 |
| 270525 | LASS5 | LAG1 longevity assurance homolog 5 (*S. cerevisiae*) | 111.31 | 73.14 | 0.379 | 57.78 |
| 270869 | ZNF410 | Zinc finger protein 410 | 135.77 | 84.28 | 0.172 | 53.74 |
| 271135 | ATP5C1 | ATP synthase, H+ transporting, mitochondrial F1 complex, gamma polypeptide 1 | 448.47 | 176.19 | 0.172 | 135.97 |
| 271695 | NOB1 | NIN1/RPN12 binding protein 1 homolog (*S. cerevisiae*) | 111.46 | 73.07 | 0.310 | 47.43 |
| 272062 | PTPRF | Protein tyrosine phosphatase. receptor type. F | 269.10 | 88.46 | 0.310 | 119.22 |
| 272168 | SERINC3 | Serine incorporator 3 | 121.11 | 72.44 | 0.138 | 39.75 |
| 272630 | ATP6V1D | ATPase, H+ transporting, lysosomal 34 kDa, V1 subunit D | 149.33 | 85.72 | 0.207 | 78.13 |
| 272927 | SEC23A | Sec23 homolog A (*S. cerevisiae*) | 128.24 | 74.07 | 0.379 | 52.45 |
| 273077 | TMEM14B | Transmembrane protein 14B | 128.20 | 70.29 | 0.345 | 63.88 |
| 274184 | TFE3 | Transcription factor binding to IGHM enhancer 3 | 111.31 | 57.20 | 0.276 | 57.28 |
| 274772 | C15orf15 | Chromosome 15 open reading frame 15 | 1163.64 | 205.16 | 0.172 | 82.77 |
| 274873 | CARS | Cysteinyl-tRNA synthetase | 176.72 | 76.48 | 0.207 | 82.54 |
| 275243 | S100A6 | S100 calcium binding protein A6 (calcyclin) | 361.59 | 101.08 | 0.103 | 591.93 |
| 275775 | SEPP1 | Selenoprotein P, plasma, 1 | 543.33 | 189.21 | 0.379 | 121.63 |
| 275865 | PCNP | PEST-containing nuclear protein | 315.34 | 88.79 | 0.069 | 83.52 |
| 276878 | NUP93 | Nucleoporin 93 kDa | 101.32 | 60.26 | 0.241 | 65.66 |
| 277035 | MGLL | Monoglyceride lipase | 399.51 | 211.97 | 0.379 | 116.25 |
| 277517 | C11orf2 | Chromosome 11 open reading frame 2 | 193.83 | 84.84 | 0.241 | 127.65 |
| 278186 | ARHGEF1 | Rho guanine nucleotide exchange factor (GEF) 1 | 194.28 | 91.63 | 0.345 | 73.95 |
| 278362 | MEA1 | Male-enhanced antigen 1 | 152.60 | 83.00 | 0.276 | 98.75 |
| 278426 | PDAP1 | PDGFA associated protein 1 | 184.93 | 86.49 | 0.172 | 106.94 |
| 278429 | C9orf78 | Chromosome 9 open reading frame 78 | 109.74 | 79.17 | 0.276 | 63.78 |
| 278500 | GNPDA1 | Glucosamine-6-phosphate deaminase 1 | 174.64 | 74.75 | 0.241 | 80.44 |
| 278569 | SNX17 | Sorting nexin 17 | 297.66 | 66.25 | 0.069 | 132.92 |
| 278573 | CD59 | CD59 antigen p18-20 (antigen identified by monoclonal antibodies 16.3A5, EJ16, EJ30, EL32 and G344) | 336.75 | 91.21 | 0.138 | 154.72 |
| 278721 | SLC39A7 | Solute carrier family 39 (zinc transporter), member 7 | 147.65 | 72.58 | 0.379 | 71.42 |
| 279061 | GLOD4 | Glyoxalase domain containing 4 | 148.90 | 76.66 | 0.172 | 65.97 |
| 279245 | TACC1 | Transforming. acidic coiled-coil containing protein 1 | 186.16 | 79.86 | 0.241 | 103.52 |
| 279257 | PCMT1 | Protein-L-isoaspartate (D-aspartate) O-methyltransferase | 172.73 | 62.20 | 0.103 | 102.09 |
| 279413 | POLDI | Polymerase (DNA directed). delta 1. catalytic subunit 125 kDa | 164.91 | 99.93 | 0.276 | 75.52 |
| 279529 | PRELID1 | PRELI domain containing 1 | 224.95 | 77.28 | 0.172 | 102.94 |
| 279583 | METTL9 | Methyltransferase like 9 | 183.44 | 155.70 | 0.241 | 146.63 |
| 279623 | SEPX1 | Selenoprotein X, 1 | 117.70 | 54.66 | 0.345 | 47.48 |

TABLE 2-continued

A list of 2087 candidate endogenous reference genes

| | | | | | | |
|---|---|---|---|---|---|---|
| 279640 | TPR | Translocated promoter region (to activated MET oncogene) | 94.90 | 66.61 | 0.310 | 69.84 |
| 279652 | MRPL4 | Mitochondrial ribosomal protein L4 | 173.40 | 73.00 | 0.276 | 110.73 |
| 279669 | TUBG1 | Tubulin, gamma 1 | 169.58 | 65.01 | 0.310 | 72.06 |
| 279696 | SUMF2 | Sulfatase modifying factor 2 | 149.85 | 83.02 | 0.345 | 127.55 |
| 279806 | DDX5 | RNA-binding protein 45 (RBP45). putative | 457.60 | 87.95 | 0.103 | 856.99 |
| 279836 | COMMD9 | COMM domain containing 9 | 104.98 | 49.94 | 0.379 | 60.58 |
| 279920 | YWHAB | Tyrosine 3-monooxygenase/tryptophan 5-monooxygenase activation protein. beta polypeptide | 288.39 | 87.94 | 0.034 | 251.99 |
| 279929 | TMED9 | Transmembrane emp24 protein transport domain containing 9 | 291.55 | 91.04 | 0.069 | 202.03 |
| 280202 | SBF1 | SET binding factor 1 | 382.01 | 317.21 | 0.310 | 36.29 |
| 280342 | PRKAR1A | Protein kinase, cAMP-dependent, regulatory, type I. alpha (tissue specific extinguisher 1) | 266.02 | 111.27 | 0.103 | 209.46 |
| 280378 | SNRPB2 | Small nuclear ribonucleoprotein polypeptide B" | 243.47 | 100.43 | 0.310 | 68.06 |
| 282410 | CALM1 | Calmodulin 1 (phosphorylase kinase, delta) | 246.78 | 67.76 | 0.103 | 513.80 |
| 282700 | SPCS2 | Signal peptidase complex subunit 2 homolog (*S. cerevisiae*) | 232.99 | 84.36 | 0.207 | 59.54 |
| 282901 | RBM39 | RNA binding motif protein 39 | 166.92 | 85.70 | 0.138 | 181.79 |
| 282998 | RBM9 | RNA binding motif protein 9 | 477.00 | 221.29 | 0.103 | 145.15 |
| 283111 | C14orf124 | Chromosome 14 open reading frame 124 | 168.06 | 139.52 | 0.207 | 73.74 |
| 283454 | BNIP2 | BCL2/adenovirus E1B 19 kDa interacting protein 2 | 130.03 | 68.79 | 0.310 | 47.89 |
| 283521 | RHEB | Ras homolog enriched in brain | 193.25 | 113.28 | 0.310 | 92.73 |
| 283610 | ATG4B | ATG4 autophagy related 4 homolog B (*S. cerevisiae*) | 180.36 | 88.44 | 0.172 | 49.24 |
| 283652 | IDI1 | Isopentenyl-diphosphate delta isomerase 1 | 233.34 | 102.32 | 0.241 | 58.55 |
| 283739 | UBQLN4 | Ubiquitin 4 | 165.35 | 84.58 | 0.207 | 62.49 |
| 284208 | ANKRD25 | Ankyrin repeat domain 25 | 124.68 | 85.84 | 0.379 | 46.63 |
| 284279 | HMOX2 | Heme oxygenase (decycling) 2 | 151.53 | 85.91 | 0.310 | 50.68 |
| 284286 | MRPS24 | Mitochondrial ribosomal protein S24 | 136.83 | 77.51 | 0.345 | 71.40 |
| 284491 | PDXK | Pyridoxal (pyridoxine, vitamin B6) kinase | 235.50 | 93.74 | 0.138 | 787.92 |
| 285354 | MAX | MYC associated factor X | 109.16 | 60.60 | 0.345 | 64.26 |
| 285976 | LASS2 | LAG1 longevity assurance homolog 2 (*S. cerevisiae*) | 203.17 | 82.28 | 0.172 | 132.14 |
| 286221 | ARF1 | ADP-ribosylation factor 1 | 704.87 | 66.67 | 0.069 | 199.12 |
| 286226 | MYO1C | Myosin IC | 253.69 | 114.87 | 0.310 | 90.05 |
| 288193 | KPNA4 | Karyopherin alpha 4 (importin alpha 3) | 144.60 | 134.58 | 0.379 | 59.34 |
| 288856 | PFDN5 | Prefoldin 5 | 226.65 | 96.63 | 0.103 | 320.21 |
| 288969 | NMRAL1 | NmrA-like family domain containing 1 | 126.04 | 77.91 | 0.379 | 34.41 |
| 289008 | NUS1 | Nuclear undecaprenyl pyrophosphate synthase 1 homolog (*S. cerevisiae*) | 157.63 | 95.67 | 0.310 | 68.14 |
| 289092 | COTL1 | Coactosin-like 1 (*Dictyostelium*) | 315.93 | 109.13 | 0.172 | 167.69 |
| 289123 | DCTN2 | Dynactin 2 (p50) | 261.39 | 105.34 | 0.069 | 89.02 |
| 289271 | CYC1 | Cytochrome c-1 | 345.69 | 78.79 | 0.172 | 242.81 |
| 290243 | GBF1 | Golgi-specific brefeldin A resistance factor 1 | 241.54 | 85.11 | 0.310 | 632.98 |
| 290404 | SLC25A3 | Solute carrier family 25 (mitochondrial carrier; phosphate carrier), member 3 | 1579.85 | 87.93 | 0.034 | 45.05 |
| 290758 | DDB1 | Damage-specific DNA binding protein 1, 127 kDa | 452.78 | 82.29 | 0.138 | 190.14 |
| 291587 | ARID1B | AT rich interactive domain 1B (SWI1-like) | 135.97 | 82.06 | 0.310 | 73.22 |
| 292026 | EIF4E2 | Eukaryotic translation initiation factor 4E member 2 | 186.78 | 88.38 | 0.138 | 46.59 |
| 292063 | EIF4B | Hypothetical protein PRO1843 | 439.43 | 110.97 | 0.103 | 148.75 |
| 292078 | LARP1 | La ribonucleoprotein domain family. member 1 | 246.82 | 65.22 | 0.069 | 105.37 |
| 292265 | ZMYND11 | Zinc finger, MYND domain containing 1 | 133.13 | 109.13 | 0.207 | 56.47 |
| 292457 | SNHG5 | Small nucleolar RNA host gene (non-protein coding) 5 | 400.14 | 267.50 | 0.276 | 289.85 |
| 292493 | XRCC6 | X-ray repair complementing defective repair in Chinese hamster cells 6 (Ku autoantigen, 70 kDa) | 691.10 | 100.07 | 0.034 | 318.36 |
| 292524 | CCNH | Cyclin H | 158.48 | 96.80 | 0.276 | 32.70 |
| 292579 | PTDSS1 | Phosphatidylserine synthase 1 | 195.76 | 80.55 | 0.276 | 67.07 |
| 293563 | C1orf108 | Chromosome 1 open reading frame 108 | 144.99 | 87.81 | 0.172 | 65.61 |
| 295917 | ATP6V1B2 | ATPase, H+ transporting. lysosomal 56/58 kDa, VI subunit B, isoform 2 | 151.09 | 76.58 | 0.207 | 62.97 |
| 297324 | TIMP3 | TIMP metallopeptidase inhibitor 3 (Sorsby fundus dystrophy. pseudoinflammatory) | 505.19 | 227.34 | 0.310 | 200.02 |
| 298198 | CMTM3 | CKLF-like MARVEL transmembrane domain containing 3 | 127.34 | 71.77 | 0.310 | 95.15 |
| 298280 | ATP5A1 | ATP synthase, H+ transporting, mitochondrial F1 complex. alpha subunit. isoform 1. cardiac muscle | 1791.25 | 357.36 | 0.000 | 473.59 |
| 298654 | DUSP6 | Dual specificity phosphatase 6 | 208.26 | 87.60 | 0.310 | 98.88 |
| 299002 | FBL | Fibrillarin | 591.46 | 179.47 | 0.138 | 162.19 |
| 299055 | GDI2 | GDP dissociation inhibitor 2 | 323.73 | 77.59 | 0.069 | 72.16 |
| 300141 | RPL39 | Ribosomal protein L39 | 775.36 | 419.08 | 0.172 | 791.80 |
| 300684 | RCP9 | Calcitonin gene-related peptide-receptor component protein | 79.62 | 45.89 | 0.241 | 39.78 |
| 300772 | TPM2 | Tropomyosin 2 (beta) | 861.72 | 370.12 | 0.345 | 294.55 |
| 300816 | RAB1B | RAB1B. member RAS oncogene family | 228.92 | 96.00 | 0.172 | 175.17 |
| 300834 | GALNT2 | UDP-N-acetyl-alpha-D-galactosamine: polypeptide N-acetylgaladosaminyltransferase 2 (GalNAc-T2) | 155.76 | 89.15 | 0.241 | 76.65 |
| 301404 | RBM3 | RNA binding motif (RNP1, RRM) protein 3 | 325.81 | 102.69 | 0.172 | 117.20 |
| 301412 | UFC1 | Ubiquitin-fold modifier conjugating enzyme 1 | 142.19 | 76.03 | 0.276 | 155.60 |
| 302742 | MRPS6 | Mitochondrial ribosomal protein S6 | 184.15 | 77.33 | 0.276 | 99.50 |
| 302903 | UBE2I | Ubiquitin-conjugating enzyme E2I (UBC9 homolog, yeast) | 178.40 | 82.89 | 0.172 | 95.85 |
| 303676 | G3BP2 | Ras-GTPase activating protein SH3 domain-binding protein 2 | 149.92 | 66.30 | 0.241 | 98.85 |
| 304192 | DSTN | Destrin (actin depolymerizing factor) | 223.11 | 77.62 | 0.207 | 79.90 |
| 304682 | CST3 | Cystatin C (amyloid angiopathy and cerebral hemorrhage) | 266.47 | 126.42 | 0.172 | 802.25 |
| 306123 | MAGEF1 | Melanoma antigen family F, 1 | 183.67 | 83.29 | 0.379 | 64.12 |

TABLE 2-continued

A list of 2087 candidate endogenous reference genes

| | | | | | | |
|---|---|---|---|---|---|---|
| 306242 | RANBP9 | RAN binding protein 9 | 116.92 | 67.43 | 0.310 | 66.12 |
| 306329 | ZFAND6 | Zinc finger, AN1-type domain 6 | 247.28 | 99.07 | 0.276 | 111.07 |
| 306425 | IBTK | Inhibitor of Bruton agammaglobulinemia tyrosine kinase | 104.18 | 51.87 | 0.379 | 71.02 |
| 308122 | ITPK1 | Inositol 1,3,4-triphosphate 5/6 kinase | 254.52 | 81.30 | 0.276 | 53.88 |
| 308340 | NUP188 | Nucleoporin 188 kDa | 329.72 | 144.04 | 0.241 | 50.55 |
| 308709 | PDIA3 | Protein disulfide isomerase family A, member 3 | 204.27 | 87.48 | 0.069 | 175.08 |
| 309090 | SFRS7 | Splicing factor, arginine/serine-rich 7, 35 kDa | 189.69 | 89.49 | 0.172 | 104.22 |
| 309231 | C6orf153 | Chromosome 6 open reading frame 153 | 157.44 | 80.31 | 0.310 | 66.08 |
| 309641 | RNF11 | Ring finger protein 11 | 162.82 | 68.82 | 0.172 | 187.15 |
| 309753 | STARD3NL | STARD3 N-terminal like | 119.30 | 74.99 | 0.310 | 95.69 |
| 309849 | C14orf159 | Chromosome 14 open reading frame 159 | 122.74 | 74.53 | 0.379 | 43.93 |
| 310542 | TOMM40 | Translocase of outer mitochondrial membrane 40 homolog (yeast) | 267.48 | 79.87 | 0.138 | 50.95 |
| 310645 | RAB1A | RAB1A. member RAS oncogene family | 252.99 | 84.41 | 0.241 | 104.46 |
| 311072 | MRPS35 | Mitochondrial ribosomal protein S35 | 138.81 | 64.82 | 0.345 | 40.18 |
| 311346 | CMAS | Cytidine monophosphate N-acetylneuraminic acid synthetase | 109.31 | 97.45 | 0.345 | 48.58 |
| 311609 | DDX39 | DEAD (Asp-Glu-Ala-Asp) box polypeptide 39 | 260.02 | 110.28 | 0.138 | 102.82 |
| 311640 | RPS27A | Ribosomal protein S27a | 524.64 | 119.16 | 0.034 | 830.70 |
| 312098 | ADAM15 | ADAM metallopeptidase domain 15 (metargidin) | 200.26 | 132.76 | 0.345 | 77.56 |
| 313847 | TXNDC11 | Thioredoxin domain containing 11 | 106.99 | 71.40 | 0.345 | 35.55 |
| 314263 | BAZ2A | Bromodomain adjacent to zinc finger domain, 2A | 164.92 | 91.68 | 0.241 | 70.15 |
| 314359 | EIF3S12 | Eukaryotic translation initiation factor 3, subunit 12 | 248.91 | 116.13 | 0.103 | 350.37 |
| 315177 | IFRD2 | Interferon-related developmental regulator 2 | 180.25 | 60.11 | 0.276 | 58.92 |
| 315230 | EIF1B | Eukaryotic translation initiation factor 1B | 166.77 | 108.63 | 0.207 | 160.77 |
| 319334 | NASP | Nuclear autoantigenic sperm protein (histone-binding) | 320.92 | 87.44 | 0.103 | 131.55 |
| 321391 | ELOF1 | Elongation factor 1 homolog (*S. cerevisiae*) | 119.51 | 68.26 | 0.345 | 60.37 |
| 321541 | RAB11A | RAB11A, member RAS oncogene family | 193.82 | 99.65 | 0.172 | 123.34 |
| 323363 | ATG9A | ATG9 autophagy related 9 homolog A (*S. cerevisiae*) | 159.62 | 88.11 | 0.276 | 47.64 |
| 323489 | PTCD3 | Pentatricopeptide repeat domain 3 | 153.29 | 80.62 | 0.172 | 49.53 |
| 324250 | NDUFB2 | NADH dehydrogenase (ubiquinone) 1 beta subcomplex, 2, 8 kDa | 245.74 | 182.66 | 0.379 | 183.95 |
| 324844 | VKORC1 | Vitamin K epoxide reductase complex. subunit 1 | 151.74 | 66.24 | 0.276 | 138.96 |
| 325650 | EHD2 | EH-domain containing 2 | 160.03 | 99.53 | 0.379 | 116.94 |
| 326387 | MORF4L2 | Mortality factor 4 like 2 | 313.02 | 109.69 | 0.103 | 189.57 |
| 330384 | CORO1C | Coronin. actin binding protein. 1C | 171.53 | 69.53 | 0.103 | 118.15 |
| 331431 | SCC-112 | SCC-112 protein | 242.38 | 75.28 | 0.069 | 64.31 |
| 333388 | EEF1D | Eukaryotic translation elongation factor 1 delta (guanine nucleotide exchange protein) | 899.57 | 105.63 | 0.000 | 404.01 |
| 333579 | HSPC152 | Hypothetical protein HSPC152 | 209.20 | 133.84 | 0.172 | 163.96 |
| 333786 | PSMA2 | Proteasome (prosome. macropain) subunit, alpha type. 2 | 207.24 | 97.57 | 0.138 | 197.41 |
| 333823 | MRPL13 | Mitochondrial ribosomal protein L13 | 113.33 | 69.75 | 0.345 | 44.81 |
| 334017 | TUBA1B | Tubulin. alpha 1b | 1834.27 | 95.82 | 0.000 | 1202.13 |
| 334479 | TRAF7 | TNF receptor-associated factor 7 | 242.13 | 130.36 | 0.138 | 56.99 |
| 334534 | GNS | Glucosamine (N-acetyl)-6-sulfatase (Sanfilippo disease IIID) | 129.18 | 72.76 | 0.276 | 73.76 |
| 334587 | RBPMS | RNA binding protein with multiple splicing | 136.68 | 59.93 | 0.345 | 76.18 |
| 334713 | UBL7 | Ubiquitin-like 7 (bone marrow stromal cell-derived) | 192.75 | 67.45 | 0.207 | 71.93 |
| 334851 | LASP1 | LIM and SH3 protein 1 | 297.69 | 80.06 | 0.034 | 98.51 |
| 334868 | PPP2R5E | Protein phosphatase 2, regulatory subunit B (B56), epsilon isoform | 111.74 | 78.51 | 0.345 | 40.49 |
| 335003 | ANKRD11 | Ankyrin repeat domain 11 | 152.63 | 135.85 | 0.276 | 85.85 |
| 335057 | SEPT2 | Septin 2 | 321.91 | 90.60 | 0.069 | 203.38 |
| 335163 | LIMCH1 | LIM and calponin homology domains 1 | 217.46 | 84.47 | 0.379 | 58.83 |
| 335918 | FDPS | Farnesyl diphosphate synthase (farnesyl pyrophosphate synthetase. dimethylallyltranstransferase, geranyltranstransferase | 635.55 | 104.20 | 0.034 | 75.25 |
| 337295 | STIP1 | Stress-induced-phosphoprotein 1 (Hsp70/Hsp90-organizing | 326.55 | 78.19 | 0.172 | 108.95 |
| 337766 | TXNRD1 | Thioredoxin reductase 1 | 641.30 | 103.44 | 0.034 | 227.03 |
| 339278 | COPB1 | Coatomer protein complex. subunit beta 1 | 144.35 | 59.14 | 0.241 | 121.58 |
| 339639 | COX7A2L | Cytochrome c oxidase subunit VIIa polypeptide 2 like | 222.21 | 84.81 | 0.241 | 200.80 |
| 339697 | GRINA | Glutamate receptor, ionotropic, N-methyl D-asparate-associated protein 1 (glutamate binding) | 287.06 | 90.28 | 0.103 | 251.13 |
| 343911 | EI24 | Etoposide induced 2.4 mRNA | 172.38 | 72.77 | 0.103 | 162.16 |
| 345694 | KCMF1 | Potassium channel modulatory factor 1 | 114.01 | 57.72 | 0.345 | 54.57 |
| 346868 | EBNA1BP2 | EBNA1 binding protein 2 | 190.81 | 79.22 | 0.276 | 75.67 |
| 348418 | DR1 | Down-regulator of transcription 1. TBP-binding (negative cofactor | 109.41 | 77.62 | 0.207 | 45.01 |
| 349656 | SCARB2 | Scavenger receptor class B, member 2 | 147.31 | 89.03 | 0.241 | 210.49 |
| 350194 | ZMAT2 | Zinc finger. matrin type 2 | 115.49 | 53.42 | 0.207 | 37.72 |
| 350229 | CASC3 | Cancer susceptibility candidate 3 | 124.19 | 53.21 | 0.241 | 114.41 |
| 350268 | IRF2BP2 | Interferon regulatory factor 2 binding protein 2 | 153.03 | 81.62 | 0.276 | 118.60 |
| 350364 | FAM120AOS | Family with sequence similarity 120A opposite strand | 107.30 | 65.11 | 0.379 | 41.56 |
| 350927 | SLC25A6 | Solute carrier family 25 (mitochondrial carrier: adenine nucleotide translocator). member 6 | 952.99 | 85.55 | 0.000 | 444.35 |
| 351099 | FLJ10241 | Hypothetical protein FLJ10241 | 126.93 | 65.83 | 0.276 | 39.55 |
| 351296 | LOC51035 | SAPK substrate protein 1 | 210.44 | 71.71 | 0.172 | 87.27 |
| 351316 | TM4SF1 | Transmembrane 4 L six family member 1 | 422.43 | 110.13 | 0.276 | 449.98 |
| 351474 | PAQR4 | Progestin and adipoQ receptor family member IV | 212.87 | 153.70 | 0.345 | 84.43 |
| 351680 | | CDNA clone IMAGE: 5302006 | 133.19 | 88.88 | 0.276 | 120.23 |
| 351875 | COX6C | Cytochrome c oxidase subunit VIc | 304.69 | 180.70 | 0.310 | 559.91 |
| 352341 | STCH | Stress 70 protein chaperone, microsome-associated. 60 kDa | 121.74 | 86.32 | 0.379 | 58.92 |
| 352656 | GHITM | Growth hormone inducible transmembrane protein | 363.92 | 99.19 | 0.103 | 63.14 |
| 352768 | PSMB1 | Proteasome (prosome, macropain) subunit, beta type, 1 | 292.02 | 82.24 | 0.103 | 177.54 |
| 354056 | POR | P450 (cytochrome) oxidoreductase | 227.09 | 82.79 | 0.379 | 74.23 |

TABLE 2-continued

A list of 2087 candidate endogenous reference genes

| | | | | | | |
|---|---|---|---|---|---|---|
| 355141 | TNIP1 | TNFAIP3 interacting protein 1 | 269.81 | 97.79 | 0.241 | 102.36 |
| 355606 | TMEM167 | Transmembrane protein 167 | 211.08 | 149.60 | 0.276 | 80.22 |
| 355643 | RNPS1 | RNA binding protein S1, serine-rich domain | 423.42 | 65.75 | 0.103 | 105.94 |
| 355708 | TMEM127 | Transmembrane protein 127 | 77.31 | 49.24 | 0.379 | 45.95 |
| 355750 | JOSD3 | Josephin domain containing 3 | 117.50 | 61.17 | 0.379 | 147.10 |
| 355753 | AGPAT6 | 1-acylglycerol-3-phosphate O-acyltransferase 6 (lysophosphatidic acid acyltransferase. zeta) | 150.13 | 73.56 | 0.345 | 47.02 |
| 355867 | MARS | Methionine-tRNA synthetase | 323.10 | 233.26 | 0.069 | 59.52 |
| 355927 | VDAC2 | Voltage-dependent anion channel 2 | 242.40 | 82.56 | 0.103 | 141.28 |
| 355934 | SFPQ | Splicing factor proline/glutamine-rich (polypyrimidine tract binding protein associated) | 269.46 | 133.96 | 0.138 | 128.50 |
| 355983 | BZW1 | Basic leucine zipper and W2 domains 1 | 338.32 | 108.39 | 0.103 | 181.32 |
| 356061 | MAP1LC3B | Microtubule-associated protein 1 light chain 3 beta | 126.69 | 74.25 | 0.207 | 166.48 |
| 356096 | MAP7D1 | MAP7 domain containing 1 | 191.33 | 92.49 | 0.207 | 152.55 |
| 356190 | UBB | Ubiquitin B | 742.69 | 74.99 | 0.000 | 716.73 |
| 356270 | SDHD | Succinate dehydrogenase complex, subunit D, integral membrane protein | 977.72 | 187.08 | 0.207 | 47.58 |
| 356285 | HMGN1 | High-mobility group nucleosome binding domain 1 | 279.36 | 80.39 | 0.138 | 330.79 |
| 356331 | PPIA | Peptidylprolyl isomerase A (cyclophilin A) | 1225.70 | 78.02 | 0.034 | 1646.83 |
| 356366 | RPS2 | Ribosomal protein S2 | 5031.59 | 91.00 | 0.000 | 1894.42 |
| 356371 | RPL28 | Ribosomal protein L28 | 622.10 | 176.27 | 0.034 | 2001.52 |
| 356377 | RNF187 | Ring finger protein 187 | 188.84 | 96.73 | 0.207 | 92.73 |
| 356467 | C19orf42 | Chromosome 19 open reading frame 42 | 148.32 | 80.69 | 0.034 | 76.36 |
| 356501 | PHF6 | PHD finger protein 6 | 145.65 | 87.04 | 0.310 | 160.28 |
| 356502 | RPLP1 | Ribosomal protein, large, P1 | 881.03 | 208.46 | 0.000 | 2388.08 |
| 356549 | SNRPD3 | Small nuclear ribonucleoprotein D3 polypeptide 18 kDa | 153.63 | 84.17 | 0.276 | 81.89 |
| 356630 | NUTF2 | Nuclear transport factor 2 | 144.29 | 83.13 | 0.103 | 186.27 |
| 356647 | SNX6 | Sorting nexin 6 | 134.10 | 84.57 | 0.310 | 94.88 |
| 356654 | PSMC1 | Proteasome (prosome, macropain) 26S subunit, ATPase, 1 | 154.97 | 82.94 | 0.172 | 80.59 |
| 356766 | C20orf199 | Chromosome 20 open reading frame 199 | 227.51 | 154.61 | 0.310 | 203.56 |
| 356769 | MAN2B1 | Mannosidase, alpha, class 2B. member 1 | 166.87 | 97.57 | 0.310 | 102.94 |
| 356799 | RPL41 | Ribosomal protein L41 | 336.21 | 165.15 | 0.345 | 350.34 |
| 357901 | SOX4 | SRY (sex determining region Y)-box 4 | 163.64 | 90.74 | 0.345 | 273.44 |
| 362728 | SEP15 | 15 kDa selenoprotein | 302.87 | 139.54 | 0.138 | 110.63 |
| 365116 | U2AF1 | U2(RNU2) small nuclear RNA auxiliary factor 1 | 152.30 | 63.70 | 0.241 | 103.78 |
| 368084 | LRPPRC | Leucine-rich PPR-motif containing | 180.31 | 95.65 | 0.241 | 70.90 |
| 368149 | CCT7 | Chaperonin containing TCP1. subunit 7 (eta) | 968.98 | 94.04 | 0.069 | 253.53 |
| 368157 | PYGB | Phosphorylase. glycogen; brain | 289.40 | 94.26 | 0.241 | 262.01 |
| 368240 | DYRK1A | Dual-specificity tyrosine-(Y)-phosphorylation regulated kinase 1A | 132.39 | 93.19 | 0.379 | 80.76 |
| 368264 | PPP2R5C | Protein phosphatase 2. regulatory subunit B (B56), gamma | 235.30 | 135.72 | 0.103 | 78.57 |
| 368376 | SRPR | Signal recognition particle receptor ('docking protein') | 170.10 | 91.17 | 0.138 | 64.69 |
| 368402 | C8orf55 | Chromosome 8 open reading frame 55 | 129.24 | 75.63 | 0.379 | 50.69 |
| 368404 | EXT2 | Exostoses (multiple) 2 | 144.25 | 80.41 | 0.345 | 64.81 |
| 368525 | PDLIM1 | PDZ and LIM domain 1 (elfin) | 285.39 | 113.52 | 0.241 | 94.01 |
| 368598 | ZC3H15 | Zinc finger CCCH-type containing 15 | 153.03 | 73.26 | 0.172 | 63.93 |
| 368934 | C17orf45 | Chromosome 17 open reading frame 45 | 538.27 | 122.37 | 0.103 | 510.24 |
| 368985 | TRIP12 | Thyroid hormone receptor interactor 12 | 160.59 | 66.50 | 0.345 | 74.13 |
| 369017 | RAB2A | RAB2A, member RAS oncogene family | 185.09 | 87.27 | 0.172 | 120.37 |
| 369052 | SELT | Selenoprotein T | 368.37 | 150.53 | 0.172 | 114.17 |
| 369068 | DYNC1LI2 | Dynein, cytoplasmic 1, light intermediate chain 2 | 158.56 | 97.53 | 0.138 | 167.20 |
| 369125 | PSMD14 | Proteasome (prosome, macropain) 26S subunit, non-ATPase. 14 | 166.50 | 83.15 | 0.103 | 74.34 |
| 369285 | INTS7 | Integrator complex subunit 7 | 112.06 | 98.19 | 0.379 | 266.65 |
| 369356 | MLL5 | Myeloid/lymphoid or mixed-lineage leukemia 5 (trithorax homolog, Drosophila) | 156.73 | 73.07 | 0.276 | 76.27 |
| 369606 | CPSF6 | Cleavage and polyadenylation specific factor 6, 68 kDa | 132.90 | 65.76 | 0.207 | 63.91 |
| 369607 | GAK | Cyclin G associated kinase | 139.66 | 91.16 | 0.379 | 72.66 |
| 369614 | COPS2 | COP9 constitutive photomorphogenic homolog subunit 2 (Arabidopsis) | 138.58 | 64.46 | 0.241 | 36.98 |
| 369615 | SLC25A38 | Solute carrier family 25. member 38 | 148.69 | 73.93 | 0.345 | 43.41 |
| 369761 | DAZAP2 | DAZ associated protein 2 | 432.10 | 77.51 | 0.069 | 187.75 |
| 369785 | C19orf50 | Chromosome 19 open reading frame 50 | 176.53 | 91.76 | 0.207 | 85.83 |
| 369920 | RAP1B | RAP1B. member of RAS oncogene family | 160.45 | 86.70 | 0.138 | 172.27 |
| 370024 | SEC31A | SEC31 homolog A (S. cerevisiae) | 162.54 | 73.78 | 0.138 | 159.51 |
| 370247 | APLP2 | Amyloid beta (A4) precursor-like protein 2 | 331.96 | 98.29 | 0.207 | 295.17 |
| 370292 | BCCIP | BRCA2 and CDKN1A interacting protein | 116.14 | 69.62 | 0.172 | 54.66 |
| 370312 | FNTA | Farnesyltransferase, CAAX box, alpha | 113.75 | 73.97 | 0.172 | 56.14 |
| 370408 | COMT | Catechol-O-methyltransferase | 269.48 | 182.45 | 0.138 | 81.80 |
| 370581 | CAP1 | CAP. adenylate cyclase-associated protein 1 (yeast) | 429.82 | 79.15 | 0.069 | 202.38 |
| 370770 | XPO1 | Exportin 1 (CRM1 homolog, yeast) | 218.71 | 75.18 | 0.172 | 86.09 |
| 370771 | CDKN1A | Cyclin-dependent kinase inhibitor 1A (p21, Cip1) | 406.91 | 129.23 | 0.207 | 221.01 |
| 370895 | RPN2 | Ribophorin II | 431.77 | 115.24 | 0.069 | 151.28 |
| 370927 | LRRC59 | Leucine rich repeat containing 59 | 338.69 | 149.06 | 0.138 | 68.76 |
| 370937 | TAPBP | TAP binding protein (tapasin) | 159.24 | 70.81 | 0.310 | 115.35 |
| 371001 | EIF3S9 | Eukaryotic translation initiation factor 3, subunit 9 eta, 116 kDa | 343.76 | 63.64 | 0.103 | 193.59 |
| 371416 | CARM1 | Coactivator-associated arginine methyltransferase 1 | 186.54 | 108.72 | 0.276 | 44.92 |
| 371563 | RAB14 | RAB14. member RAS oncogene family | 154.08 | 65.54 | 0.310 | 90.16 |
| 371788 | C1orf77 | Chromosome 1 open reading frame 77 | 121.36 | 60.36 | 0.207 | 40.80 |
| 371889 | ATP1A1 | Hypothetical protein MGC16179 | 910.43 | 156.53 | 0.069 | 245.88 |

TABLE 2-continued

A list of 2087 candidate endogenous reference genes

| 372003 | FAM120A | Family with sequence similarity 120A | 211.67 | 121.79 | 0.241 | 130.10 |
|---|---|---|---|---|---|---|
| 372050 | YIPF5 | Yip1 domain family, member 5 | 117.56 | 66.39 | 0.276 | 58.15 |
| 372286 | CUL3 | Cullin 3 | 131.34 | 66.77 | 0.207 | 55.91 |
| 372331 | SPTAN1 | Spectrin, alpha. non-erythrocytic 1 (alpha-fodrin) | 187.03 | 76.74 | 0.207 | 141.12 |
| 372541 | KBTBD2 | Kelch repeat and BTB (POZ) domain containing 2 | 100.18 | 63.32 | 0.310 | 72.26 |
| 372616 | ARL1 | ADP-ribosylation factor-like 1 | 107.60 | 50.60 | 0.345 | 53.90 |
| 372914 | NDRG1 | N-myc downstream regulated gene 1 | 214.33 | 101.47 | 0.241 | 84.08 |
| 373550 | TGIF1 | TGFB-induced factor homeobox 1 | 109.97 | 67.30 | 0.379 | 133.12 |
| 373741 | HM13 | Histocompatibility (minor) 13 | 280.09 | 120.85 | 0.069 | 144.47 |
| 373763 | HNRPR | Heterogeneous nuclear ribonucleoprotein R | 210.83 | 74.59 | 0.103 | 190.45 |
| 373952 | CAMTA2 | Calmodulin binding transcription activator 2 | 181.38 | 88.37 | 0.345 | 50.38 |
| 373959 | VGLL4 | Vestigial like 4 (*Drosophila*) | 141.11 | 70.42 | 0.310 | 71.58 |
| 374043 | ASXL1 | Additional sex combs like 1 (*Drosophila*) | 130.97 | 88.31 | 0.241 | 116.01 |
| 374257 | LOC28616 | Hypothetical protein LOC286167 | 151.79 | 112.19 | 0.276 | 73.50 |
| 374378 | CKS1B | CDC28 protein kinase regulatory subunit 1B | 179.04 | 67.28 | 0.172 | 113.85 |
| 374477 | EWSR1 | Ewing sarcoma breakpoint region 1 | 423.33 | 116.42 | 0.069 | 133.82 |
| 374503 | MORF4L1 | Mortality factor 4 like 1 | 292.45 | 60.67 | 0.069 | 303.22 |
| 374588 | RPL17 | Ribosomal protein L17 | 907.22 | 138.52 | 0.034 | 1232.67 |
| 374596 | TPT1 | Tumor protein. translationally-controlled 1 | 987.59 | 77.14 | 0.034 | 3569.27 |
| 374650 | IFITM3 | Interferon induced transmembrane protein 3 (1-8U) | 366.99 | 97.80 | 0.276 | 406.62 |
| 374973 | PRPF4 | PRP4 pre-mRNA processing factor 4 homolog (yeast) | 103.66 | 65.33 | 0.207 | 44.01 |
| 375001 | TLN1 | Talin 1 | 392.09 | 120.61 | 0.138 | 109.38 |
| 375108 | CD24 | CD24 antigen (small cell lung carcinoma cluster 4 antigen) | 239.14 | 95.21 | 0.310 | 518.62 |
| 375217 | RNF31 | Ring finger protein 31 | 104.06 | 73.05 | 0.379 | 50.53 |
| 376046 | BTN3A2 | Butyrophilin, subfamily 3. member A2 | 149.93 | 123.05 | 0.310 | 52.79 |
| 376933 | GUK1 | Guanylate kinase 1 | 401.68 | 92.59 | 0.276 | 308.91 |
| 377155 | MTDH | Metadherin | 214.89 | 91.52 | 0.138 | 132.35 |
| 378103 | RPS5 | Ribosomal protein S5 | 1006.11 | 134.01 | 0.069 | 568.97 |
| 378532 | HBS1L | HBS1-like (*S. cerevisiae*) | 131.17 | 80.02 | 0.241 | 36.24 |
| 378808 | EIF2A | Eukaryotic translation initiation factor 2A. 65 kDa | 197.55 | 75.77 | 0.138 | 71.81 |
| 380403 | BMI1 | BMI1 polycomb ring finger oncogene | 103.02 | 59.56 | 0.276 | 49.37 |
| 380774 | DDX3X | DEAD (Asp-Glu-Ala-Asp) box polypeptide 3, X-linked | 183.86 | 64.56 | 0.241 | 292.30 |
| 380953 | RPL38 | Ribosomal protein L38 | 472.88 | 260.03 | 0.138 | 1234.08 |
| 380973 | SUMO2 | SMT3 suppressor of mif two 3 homolog 2 (yeast) | 634.74 | 241.40 | 0.103 | 516.19 |
| 381008 | HLA-E | Major histocompatibility complex, class I. E | 476.57 | 108.00 | 0.103 | 189.44 |
| 381058 | KIAA0146 | KIAA0146 protein | 136.13 | 82.82 | 0.276 | 58.75 |
| 381072 | PPIF | Peptidylprolyl isomerase F (cyclophilin F) | 236.14 | 96.10 | 0.034 | 101.71 |
| 381123 | RPL21 | Ribosomal protein L21 | 1087.11 | 152.34 | 0.069 | 2223.30 |
| 381126 | RPS14 | Ribosomal protein S14 | 312.13 | 120.35 | 0.172 | 890.77 |
| 381189 | CBX3 | Chromobox homolog 3 (HP1 gamma homolog. *Drosophila*) | 352.70 | 90.90 | 0.138 | 202.41 |
| 381219 | RPL15 | Ribosomal protein L15 | 454.76 | 118.60 | 0.034 | 690.41 |
| 381256 | GLTP | Glycolipid transfer protein | 107.14 | 53.95 | 0.379 | 107.25 |
| 382044 | MRPS2 | Mitochondrial ribosomal protein S2 | 171.06 | 80.19 | 0.207 | 63.91 |
| 382168 | NCOA3 | Nuclear receptor coactivator 3 | 166.37 | 135.20 | 0.345 | 47.57 |
| 385913 | ANP32E | Acidic (leucine-rich) nuclear phosphoprotein 32 family, member E | 183.06 | 71.26 | 0.345 | 98.67 |
| 385986 | UBE2B | Ubiquitin-conjugating enzyme E2B (RAD6 homolog) | 135.72 | 71.52 | 0.345 | 133.50 |
| 386434 | ANXA7 | Annexin A7 | 173.87 | 70.85 | 0.138 | 79.18 |
| 386465 | CHERP | Calcium homeostasis endoplasmic reticulum protein | 177.08 | 80.21 | 0.345 | 43.91 |
| 386939 | USP7 | Ubiquitin specific peptidase 7 (herpes virus-associated) | 181.20 | 217.36 | 0.207 | 49.17 |
| 387208 | FAU | Finkel-Biskis-Reilly murine sarcoma virus (FBR-MuSV) ubiquitously expressed (fox derived); ribosomal protein S30 | 336.62 | 163.47 | 0.103 | 653.75 |
| 387804 | PABPC1 | Poly(A) binding protein, cytoplasmic 1 | 625.68 | 87.04 | 0.000 | 382.83 |
| 388034 | RXRB | Retinoid X receptor. beta | 142.87 | 89.88 | 0.310 | 38.31 |
| 388654 | ATP6V1G1 | ATPase, H+ transporting, lysosomal 13 kDa, V1 subunit G isoform 1 | 234.65 | 112.64 | 0.172 | 97.60 |
| 388664 | RPL11 | Ribosomal protein L11 | 672.13 | 137.34 | 0.034 | 1553.26 |
| 388739 | XRCC5 | X-ray repair complementing defective repair in Chinese hamster cells 5 (double-strand-break rejoining; Ku autoantigen, 80 kDa) | 346.39 | 73.79 | 0.034 | 162.11 |
| 388927 | YY1 | YY1 transcription factor | 136.53 | 65.73 | 0.103 | 127.70 |
| 388956 | C19orf22 | Chromosome 19 open reading frame 22 | 133.57 | 84.00 | 0.345 | 55.36 |
| 389037 | MCM3APAS | MCM3 minichromosome maintenance deficient 3 (*S. cerevisiae*) associated protein | 152.46 | 115.81 | 0.207 | 70.85 |
| 389107 | ATP6V0C | ATPase, H+ transporting. lysosomal 16 kDa, V0 subunit c | 237.34 | 79.84 | 0.172 | 238.25 |
| 389171 | PINK1 | PTEN induced putative kinase 1 | 126.44 | 98.97 | 0.207 | 74.04 |
| 389649 | EIF4A3 | Eukaryotic translation initiation factor 4A. isoform 3 | 193.85 | 75.13 | 0.138 | 88.57 |
| 389734 | TCEAL8 | Transcription elongation factor A (SII)-like 8 | 155.08 | 72.63 | 0.345 | 43.98 |
| 389996 | CHCHD2 | Coiled-coil-helix-coiled-coil-helix domain containing 2 | 373.11 | 68.47 | 0.034 | 337.24 |
| 390667 | GSTK1 | Glutathione S-transferase kappa 1 | 168.35 | 104.34 | 0.241 | 152.19 |
| 393201 | ACTR2 | ARP2 actin-related protein 2 homolog (yeast) | 328.49 | 139.01 | 0.172 | 119.86 |
| 395482 | PTK2 | PTK2 protein tyrosine kinase 2 | 177.88 | 103.98 | 0.207 | 42.01 |
| 396644 | PAIP2 | Poly(A) binding protein interacting protein 2 | 198.13 | 69.25 | 0.103 | 96.51 |
| 396740 | NIP30 | NEFA-interacting nuclear protein NIP30 | 96.64 | 53.08 | 0.241 | 47.28 |
| 396783 | SLC9A3R1 | Solute carrier family 9 (sodium/hydrogen exchanger). member 3 regulator 1 | 165.70 | 98.11 | 0.276 | 107.54 |
| 397609 | RPS16 | Ribosomal protein S16 | 1470.38 | 224.21 | 0.069 | 1068.13 |
| 399800 | AKAP8L | A kinase (PRKA) anchor protein 8-like | 166.62 | 90.19 | 0.310 | 63.09 |
| 400295 | RPL30 | Ribosomal protein L30 | 473.07 | 139.61 | 0.103 | 2027.75 |
| 401509 | RBM10 | RNA binding motif protein 10 | 170.05 | 75.56 | 0.172 | 69.36 |

TABLE 2-continued

A list of 2087 candidate endogenous reference genes

| 401903 | COX5A | Cytochrome c oxidase subunit Va | 149.97 | 93.76 | 0.379 | 296.35 |
|---|---|---|---|---|---|---|
| 401929 | RPL10 | Ribosomal protein L10 | 1521.64 | 147.31 | 0.000 | 2240.90 |
| 403917 | STK24 | Serine/threonine kinase 24 (STE20 homolog. yeast) | 150.48 | 84.52 | 0.276 | 83.03 |
| 404056 | EIF3S1 | Eukaryotic translation initiation factor 3. subunit 1 alpha. 35 kDa | 140.93 | 90.80 | 0.310 | 62.42 |
| 404321 | GARS | Glycyl-tRNA synthetase | 247.29 | 80.31 | 0.034 | 166.21 |
| 405144 | SFRS3 | Splicing factor, arginine/serine-rich 3 | 526.80 | 137.87 | 0.034 | 293.88 |
| 405410 | OGT | O-linked N-acetylglucosamine (GlcNAc) transferase (UDP-N-acetylglucosamine: polypeptide-N-acetylglucosaminyl transferase) | 153.55 | 55.45 | 0.379 | 87.05 |
| 405514 | KIAA1267 | KIAA1267 | 114.08 | 65.11 | 0.345 | 72.89 |
| 405590 | EIF3S6 | Eukaryotic translation initiation factor 3. subunit 6 48 kDa | 654.44 | 113.72 | 0.069 | 174.41 |
| 405880 | MRPS21 | Mitochondrial ribosomal protein S21 | 141.88 | 82.93 | 0.276 | 145.69 |
| 405942 | CCDC137 | Coiled-coil domain containing 137 | 133.03 | 86.11 | 0.241 | 77.12 |
| 406062 | NDUFA11 | NADH dehydrogenase (ubiquinone) 1 alpha subcomplex, 11. 14.7 kDa | 173.17 | 93.80 | 0.345 | 194.39 |
| 406068 | UBE2M | Ubiquitin-conjugating enzyme E2M (UBC12 homolog, yeast) | 132.46 | 80.88 | 0.345 | 94.66 |
| 406096 | ZFAND5 | Zinc finger. AN1-type domain 5 | 192.43 | 93.38 | 0.345 | 318.23 |
| 406277 | SF3A1 | Splicing factor 3a, subunit 1, 120 kDa | 296.74 | 89.39 | 0.276 | 83.36 |
| 406300 | RPL23 | Ribosomal protein L23 | 696.30 | 308.79 | 0.069 | 1844.46 |
| 406423 | SF3B2 | Splicing factor 3b, subunit 2, 145 kDa | 355.96 | 73.17 | 0.069 | 58.42 |
| 406510 | ATP5B | ATP synthase, H+ transporting, mitochondrial F1 complex, beta polypeptide | 1002.07 | 88.90 | 0.034 | 206.51 |
| 406520 | LOC38954 | Similar to CG14977-PA | 124.27 | 87.28 | 0.276 | 188.85 |
| 406534 | HMG20B | High-mobility group 20B | 281.92 | 155.98 | 0.103 | 66.80 |
| 406590 | MRFAP1 | Mof4 family associated protein 1 | 256.02 | 73.95 | 0.207 | 195.87 |
| 406620 | RPS10 | Ribosomal protein S10 | 1185.80 | 153.87 | 0.034 | 437.99 |
| 406683 | RPS15 | Ribosomal protein S15 | 521.25 | 123.23 | 0.069 | 137.98 |
| 406799 | RAB18 | RAB18. member RAS oncogene family | 127.87 | 57.58 | 0.310 | 50.22 |
| 406840 | SLC35A4 | Solute carrier family 35. member A4 | 186.45 | 71.30 | 0.103 | 42.86 |
| 407368 | LSM14A | LSM14A, SCD6 homolog A (*S. cerevisiae*) | 151.28 | 68.77 | 0.207 | 296.81 |
| 407580 | PKP4 | Plakophilin 4 | 130.61 | 101.53 | 0.207 | 111.02 |
| 407995 | MIF | Macrophage migration inhibitory factor (glycosylation-inhibiting factor) | 520.62 | 161.06 | 0.241 | 820.62 |
| 408018 | RPL36 | Ribosomal protein L36 | 426.58 | 200.20 | 0.276 | 1665.77 |
| 408073 | RPS6 | Ribosomal protein S6 | 1753.93 | 92.01 | 0.034 | 1215.89 |
| 408236 | TXNL5 | Thioredoxin-like 5 | 137.51 | 78.57 | 0.276 | 189.91 |
| 408257 | NDUFS6 | NADH dehydrogenase (ubiquinone) Fe—S protein 6, 13 kDa (NADH-coenzyme Q reductase) | 167.98 | 115.41 | 0.379 | 166.96 |
| 408293 | CEP170 | Centrosomal protein 170 kDa | 95.55 | 57.63 | 0.379 | 56.47 |
| 408324 | FLJ10769 | Hypothetical protein FLJ10769 | 179.63 | 110.86 | 0.345 | 54.49 |
| 408428 | FOXN3 | Forkhead box N3 | 171.98 | 93.85 | 0.379 | 87.86 |
| 408581 | SVIL | Supervillin | 150.79 | 78.33 | 0.276 | 98.78 |
| 408909 | GOLPH3 | Golgi phosphoprotein 3 (coat-protein) | 149.55 | 90.99 | 0.207 | 103.46 |
| 409140 | ATP5O | ATP synthase, H+ transporting, mitochondrial F1 complex, O subunit (oligomycin sensitivity conferring protein) | 238.76 | 77.50 | 0.138 | 187.51 |
| 409223 | SSR4 | Signal sequence receptor, delta (translocon-associated protein delta) | 187.19 | 88.00 | 0.138 | 154.53 |
| 409230 | AGPAT1 | 1-acylglycerol-3-phosphate O-acyltransferase 1 (lysophosphatidic acid acyltransferase, alpha) | 188.83 | 78.43 | 0.207 | 71.39 |
| 409834 | PHPT1 | Phosphohistidine phosphatase 1 | 129.72 | 80.15 | 0.379 | 132.98 |
| 410197 | IDH3G | Isocitrate dehydrogenase 3 (NAD+) gamma | 142.89 | 74.63 | 0.276 | 43.88 |
| 410596 | WDR68 | WD repeat domain 68 | 190.39 | 78.19 | 0.069 | 37.03 |
| 410817 | RPL13 | Ribosomal protein L13 | 1259.59 | 96.20 | 0.034 | 2237.70 |
| 411480 | AUP1 | Ancient ubiquitous protein 1 | 197.34 | 72.07 | 0.103 | 130.09 |
| 411641 | EIF4EBP1 | Eukaryotic translation initiation factor 4E binding protein 1 | 185.54 | 87.93 | 0.310 | 96.89 |
| 411847 | MAPK6 | Mitogen-activated protein kinase 6 | 143.89 | 100.65 | 0.207 | 67.09 |
| 412103 | EFHA1 | EF-hand domain family. member A1 | 130.69 | 68.19 | 0.276 | 74.51 |
| 412117 | ANXA6 | Annexin A6 | 173.96 | 90.66 | 0.172 | 81.81 |
| 412196 | IFT57 | Intraflagellar transport 57 homolog (*Chlamydomonas*) | 109.98 | 56.91 | 0.379 | 49.42 |
| 412433 | AIP | Aryl hydrocarbon receptor interacting protein | 157.20 | 76.87 | 0.207 | 95.68 |
| 412468 | KLHDC3 | Kelch domain containing 3 | 366.49 | 77.49 | 0.172 | 60.90 |
| 412842 | CDC123 | Cell division cycle 123 homolog (*S. cerevisiae*) | 155.00 | 62.20 | 0.207 | 68.47 |
| 413036 | WBSCR22 | Williams Beuren syndrome chromosome region 22 | 181.29 | 60.06 | 0.103 | 73.81 |
| 413482 | C21orf33 | Chromosome 21 open reading frame 33 | 220.73 | 103.88 | 0.172 | 72.11 |
| 414579 | SCOTIN | Scotin | 344.80 | 79.60 | 0.138 | 89.15 |
| 415342 | TCF25 | Transcription factor 25 (basic helix-loop-helix) | 132.99 | 67.57 | 0.172 | 122.55 |
| 416049 | TNPO2 | Transportin 2 (importin 3, karyopherin beta 2b) | 121.80 | 74.72 | 0.345 | 77.32 |
| 416436 | TRIM50 | Tripartite motif-containing 50 | 253.97 | 118.36 | 0.138 | 85.38 |
| 417004 | S100A11 | S100 calcium binding protein A11 (calgizzarin) | 282.02 | 146.47 | 0.138 | 317.66 |
| 417029 | C17orf81 | Chromosome 17 open reading frame 81 | 116.93 | 60.21 | 0.379 | 84.10 |
| 418123 | CTSLL3 | Cathepsin L-like 3 | 196.99 | 151.69 | 0.345 | 94.78 |
| 418175 | VPS28 | Vacuolar protein sorting 28 (yeast) | 137.80 | 101.08 | 0.345 | 126.20 |
| 418233 | MRPL24 | Mitochondrial ribosomal protein L24 | 111.66 | 117.93 | 0.345 | 91.94 |
| 418450 | MRPL11 | Mitochondrial ribosomal protein L11 | 169.41 | 63.02 | 0.310 | 53.11 |
| 418533 | BUB3 | BUB3 budding uninhibited by benzimidazoles 3 homolog (yeast) | 180.32 | 113.91 | 0.172 | 73.29 |
| 418668 | ATP5D | ATP synthase, H+ transporting. mitochondrial F1 complex. delta subunit | 142.90 | 94.88 | 0.276 | 249.44 |
| 419640 | PARK7 | Parkinson disease (autosomal recessive, early onset) 7 | 255.09 | 75.95 | 0.172 | 80.33 |
| 420269 | COL6A2 | Collagen. type VI. alpha 2 | 425.15 | 132.41 | 0.379 | 327.11 |

TABLE 2-continued

A list of 2087 candidate endogenous reference genes

| | | | | | | |
|---|---|---|---|---|---|---|
| 420272 | H2AFY | H2A histone family. member Y | 236.54 | 78.85 | 0.069 | 156.87 |
| 421257 | RPL7 | Ribosomal protein L7 | 148.01 | 111.08 | 0.138 | 773.71 |
| 421509 | CCT4 | Chaperonin containing TCP1, subunit 4 (delta) | 245.54 | 69.17 | 0.138 | 100.96 |
| 422113 | ZNF511 | Zinc finger protein 511 | 92.03 | 40.84 | 0.379 | 56.61 |
| 423935 | RDBP | RD RNA binding protein | 114.07 | 56.49 | 0.241 | 90.04 |
| 423968 | FIS1 | Fission 1 (mitochondrial outer membrane) homolog (*S. cerevisiae*) | 140.14 | 94.84 | 0.379 | 184.40 |
| 424126 | SERF2 | Small EDRK-rich factor 2 | 421.90 | 169.35 | 0.103 | 442.70 |
| 424908 | LSM5 | LSM5 homolog, U6 small nuclear RNA associated (*S. cerevisiae*) | 118.18 | 94.48 | 0.310 | 84.59 |
| 425777 | UBE2L6 | Ubiquitin-conjugating enzyme E2L 6 | 176.08 | 83.76 | 0.345 | 95.06 |
| 426296 | C10orf104 | Chromosome 10 open reading frame 104 | 193.46 | 94.72 | 0.207 | 104.09 |
| 426359 | PRR13 | proline rich 13 | 204.04 | 77.90 | 0.345 | 127.55 |
| 429052 | ITGB1 | Integrin. beta 1 (fibronectin receptor. beta polypeptide. antigen CD29 includes MDF2. MSK12) | 343.25 | 71.08 | 0.207 | 216.47 |
| 429353 | SEPN1 | Selenoprotein N, 1 | 163.54 | 91.46 | 0.241 | 102.88 |
| 429581 | RTN4 | Reticulon 4 | 587.74 | 263.68 | 0.069 | 320.92 |
| 429819 | PITPNA | Phosphatidylinositol transfer protein, alpha | 132.54 | 66.33 | 0.241 | 119.10 |
| 429839 | BTF3L4 | Basic transcription factor 3-like 4 | 128.62 | 88.13 | 0.379 | 63.92 |
| 430425 | GNB1 | Guanine nucleotide binding protein (G protein). beta polypeptide 1 | 348.68 | 72.19 | 0.069 | 129.12 |
| 430551 | IQGAP1 | IQ motif containing GTPase activating protein 1 | 168.69 | 68.30 | 0.241 | 88.02 |
| 430606 | CS | Citrate synthase | 377.31 | 109.46 | 0.034 | 147.21 |
| 430657 | ARF5 | ADP-ribosylation factor 5 | 184.36 | 99.34 | 0.310 | 83.08 |
| 430733 | CLNS1A | Chloride channel. nucleotide-sensitive. 1A | 147.58 | 71.03 | 0.207 | 62.07 |
| 431101 | GNG12 | Guanine nucleotide binding protein (G protein). gamma 12 | 197.95 | 72.99 | 0.310 | 108.86 |
| 431367 | VTA1 | Vps20-associated 1 homolog (*S. cerevisiae*) | 154.26 | 81.47 | 0.172 | 43.97 |
| 431498 | FOXP1 | Forkhead box P1 | 158.95 | 84.08 | 0.345 | 98.20 |
| 431550 | MAP4K4 | Mitogen-activated protein kinase kinase kinase kinase 4 | 150.49 | 75.85 | 0.241 | 138.08 |
| 431668 | COX6B1 | Cytochrome c oxidase subunit Vib polypeptide 1 (ubiquitous) | 249.30 | 171.30 | 0.207 | 425.55 |
| 431850 | MAPK1 | Mitogen-activated protein kinase 1 | 147.43 | 68.90 | 0.241 | 66.06 |
| 431861 | PPP5C | Protein phosphatase 5, catalytic subunit | 203.35 | 97.62 | 0.138 | 99.20 |
| 431926 | NFKB1 | Nuclear factor of kappa light polypeptide gene enhancer in B-cells 1 (p105) | 118.70 | 65.79 | 0.310 | 59.70 |
| 432121 | PRDX2 | Peroxiredoxin 2 | 328.05 | 98.46 | 0.069 | 287.03 |
| 432438 | EML4 | Echinoderm microtubule associated protein like 4 | 127.17 | 67.00 | 0.345 | 67.18 |
| 432491 | ESD | Esterase D/formylglutathione hydrolase | 181.49 | 81.57 | 0.103 | 68.19 |
| 432690 | SLC39A9 | Solute carrier family 39 (zinc transporter), member 9 | 123.27 | 74.29 | 0.207 | 62.18 |
| 432760 | CAPZB | Capping protein (actin filament) muscle Z-line. beta | 189.76 | 70.34 | 0.069 | 950.43 |
| 432898 | RPL4 | Mitogen-activated protein kinase kinase kinase 13 | 2173.97 | 96.68 | 0.000 | 1111.01 |
| 432976 | NR1H2 | Nuclear receptor subfamily 1, group H. member 2 | 190.02 | 112.04 | 0.241 | 79.20 |
| 433154 | PLSCR3 | Phospholipid scramblase 3 | 118.46 | 78.13 | 0.345 | 42.73 |
| 433201 | CDK2AP1 | CDK2-associated protein 1 | 137.33 | 80.77 | 0.241 | 153.26 |
| 433222 | NPC2 | Niemann-Pick disease, type C2 | 218.82 | 98.64 | 0.069 | 149.92 |
| 433291 | ARD1A | ARD1 homolog A, N-acetyltransferase (*S. cerevisiae*) | 119.07 | 75.05 | 0.207 | 64.82 |
| 433307 | BCKDHA | Branched chain keto acid dehydrogenase E1, alpha polypeptide (maple syrup urine disease) | 166.35 | 84.74 | 0.379 | 89.54 |
| 433343 | SRRM2 | Serine/arginine repetitive matrix 2 | 179.81 | 99.94 | 0.103 | 178.03 |
| 433345 | | Full-length cDNA clone CL0BB014ZH04 of Neuroblastoma of *Homo sapiens* (human) | 131.69 | 72.43 | 0.241 | 109.07 |
| 433419 | COX4I1 | Cytochrome c oxidase subunit IV isoform 1 | 291.96 | 97.81 | 0.103 | 402.93 |
| 433512 | ACTR3 | ARP3 actin-related protein 3 homolog (yeast) | 202.84 | 72.82 | 0.103 | 95.46 |
| 433529 | RPS11 | Ribosomal protein S11 | 659.56 | 130.65 | 0.069 | 457.96 |
| 433540 | DNAJC8 | DnaJ (Hsp40) homolog, subfamily C. member 8 | 164.57 | 66.59 | 0.172 | 102.38 |
| 433573 | C11orf68 | Chromosome 11 open reading frame 68 | 109.74 | 74.58 | 0.379 | 76.09 |
| 433615 | TUBB2C | Tubulin. beta 2C | 1313.99 | 109.59 | 0.034 | 501.20 |
| 433701 | RPL37A | Ribosomal protein L37a | 941.22 | 280.38 | 0.034 | 2360.84 |
| 433722 | KIAA1967 | KIAA1967 | 137.26 | 57.51 | 0.345 | 37.39 |
| 433732 | CLK1 | CDC-like kinase 1 | 179.68 | 71.24 | 0.379 | 66.75 |
| 433750 | EIF4G1 | Eukaryotic translation initiation factor 4 gamma. 1 | 509.92 | 79.20 | 0.138 | 129.41 |
| 433759 | BANF1 | Barrier to autointegration factor 1 | 185.36 | 115.51 | 0.103 | 199.75 |
| 433795 | SHC1 | SHC (Src homology 2 domain containing) transforming protein 1 | 307.01 | 110.48 | 0.103 | 93.40 |
| 433863 | PEBP1 | Phosphatidylethanolamine binding protein 1 | 349.44 | 89.20 | 0.034 | 565.16 |
| 433901 | COX8A | Cytochrome c oxidase subunit 8A (ubiquitous) | 335.34 | 202.06 | 0.207 | 527.55 |
| 433951 | GPX4 | Glutathione peroxidase 4 (phospholipid hydroperoxidase) | 265.60 | 84.94 | 0.207 | 646.53 |
| 434102 | HMGB1 | High-mobility group box 1 | 638.86 | 104.01 | 0.000 | 439.56 |
| 434207 | HARS2 | Histidyl-tRNA synthetase 2 | 146.76 | 94.43 | 0.276 | 50.79 |
| 434219 | ANKHD1 | Ankyrin repeat and KH domain containing 1 | 190.31 | 76.42 | 0.103 | 265.78 |
| 434401 | ZNF638 | Zinc finger protein 638 | 127.61 | 80.05 | 0.276 | 97.81 |
| 434937 | PPIB | Peptidylprolyl isomerase B (cyclophilin B) | 258.12 | 78.54 | 0.069 | 426.54 |
| 434953 | HMGB2 | High-mobility group box 2 | 275.63 | 95.40 | 0.138 | 90.55 |
| 434980 | APP | Amyloid beta (A4) precursor protein (peptidase nexin-II. Alzheimers disease) | 228.56 | 92.10 | 0.172 | 645.54 |
| 435044 | TBC1D22A | TBC1 domain family, member 22A | 160.02 | 137.97 | 0.310 | 159.88 |
| 435064 | DENND1A | DENN/MADD domain containing 1A | 99.58 | 55.26 | 0.379 | 37.16 |
| 435120 | KIF1C | Kinesin family member 1C | 210.09 | 68.46 | 0.241 | 114.26 |
| 435136 | TXN | Thioredoxin | 346.61 | 189.66 | 0.276 | 221.38 |
| 435166 | LBR | Lamin B receptor | 188.22 | 185.85 | 0.310 | 68.73 |
| 435231 | ZFR | Zinc finger RNA binding protein | 158.35 | 73.83 | 0.172 | 48.65 |
| 435255 | UBXD1 | UBX domain containing 1 | 173.66 | 118.04 | 0.241 | 59.99 |
| 435326 | ACTL6A | Actin-like 6A | 152.42 | 64.63 | 0.172 | 41.79 |

TABLE 2-continued

A list of 2087 candidate endogenous reference genes

| | | | | | | |
|---|---|---|---|---|---|---|
| 435512 | PPP3CA | Protein phosphatase 3 (formerly 2B), catalytic subunit, alpha isoform (calcineurin A alpha) | 156.63 | 85.19 | 0.345 | 114.98 |
| 435535 | ZNF395 | Zinc finger protein 395 | 126.06 | 79.86 | 0.310 | 50.14 |
| 435610 | WAC | WW domain containing adaptor with coiled-coil | 197.21 | 111.45 | 0.172 | 100.47 |
| 435741 | GCSH | IQ motif and WD repeats 1 | 165.11 | 72.41 | 0.138 | 121.99 |
| 435759 | THAP4 | THAP domain containing 4 | 133.58 | 83.98 | 0.379 | 45.48 |
| 435771 | API5 | Apoptosis inhibitor 5 | 191.29 | 106.97 | 0.276 | 59.57 |
| 435841 | TNRC15 | Trinucleotide repeat containing 15 | 115.02 | 60.28 | 0.310 | 37.44 |
| 435850 | LYPLA1 | Lysophospholipase I | 278.94 | 98.93 | 0.138 | 132.98 |
| 435933 | PHF10 | Chromosome 6 open reading frame 120 | 160.27 | 71.75 | 0.276 | 72.80 |
| 435948 | ATAD1 | ATPase family, AAA domain containing 1 | 119.77 | 79.07 | 0.310 | 46.76 |
| 435952 | CDK5RAP1 | CDK5 regulatory subunit associated protein 1 | 122.11 | 83.77 | 0.310 | 40.84 |
| 435974 | MTHFD1 | Methylenetetrahydrofolate dehydrogenase (NADP+ dependent) 1, methenyltetrahydrofolate cyclohydrolase, formyltetrahydrofolate synthetase | 193.28 | 103.81 | 0.172 | 55.52 |
| 436035 | TUBA1C | Tubulin, alpha 1c | 3419.68 | 98.12 | 0.000 | 275.68 |
| 436093 | BAT2 | HLA-B associated transcript 2 | 414.35 | 96.65 | 0.172 | 98.56 |
| 436204 | ZNF289 | Zinc finger protein 289, ID1 regulated | 187.48 | 70.10 | 0.138 | 33.87 |
| 436298 | EMP1 | Epithelial membrane protein 1 | 139.81 | 90.61 | 0.310 | 164.61 |
| 436405 | IDH3B | Isocitrate dehydrogenase 3 (NAD+) beta | 233.17 | 64.64 | 0.172 | 72.68 |
| 436437 | ALDH2 | Aldehyde dehydrogenase 2 family (mitochondrial) | 213.99 | 91.66 | 0.207 | 112.73 |
| 436446 | ARMET | Arginine-rich, mutated in early stage tumors | 238.76 | 107.79 | 0.379 | 112.15 |
| 436500 | DBNL | Drebrin-like | 322.18 | 106.61 | 0.241 | 68.08 |
| 436568 | CD74 | CD74 antigen (invariant polypeptide of major histocompatibility complex, class II antigen-associated) | 3672.46 | 211.82 | 0.345 | 1315.63 |
| 436578 | POLR2F | Polymerase (RNA) II (DNA directed) polypeptide F | 106.90 | 73.50 | 0.345 | 88.14 |
| 436657 | CLU | Clusterin (complement lysis inhibitor. SP-40, 40, sulfated glycoprotein 2, testosterone-repressed prostate message 2, apolipoprotein J) | 586.91 | 158.76 | 0.241 | 1709.53 |
| 436687 | SET | SET translocation (myeloid leukemia-associated) | 285.02 | 84.84 | 0.034 | 483.49 |
| 436803 | VBP1 | Von Hippel-Lindau binding protein 1 | 182.84 | 93.52 | 0.207 | 77.53 |
| 437056 | SUPT5H | Suppressor of Ty 5 homolog (S. cerevisiae) | 216.64 | 117.71 | 0.207 | 47.97 |
| 437060 | CYCS | Cytochrome c, somatic | 1874.90 | 252.41 | 0.207 | 102.41 |
| 437110 | ANXA2 | Annexin A2 | 2060.10 | 130.61 | 0.034 | 483.00 |
| 437178 | ACADVL | Acyl-Coenzyme A dehydrogenase, very long chain | 288.37 | 92.69 | 0.069 | 176.48 |
| 437256 | GRINL1A | Glutamate receptor, ionotropic, N-methyl D-aspartate-like 1A | 151.07 | 83.14 | 0.345 | 42.69 |
| 437277 | MGAT4B | Mannosyl (alpha-1,3-)-glycoprotein beta-1,4-N-acetylglucosaminyltransferase, isoenzyme B | 1083.50 | 147.46 | 0.103 | 98.94 |
| 437367 | GBAS | Glioblastoma amplified sequence | 143.22 | 113.71 | 0.276 | 128.35 |
| 437388 | PIGT | Phosphatidylinositol glycan, class T | 227.91 | 106.45 | 0.103 | 55.36 |
| 437403 | PPA1 | Pyrophosphatase (inorganic) 1 | 159.06 | 72.02 | 0.138 | 83.72 |
| 437594 | RPLP2 | Ribosomal protein, large, P2 | 498.18 | 148.73 | 0.034 | 2903.18 |
| 437638 | XBP1 | X-box binding protein 1 | 319.21 | 100.78 | 0.069 | 381.08 |
| 437779 | C11orf10 | Chromosome 11 open reading frame 10 | 241.39 | 149.44 | 0.345 | 178.08 |
| 437831 | C14orf32 | Chromosome 14 open reading frame 32 | 175.37 | 74.13 | 0.241 | 47.62 |
| 438072 | UNC84A | Unc-84 homolog A (C. elegans) | 146.52 | 82.20 | 0.345 | 53.45 |
| 438219 | GPS2 | G protein pathway suppressor 2 | 172.78 | 109.64 | 0.172 | 71.49 |
| 438429 | RPS19 | Ribosomal protein S19 | 721.53 | 169.75 | 0.103 | 3026.84 |
| 438678 | TALDO1 | Transaldolase 1 | 280.29 | 75.06 | 0.138 | 109.07 |
| 438720 | MCM7 | MCM7 minichromosome maintenance deficient 7 (S. cerevisiae) | 548.49 | 107.89 | 0.138 | 192.09 |
| 438970 | TBL1XR1 | Transducin (beta)-like 1X-linked receptor 1 | 185.70 | 86.87 | 0.241 | 73.49 |
| 438974 | CUTL1 | Cut-like 1. CCAAT displacement protein (Drosophila) | 159.65 | 95.91 | 0.310 | 59.88 |
| 439480 | RBM5 | RNA binding motif protein 5 | 145.24 | 117.34 | 0.379 | 56.89 |
| 439481 | SUPT4H1 | Suppressor of Ty 4 homolog 1 (S. cerevisiae) | 139.55 | 62.12 | 0.207 | 121.04 |
| 439548 | FAM96A | Family with sequence similarity 96. member A | 155.35 | 85.81 | 0.241 | 32.78 |
| 439552 | MAP2K3 | Mitogen-activated protein kinase kinase 3 | 2617.77 | 147.47 | 0.000 | 97.32 |
| 439815 | HBXIP | Hepatitis B virus x interacting protein | 127.08 | 97.39 | 0.310 | 188.94 |
| 440382 | TRIM27 | Tripartite motif-containing 27 | 155.33 | 68.54 | 0.172 | 80.66 |
| 440544 | CLIC4 | Chloride intracellular channel 4 | 337.71 | 121.54 | 0.103 | 116.71 |
| 440599 | DDX1 | DEAD (Asp-Glu-Ala-Asp) box polypeptide 1 | 433.83 | 283.30 | 0.103 | 194.20 |
| 440604 | PSMD7 | Proteasome (prosome. macropain) 26S subunit, non-ATPase, 7 (Mov34 homolog) | 156.07 | 77.17 | 0.138 | 99.15 |
| 440899 | TTYH3 | Tweety homolog 3 (Drosophila) | 229.54 | 97.64 | 0.172 | 81.97 |
| 440932 | SEPT9 | Septin 9 | 361.78 | 96.86 | 0.034 | 158.17 |
| 440960 | RAD23A | RAD23 homolog A (S. cerevisiae) | 214.38 | 69.61 | 0.207 | 56.98 |
| 440961 | CAST | Calpastatin | 194.31 | 90.01 | 0.207 | 86.43 |
| 441072 | POLR2L | Polymerase (RNA) II (DNA directed) polypeptide L, 7.6 kDa | 225.44 | 138.68 | 0.379 | 278.78 |
| 441550 | ABHD12 | Abhydrolase domain containing 12 | 215.47 | 106.70 | 0.241 | 69.22 |
| 442344 | IRS2 | Insulin receptor substrate 2 | 134.97 | 79.52 | 0.379 | 117.65 |
| 442798 | RNF10 | Ring finger protein 10 | 210.73 | 75.43 | 0.103 | 80.34 |
| 443134 | GBA2 | Glucosidase. beta (bile acid) 2 | 132.85 | 60.27 | 0.379 | 64.55 |
| 443379 | PSMD11 | Proteasome (prosome, macropain) 26S subunit. non-ATPase. 11 | 180.98 | 64.45 | 0.172 | 49.98 |
| 443837 | NPEPPS | Aminopeptidase puromycin sensitive | 173.54 | 73.65 | 0.172 | 51.38 |
| 443914 | SOD1 | Superoxide dismutase 1. soluble (amyotrophic lateral sclerosis 1 (adult)) | 341.06 | 88.95 | 0.103 | 267.67 |
| 444279 | GPBP1 | GC-rich promoter binding protein 1 | 132.98 | 56.92 | 0.241 | 63.11 |
| 444356 | GRB2 | Growth factor receptor-bound protein 2 | 167.92 | 61.94 | 0.172 | 146.51 |

TABLE 2-continued

A list of 2087 candidate endogenous reference genes

| 444468 | CTDSP1 | CTD (carboxy-terminal domain, RNA polymerase II, polypeptide A small phosphatase 1 | 187.59 | 76.37 | 0.241 | 92.85 |
| --- | --- | --- | --- | --- | --- | --- |
| 444472 | SDHC | Succinate dehydrogenase complex. subunit C. integral membrane protein, 15 kDa | 175.42 | 71.22 | 0.207 | 45.51 |
| 444569 | TMEM49 | Transmembrane protein 49 | 212.58 | 83.31 | 0.241 | 197.09 |
| 444673 | CLPTM1L | CLPTM1-like | 229.08 | 106.76 | 0.207 | 91.56 |
| 444724 | AZI2 | 5-azacytidine induced 2 | 132.28 | 73.71 | 0.345 | 44.74 |
| 444818 | CGGBP1 | CGG triplet repeat binding protein 1 | 177.53 | 83.72 | 0.241 | 66.90 |
| 444931 | CRSP6 | Cofactor required for Sp1 transcriptional activation, subunit 6, 77 kDa | 88.71 | 48.78 | 0.379 | 43.14 |
| 444969 | MEMO1 | Mediator of cell motility 1 | 96.52 | 59.19 | 0.276 | 59.89 |
| 444986 | METAP2 | Methionyl aminopeptidase 2 | 169.09 | 73.08 | 0.172 | 54.25 |
| 445081 | OAF | OAF homolog (*Drosophila*) | 113.21 | 58.71 | 0.345 | 57.76 |
| 445351 | LGALS1 | Lectin. galactoside-binding. soluble, 1 (galectin 1) | 564.16 | 197.93 | 0.241 | 1304.52 |
| 445394 | VPS29 | Vacuolar protein sorting 29 (yeast) | 276.97 | 108.32 | 0.138 | 82.01 |
| 445498 | SNW1 | SNW domain containing 1 | 143.71 | 69.55 | 0.138 | 43.68 |
| 445511 | RIOK3 | RIO kinase 3 (yeast) | 110.92 | 105.70 | 0.379 | 54.46 |
| 445570 | CD63 | CD63 antigen (melanoma 1 antigen) | 489.45 | 199.49 | 0.034 | 182.09 |
| 445803 | DC2 | DC2 protein | 658.16 | 215.09 | 0.138 | 77.15 |
| 445893 | KHDRBS1 | KH domain containing, RNA binding. signal transduction associated 1 | 227.64 | 88.75 | 0.138 | 189.36 |
| 445977 | GTF3A | General transcription factor IIIA | 160.66 | 73.81 | 0.172 | 82.05 |
| 446017 | WSB1 | WD repeat and SOCS box-containing 1 | 239.91 | 93.71 | 0.276 | 231.33 |
| 446091 | WTAP | Wilms tumor 1 associated protein | 119.70 | 95.46 | 0.379 | 83.46 |
| 446123 | CAPZA2 | Capping protein (actin filament) muscle Z-line, alpha 2 | 370.83 | 95.48 | 0.138 | 88.07 |
| 446149 | LDHB | Lactate dehydrogenase B | 1544.78 | 120.53 | 0.000 | 250.91 |
| 446260 | PSMA6 | Proteasome (prosome, macropain) subunit, alpha type. 6 | 224.07 | 106.72 | 0.172 | 227.02 |
| 446336 | PXN | Paxillin | 259.56 | 97.96 | 0.138 | 155.02 |
| 446345 | FTH1 | Ferritin, heavy polypeptide 1 | 2359.77 | 133.58 | 0.034 | 3636.50 |
| 446414 | CD47 | CD47 antigen (Rh-related antigen. integrin-associated signal transducer) | 165.59 | 95.67 | 0.310 | 83.15 |
| 446427 | OAZ1 | Ornithine decarboxylase antizyme 1 | 673.68 | 62.71 | 0.069 | 576.39 |
| 446445 | YIF1A | Yip1 interacting factor homolog A (*S. cerevisiae*) | 151.87 | 80.99 | 0.276 | 76.17 |
| 446450 | ITM2B | Integral membrane protein 2B | 511.62 | 115.21 | 0.138 | 528.00 |
| 446574 | TMSB10 | Thymosin. beta 10 | 524.43 | 177.08 | 0.103 | 1381.46 |
| 446588 | RPS13 | Ribosomal protein S13 | 183.34 | 95.13 | 0.345 | 603.82 |
| 446623 | HNRPL | Heterogeneous nuclear ribonucleoprotein L | 113.61 | 53.54 | 0.276 | 351.95 |
| 446628 | RPS4X | Ribosomal protein S4, X-linked | 1285.06 | 89.84 | 0.000 | 2026.83 |
| 446641 | ARAF | V-raf murine sarcoma 3611 viral oncogene homolog | 176.49 | 69.57 | 0.241 | 54.08 |
| 446852 | EIF3S6IP | Eukaryotic translation initiation factor 3. subunit 6 interacting protein | 925.97 | 188.87 | 0.034 | 160.77 |
| 447477 | ST13 | Suppression of tumorigenicity 13 (colon carcinoma) (Hsp70 interacting protein) | 272.29 | 141.17 | 0.103 | 139.88 |
| 447492 | PGAM1 | Phosphoglycerate mutase 1 (brain) | 781.46 | 84.70 | 0.034 | 498.68 |
| 447547 | VPS35 | Hypothetical protein MGC34800 | 195.14 | 67.15 | 0.103 | 121.44 |
| 448226 | RPLP0 | Ribosomal protein, large, P0 | 3809.20 | 75.92 | 0.000 | 1108.65 |
| 448588 | NGFRAP1 | Nerve growth factor receptor (TNFRSF16) associated protein 1 | 218.09 | 83.14 | 0.310 | 364.70 |
| 448646 | RPL27A | Ribosomal protein L27a | 766.60 | 139.37 | 0.276 | 3106.03 |
| 448879 | LOC38834 | similar to ribosomal protein L13 | 471.24 | 99.11 | 0.069 | 126.52 |
| 449114 | HNRPC | Heterogeneous nuclear ribonucleoprotein C (C1/C2) | 803.24 | 90.38 | 0.034 | 241.77 |
| 449171 | HNRPK | Heterogeneous nuclear ribonucleoprotein K | 403.79 | 69.90 | 0.034 | 266.35 |
| 454534 | USF2 | Upstream transcription factor 2, c-fos interacting | 111.98 | 76.53 | 0.310 | 62.62 |
| 454699 | IL6ST | Interleukin 6 signal transducer (gp130. oncostatin M receptor) | 266.74 | 139.73 | 0.103 | 48.68 |
| 456507 | KIAA0319L | KIAA0319-like | 131.45 | 85.77 | 0.241 | 73.31 |
| 456557 | C1orf164 | chromosome 1 open reading frame 164 | 143.89 | 71.60 | 0.276 | 116.20 |
| 458320 | C3orf37 | chromosome 3 open reading frame 37 | 170.49 | 148.07 | 0.310 | 35.84 |
| 458358 | TSPYL1 | Squamous cell carcinoma antigen recognized by T cells 2 | 101.91 | 73.81 | 0.345 | 127.17 |
| 458414 | IFITM1 | Interferon induced transmembrane protein 1 (9-27) | 278.31 | 223.88 | 0.345 | 119.42 |
| 458458 | FAM108A1 | Family with sequence similarity 108. member A1 | 149.77 | 96.59 | 0.276 | 93.53 |
| 458747 | ANP32A | Acidic (leucine-rich) nuclear phosphoprotein 32 family, member A | 197.57 | 100.71 | 0.172 | 46.30 |
| 459106 | AZIN1 | Antizyme inhibitor 1 | 209.63 | 95.22 | 0.207 | 49.61 |
| 459149 | BTBD1 | BTB (POZ) domain containing 1 | 136.20 | 84.67 | 0.310 | 54.21 |
| 459174 | FAM91A1 | Family with sequence similarity 91, member A1 | 133.90 | 80.72 | 0.379 | 82.35 |
| 459211 | AKAP13 | A kinase (PRKA) anchor protein 13 | 217.52 | 97.30 | 0.310 | 70.77 |
| 459596 | MPG | N-methylpurine-DNA glycosylase | 110.09 | 94.77 | 0.241 | 78.83 |
| 459649 | CLCN7 | Chloride channel 7 | 161.09 | 107.31 | 0.207 | 57.89 |
| 459927 | PTMA | Prothymosin. alpha (gene sequence 28) | 1066.55 | 86.69 | 0.000 | 1205.32 |
| 459940 | LITAF | Lipopolysaccharide-induced TNF factor | 184.70 | 98.75 | 0.069 | 118.47 |
| 460238 | SH3GLB2 | SH3-domain GRB2-like endophilin B2 | 146.60 | 86.41 | 0.207 | 54.58 |
| 460317 | SETX | Senataxin | 132.56 | 111.94 | 0.310 | 59.22 |
| 460336 | GGA2 | Golgi associated. gamma adaptin ear containing. ARF binding protein 2 | 253.27 | 171.03 | 0.241 | 51.31 |
| 460468 | XPO6 | Exportin 6 | 212.84 | 80.39 | 0.172 | 58.36 |
| 460499 | ATXN2L | Ataxin 2-like | 228.25 | 84.67 | 0.310 | 66.95 |
| 460574 | LOC12444 | Hypothetical protein BC017488 | 125.84 | 87.37 | 0.379 | 74.28 |
| 460923 | CNOT1 | CCR4-NOT transcription complex. subunit 1 | 173.85 | 65.75 | 0.207 | 67.45 |
| 460929 | GOT2 | Glutamic-oxaloacetic transaminase 2, mitochondrial (aspartate aminotransferase 2) | 397.62 | 79.42 | 0.103 | 126.69 |

TABLE 2-continued

A list of 2087 candidate endogenous reference genes

| 460978 | APPBP1 | Amyloid beta precursor protein binding protein 1 | 133.67 | 64.71 | 0.241 | 46.47 |
|---|---|---|---|---|---|---|
| 461047 | G6PD | Glucose-6-phosphate dehydrogenase | 274.16 | 130.32 | 0.207 | 81.94 |
| 461131 | CYB5B | Cytochrome b5 type B (outer mitochondrial membrane) | 192.30 | 75.56 | 0.138 | 76.12 |
| 461361 | CFDP1 | Craniofacial development protein 1 | 111.79 | 67.73 | 0.310 | 79.79 |
| 461379 | GABARAPL2 | GABA(A) receptor-associated protein-like 2 | 122.55 | 63.48 | 0.345 | 184.34 |
| 461722 | TRAPPC2L | Trafficking protein particle complex 2-like | 97.91 | 62.09 | 0.379 | 78.84 |
| 461777 | CHMP1A | Chromatin modifying protein 1A | 171.31 | 77.92 | 0.207 | 77.23 |
| 461896 | CRK | V-crk sarcoma virus CT10 oncogene homolog (avian) | 158.10 | 68.61 | 0.276 | 68.65 |
| 461925 | RPA1 | Replication protein A1. 70 kDa | 160.13 | 72.42 | 0.103 | 83.76 |
| 462035 | UBE2G1 | Ubiquitin-conjugating enzyme E2G 1 (UBC7 homolog, yeast) | 149.46 | 102.82 | 0.207 | 72.02 |
| 462086 | RPAIN | RPA interacting protein | 129.54 | 77.35 | 0.379 | 70.39 |
| 462306 | UBE2S | Ubiquitin-conjugating enzyme E2S | 216.54 | 74.27 | 0.310 | 226.76 |
| 462316 | TTC19 | Hypothetical protein LOC125150 | 116.49 | 89.17 | 0.241 | 83.84 |
| 462492 | USP22 | Ubiquitin specific peptidase 22 | 379.95 | 165.78 | 0.138 | 95.69 |
| 462550 | PIGS | Phosphatidylinositol glycan. class S | 164.57 | 97.00 | 0.345 | 61.36 |
| 462956 | PPARBP | PPAR binding protein | 106.51 | 76.59 | 0.379 | 65.65 |
| 462998 | IGFBP4 | Insulin-like growth factor binding protein 4 | 345.88 | 87.71 | 0.207 | 238.31 |
| 463010 | SMARCE1 | SWI/SNF related, matrix associated, actin dependent regulator of chromatin. subfamily e. member 1 | 173.85 | 56.13 | 0.069 | 51.34 |
| 463035 | FKBP10 | FK506 binding protein 10. 65 kDa | 164.51 | 91.24 | 0.310 | 88.10 |
| 463041 | RERE | Arginine-glutamic acid dipeptide (RE) repeats | 200.18 | 92.99 | 0.276 | 112.05 |
| 463059 | STAT3 | Signal transducer and activator of transcription 3 (acute-phase response factor) | 205.74 | 114.93 | 0.207 | 286.52 |
| 463295 | CDC27 | Cell division cycle 27 | 115.34 | 79.50 | 0.310 | 47.81 |
| 463506 | AKAP1 | A kinase (PRKA) anchor protein 1 | 124.11 | 52.64 | 0.345 | 401.26 |
| 463702 | BCAS3 | Breast carcinoma amplified sequence 3 | 98.88 | 74.57 | 0.379 | 44.08 |
| 463797 | MRTO4 | mRNA turnover 4 homolog (*S. cerevisiae*) | 142.20 | 59.85 | 0.276 | 48.55 |
| 464071 | PGD | Phosphogluconate dehydrogenase | 338.78 | 85.70 | 0.138 | 159.65 |
| 464137 | ACOX1 | Acyl-Coenzyme A oxidase 1, palmitoyl | 103.04 | 66.74 | 0.241 | 64.57 |
| 464210 | SYNGR2 | Synaptogyrin 2 | 348.69 | 97.83 | 0.276 | 159.36 |
| 464336 | P4HB | Procollagen-proline, 2-oxoglutarate 4-dioxygenase (proline 4-hydroxylase). beta polypeptide (protein disulfide isomerase-associated 1) | 859.74 | 89.54 | 0.069 | 354.48 |
| 464438 | AGTRAP | Angiotensin II receptor-associated protein | 117.55 | 68.62 | 0.379 | 100.58 |
| 464472 | MRLC2 | Myosin regulatory light chain MRLC2 | 233.35 | 102.50 | 0.034 | 303.55 |
| 464595 | PPP4R1 | Protein phosphatase 4. regulatory subunit 1 | 181.18 | 80.16 | 0.241 | 61.71 |
| 464652 | TNFSF5IP1 | Tumor necrosis factor superfamily, member 5-induced protein 1 | 145.59 | 119.46 | 0.345 | 59.73 |
| 464912 | P15RS | Hypothetical protein FLJ10656 | 142.03 | 83.19 | 0.276 | 65.87 |
| 465224 | NARS | Asparaginyl-tRNA synthetase | 220.96 | 70.84 | 0.103 | 91.32 |
| 465374 | EFHD2 | EF-hand domain family. member D2 | 265.91 | 113.85 | 0.241 | 121.77 |
| 465498 | TXNL4A | Thioredoxin-like 4A | 121.61 | 80.29 | 0.276 | 118.06 |
| 465529 | MIDN | Midnolin | 139.65 | 96.07 | 0.345 | 77.19 |
| 465543 | BTBD2 | BTB (POZ) domain containing 2 | 204.49 | 98.92 | 0.207 | 90.71 |
| 465627 | MAP2K2 | Mitogen-activated protein kinase kinase 2 | 154.59 | 85.81 | 0.310 | 176.08 |
| 465645 | C19orf10 | Chromosome 19 open reading frame 10 | 204.93 | 79.48 | 0.276 | 122.81 |
| 465808 | HNRPM | Heterogeneous nuclear ribonucleoprotein M | 258.95 | 99.76 | 0.103 | 126.89 |
| 465849 | PIN1 | Protein (peptidyl-prolyl cis/trans isomerase) NIMA-interacting 1 | 121.36 | 61.35 | 0.310 | 157.79 |
| 465924 | SDHB | Succinate dehydrogenase complex. subunit B. iron sulfur (Ip) | 161.79 | 65.94 | 0.241 | 76.80 |
| 466044 | PKN1 | Protein kinase N1 | 252.31 | 87.50 | 0.276 | 62.96 |
| 466088 | TPM4 | Tropomyosin 4 | 139.00 | 71.29 | 0.345 | 150.55 |
| 466148 | NR2F6 | Nuclear receptor subfamily 2, group F, member 6 | 179.12 | 94.04 | 0.379 | 157.14 |
| 466471 | GPI | Glucose phosphate isomerase | 502.15 | 94.80 | 0.069 | 172.27 |
| 466693 | SIRT2 | Sirtuin (silent mating type information regulation 2 homolog) 2 (*S. cerevisiae*) | 214.11 | 113.63 | 0.379 | 122.41 |
| 466766 | LTBP4 | Latent transforming growth factor beta binding protein 4 | 174.46 | 77.33 | 0.379 | 68.26 |
| 466775 | SNRPA | Small nuclear ribonucleoprotein polypeptide A | 196.94 | 63.74 | 0.138 | 58.13 |
| 467084 | EIF4G3 | Eukaryotic translation initiation factor 4 gamma. 3 | 102.77 | 64.71 | 0.310 | 58.39 |
| 467097 | SNRP70 | Small nuclear ribonucleoprotein 70 kDa polypeptide (RNP antigen) | 294.48 | 80.04 | 0.103 | 100.15 |
| 467192 | PPP2R1A | Protein phosphatase 2 (formerly 2A), regulatory subunit A (PR 65) alpha isoform | 475.55 | 80.67 | 0.069 | 102.67 |
| 467279 | LENG4 | Leukocyte receptor cluster (LRC) member 4 | 315.24 | 116.72 | 0.310 | 169.43 |
| 467284 | RPS9 | Ribosomal protein S9 | 986.04 | 73.58 | 0.069 | 638.08 |
| 467408 | TRIM28 | Tripartite motif-containing 28 | 715.33 | 79.78 | 0.138 | 235.85 |
| 467637 | CDC42 | Cell division cycle 42 (GTP binding protein. 25 kDa) | 158.07 | 97.05 | 0.138 | 282.31 |
| 467696 | HPCAL1 | Hippocalcin-like 1 | 172.64 | 83.71 | 0.379 | 94.69 |
| 467701 | ODC1 | Ornithine decarboxylase 1 | 351.16 | 77.30 | 0.103 | 112.30 |
| 467807 | LAPTM4A | Lysosomal-associated protein transmembrane 4 alpha | 482.50 | 88.89 | 0.069 | 380.71 |
| 467824 | PUM2 | Pumilio homolog 2 (*Drosophila*) | 153.26 | 86.50 | 0.207 | 60.01 |
| 467960 | RAB10 | RAB10. member RAS oncogene family | 162.79 | 57.31 | 0.103 | 100.37 |
| 468018 | PPP1CB | Protein phosphatase 1, catalytic subunit. beta isoform | 203.84 | 64.65 | 0.207 | 243.47 |
| 468415 | PIGF | Phosphatidylinositol glycan, class F | 150.01 | 71.46 | 0.241 | 85.62 |
| 468442 | CALM2 | Calmodulin 2 (phosphorylase kinase. delta) | 1841.31 | 235.41 | 0.000 | 448.88 |
| 468760 | AFTPH | Aftiphilin | 93.25 | 61.52 | 0.310 | 56.19 |
| 469022 | DGUOK | Deoxyguanosine kinase | 116.26 | 75.71 | 0.241 | 55.33 |
| 469171 | C1orf160 | Chromosome 1 open reading frame 160 | 116.05 | 66.17 | 0.172 | 59.47 |
| 469331 | STARD7 | START domain containing 7 | 312.84 | 91.19 | 0.138 | 3007.75 |
| 469820 | RALB | V-ral simian leukemia viral oncogene homolog B (ras related: GTF binding protein) | 125.95 | 59.65 | 0.379 | 51.68 |

TABLE 2-continued

A list of 2087 candidate endogenous reference genes

| | | | | | | |
|---|---|---|---|---|---|---|
| 469863 | YWHAZ | Tyrosine 3-monooxygenase/tryptophan 5-monooxygenase activation protein. zeta polypeptide | 385.89 | 74.53 | 0.034 | 262.56 |
| 469925 | FAM128B | Family with sequence similarity 128, member B | 157.81 | 62.74 | 0.345 | 481.47 |
| 469970 | SFRS4 | Splicing factor, arginine/serine-rich 4 | 134.13 | 54.16 | 0.310 | 62.81 |
| 470091 | YWHAE | Tyrosine 3-monooxygenase/tryptophan 5-monooxygenase activation protein. epsilon polypeptide | 330.87 | 97.70 | 0.069 | 590.76 |
| 470233 | ARL5A | ADP-ribosylation factor-like 5A | 137.43 | 81.25 | 0.345 | 39.57 |
| 470417 | PEF1 | Penta-EF-hand domain containing 1 | 144.07 | 63.57 | 0.241 | 62.85 |
| 470477 | PTP4A2 | Protein tyrosine phosphatase type IVA. member 2 | 163.45 | 69.99 | 0.103 | 138.21 |
| 470577 | EIF2S2 | Eukaryotic translation initiation factor 2. subunit 2 beta. 38 kDa | 175.54 | 98.23 | 0.379 | 164.48 |
| 470588 | KPNA6 | Karyopherin alpha 6 (importin alpha 7) | 105.07 | 66.63 | 0.207 | 91.23 |
| 470943 | STAT1 | Signal transducer and activator of transcription 1. 91 kDa | 204.00 | 91.39 | 0.207 | 99.04 |
| 471011 | SF3B1 | Splicing factor 3b, subunit 1, 155 kDa | 171.22 | 65.74 | 0.276 | 54.27 |
| 471104 | NOP5/NOP58 | Nucleolar protein NOP5/NOP58 | 119.95 | 77.84 | 0.207 | 107.80 |
| 471207 | NDUFS1 | NADH dehydrogenase (ubiquinone) Fe—S protein 1, 75 kDa (NADH-coenzyme Q reductase) | 152.75 | 64.26 | 0.207 | 53.27 |
| 471441 | PSMB2 | Proteasome (prosome. macropain) subunit, beta type, 2 | 160.02 | 84.75 | 0.207 | 132.08 |
| 471461 | ACSL3 | Acyl-CoA synthetase long-chain family member 3 | 143.25 | 48.15 | 0.207 | 55.56 |
| 471593 | CAB39 | Calcium binding protein 39 | 125.47 | 90.94 | 0.276 | 71.62 |
| 471768 | STK40 | Serine/threonine kinase 40 | 150.57 | 81.43 | 0.310 | 76.01 |
| 471818 | CAPRIN1 | Cell cycle associated protein 1 | 233.39 | 93.24 | 0.069 | 48.75 |
| 471851 | HDLBP | High density lipoprotein binding protein (vigilin) | 770.41 | 90.63 | 0.034 | 284.45 |
| 471873 | DTYMK | Deoxythymidylate kinase (thymidylate kinase) | 151.55 | 81.98 | 0.276 | 61.06 |
| 471933 | FKBP1A | FK506 binding protein 1A. 12 kDa | 264.05 | 83.21 | 0.138 | 166.80 |
| 471975 | C20orf116 | Chromosome 20 open reading frame 116 | 168.09 | 95.60 | 0.379 | 46.80 |
| 472010 | PRNP | Prion protein (p27-30) (Creutzfeld-Jakob disease, Gerstmann-Strausler-Scheinker syndrome, fatal familial insomnia) | 151.22 | 82.78 | 0.276 | 217.32 |
| 472024 | C20orf30 | Chromosome 20 open reading frame 30 | 180.50 | 82.62 | 0.138 | 87.82 |
| 472031 | UBE2D3 | Ubiquitin-conjugating enzyme E2D 3 (UBC4/5 homolog, yeast) | 305.38 | 72.17 | 0.069 | 161.41 |
| 472038 | UTP11L | UTP11-like, U3 small nucleolar ribonucleoprotein, (yeast) | 116.49 | 107.41 | 0.379 | 46.16 |
| 472056 | SYNCRIP | Synaptotagmin binding, cytoplasmic RNA interacting protein | 198.01 | 71.24 | 0.103 | 97.30 |
| 472119 | MKKS | McKusick-Kaufman syndrome | 110.70 | 82.99 | 0.276 | 43.01 |
| 472185 | NDUFS5 | NADH dehydrogenase (ubiquinone) Fe—S protein 5, 15 kDa (NADH-coenzyme Q reductase) | 317.85 | 115.06 | 0.172 | 175.84 |
| 472213 | RRBP1 | Ribosome binding protein 1 homolog 180 kDa (dog) | 194.55 | 81.99 | 0.276 | 81.63 |
| 472330 | C20orf3 | Chromosome 20 open reading frame 3 | 210.62 | 71.28 | 0.345 | 111.23 |
| 472475 | MACF1 | Glycine-rich protein (GRP3S) | 170.84 | 81.77 | 0.310 | 117.24 |
| 472535 | AURKAIP1 | Aurora kinase A interacting protein 1 | 236.28 | 92.32 | 0.345 | 87.41 |
| 472558 | ERGIC3 | ERGIC and golgi 3 | 273.22 | 82.09 | 0.138 | 150.94 |
| 472651 | BLCAP | Bladder cancer associated protein | 174.08 | 74.85 | 0.241 | 69.65 |
| 472737 | TOP1 | Topoisomerase (DNA) I | 145.07 | 71.88 | 0.310 | 79.62 |
| 473296 | TPD52L2 | Tumor protein D52-like 2 | 198.42 | 74.39 | 0.172 | 87.51 |
| 473583 | YBX1 | Y box binding protein 1 | 706.53 | 98.38 | 0.034 | 340.36 |
| 473648 | GART | Phosphoribosylglycinamide formyltransferase, phosphoribosylglycinamide synthetase, phosphoribosylaminoimidazole synthetase | 159.98 | 70.49 | 0.138 | 51.98 |
| 473721 | SLC2A1 | Solute carrier family 2 (facilitated glucose transporter), member 1 | 496.75 | 142.19 | 0.345 | 157.66 |
| 473761 | RTN3 | Reticulon 3 | 222.45 | 76.58 | 0.103 | 160.89 |
| 473788 | OTUB1 | OTU domain, ubiquitin aldehyde binding 1 | 235.08 | 75.48 | 0.207 | 93.09 |
| 474005 | SUMO3 | SMT3 suppressor of mif two 3 homolog 3 (yeast) | 224.13 | 104.97 | 0.138 | 71.57 |
| 474010 | PTTG1IP | Pituitary tumor-transforming 1 interacting protein | 472.39 | 85.43 | 0.138 | 111.37 |
| 474053 | COL6A1 | Collagen, type VI, alpha 1 | 240.21 | 60.68 | 0.345 | 421.26 |
| 474083 | B4GALT2 | UDP-Gal: betaGlcNAc beta 1,4-galactosyltransferase, polypeptide 2 | 118.57 | 65.47 | 0.345 | 74.49 |
| 474213 | UFD1L | Ubiquitin fusion degradation 1 like (yeast) | 117.12 | 72.56 | 0.276 | 42.38 |
| 474584 | AKR1A1 | Aldo-keto reductase family 1. member A1 (aldehyde reductase) | 216.03 | 70.29 | 0.138 | 94.42 |
| 474643 | C22orf28 | Chromosome 22 open reading frame 28 | 331.66 | 109.80 | 0.138 | 100.93 |
| 474751 | MYH9 | Myosin. heavy polypeptide 9, non-muscle | 426.57 | 109.52 | 0.069 | 127.27 |
| 474833 | CSNK1E | Casein kinase 1, epsilon | 193.49 | 86.78 | 0.138 | 68.93 |
| 474914 | RUTBC3 | RUN and TBC1 domain containing 3 | 190.23 | 157.68 | 0.345 | 74.06 |
| 474938 | SLC25A17 | Solute carrier family 25 (mitochondrial carrier; peroxisomal membrane protein, 34 kDa). member 17 | 113.70 | 81.93 | 0.345 | 33.74 |
| 474949 | RBX1 | Ring-box 1 | 145.55 | 82.29 | 0.241 | 69.67 |
| 474982 | ACO2 | Aconitase 2, mitochondrial | 307.04 | 91.01 | 0.034 | 105.23 |
| 475125 | ATXN10 | Ataxin 10 | 198.54 | 95.44 | 0.172 | 118.31 |
| 475319 | LRRFIP2 | Leucine rich repeat (in FLII) interacting protein 2 | 104.35 | 72.12 | 0.310 | 69.04 |
| 475382 | MTMR14 | Myotubularin related protein 14 | 149.47 | 83.39 | 0.172 | 114.62 |
| 475392 | TMEM111 | Transmembrane protein 111 | 136.12 | 88.37 | 0.379 | 46.89 |
| 475663 | RAB5A | RAB5A, member RAS oncogene family | 119.70 | 91.27 | 0.241 | 74.69 |
| 475733 | TOP2B | Topoisomerase (DNA) II beta 180 kDa | 180.06 | 113.03 | 0.172 | 121.72 |
| 475812 | STT3B | STT3, subunit of the oligosaccharyltransferase complex. homolog B (*S. cerevisiae*) | 108.24 | 76.02 | 0.310 | 55.56 |
| 476018 | CTNNB1 | Catenin (cadherin-associated protein), beta 1, 88 kDa | 138.21 | 58.20 | 0.310 | 215.94 |
| 476033 | TXNDC12 | Thioredoxin domain containing 12 (endoplasmic reticulum) | 146.57 | 70.89 | 0.172 | 52.90 |
| 476179 | SMARCC1 | SWI/SNF related, matrix associated, actin dependent regulator of chromatin, subfamily c, member 1 | 171.16 | 127.75 | 0.138 | 91.06 |
| 476221 | IHPK2 | Inositol hexaphosphate kinase 2 | 145.26 | 55.31 | 0.241 | 77.62 |
| 476231 | IMPDH2 | IMP (inosine monophosphate) dehydrogenase 2 | 1006.91 | 110.38 | 0.034 | 120.62 |

TABLE 2-continued

A list of 2087 candidate endogenous reference genes

| | | | | | | |
|---|---|---|---|---|---|---|
| 476308 | ALAS1 | Aminolevulinate, delta-, synthase 1 | 132.82 | 82.50 | 0.345 | 50.43 |
| 476365 | SCP2 | Sterol carrier protein 2 | 690.56 | 180.11 | 0.276 | 125.14 |
| 476448 | FLNB | Filamin B, beta (actin binding protein 278) | 189.01 | 103.49 | 0.310 | 56.29 |
| 476706 | MRPL37 | Mitochondrial ribosomal protein L37 | 249.66 | 66.27 | 0.172 | 97.03 |
| 476930 | CHMP2B | Chromatin modifying protein 2B | 143.22 | 100.41 | 0.310 | 73.54 |
| 477157 | DULLARD | Dullard homolog (*Xenopus laevis*) | 158.37 | 96.36 | 0.103 | 97.30 |
| 477789 | ATP1B3 | ATPase. Na+/K+ transporting. beta 3 polypeptide | 167.45 | 84.60 | 0.138 | 135.93 |
| 477892 | GYG1 | Glycogenin 1 | 151.92 | 63.62 | 0.345 | 54.22 |
| 478000 | MBNL1 | Muscleblind-like (*Drosophila*) | 304.13 | 90.08 | 0.241 | 61.18 |
| 478044 | PA2G4 | Proliferation-associated 2G4, 38 kDa | 460.10 | 87.56 | 0.103 | 157.68 |
| 478553 | EIF4A2 | Eukaryotic translation initiation factor 4A, isoform 2 | 403.21 | 91.85 | 0.069 | 357.47 |
| 479208 | FBXL5 | F-box and leucine-rich repeat protein 5 | 140.68 | 84.67 | 0.276 | 55.97 |
| 479264 | LAP3 | Leucine aminopeptidase 3 | 140.16 | 84.68 | 0.241 | 106.91 |
| 479634 | SLC30A9 | Solute carrier family 30 (zinc transporter), member 9 | 123.90 | 63.55 | 0.379 | 75.32 |
| 479693 | SFRS11 | Splicing factor, arginine/serine-rich 11 | 189.39 | 69.99 | 0.172 | 199.97 |
| 479728 | GAPDH | Glyceraldehyde-3-phosphate dehydrogenase | 7330.72 | 80.18 | 0.000 | 3167.05 |
| 479747 | BCAR1 | Breast cancer anti-estrogen resistance 1 | 183.08 | 85.45 | 0.310 | 58.32 |
| 479814 | POLR2B | Polymerase (RNA) II (DNA directed) polypeptide B, 140 kDa | 170.30 | 62.57 | 0.310 | 102.92 |
| 480073 | HNRPD | Heterogeneous nuclear ribonucleoprotein D (AU-rich element RNA binding protein 1, 37 kDa) | 229.02 | 68.01 | 0.103 | 241.33 |
| 480311 | PDLIM5 | PDZ and LIM domain 5 | 273.24 | 235.65 | 0.241 | 95.21 |
| 480465 | SCYE1 | Small inducible cytokine subfamily E. member 1 (endothelial monocyte-activating) | 107.39 | 55.27 | 0.276 | 55.39 |
| 480653 | ANXA5 | Annexin A5 | 303.60 | 104.16 | 0.069 | 169.77 |
| 481571 | UQCRH | Similar to Ubiquinol-cytochrome C reductase complex 11 kDa protein. mitochondrial precursor (Mitochondrial hinge protein) (Cytochrome C1, nonheme 11 kDa protein) (Complex III subunit VIII) | 229.54 | 102.84 | 0.138 | 431.88 |
| 481720 | MYO10 | Myosin X | 140.50 | 130.53 | 0.310 | 91.75 |
| 481898 | CCBL2 | Cysteine conjugate-beta lyase 2 | 134.41 | 54.32 | 0.310 | 48.63 |
| 482144 | RPL26 | Similar to 60S ribosomal protein L26 | 447.43 | 95.30 | 0.034 | 699.37 |
| 482363 | SLC30A5 | Solute carrier family 30 (zinc transporter), member 5 | 78.30 | 56.98 | 0.379 | 57.46 |
| 482526 | TINP1 | TGF beta-inducible nuclear protein 1 | 121.52 | 61.06 | 0.241 | 173.99 |
| 482868 | KIAA0372 | KIAA0372 | 126.07 | 60.99 | 0.241 | 71.13 |
| 483036 | PJA2 | Praja 2, RING-H2 motif containing | 158.62 | 65.91 | 0.276 | 72.48 |
| 483067 | C5orf13 | Chromosome 5 open reading frame 13 | 318.12 | 190.12 | 0.379 | 195.11 |
| 483305 | HINT1 | Histidine triad nucleotide binding protein 1 | 236.40 | 118.42 | 0.207 | 113.38 |
| 483408 | PPP2CA | Protein phosphatase 2 (formerly 2A). catalytic subunit, alpha isoform | 230.50 | 94.12 | 0.138 | 105.32 |
| 483454 | CNN3 | Calponin 3, acidic | 211.93 | 89.89 | 0.207 | 399.33 |
| 483486 | JMJD1B | Jumonji domain containing 1B | 107.12 | 52.95 | 0.310 | 64.58 |
| 484138 | FBXW11 | F-box and WD-40 domain protein 11 | 117.64 | 68.50 | 0.379 | 109.27 |
| 484188 | ATP6V0E1 | ATPase, H+ transporting, lysosomal 9 kDa, V0 subunit e1 | 159.10 | 68.32 | 0.138 | 71.54 |
| 484242 | UBXD8 | UBX domain containing 8 | 125.98 | 75.93 | 0.207 | 66.51 |
| 484288 | DDX41 | DEAD (Asp-Glu-Ala-Asp) box polypeptide 41 | 214.13 | 74.98 | 0.138 | 47.70 |
| 484363 | RNF130 | Ring finger protein 130 | 97.65 | 67.32 | 0.138 | 111.91 |
| 484551 | CPM | Carboxypeptidase M | 186.28 | 78.16 | 0.310 | 71.14 |
| 484813 | DEK | DEK oncogene (DNA binding) | 260.77 | 83.22 | 0.172 | 144.27 |
| 485155 | RPL35 | Ribosomal protein L35 | 281.04 | 111.39 | 0.172 | 1995.97 |
| 485195 | SORT1 | Sortilin 1 | 150.82 | 80.52 | 0.345 | 91.72 |
| 485246 | PSMA5 | Proteasome (prosome, macropain) subunit, alpha type. 5 | 164.31 | 83.49 | 0.207 | 72.99 |
| 485262 | MTCH1 | Mitochondrial carrier homolog 1 (*C. elegans*) | 364.72 | 91.85 | 0.103 | 222.02 |
| 485365 | AHCYL1 | S-adenosylhomocysteine hydrolase-like 1 | 182.57 | 61.85 | 0.207 | 87.98 |
| 485616 | DST | Dystonin | 144.43 | 74.83 | 0.276 | 159.14 |
| 486542 | BCLAF1 | BCL2-associated transcription factor 1 | 184.76 | 58.42 | 0.207 | 57.11 |
| 487027 | VIL2 | Villin 2 (ezrin) | 228.59 | 71.02 | 0.138 | 203.46 |
| 487054 | TCP1 | T-complex 1 | 209.76 | 78.62 | 0.138 | 162.70 |
| 487635 | BZW2 | Basic leucine zipper and W2 domains 2 | 250.31 | 146.18 | 0.172 | 96.11 |
| 487774 | HNRPA2B1 | Heterogeneous nuclear ribonucleoprotein A2/B1 | 218.53 | 87.55 | 0.103 | 476.18 |
| 488171 | NUDCD3 | NudC domain containing 3 | 607.73 | 183.50 | 0.034 | 2935.95 |
| 488181 | OGDH | Oxoglutarate (alpha-ketoglutarate) dehydrogenase (lipoamide) | 245.90 | 110.90 | 0.207 | 93.55 |
| 488307 | ECOP | EGFR-coamplified and overexpressed protein | 151.47 | 75.46 | 0.345 | 105.70 |
| 488478 | C7orf42 | Chromosome 7 open reading frame 42 | 151.66 | 70.90 | 0.207 | 70.53 |
| 488671 | BAZ1B | Bromodomain adjacent to zinc finger domain. 1B | 114.54 | 65.20 | 0.207 | 97.87 |
| 489207 | ASNS | Asparagine synthetase | 262.06 | 124.38 | 0.172 | 159.98 |
| 489284 | ARPC1B | Actin related protein 2/3 complex. subunit 1B. 41 kDa | 555.08 | 109.32 | 0.103 | 249.26 |
| 489287 | CPSF4 | Cleavage and polyadenylation specific factor 4, 30 kDa | 171.76 | 69.89 | 0.172 | 88.36 |
| 489336 | SYAP1 | Synapse associated protein 1. SAP47 homolog (*Drosophila*) | 126.10 | 45.09 | 0.310 | 51.70 |
| 489615 | PBEF1 | Pre-B-cell colony enhancing factor 1 | 211.67 | 111.85 | 0.276 | 110.09 |
| 490203 | CALD1 | Caldesmon 1 | 242.44 | 103.25 | 0.207 | 84.05 |
| 490394 | SSBP1 | Single-stranded DNA binding protein 1 | 444.28 | 309.52 | 0.241 | 86.70 |
| 490415 | ZYX | Zyxin | 259.67 | 90.01 | 0.138 | 278.36 |
| 490745 | DNAJB6 | DnaJ (Hsp40) homolog. subfamily B. member 6 | 182.26 | 74.39 | 0.103 | 170.33 |
| 490795 | FAM62B | Family with sequence similarity 62 (C2 domain containing) member B | 256.81 | 139.32 | 0.276 | 67.48 |
| 490874 | MTX1 | Metaxin 1 | 139.52 | 83.02 | 0.310 | 62.57 |
| 491336 | ELP3 | Elongation protein 3 homolog (*S. cerevisiae*) | 98.38 | 59.66 | 0.379 | 43.04 |
| 491359 | LMNA | Lamin A/C | 797.11 | 108.53 | 0.138 | 415.19 |

TABLE 2-continued

A list of 2087 candidate endogenous reference genes

| 491440 | PPP2CB | Protein phosphatase 2 (formerly 2A). catalytic subunit. beta isoform | 146.90 | 77.42 | 0.276 | 218.31 |
|---|---|---|---|---|---|---|
| 491494 | CCT3 | Chaperonin containing TCP1, subunit 3 (gamma) | 1152.31 | 109.73 | 0.034 | 207.97 |
| 491597 | VDAC3 | Voltage-dependent anion channel 3 | 189.10 | 60.03 | 0.207 | 82.40 |
| 491695 | UBE2V2 | Ubiquitin-conjugating enzyme E2 variant 2 | 1324.03 | 205.58 | 0.276 | 58.78 |
| 491745 | TCEA1 | Transcription elongation factor A (SII). 1 | 180.17 | 63.49 | 0.241 | 69.36 |
| 491988 | TRAM1 | Translocation associated membrane protein 1 | 151.74 | 62.44 | 0.172 | 147.67 |
| 492236 | WDR42A | WD repeat domain 42A | 135.63 | 62.96 | 0.310 | 61.94 |
| 492314 | LAPTM4B | Lysosomal associated protein transmembrane 4 beta | 315.85 | 98.92 | 0.138 | 124.30 |
| 492445 | UBR5 | Ubiquitin protein ligase E3 component n-recognin 5 | 133.59 | 70.25 | 0.345 | 51.32 |
| 492599 | EIF3S3 | Eukaryotic translation initiation factor 3, subunit 3 gamma, 40 kDa | 457.44 | 91.86 | 0.069 | 165.21 |
| 492805 | NMD3 | NMD3 homolog (S. cerevisiae) | 154.69 | 68.25 | 0.276 | 64.99 |
| 493362 | AK3L1 | Adenylate kinase 3 | 138.22 | 63.01 | 0.241 | 49.75 |
| 493750 | WDR40A | WD repeat domain 40A | 158.95 | 64.13 | 0.345 | 28.58 |
| 494173 | ANXA1 | Annexin A1 | 663.71 | 206.40 | 0.138 | 439.06 |
| 494419 | LAMP1 | Lysosomal-associated membrane protein 1 | 278.30 | 123.84 | 0.276 | 112.59 |
| 494457 | NINJ1 | Ninjurin 1 | 146.99 | 120.17 | 0.379 | 192.87 |
| 494604 | ANP32B | Acidic (leucine-rich) nuclear phosphoprotein 32 family. member B | 297.30 | 74.71 | 0.069 | 142.74 |
| 494614 | BAT2D1 | BAT2 domain containing 1 | 103.03 | 72.44 | 0.310 | 133.29 |
| 494691 | PFN1 | Profilin 1 | 582.68 | 96.95 | 0.069 | 1198.54 |
| 494700 | SLC44A1 | Solute carrier family 44, member 1 | 156.34 | 79.78 | 0.379 | 88.15 |
| 494985 | FBXW2 | F-box and WD-40 domain protein 2 | 97.45 | 68.65 | 0.379 | 40.27 |
| 495039 | NDUFA8 | NADH dehydrogenase (ubiquinone) 1 alpha subcomplex. 8, 19 | 100.91 | 70.67 | 0.345 | 82.23 |
| 495349 | KIAA0515 | KIAA0515 | 213.73 | 62.92 | 0.069 | 129.84 |
| 495471 | PMPCA | Peptidase (mitochondrial processing) alpha | 174.09 | 84.07 | 0.172 | 85.88 |
| 495605 | CD99 | CD99 antigen | 171.31 | 62.16 | 0.138 | 198.26 |
| 495851 | APOO | Apolipoprotein O | 144.33 | 80.53 | 0.345 | 129.92 |
| 495960 | ATP6AP2 | ATPase. H+ transporting. lysosomal accessory protein 2 | 177.66 | 91.25 | 0.276 | 67.87 |
| 496068 | PCTK1 | PCTAIRE protein kinase 1 | 177.60 | 80.15 | 0.207 | 56.40 |
| 496098 | OTUD5 | OTU domain containing 5 | 171.08 | 119.61 | 0.207 | 43.34 |
| 496271 | ? | Full-length cDNA clone CS0DJ002YF04 of T cells (Jurkat cell line) Cot 10-normalized of Homo sapiens (human) | 552.58 | 198.74 | 0.172 | 70.79 |
| 496487 | ATF4 | Activating transcription factor 4 (tax-responsive enhancer element B67) | 644.83 | 92.22 | 0.069 | 179.34 |
| 496646 | IL13RA1 | Interleukin 13 receptor. alpha 1 | 117.23 | 77.35 | 0.310 | 54.24 |
| 496684 | LAMP2 | Lysosomal-associated membrane protein 2 | 175.62 | 85.98 | 0.241 | 127.56 |
| 497183 | IVNS1ABP | Influenza virus NS1A binding protein | 156.30 | 56.55 | 0.241 | 76.25 |
| 497599 | WARS | Tryptophanyl-tRNA synthetase | 328.30 | 141.43 | 0.103 | 158.85 |
| 497692 | NSL1 | NSL1, MIND kinetochore complex component. homolog (S. cerevisiae) | 142.41 | 132.49 | 0.379 | 45.74 |
| 497893 | ENAH | Enabled homolog (Drosophila) | 133.62 | 90.22 | 0.276 | 73.14 |
| 498239 | FH | Fumarate hydratase | 304.63 | 108.28 | 0.276 | 51.25 |
| 498313 | ADSS | Adenylosuccinate synthase | 138.41 | 96.89 | 0.276 | 66.59 |
| 498317 | C1orf121 | Chromosome 1 open reading frame 121 | 139.90 | 108.25 | 0.379 | 67.33 |
| 498455 | LARP5 | La ribonucleoprotein domain family, member 5 | 142.32 | 72.97 | 0.241 | 56.84 |
| 498548 | RBM17 | RNA binding motif protein 17 | 119.60 | 106.34 | 0.207 | 84.57 |
| 498727 | DHCR24 | 24-dehydrocholesterol reductase | 380.21 | 178.18 | 0.207 | 125.92 |
| 499145 | YME1L1 | YME1-like 1 (S. cerevisiae) | 218.20 | 87.96 | 0.241 | 85.44 |
| 499158 | GGA1 | Golgi associated. gamma adaptin ear containing. ARF binding protein 1 | 149.92 | 94.46 | 0.276 | 59.38 |
| 499594 | TIMM23 | Translocase of inner mitochondrial membrane 23 homolog (yeast) | 116.05 | 77.66 | 0.241 | 46.30 |
| 499833 | REEP3 | Receptor accessory protein 3 | 97.26 | 86.49 | 0.345 | 48.48 |
| 499891 | HNRPH3 | Heterogeneous nuclear ribonucleoprotein H3 (2H9) | 152.75 | 70.91 | 0.103 | 103.56 |
| 499925 | VPS26A | Vacuolar protein sorting 26 homolog A (S. pombe) | 129.39 | 63.83 | 0.172 | 66.21 |
| 499960 | SAR1A | SAR1 gene homolog A (S. cerevisiae) | 122.18 | 69.10 | 0.172 | 87.25 |
| 500067 | PPP3CB | Protein phosphatase 3 (formerly 2B). catalytic subunit. beta isoform (calcineurin A beta) | 120.27 | 66.72 | 0.241 | 124.28 |
| 500101 | VCL | Vinculin | 197.78 | 102.19 | 0.207 | 122.06 |
| 500375 | ENTPD6 | Ectonucleoside triphosphate diphosphohydrolase 6 (putative function) | 163.42 | 84.78 | 0.276 | 93.92 |
| 500409 | GLUD1 | Glutamate dehydrogenase 1 | 161.37 | 95.54 | 0.138 | 228.78 |
| 500546 | IDE | Insulin-degrading enzyme | 112.83 | 68.82 | 0.310 | 46.45 |
| 500674 | TM9SF3 | Transmembrane 9 superfamily member 3 | 215.50 | 58.43 | 0.207 | 132.96 |
| 500775 | ZNF207 | Zinc finger protein 207 | 233.29 | 62.27 | 0.034 | 165.68 |
| 500842 | MGEA5 | Meningioma expressed antigen 5 (hyaluronidase) | 179.67 | 93.93 | 0.310 | 194.92 |
| 500874 | CUEDC2 | CUE domain containing 2 | 129.96 | 52.06 | 0.310 | 136.22 |
| 501012 | ADD3 | Adducin 3 (gamma) | 223.70 | 119.75 | 0.310 | 80.79 |
| 501023 | MXI1 | MAX interactor 1 | 94.44 | 62.74 | 0.345 | 62.06 |
| 501203 | TIAL1 | TIA1 cytotoxic granule-associated RNA binding protein-like 1 | 146.01 | 73.16 | 0.276 | 75.46 |
| 501293 | BSG | Basigin (OK blood group) | 737.88 | 112.29 | 0.103 | 664.58 |
| 501309 | CIRBP | Cold inducible RNA binding protein | 265.44 | 117.90 | 0.034 | 203.81 |
| 501353 | PLEKHJ1 | Pleckstrin homology domain containing, family J member 1 | 100.87 | 56.61 | 0.379 | 75.27 |
| 501376 | UROS | Uroporphyrinogen III synthase (congenital erythropoietic porphyria) | 130.07 | 71.33 | 0.241 | 54.58 |
| 501420 | NCLN | Nicalin homolog (zebrafish) | 177.01 | 86.48 | 0.241 | 51.28 |
| 501629 | IER2 | Immediate early response 2 | 140.79 | 60.99 | 0.241 | 197.55 |
| 501684 | NAP1L4 | Nucleosome assembly protein 1-like 4 | 166.93 | 111.13 | 0.138 | 77.93 |
| 501735 | STIM1 | Stromal interaction molecule 1 | 117.62 | 71.87 | 0.276 | 85.58 |
| 501853 | TMEM9B | TMEM9 domain family, member B | 110.79 | 91.41 | 0.379 | 55.61 |

TABLE 2-continued

A list of 2087 candidate endogenous reference genes

| | | | | | | |
|---|---|---|---|---|---|---|
| 501924 | USP47 | Ubiquitin specific peptidase 47 | 132.14 | 118.32 | 0.345 | 43.63 |
| 501991 | MLSTD2 | Male sterility domain containing 2 | 96.74 | 62.95 | 0.379 | 51.17 |
| 502302 | CAT | Catalase | 158.19 | 107.96 | 0.345 | 78.26 |
| 502328 | CD44 | CD44 antigen (homing function and Indian blood group system) | 366.11 | 100.63 | 0.172 | 183.18 |
| 502461 | DGKZ | Diacylglycerol kinase. zeta 104 kDa | 109.99 | 96.64 | 0.310 | 78.41 |
| 502528 | NDUFS3 | NADH dehydrogenase (ubiquinone) Fe—S protein 3. 30 kDa (NADH-coenzyme Q reductase) | 119.28 | 75.88 | 0.207 | 151.30 |
| 502630 | C11orf31 | Chromosome 11 open reading frame 31 | 170.27 | 98.83 | 0.276 | 149.13 |
| 502659 | RHOC | Ras homolog gene family, member C | 253.62 | 101.47 | 0.138 | 234.42 |
| 502705 | PRPF19 | PRP19/PSO4 pre-mRNA processing factor 19 homolog (*S. cerevisiae*) | 198.31 | 100.04 | 0.276 | 84.60 |
| 502745 | FADS2 | Fatty acid desaturase 2 | 266.18 | 116.45 | 0.276 | 221.93 |
| 502769 | SLC3A2 | Solute carrier family 3 (activators of dibasic and neutral amino acid transport). member 2 | 276.24 | 84.47 | 0.138 | 123.67 |
| 502773 | ADI1 | Acireductone dioxygenase 1 | 159.84 | 55.74 | 0.103 | 57.70 |
| 502823 | PRDX5 | Peroxiredoxin 5 | 183.65 | 76.11 | 0.241 | 216.88 |
| 502829 | SF1 | Splicing factor 1 | 263.86 | 66.20 | 0.069 | 141.67 |
| 502836 | ARL2 | ADP-ribosylation factor-like 2 | 134.06 | 114.72 | 0.310 | 119.31 |
| 502842 | CAPN1 | Calpain 1. (mu/l) large subunit | 287.11 | 101.89 | 0.207 | 88.58 |
| 502872 | MAP3K11 | Mitogen-activated protein kinase kinase kinase 11 | 128.70 | 82.13 | 0.276 | 72.97 |
| 502876 | RHOB | Ras homolog gene family, member B | 165.00 | 92.57 | 0.310 | 283.76 |
| 503093 | ZFP36L2 | Zinc finger protein 36, C3H type-like 2 | 150.79 | 67.83 | 0.207 | 280.17 |
| 503222 | RAB6A | RAB6A, member RAS oncogene family | 152.69 | 73.96 | 0.241 | 119.21 |
| 503251 | PPME1 | Protein phosphatase methylesterase 1 | 123.71 | 52.56 | 0.207 | 59.51 |
| 503597 | HSPC148 | Hypothetical protein HSPC148 | 107.89 | 76.02 | 0.276 | 58.03 |
| 503709 | TMEM123 | Transmembrane protein 123 | 339.10 | 161.64 | 0.172 | 79.34 |
| 503716 | DCUN1D5 | DCN1, defective in cullin neddylation 1. domain containing 5 (*S. cerevisiae*) | 167.32 | 87.13 | 0.138 | 54.63 |
| 503787 | DARS | Aspartyl-tRNA synthetase | 147.34 | 55.17 | 0.138 | 100.30 |
| 504237 | STT3A | STT3, subunit of the oligosaccharyltransferase complex. homolog A (*S. cerevisiae*) | 117.19 | 108.95 | 0.345 | 77.26 |
| 504517 | RPS27 | Tetraspanin 9 | 176.40 | 121.62 | 0.379 | 2547.00 |
| 504613 | PTMS | Parathymosin | 175.13 | 81.37 | 0.345 | 308.10 |
| 504620 | PHB2 | Prohibitin 2 | 506.51 | 79.86 | 0.069 | 136.79 |
| 504687 | MYL9 | Elongation factor Tu family protein | 343.66 | 100.94 | 0.379 | 340.49 |
| 504828 | DDX47 | DEAD (Asp-Glu-Ala-Asp) box polypeptide 47 | 130.63 | 59.08 | 0.379 | 43.21 |
| 504895 | STRAP | Serine/threonine kinase receptor associated protein | 221.43 | 95.09 | 0.138 | 122.68 |
| 505033 | KRAS | v-Ki-ras2 Kirsten rat sarcoma viral oncogene homolog | 115.82 | 83.04 | 0.310 | 57.38 |
| 505059 | PSMD4 | Proteasome (prosome, macropain) 26S subunit, non-ATPase, 4 | 259.00 | 62.63 | 0.103 | 180.27 |
| 505625 | C12orf10 | Chromosome 12 open reading frame 10 | 105.33 | 77.88 | 0.345 | 80.93 |
| 505652 | COPZ1 | Coatomer protein complex, subunit zeta 1 | 204.89 | 87.20 | 0.000 | 217.03 |
| 505676 | CIP29 | Cytokine induced protein 29 kDa | 184.81 | 88.39 | 0.241 | 118.62 |
| 505705 | MYL6 | Myosin, light polypeptide 6, alkali, smooth muscle and non-muscle | 438.52 | 109.87 | 0.069 | 1121.48 |
| 505806 | PBXIP1 | Pre-B-cell leukemia transcription factor interacting protein 1 | 115.75 | 83.63 | 0.310 | 72.04 |
| 505824 | SAMM50 | Sorting and assembly machinery component 50 homolog (*S. cerevisiae*) | 242.60 | 117.59 | 0.172 | 59.28 |
| 506215 | RARS | Arginyl-tRNA synthetase | 192.15 | 85.96 | 0.172 | 103.05 |
| 506325 | NUDT4 | Nudix (nucleoside diphosphate linked moiety X)-type motif 4 pseudogene 2 | 121.40 | 87.04 | 0.379 | 161.89 |
| 506759 | ATP2A2 | ATPase. Ca++ transporting. cardiac muscle. slow twitch 2 | 375.19 | 241.76 | 0.241 | 195.37 |
| 506861 | DDX54 | DEAD (Asp-Glu-Ala-Asp) box polypeptide 54 | 199.70 | 104.77 | 0.241 | 74.73 |
| 507074 | KIAA0152 | KIAA0152 | 244.90 | 89.86 | 0.069 | 77.13 |
| 507162 | VPS37B | Vacuolar protein sorting 37 homolog B (*S. cerevisiae*) | 142.45 | 79.66 | 0.276 | 143.42 |
| 507584 | POLR1D | Polymerase (RNA) I polypeptide D. 16 kDa | 121.94 | 73.07 | 0.241 | 107.77 |
| 507680 | PFAAP5 | Phosphonoformate immuno-associated protein 5 | 143.30 | 68.40 | 0.345 | 63.32 |
| 507910 | PGRMC2 | Progesterone receptor membrane component 2 | 131.09 | 75.85 | 0.207 | 124.83 |
| 507916 | TSC22D1 | TSC22 domain family. member 1 | 344.52 | 102.84 | 0.172 | 243.46 |
| 508010 | FNDC3A | Fibronectin type III domain containing 3A | 264.21 | 157.30 | 0.241 | 110.98 |
| 508644 | FLJ10154 | Hypothetical protein FLJ10154 | 183.99 | 75.88 | 0.310 | 65.60 |
| 509163 | ERGIC1 | Endoplasmic reticulum-golgi intermediate compartment (ERGIC) | 1147.54 | 71.85 | 0.103 | 94.35 |
| 509226 | FKBP3 | FK506 binding protein 3, 25 kDa | 146.28 | 97.77 | 0.241 | 140.21 |
| 509264 | KLHDC2 | Kelch domain containing 2 | 117.21 | 72.23 | 0.207 | 121.90 |
| 509414 | KTN1 | Kinectin 1 (kinesin receptor) | 196.92 | 103.65 | 0.207 | 88.75 |
| 509622 | RGL2 | Ral guanine nucleotide dissociation stimulator-like 2 | 136.36 | 70.20 | 0.345 | 93.28 |
| 509736 | HSP90AB1 | Heat shock protein 90 kDa alpha (cytosolic), class B member 1 | 2045.82 | 87.83 | 0.000 | 550.72 |
| 509791 | ERH | Enhancer of rudimentary homolog (*Drosophila*) | 148.95 | 80.20 | 0.207 | 256.46 |
| 509909 | NUMB | Numb homolog (*Drosophila*) | 115.97 | 62.99 | 0.241 | 58.22 |
| 510087 | ENSA | Endosulfine alpha | 196.15 | 70.81 | 0.034 | 159.53 |
| 510328 | DDX24 | DEAD (Asp-Glu-Ala-Asp) box polypeptide 24 | 446.38 | 126.73 | 0.103 | 75.63 |
| 510402 | CD46 | CD46 molecule, complement regulatory protein | 255.43 | 87.89 | 0.276 | 81.27 |
| 511067 | FAM82C | Family with sequence similarity 82. member C | 193.94 | 125.16 | 0.345 | 39.66 |
| 511138 | TMEM87A | Transmembrane protein 87A | 153.90 | 71.25 | 0.241 | 82.26 |
| 511149 | SNAP23 | Synaptosomal-associated protein, 23 kDa | 159.76 | 70.15 | 0.276 | 51.21 |
| 511425 | SRP9 | Signal recognition particle 9 kDa | 1439.84 | 206.14 | 0.069 | 454.09 |
| 511504 | TCF12 | Transcription factor 12 (HTF4. helix-loop-helix transcription factors 4) | 175.22 | 83.75 | 0.276 | 69.32 |
| 511862 | | Similar to 60S acidic ribosomal protein P1 | 182.40 | 88.27 | 0.379 | 84.86 |
| 511952 | CBX6 | Chromobox homolog 6 | 153.88 | 81.20 | 0.276 | 64.59 |

TABLE 2-continued

A list of 2087 candidate endogenous reference genes

| | | | | | | |
|---|---|---|---|---|---|---|
| 512005 | ARPC3 | Actin related protein 2/3 complex. subunit 3, 21 kDa | 175.09 | 73.61 | 0.241 | 119.68 |
| 512465 | SURF4 | Surfeit 4 | 272.49 | 79.31 | 0.069 | 106.55 |
| 512525 | RPS17 | Ribosomal protein S17 | 1561.21 | 128.47 | 0.069 | 599.75 |
| 512607 | MIR16 | Membrane interacting protein of RGS16 | 243.63 | 112.71 | 0.207 | 98.46 |
| 512640 | PRKCSH | Protein kinase C substrate 80K-H | 369.95 | 87.75 | 0.172 | 131.74 |
| 512661 | ISY1 | ISY1 splicing factor homolog (S. cerevisiae) | 247.17 | 110.21 | 0.241 | 115.05 |
| 512676 | RPS25 | Ribosomal protein S25 | 200.49 | 132.68 | 0.241 | 286.69 |
| 512693 | METT11D1 | Methyltransferase 11 domain containing 1 | 119.37 | 86.98 | 0.345 | 29.73 |
| 512756 | THAP7 | THAP domain containing 7 | 139.40 | 88.58 | 0.345 | 51.73 |
| 512815 | AP3D1 | Adaptor-related protein complex 3, delta 1 subunit | 260.40 | 98.20 | 0.034 | 107.57 |
| 512857 | CD151 | CD151 antigen | 289.17 | 93.65 | 0.207 | 378.94 |
| 512867 | CASC4 | Cancer susceptibility candidate 4 | 130.94 | 70.38 | 0.207 | 100.14 |
| 512908 | ARPP-19 | Cyclic AMP phosphoprotein. 19 kD | 226.51 | 76.75 | 0.207 | 146.97 |
| 513043 | IMP3 | IMP3, U3 small nucleolar ribonucleoprotein, homolog (yeast) | 135.64 | 58.16 | 0.310 | 47.55 |
| 513055 | WDR61 | WD repeat domain 61 | 114.60 | 53.12 | 0.345 | 70.68 |
| 513057 | RANBP5 | RAN binding protein 5 | 280.02 | 118.69 | 0.172 | 101.08 |
| 513058 | TMED3 | Transmembrane emp24 protein transport domain containing 3 | 180.01 | 81.33 | 0.138 | 114.71 |
| 513071 | MESDC1 | Mesoderm development candidate 1 | 153.38 | 113.49 | 0.276 | 50.82 |
| 513083 | RPL9 | Ribosomal protein L9 | 1564.85 | 164.78 | 0.034 | 740.57 |
| 513141 | IDH2 | Isocitrate dehydrogenase 2 (NADP+). mitochondrial | 276.13 | 73.73 | 0.103 | 172.64 |
| 513145 | NGRN | Neugrin. neurite outgrowth associated | 292.66 | 85.21 | 0.034 | 91.71 |
| 513153 | FURIN | Furin (paired basic amino acid cleaving enzyme) | 171.95 | 95.68 | 0.379 | 67.56 |
| 513230 | MRPL28 | Mitochondrial ribosomal protein L28 | 206.58 | 141.00 | 0.241 | 67.94 |
| 513242 | RHOT2 | Ras homolog gene family. member T2 | 146.56 | 66.79 | 0.345 | 59.56 |
| 513261 | HN1L | Hematological and neurological expressed 1-like | 169.07 | 73.84 | 0.138 | 62.28 |
| 513266 | NDUFB10 | NADH dehydrogenase (ubiquinone) 1 beta subcomplex, 10, 22 | 141.77 | 93.82 | 0.345 | 42.16 |
| 513470 | NFATC2IP | Nuclear factor of activated T-cells, cytoplasmic. calcineurin-dependent 2 interacting protein | 123.18 | 55.34 | 0.310 | 30.57 |
| 513488 | MVP | Major vault protein | 276.00 | 95.97 | 0.276 | 79.08 |
| 513490 | ALDOA | Aldolase A. fructose-bisphosphate | 1575.38 | 81.23 | 0.034 | 916.32 |
| 513520 | BCKDK | Branched chain ketoacid dehydrogenase kinase | 181.01 | 99.21 | 0.276 | 51.25 |
| 513522 | FUS | Fusion (involved in t(12; 16) in malignant liposarcoma) | 402.21 | 88.89 | 0.034 | 172.34 |
| 513631 | ARL2BP | ADP-ribosylation factor-like 2 binding protein | 133.32 | 76.06 | 0.379 | 60.80 |
| 513856 | DPH1 | DPH1 homolog (S. cerevisiae) | 153.80 | 77.15 | 0.172 | 162.16 |
| 513984 | FLII | Flightless 1 homolog (Drosophila) | 218.66 | 80.64 | 0.103 | 61.58 |
| 514012 | MAP2K3 | Mitogen-activated protein kinase kinase 3 | 206.91 | 198.73 | 0.379 | 68.18 |
| 514036 | SDF2 | Stromal cell-derived factor 2 | 139.48 | 83.16 | 0.379 | 49.32 |
| 514038 | FLOT2 | Flotillin 2 | 205.94 | 75.37 | 0.241 | 103.22 |
| 514174 | JUP | Junction plakoglobin | 311.95 | 175.04 | 0.310 | 204.87 |
| 514196 | RPL27 | Ribosomal protein L27 | 445.53 | 163.18 | 0.103 | 927.28 |
| 514211 | TMEM101 | Transmembrane protein 101 | 207.70 | 66.43 | 0.345 | 109.02 |
| 514216 | SLC25A39 | Solute carrier family 25. member 39 | 372.09 | 78.71 | 0.103 | 162.85 |
| 514220 | GRN | Granulin | 569.94 | 118.75 | 0.103 | 216.06 |
| 514297 | UBE2Z | Ubiquitin-conjugating enzyme E2Z (putative) | 149.22 | 70.83 | 0.172 | 84.41 |
| 514303 | PHB | Prohibitin | 337.86 | 78.21 | 0.103 | 142.93 |
| 514435 | SF3B3 | Splicing factor 3b, subunit 3. 130 kDa | 245.52 | 67.98 | 0.138 | 44.20 |
| 514489 | WBP2 | WW domain binding protein 2 | 367.18 | 97.07 | 0.138 | 147.04 |
| 514535 | LGALS3BP | Lectin. galactoside-binding. soluble. 3 binding protein | 714.12 | 134.59 | 0.172 | 117.40 |
| 514581 | ACTG1 | Actin, gamma 1 | 6790.08 | 96.54 | 0.000 | 1374.42 |
| 514590 | HGS | Hepatocyte growth factor-regulated tyrosine kinase substrate | 234.48 | 89.80 | 0.241 | 88.17 |
| 514819 | AP2B1 | Adaptor-related protein complex 2, beta 1 subunit | 184.47 | 53.67 | 0.207 | 92.79 |
| 514870 | ATP5F1 | ATP synthase, H+ transporting, mitochondrial F0 complex, subunit b, isoform 1 | 441.56 | 130.47 | 0.034 | 84.88 |
| 514920 | CALCOCO | Calcium binding and coiled-coil domain 2 | 151.26 | 76.62 | 0.241 | 46.59 |
| 514934 | CAPZA1 | Capping protein (actin filament) muscle Z-line, alpha 1 | 232.49 | 84.07 | 0.276 | 101.72 |
| 515003 | C19orf6 | Chromosome 19 open reading frame 6 | 218.92 | 96.61 | 0.172 | 96.49 |
| 515005 | STK11 | Serine/threonine kinase 11 (Peutz-Jeghers syndrome) | 127.27 | 85.12 | 0.379 | 66.15 |
| 515018 | GNA13 | Guanine nucleotide binding protein (G protein). alpha 13 | 162.22 | 105.65 | 0.345 | 72.69 |
| 515053 | AES | Amino-terminal enhancer of split | 314.90 | 95.73 | 0.138 | 258.48 |
| 515070 | EEF2 | Eukaryotic translation elongation factor 2 | 403.41 | 101.00 | 0.034 | 2097.60 |
| 515092 | CLPP | ClpP caseinolytic peptidase, ATP-dependent, proteolytic subunit homolog (E. coli) | 173.03 | 103.29 | 0.241 | 50.27 |
| 515155 | C19orf43 | Chromosome 19 open reading frame 43 | 161.94 | 77.42 | 0.138 | 117.34 |
| 515162 | CALR | Calreticulin | 575.58 | 88.03 | 0.034 | 110.24 |
| 515164 | GADD45GIP1 | Growth arrest and DNA-damage-inducible, gamma interacting protein 1 | 191.12 | 69.42 | 0.276 | 107.72 |
| 515210 | DNAJB1 | DnaJ (Hsp40) homolog, subfamily B. member 1 | 233.68 | 80.33 | 0.207 | 330.45 |
| 515255 | LSM4 | LSM4 homolog. U6 small nuclear RNA associated (S. cerevisiae) | 266.66 | 105.98 | 0.276 | 139.77 |
| 515266 | UPF1 | UPF1 regulator of nonsense transcripts homolog (yeast) | 163.88 | 99.99 | 0.276 | 60.23 |
| 515271 | SFRS14 | Splicing factor, arginine/serine-rich 14 | 124.30 | 81.86 | 0.310 | 47.59 |
| 515329 | RPL22 | Ribosomal protein L22 | 191.43 | 75.49 | 0.138 | 455.30 |
| 515371 | CAPNS1 | Calpain. small subunit 1 | 404.46 | 95.10 | 0.069 | 519.15 |
| 515406 | AKT2 | V-akt murine thymoma viral oncogene homolog 2 | 139.00 | 124.72 | 0.345 | 101.41 |
| 515417 | EGLN2 | Egl nine homolog 2 (C. elegans) | 257.04 | 138.23 | 0.379 | 141.94 |
| 515432 | DEDD2 | Death effector domain containing 2 | 94.65 | 52.25 | 0.379 | 52.49 |
| 515472 | SNRPD2 | Small nuclear ribonucleoprotein D2 polypeptide 16.5 kDa | 292.31 | 154.43 | 0.207 | 250.23 |
| 515475 | SYMPK | Symplekin | 133.18 | 53.29 | 0.241 | 43.73 |
| 515487 | CALM3 | Calmodulin 3 (phosphorylase kinase. delta) | 439.26 | 95.22 | 0.069 | 170.52 |

TABLE 2-continued

A list of 2087 candidate endogenous reference genes

| | | | | | | |
|---|---|---|---|---|---|---|
| 515494 | SLC1A5 | Solute carrier family 1 (neutral amino acid transporter), member 5 | 448.32 | 106.79 | 0.138 | 90.90 |
| 515500 | SAE1 | SUMO-1 activating enzyme subunit 1 | 380.21 | 79.67 | 0.034 | 84.41 |
| 515515 | KDELR1 | KDEL (Lys-Asp-Glu-Leu) endoplasmic reticulum protein retention receptor 1 | 261.62 | 81.81 | 0.138 | 278.16 |
| 515517 | RPL18 | Ribosomal protein L18 | 743.38 | 74.48 | 0.103 | 361.65 |
| 515524 | NUCB1 | Nucleobindin 1 | 350.34 | 117.21 | 0.103 | 177.67 |
| 515540 | PTOV1 | Prostate tumor overexpressed gene 1 | 175.30 | 98.47 | 0.172 | 165.98 |
| 515550 | LOC284361 | Hematopoietic signal peptide-containing | 135.48 | 82.61 | 0.310 | 234.71 |
| 515598 | PRPF31 | PRP31 pre-mRNA processing factor 31 homolog (yeast) | 368.40 | 151.24 | 0.276 | 57.93 |
| 515607 | PPP1R12C | Protein phosphatase 1, regulatory (inhibitor) subunit 12C | 165.22 | 97.14 | 0.379 | 50.41 |
| 515642 | GPSN2 | Glycoprotein, synaptic 2 | 171.37 | 74.21 | 0.345 | 122.06 |
| 515785 | BLVRB | Biliverdin reductase B (flavin reductase (NADPH)) | 143.92 | 94.30 | 0.310 | 182.67 |
| 515846 | RUVBL2 | RuvB-like 2 (*E. coli*) | 354.78 | 98.40 | 0.138 | 97.93 |
| 515848 | HADHB | Hydroxyacyl-Coenzyme A dehydrogenase/3-ketoacyl-Coenzyme thiolase/enoyl-Coenzyme A hydratase (trifunctional protein). beta subunit | 213.42 | 90.90 | 0.103 | 98.50 |
| 515890 | YPEL5 | Yippee-like 5 (*Drosophila*) | 181.92 | 82.16 | 0.276 | 123.75 |
| 516075 | TIA1 | TIA1 cytotoxic granule-associated RNA binding protein | 183.23 | 80.58 | 0.310 | 93.19 |
| 516077 | FLJ14668 | Hypothetical protein FLJ14668 | 112.96 | 75.82 | 0.276 | 61.98 |
| 516087 | TEX261 | Testis expressed sequence 261 | 146.81 | 110.15 | 0.241 | 33.17 |
| 516111 | DCTN1 | Dynactin 1 (p150. glued homolog. *Drosophila*) | 261.96 | 94.41 | 0.103 | 64.73 |
| 516114 | WBP1 | WW domain binding protein 1 | 114.03 | 56.61 | 0.310 | 42.16 |
| 516157 | MAT2A | Methionine adenosyltransferase II. alpha | 195.52 | 68.87 | 0.172 | 242.05 |
| 516450 | SMPD4 | Sphingomyelin phosphodiesterase 4, neutral membrane (neutral sphingomyelinase-3) | 248.30 | 97.54 | 0.172 | 118.46 |
| 516522 | INTS3 | Integrator complex subunit 3 | 142.16 | 102.91 | 0.379 | 59.15 |
| 516539 | HNRPA3 | Heterogeneous nuclear ribonucleoprotein A3 | 223.52 | 72.69 | 0.138 | 168.69 |
| 516587 | UBE2Q1 | Ubiquitin-conjugating enzyme E2Q (putative) 1 | 131.58 | 55.37 | 0.345 | 69.25 |
| 516633 | NCKAP1 | NCK-associated protein 1 | 198.42 | 62.97 | 0.241 | 153.54 |
| 516711 | CHPF | Chondroitin polymerizing factor | 213.73 | 142.81 | 0.379 | 128.03 |
| 516790 | ARHGEF2 | Rho/rac guanine nucleotide exchange factor (GEF) 2 | 133.62 | 84.47 | 0.379 | 59.83 |
| 516807 | STK25 | Serine/threonine kinase 25 (STE20 homolog, yeast) | 455.41 | 109.35 | 0.138 | 64.72 |
| 516826 | TRIB3 | Tribbles homolog 3 (*Drosophila*) | 228.24 | 99.31 | 0.241 | 50.84 |
| 516855 | CENPB | Centromere protein B. 80 kDa | 202.67 | 80.52 | 0.276 | 82.21 |
| 517080 | SLC35C2 | Solute carrier family 35, member C2 | 163.93 | 94.82 | 0.207 | 60.57 |
| 517106 | CEBPB | CCAAT/enhancer binding protein (C/EBP), beta | 178.82 | 93.37 | 0.345 | 155.23 |
| 517134 | C20orf43 | Chromosome 20 open reading frame 43 | 247.39 | 69.92 | 0.069 | 79.36 |
| 517145 | ENO1 | Enolase 1, (alpha) | 3401.32 | 102.15 | 0.000 | 166.84 |
| 517168 | TAGLN2 | Transgelin 2 | 626.02 | 75.92 | 0.069 | 595.39 |
| 517216 | PEA15 | Phosphoprotein enriched in astrocytes 15 | 283.17 | 82.20 | 0.172 | 201.83 |
| 517232 | PEX19 | Peroxisomal biogenesis factor 19 | 151.27 | 57.99 | 0.207 | 78.36 |
| 517240 | IFNGR2 | Interferon gamma receptor 2 (interferon gamma transducer 1) | 158.55 | 79.26 | 0.172 | 79.49 |
| 517262 | SON | SON DNA binding protein | 197.08 | 79.92 | 0.138 | 111.91 |
| 517293 | F11R | F11 receptor | 215.86 | 109.54 | 0.276 | 1045.83 |
| 517338 | ATP6V1E1 | ATPase. H+ transporting. lysosomal 31 kDa. V1 subunit E isoform 1 | 197.20 | 81.17 | 0.069 | 122.60 |
| 517342 | DEDD | Death effector domain containing | 136.31 | 62.93 | 0.276 | 55.11 |
| 517356 | COL18A1 | Collagen, type XVIII, alpha 1 | 388.40 | 175.92 | 0.345 | 169.44 |
| 517357 | DGCR2 | DiGeorge syndrome critical region gene 2 | 214.17 | 92.03 | 0.241 | 88.38 |
| 517421 | PCQAP | PC2 (positive cofactor 2. multiprotein complex) glutamine/Q-rich-associated protein | 205.74 | 178.98 | 0.241 | 70.11 |
| 517438 | ASCC2 | Activating signal cointegrator 1 complex subunit 2 | 138.59 | 89.52 | 0.138 | 46.79 |
| 517517 | EP300 | E1A binding protein p300 | 124.61 | 92.25 | 0.379 | 70.50 |
| 517543 | PES1 | Pescadillo homolog 1, containing BRCT domain (zebrafish) | 242.64 | 124.33 | 0.276 | 66.78 |
| 517582 | MCM5 | MCM5 minichromosome maintenance deficient 5, cell division cycle 46 (*S. cerevisiae*) | 424.00 | 105.24 | 0.172 | 49.05 |
| 517622 | UNC84B | Unc-84 homolog B (*C. elegans*) | 131.34 | 80.16 | 0.310 | 86.59 |
| 517641 | L3MBTL2 | L(3)mbt-like 2 (*Drosophila*) | 116.46 | 67.43 | 0.345 | 35.18 |
| 517666 | CYB5R3 | Cytochrome b5 reductase 3 | 314.58 | 161.98 | 0.138 | 125.03 |
| 517731 | TRABD | TraB domain containing | 180.88 | 102.41 | 0.276 | 83.26 |
| 517768 | BRP44 | Brain protein 44 | 127.10 | 104.51 | 0.345 | 90.63 |
| 517792 | C3orf10 | Chromosome 3 open reading frame 10 | 175.04 | 80.24 | 0.069 | 101.16 |
| 517817 | TMEM43 | Transmembrane protein 43 | 136.66 | 75.36 | 0.310 | 40.01 |
| 517821 | | CDNA clone IMAGE: 5278517 | 120.53 | 66.29 | 0.310 | 154.05 |
| 517888 | CRTAP | Cartilage associated protein | 208.15 | 77.38 | 0.207 | 87.57 |
| 517948 | DHX30 | DEAH (Asp-Glu-Ala-His) box polypeptide 30 | 209.13 | 121.04 | 0.207 | 70.11 |
| 517949 | MAP4 | Microtubule-associated protein 4 | 306.69 | 79.18 | 0.103 | 204.68 |
| 517969 | APEH | N-acylaminoacyl-peptide hydrolase | 330.37 | 60.97 | 0.207 | 65.68 |
| 517981 | TUSC2 | Tumor suppressor candidate 2 | 129.92 | 69.61 | 0.310 | 47.18 |
| 518060 | ARL6IP5 | ADP-ribosylation-like factor 6 interacting protein 5 | 303.59 | 116.09 | 0.207 | 144.14 |
| 518123 | TFG | TRK-fused gene | 189.81 | 59.70 | 0.138 | 95.89 |
| 518236 | SEC61A1 | Sec61 alpha 1 subunit (*S. cerevisiae*) | 272.42 | 82.37 | 0.138 | 130.33 |
| 518244 | RPN1 | Ribophorin I | 232.54 | 86.03 | 0.172 | 155.16 |
| 518249 | CNBP | CCHC-type zinc finger. nucleic acid binding protein | 307.66 | 69.72 | 0.034 | 229.80 |
| 518250 | COPG | Coatomer protein complex, subunit gamma | 205.51 | 104.21 | 0.276 | 130.03 |
| 518265 | CDV3 | CDV3 homolog (mouse) | 192.56 | 91.81 | 0.138 | 187.87 |
| 518326 | SERP1 | Stress-associated endoplasmic reticulum protein 1 | 233.71 | 64.27 | 0.069 | 106.11 |

TABLE 2-continued

A list of 2087 candidate endogenous reference genes

| | | | | | | |
|---|---|---|---|---|---|---|
| 518346 | SSR3 | Signal sequence receptor, gamma (translocon-associated protein gamma) | 133.69 | 62.65 | 0.241 | 92.36 |
| 518374 | QSOX1 | Quiescin Q6 sulfhydryl oxidase 1 | 151.71 | 84.80 | 0.310 | 145.16 |
| 518424 | NDUFB5 | NADH dehydrogenase (ubiquinone) 1 beta subcomplex, 5, 16 kDa | 625.19 | 180.45 | 0.276 | 63.18 |
| 518460 | AP2M1 | Adaptor-related protein complex 2, mu 1 subunit | 584.10 | 76.35 | 0.069 | 110.88 |
| 518464 | PSMD2 | Proteasome (prosome, macropain) 26S subunit, non-ATPase. 2 | 538.23 | 93.02 | 0.103 | 173.46 |
| 518525 | GLUL | Glutamate-ammonia ligase (glutamine synthetase) | 326.37 | 86.68 | 0.138 | 580.48 |
| 518551 | RPL31 | Ribosomal protein L31 | 883.50 | 204.46 | 0.103 | 1315.12 |
| 518608 | MRFAP1L1 | Morf4 family associated protein 1-like 1 | 107.24 | 53.27 | 0.172 | 87.02 |
| 518609 | ARPC5 | Actin related protein 2/3 complex, subunit 5, 16 kDa | 226.65 | 65.59 | 0.172 | 86.13 |
| 518750 | OCIAD1 | OCIA domain containing 1 | 121.73 | 78.62 | 0.172 | 557.63 |
| 518805 | HMGA1 | High mobility group AT-hook 1 | 1583.57 | 131.69 | 0.172 | 519.78 |
| 518827 | CCNI | Cyclin I | 495.99 | 157.57 | 0.034 | 378.10 |
| 519276 | MAPKAPK2 | Mitogen-activated protein kinase-activated protein kinase 2 | 172.89 | 87.16 | 0.172 | 110.38 |
| 519304 | PELO | Pelota homolog (*Drosophila*) | 204.10 | 151.63 | 0.310 | 91.66 |
| 519346 | ERBB2IP | Erbb2 interacting protein | 171.05 | 83.90 | 0.241 | 52.83 |
| 519347 | SFRS12 | Splicing factor. arginine/serine-rich 12 | 99.98 | 49.97 | 0.310 | 53.48 |
| 519520 | RPS25 | Ribosomal protein S25 | 717.45 | 181.09 | 0.034 | 1253.26 |
| 519523 | SERPINB6 | Serpin peptidase inhibitor, clade B (ovalbumin). member 6 | 180.64 | 74.06 | 0.172 | 97.35 |
| 519557 | TMEM14C | Transmembrane protein 14C | 139.62 | 70.39 | 0.276 | 71.79 |
| 519718 | TTC1 | Tetratricopeptide repeat domain 1 | 119.41 | 63.74 | 0.276 | 51.02 |
| 519756 | STK10 | Serine/threonine kinase 10 | 131.85 | 89.36 | 0.379 | 33.36 |
| 519818 | MGAT1 | Mannosyl (alpha-1,3-)-glycoprotein beta-1,2-N-acetylglucosaminyltransferase | 179.60 | 85.97 | 0.138 | 124.43 |
| 519909 | MARCKS | Myristoylated alanine-rich protein kinase C substrate | 360.12 | 219.46 | 0.310 | 315.50 |
| 519930 | C6orf62 | Chromosome 6 open reading frame 62 | 131.39 | 63.83 | 0.138 | 140.39 |
| 520026 | VARS2 | Valyl-tRNA synthetase | 317.40 | 77.78 | 0.241 | 122.24 |
| 520028 | HSPA1A | Heat shock 70 kDa protein 1A | 267.63 | 174.20 | 0.241 | 697.50 |
| 520037 | NEU1 | Sialidase 1 (lysosomal sialidase) | 229.35 | 119.62 | 0.310 | 108.45 |
| 520070 | CUTA | CutA divalent cation tolerance homolog (*E. coli*) | 154.48 | 68.26 | 0.207 | 234.43 |
| 520140 | SRF | Serum response factor (c-fos serum response element-binding transcription factor) | 130.75 | 59.73 | 0.379 | 78.21 |
| 520189 | ELOVL5 | ELOVL family member 5. elongation of long chain fatty acids (FEN1/Elo2, SUR4/Elo3-like, yeast) | 137.81 | 70.07 | 0.276 | 92.84 |
| 520205 | EIF2AK1 | Eukaryotic translation initiation factor 2-alpha kinase 1 | 238.20 | 66.39 | 0.138 | 137.26 |
| 520210 | KDELR2 | KDEL (Lys-Asp-Glu-Leu) endoplasmic reticulum protein retention receptor 2 | 225.97 | 94.83 | 0.138 | 163.28 |
| 520287 | C6orf111 | Chromosome 6 open reading frame 111 | 170.77 | 69.67 | 0.207 | 51.33 |
| 520313 | CD164 | CD164 antigen. sialomucin | 387.43 | 78.65 | 0.172 | 179.75 |
| 520383 | STX7 | Syntaxin 7 | 200.61 | 198.70 | 0.379 | 62.05 |
| 520421 | PERP | PERP. TP53 apoptosis effector | 278.10 | 105.31 | 0.379 | 142.93 |
| 520459 | GTF2I | General transcription factor II. i | 179.36 | 111.40 | 0.345 | 291.72 |
| 520623 | C7orf27 | Chromosome 7 open reading frame 27 | 107.46 | 71.73 | 0.345 | 33.85 |
| 520640 | ACTB | Actin, beta | 4381.34 | 95.98 | 0.034 | 1348.49 |
| 520740 | SCRN1 | Secernin 1 | 162.41 | 76.80 | 0.276 | 116.36 |
| 520794 | YKT6 | SNARE protein Ykt6 | 322.61 | 99.65 | 0.276 | 50.36 |
| 520898 | CTSB | Cathepsin B | 555.78 | 100.98 | 0.034 | 454.52 |
| 520943 | EIF4H | Eukaryotic translation initiation factor 4H | 520.03 | 71.02 | 0.069 | 219.24 |
| 520967 | MDH2 | Malate dehydrogenase 2, NAD (mitochondrial) | 368.83 | 66.26 | 0.069 | 186.05 |
| 520973 | HSPB1 | Heat shock 27 kDa protein 1 | 608.95 | 126.99 | 0.138 | 466.81 |
| 520974 | YWHAG | Tyrosine 3-monooxygenase/tryptophan 5-monooxygenase activation protein, gamma polypeptide | 171.99 | 87.92 | 0.310 | 260.44 |
| 521064 | ZNF655 | Zinc finger protein 655 | 100.31 | 68.90 | 0.379 | 78.88 |
| 521151 | ZNF672 | Zinc finger protein 672 | 185.36 | 113.36 | 0.310 | 46.43 |
| 521289 | REPIN1 | Replication initiator 1 | 220.03 | 101.31 | 0.172 | 86.72 |
| 521487 | TMEM66 | Transmembrane protein 66 | 276.62 | 74.21 | 0.138 | 363.27 |
| 521640 | RAD23B | RAD23 homolog B (*S. cerevisiae*) | 334.78 | 294.31 | 0.241 | 1470.83 |
| 521809 | RP13-122B23.3 | Cofactor of BRCA1 | 180.78 | 84.61 | 0.172 | 78.57 |
| 521903 | LY6E | Lymphocyte antigen 6 complex, locus E | 425.61 | 138.70 | 0.172 | 224.92 |
| 521924 | SIAHBP1 | Fuse-binding protein-interacting repressor | 381.93 | 82.10 | 0.103 | 89.56 |
| 521969 | NDUFB11 | NADH dehydrogenase (ubiquinone) 1 beta subcomplex, 11. 17.3 kDa | 144.58 | 114.75 | 0.379 | 136.30 |
| 521973 | WDR13 | WD repeat domain 13 | 177.47 | 106.14 | 0.172 | 49.95 |
| 522074 | TSC22D3 | TSC22 domain family, member 3 | 194.82 | 93.94 | 0.207 | 98.72 |
| 522110 | CREB3 | CAMP responsive element binding protein 3 | 153.05 | 94.31 | 0.241 | 42.72 |
| 522114 | CLTA | Clathrin, light polypeptide (Lca) | 317.85 | 88.44 | 0.103 | 155.26 |
| 522310 | NANS | N-acetylneuraminic acid synthase (sialic acid synthase) | 114.60 | 62.52 | 0.310 | 91.19 |
| 522373 | GSN | Gelsolin (amyloidosis. Finnish type) | 434.41 | 204.85 | 0.138 | 323.96 |
| 522394 | HSPA5 | Heat shock 70 kDa protein 5 (glucose-regulated protein. 78 kDa) | 367.53 | 102.24 | 0.172 | 784.29 |
| 522463 | EEF1A1 | Eukaryotic translation elongation factor 1 alpha 1 | 9324.87 | 148.86 | 0.000 | 3936.86 |
| 522507 | FBXW5 | F-box and WD-40 domain protein 5 | 199.15 | 90.48 | 0.276 | 108.16 |
| 522584 | TMSB4X | Thymosin, beta 4, X-linked | 1362.45 | 161.68 | 0.172 | 1985.02 |
| 522590 | EIF1AX | Eukaryotic translation initiation factor 1A. X-linked | 136.35 | 67.99 | 0.207 | 125.35 |
| 522632 | TIMP1 | TIMP metallopeptidase inhibitor 1 | 386.91 | 180.87 | 0.241 | 193.45 |
| 522665 | MAGED2 | Melanoma antigen family D, 2 | 430.71 | 110.49 | 0.138 | 74.89 |
| 522675 | LAS1L | LAS1-like (*S. cerevisiae*) | 201.59 | 69.13 | 0.241 | 56.35 |
| 522752 | PSMD10 | Proteasome (prosome. macropain) 26S subunit, non-ATPase, 10 | 122.91 | 60.90 | 0.276 | 74.90 |

TABLE 2-continued

A list of 2087 candidate endogenous reference genes

| | | | | | | |
|---|---|---|---|---|---|---|
| 522817 | BCAP31 | B-cell receptor-associated protein 31 | 290.93 | 84.50 | 0.172 | 110.80 |
| 522819 | IRAK1 | Interleukin-1 receptor-associated kinase 1 | 382.94 | 97.80 | 0.138 | 147.41 |
| 522823 | EMD | Emerin (Emery-Dreifuss muscular dystrophy) | 171.35 | 87.58 | 0.379 | 89.83 |
| 522932 | NCOA4 | Nuclear receptor coactivator 4 | 209.19 | 70.05 | 0.138 | 63.66 |
| 522995 | EIF4EBP2 | Eukaryotic translation initiation factor 4E binding protein 2 | 176.81 | 73.83 | 0.103 | 72.69 |
| 523004 | PSAP | Prosaposin (variant Gaucher disease and variant metachromatic leukodystrophy) | 1098.27 | 123.65 | 0.034 | 854.93 |
| 523012 | DDIT4 | DNA-damage-inducible transcript 4 | 415.15 | 125.10 | 0.276 | 174.92 |
| 523054 | TMEM50A | Transmembrane protein 50A | 139.64 | 109.41 | 0.276 | 109.08 |
| 523131 | TRAPPC3 | Trafficking protein particle complex 3 | 139.68 | 66.61 | 0.310 | 61.64 |
| 523145 | DDOST | Dolichyl-diphosphooligosaccharide-protein glycosyltransferase | 338.02 | 90.17 | 0.103 | 119.03 |
| 523215 | NDUFB8 | NADH dehydrogenase (ubiquinone) 1 beta subcomplex, 8. 19 kDa | 199.51 | 106.37 | 0.172 | 132.65 |
| 523238 | NOLC1 | Nucleolar and coiled-body phosphoprotein 1 | 176.02 | 83.34 | 0.138 | 97.37 |
| 523262 | TMEM59 | Transmembrane protein 59 | 262.49 | 95.63 | 0.069 | 168.88 |
| 523299 | EIF3S10 | Eukaryotic translation initiation factor 3, subunit 10 theta. 150/170 kDa | 180.25 | 76.56 | 0.172 | 112.29 |
| 523302 | PRDX3 | Peroxiredoxin 3 | 948.84 | 182.31 | 0.138 | 83.94 |
| 523560 | HSP90AA2 | Heat shock protein 90 kDa alpha (cytosolic), class A member 2 | 971.87 | 81.16 | 0.000 | 822.83 |
| 523680 | SSRP1 | Structure specific recognition protein 1 | 259.94 | 67.23 | 0.138 | 128.11 |
| 523789 | TncRNA | Trophoblast-derived noncoding RNA | 290.76 | 109.38 | 0.310 | 400.45 |
| 523829 | POLD4 | Polymerase (DNA-directed), delta 4 | 192.79 | 92.64 | 0.310 | 73.03 |
| 523836 | GSTP1 | Glutathione S-transferase pi | 363.83 | 79.45 | 0.103 | 390.11 |
| 523852 | CCND1 | Cyclin D1 | 257.94 | 79.21 | 0.310 | 315.81 |
| 523875 | INPPL1 | Inositol polyphosphate phosphatase-like 1 | 198.48 | 82.78 | 0.310 | 52.62 |
| 524009 | AASDHPPT | Aminoadipate-semialdehyde dehydrogenase-phosphopantetheiny transferase | 139.83 | 74.10 | 0.345 | 73.36 |
| 524081 | DPAGT1 | Dolichyl-phosphate (UDP-N-acetylglucosamine) N-acetylglucosaminephosphotransferase 1 (GlcNAc-1-P transferase | 125.85 | 78.99 | 0.345 | 43.70 |
| 524084 | RNF26 | Ring finger protein 26 | 170.50 | 95.60 | 0.310 | 45.76 |
| 524161 | RSU1 | Ras suppressor protein 1 | 173.91 | 80.13 | 0.276 | 81.94 |
| 524171 | RAD52 | RAD52 homolog (S. cerevisiae) | 128.36 | 73.88 | 0.345 | 57.90 |
| 524183 | FKBP4 | FK506 binding protein 4, 59 kDa | 345.04 | 165.12 | 0.138 | 195.27 |
| 524195 | ARHGAP2 | Rho GTPase activating protein 21 | 118.87 | 87.10 | 0.379 | 102.62 |
| 524214 | MLF2 | Myeloid leukemia factor 2 | 271.91 | 68.75 | 0.138 | 109.61 |
| 524219 | TPI1 | Triosephosphate isomerase 1 | 1085.58 | 88.77 | 0.069 | 928.11 |
| 524271 | PHC2 | Polyhomeotic-like 2 (Drosophila) | 333.79 | 105.07 | 0.138 | 59.03 |
| 524367 | CBARA1 | Calcium binding atopy-related autoantigen 1 | 133.75 | 65.29 | 0.207 | 95.25 |
| 524395 | TUBA1A | Tubulin, alpha 1a | 423.08 | 127.26 | 0.241 | 779.97 |
| 524464 | ATP5G2 | ATP synthase, H+ transporting. mitochondrial F0 complex, subunit c (subunit 9), isoform 2 | 300.01 | 124.98 | 0.172 | 295.35 |
| 524502 | RNF41 | Ring finger protein 41 | 110.38 | 68.59 | 0.241 | 55.12 |
| 524530 | CTDSP2 | CTD (carboxy-terminal domain, RNA polymerase II. polypeptide A small phosphatase 2 | 286.91 | 136.97 | 0.103 | 54.40 |
| 524590 | RAB21 | RAB21, member RAS oncogene family | 112.13 | 48.40 | 0.379 | 39.33 |
| 524599 | NAP1L1 | 60S ribosomal protein L6 (RPL6A) | 559.97 | 99.14 | 0.034 | 179.39 |
| 524690 | PPIE | Peptidylprolyl isomerase E (cyclophilin E) | 224.33 | 109.34 | 0.207 | 60.86 |
| 524788 | RAB35 | RAB35, member RAS oncogene family | 97.18 | 65.96 | 0.379 | 47.40 |
| 524809 | CLIP1 | CAP-GLY domain containing linker protein 1 | 121.91 | 90.76 | 0.345 | 71.42 |
| 524899 | SAP18 | Sin3-associated polypeptide, 18 kDa | 129.03 | 72.41 | 0.172 | 89.47 |
| 524920 | ZFP91 | Zinc finger protein 91 homolog (mouse) | 126.10 | 83.51 | 0.207 | 99.40 |
| 524969 | UFM1 | Ubiquitin-fold modifier 1 | 172.41 | 84.47 | 0.310 | 85.23 |
| 525134 | POMGNT1 | Protein O-linked mannose beta1,2-N-acetylglucosaminyltransferase | 161.82 | 102.74 | 0.345 | 77.25 |
| 525163 | ANKRD10 | Ankyrin repeat domain 10 | 156.22 | 79.59 | 0.207 | 92.10 |
| 525232 | LRP10 | Low density lipoprotein receptor-related protein 10 | 201.98 | 129.16 | 0.138 | 71.88 |
| 525238 | C14orf119 | Chromosome 14 open reading frame 119 | 141.96 | 104.26 | 0.276 | 130.29 |
| 525330 | ARF6 | ADP-ribosylation factor 6 | 191.66 | 134.63 | 0.103 | 129.69 |
| 525391 | C1orf123 | Chromosome 1 open reading frame 123 | 98.24 | 87.20 | 0.310 | 44.15 |
| 525527 | RER1 | RER1 retention in endoplasmic reticulum 1 homolog (S. cerevisiae) | 137.56 | 72.32 | 0.310 | 57.33 |
| 525626 | PACS2 | Phosphofurin acidic cluster sorting protein 2 | 126.74 | 98.42 | 0.345 | 36.14 |
| 525899 | C6orf49 | Chromosome 6 open reading frame 49 | 144.67 | 83.87 | 0.172 | 114.56 |
| 526464 | PML | Promyelocytic leukemia | 129.51 | 84.95 | 0.345 | 75.33 |
| 526521 | MDH1 | Malate dehydrogenase 1, NAD (soluble) | 414.98 | 150.61 | 0.103 | 302.75 |
| 527105 | HNRPDL | Heterogeneous nuclear ribonucleoprotein D-like | 215.39 | 95.16 | 0.207 | 425.77 |
| 527193 | RPS23 | Ribosomal protein S23 | 178.23 | 128.51 | 0.207 | 1153.32 |
| 527348 | AKAP9 | A kinase (PRKA) anchor protein (Yotiao) 9 | 103.64 | 60.76 | 0.310 | 39.34 |
| 527412 | ASAH1 | N-acylsphingosine amidohydrolase (acid ceramidase) 1 | 216.47 | 95.28 | 0.241 | 124.23 |
| 527861 | OS9 | Amplified in osteosarcoma | 317.55 | 151.86 | 0.138 | 157.27 |
| 527862 | PKD1 | Hypothetical protein LOC339047 | 142.25 | 87.72 | 0.345 | 135.27 |
| 527980 | DUT | DUTP pyrophosphatase | 150.77 | 79.02 | 0.207 | 96.02 |
| 528050 | HARS | Histidyl-tRNA synthetase | 171.62 | 84.32 | 0.138 | 39.25 |
| 528222 | NDUFS4 | NADH dehydrogenase (ubiquinone) Fe—S protein 4. 18 kDa (NADH-coenzyme Q reductase) | 112.10 | 94.04 | 0.276 | 72.79 |
| 528300 | PITRM1 | Pitrilysin metallopeptidase 1 | 122.00 | 61.07 | 0.276 | 46.35 |
| 528305 | DDX17 | DEAD (Asp-Glu-Ala-Asp) box polypeptide 17 | 298.20 | 91.95 | 0.138 | 235.95 |
| 528572 | SORBS3 | Sorbin and SH3 domain containing 3 | 187.70 | 104.57 | 0.345 | 62.31 |
| 528668 | RPL6 | Ribosomal protein L6 | 1037.68 | 85.03 | 0.034 | 572.62 |

TABLE 2-continued

A list of 2087 candidate endogenous reference genes

| 528780 | GSPT1 | G1 to S phase transition 1 | 170.88 | 56.71 | 0.138 | 73.97 |
|---|---|---|---|---|---|---|
| 528803 | UQCRC2 | Ubiquinol-cytochrome c reductase core protein II | 272.39 | 84.82 | 0.103 | 118.93 |
| 529059 | EIF3S4 | Eukaryotic translation initiation factor 3, subunit 4 delta. 44 kDa | 311.33 | 92.44 | 0.172 | 112.54 |
| 529132 | SEPW1 | Selenoprotein W. 1 | 231.08 | 110.89 | 0.276 | 115.82 |
| 529244 | NCK2 | NCK adaptor protein 2 | 236.70 | 169.13 | 0.345 | 42.17 |
| 529280 | ANAPC7 | Anaphase promoting complex subunit 7 | 94.04 | 52.31 | 0.379 | 51.63 |
| 529303 | ARPC2 | Actin related protein 2/3 complex, subunit 2. 34 kDa | 329.77 | 127.35 | 0.034 | 204.04 |
| 529369 | AFAP1 | Actin filament associated protein 1 | 101.03 | 56.96 | 0.379 | 54.85 |
| 529400 | IFNAR1 | Interferon (alpha, beta and omega) receptor 1 | 108.71 | 56.53 | 0.310 | 76.16 |
| 529420 | UBE2G2 | Ubiquitin-conjugating enzyme E2G 2 (UBC7 homolog, yeast) | 160.64 | 100.65 | 0.103 | 928.90 |
| 529591 | TLOC1 | Translocation protein 1 | 141.82 | 65.80 | 0.172 | 80.62 |
| 529618 | TFRC | Transferrin receptor (p90, CD71) | 212.76 | 85.52 | 0.241 | 89.51 |
| 529631 | RPL35A | Ribosomal protein L35a | 453.58 | 173.13 | 0.103 | 891.99 |
| 529782 | VCP | Valosin-containing protein | 532.58 | 85.03 | 0.034 | 173.75 |
| 529798 | BTF3 | Basic transcription factor 3 | 400.11 | 94.96 | 0.069 | 270.43 |
| 529862 | CSNK1A1 | Casein kinase 1. alpha 1 | 210.72 | 69.09 | 0.103 | 102.92 |
| 529890 | CANX | Calnexin | 399.31 | 129.28 | 0.069 | 448.92 |
| 529892 | SQSTM1 | Sequestosome 1 | 789.12 | 108.86 | 0.034 | 194.96 |
| 529957 | SEC63 | SEC63-like (*S. cerevisiae*) | 120.12 | 80.80 | 0.276 | 70.58 |
| 530096 | EIF3S2 | Eukaryotic translation initiation factor 3. subunit 2 beta. 36 kDa | 451.94 | 86.61 | 0.034 | 284.86 |
| 530118 | LUC7L2 | LUC7-like 2 (*S. cerevisiae*) | 132.76 | 59.55 | 0.172 | 74.65 |
| 530291 | ANXA11 | Annexin A11 | 279.25 | 86.71 | 0.069 | 75.64 |
| 530314 | SSNA1 | Sjogren's syndrome nuclear autoantigen 1 | 122.20 | 58.54 | 0.379 | 75.26 |
| 530331 | PDHA1 | Pyruvate dehydrogenase (lipoamide) alpha 1 | 179.99 | 79.37 | 0.207 | 104.89 |
| 530381 | PIM3 | Pim-3 oncogene | 114.61 | 72.86 | 0.345 | 42.02 |
| 530412 | SERBP1 | SERPINE1 mRNA binding protein 1 | 289.56 | 66.47 | 0.069 | 569.26 |
| 530436 | STXBP3 | Syntaxin binding protein 3 | 113.84 | 77.40 | 0.276 | 71.84 |
| 530479 | PMF1 | Polyamine-modulated factor 1 | 128.35 | 73.53 | 0.241 | 60.22 |
| 530687 | RNH1 | Ribonuclease/angiogenin inhibitor 1 | 342.47 | 102.27 | 0.172 | 126.29 |
| 530734 | MRPL16 | Mitochondrial ribosomal protein L16 | 106.22 | 67.89 | 0.345 | 48.51 |
| 530753 | C11orf59 | Chromosome 11 open reading frame 59 | 153.75 | 63.46 | 0.276 | 132.79 |
| 530823 | COPS7A | COP9 constitutive photomorphogenic homolog subunit 7A (*Arabidopsis*) | 202.70 | 132.83 | 0.138 | 52.43 |
| 530862 | PRKAG1 | Protein kinase. AMP-activated. gamma 1 non-catalytic subunit | 136.75 | 73.16 | 0.241 | 38.26 |
| 531081 | LGALS3 | Lectin. galactoside-binding. soluble. 3 (galectin 3) | 318.01 | 134.08 | 0.241 | 403.19 |
| 531089 | PSMA3 | Proteasome (prosome. macropain) subunit. alpha type. 3 | 218.40 | 93.16 | 0.276 | 54.35 |
| 531176 | SARS | Seryl-tRNA synthetase | 297.55 | 88.08 | 0.138 | 137.35 |
| 531330 | CBWD1 | COBW domain containing 2 | 123.09 | 79.22 | 0.310 | 125.23 |
| 531614 | BTBD14B | BTB (POZ) domain containing 14B | 123.09 | 63.39 | 0.310 | 79.33 |
| 531752 | RANBP3 | RAN binding protein 3 | 122.49 | 64.65 | 0.310 | 44.32 |
| 531856 | GAS5 | Growth arrest-specific 5 | 227.80 | 134.55 | 0.241 | 609.96 |
| 531876 | DYNLRB1 | Dynein, light chain, roadblock-type 1 | 167.51 | 104.22 | 0.241 | 122.79 |
| 531879 | RAD1 | RAD1 homolog (*S. pombe*) | 115.15 | 74.02 | 0.379 | 58.80 |
| 532359 | RPL5 | Ribosomal protein L5 | 747.39 | 72.96 | 0.000 | 682.59 |
| 532399 | ZC3H11A | Zinc finger CCCH-type containing 11A | 139.50 | 74.48 | 0.241 | 64.34 |
| 532755 | C16orf80 | Chromosome 16 open reading frame 80 | 95.17 | 63.38 | 0.207 | 37.29 |
| 532790 | NMT1 | N-myristoyltransferase 1 | 165.97 | 105.96 | 0.172 | 94.43 |
| 532793 | KPNB1 | Karyopherin (importin) beta 1 | 568.92 | 129.62 | 0.000 | 88.10 |
| 532803 | HN1 | Hematological and neurological expressed 1 | 225.82 | 90.89 | 0.103 | 218.39 |
| 532826 | MCL1 | Myeloid cell leukemia sequence 1 (BCL2-related) | 252.48 | 83.80 | 0.207 | 221.93 |
| 532853 | NDUFB7 | NADH dehydrogenase (ubiquinone) 1 beta subcomplex, 7, 18 kDa | 145.80 | 84.03 | 0.345 | 150.66 |
| 533030 | TRIOBP | TRIO and F-actin binding protein | 339.95 | 148.19 | 0.207 | 108.55 |
| 533059 | TUBB | Tubulin, beta polypeptide | 2476.41 | 87.07 | 0.000 | 423.10 |
| 533122 | SFRS10 | Splicing factor, arginine/serine-rich 10 (transformer 2 homolog, *Drosophila*) | 182.52 | 60.97 | 0.034 | 111.10 |
| 533136 | LRPAP1 | Low density lipoprotein receptor-related protein associated protein 1 | 234.76 | 108.38 | 0.207 | 119.75 |
| 533192 | TOMM20 | Translocase of outer mitochondrial membrane 20 homolog (yeast) | 208.87 | 77.43 | 0.138 | 133.51 |
| 533222 | DIMT1L | DIM1 dimethyladenosine transferase 1-like (*S. cerevisiae*) | 129.17 | 69.14 | 0.379 | 42.41 |
| 533245 | DDX46 | DEAD (Asp-Glu-Ala-Asp) box polypeptide 46 | 118.53 | 50.97 | 0.345 | 51.51 |
| 533282 | NONO | Non-POU domain containing. octamer-binding | 842.92 | 104.94 | 0.034 | 184.07 |
| 533308 | PPP2R5D | Protein phosphatase 2. regulatory subunit B (B56). delta isoform | 223.23 | 100.62 | 0.138 | 47.46 |
| 533317 | VIM | Vimentin | 1800.81 | 137.19 | 0.069 | 658.72 |
| 533437 | TCEB1 | Transcription elongation factor B (SIII). polypeptide 1 (15 kDa. elongin C) | 121.08 | 94.03 | 0.276 | 103.33 |
| 533440 | WWP1 | WW domain containing E3 ubiquitin protein ligase 1 | 146.51 | 87.93 | 0.345 | 60.09 |
| 533474 | PPP1R8 | Protein phosphatase 1, regulatory (inhibitor) subunit 8 | 95.08 | 118.26 | 0.379 | 50.60 |
| 533479 | LYPLA2 | Lysophospholipase II | 223.79 | 59.26 | 0.276 | 107.17 |
| 533526 | ATRX | Alpha thalassemia/mental retardation syndrome X-linked (RAD54 homolog, *S. cerevisiae*) | 149.83 | 61.38 | 0.276 | 73.22 |
| 533624 | H3F3A | H3 histone. family 3A | 322.44 | 81.23 | 0.103 | 986.85 |
| 533712 | RBM4 | RNA binding motif protein 4 | 169.22 | 66.18 | 0.138 | 54.47 |
| 533732 | SRP14 | Signal recognition particle 14 kDa (homologous Alu RNA binding protein) | 223.87 | 85.87 | 0.172 | 350.32 |
| 533771 | STUB1 | STIP1 homology and U-box containing protein 1 | 238.45 | 84.03 | 0.241 | 74.01 |
| 533782 | KRT8 | Keratin 8 | 1307.25 | 94.61 | 0.379 | 1096.00 |
| 533977 | TXNIP | Thioredoxin interacting protein | 429.73 | 92.27 | 0.034 | 105.46 |
| 533985 | EXOC7 | Exocyst complex component 7 | 168.92 | 93.23 | 0.276 | 83.81 |

TABLE 2-continued

A list of 2087 candidate endogenous reference genes

| | | | | | | |
|---|---|---|---|---|---|---|
| 533986 | ZMYM6 | Zinc finger, MYM-type 6 | 99.16 | 62.99 | 0.310 | 42.97 |
| 534125 | HLA-C | Major histocompatibility complex. class I. C | 610.10 | 155.80 | 0.034 | 477.32 |
| 534168 | NDUFA1 | NADH dehydrogenase (ubiquinone) 1 alpha subcomplex. 1, 7.5 kDa | 261.51 | 202.07 | 0.310 | 304.79 |
| 534212 | SEC22B | SEC22 vesicle trafficking protein homolog B (*S. cerevisiae*) | 107.96 | 68.79 | 0.379 | 57.75 |
| 534255 | B2M | Beta-2-microglobulin | 1303.98 | 172.16 | 0.000 | 2594.12 |
| 534307 | CCND3 | Cyclin D3 | 471.76 | 356.89 | 0.207 | 49.64 |
| 534314 | EIF5A | Eukaryotic translation initiation factor 5A | 438.38 | 88.29 | 0.207 | 745.09 |
| 534326 | ITGB4BP | Integrin beta 4 binding protein | 360.06 | 78.91 | 0.103 | 132.91 |
| 534338 | PPP4C | Protein phosphatase 4 (formerly X). catalytic subunit | 191.52 | 75.42 | 0.138 | 85.04 |
| 534346 | RPS7 | Ribosomal protein S7 | 572.81 | 120.27 | 0.000 | 458.06 |
| 534350 | SMARCB1 | SWI/SNF related, matrix associated, actin dependent regulator of chromatin. subfamily b. member 1 | 210.96 | 162.57 | 0.172 | 56.06 |
| 534453 | NDUFA13 | NADH dehydrogenase (ubiquinone) 1 alpha subcomplex. 13 | 194.91 | 119.87 | 0.138 | 355.30 |
| 534456 | ANAPC11 | APC11 anaphase promoting complex subunit 11 homolog (yeast) | 164.01 | 99.17 | 0.172 | 159.17 |
| 534457 | C14orf166 | Chromosome 14 open reading frame 166 | 171.37 | 66.04 | 0.138 | 73.01 |
| 534473 | TOMM22 | Translocase of outer mitochondrial membrane 22 homolog (yeast) | 144.72 | 100.10 | 0.207 | 64.20 |
| 534483 | PHF23 | PHD finger protein 23 | 123.34 | 63.04 | 0.276 | 43.74 |
| 536275 | PACS1 | Phosphofurin acidic cluster sorting protein 1 | 217.82 | 86.00 | 0.345 | 46.64 |
| 541269 | NDUFB9 | NADH dehydrogenase (ubiquinone) 1 beta subcomplex, 9. 22 kDa | 269.72 | 132.31 | 0.172 | 420.59 |
| 546248 | CTSD | Cathepsin D (lysosomal aspartyl peptidase) | 660.73 | 119.52 | 0.103 | 104.98 |
| 546250 | DYNC1I2 | Dynein. cytoplasmic 1, intermediate chain 2 | 154.54 | 71.13 | 0.172 | 166.85 |
| 546253 | FDFT1 | Farnesyl-diphosphate farnesyltransferase 1 | 249.53 | 81.90 | 0.034 | 124.83 |
| 546261 | HNRPA1 | Heterogeneous nuclear ribonucleoprotein A1 | 649.46 | 94.55 | 0.000 | 470.61 |
| 546269 | RPL10A | Ribosomal protein L10a | 706.14 | 175.46 | 0.103 | 1748.03 |
| 546271 | PCBP2 | Poly(rC) binding protein 2 | 293.34 | 87.15 | 0.103 | 451.52 |
| 546286 | RPS3 | Ribosomal protein S3 | 2290.81 | 95.60 | 0.000 | 1021.82 |
| 546289 | RPS12 | Ribosomal protein S12 | 527.74 | 281.85 | 0.103 | 1459.28 |
| 546290 | RPS18 | Ribosomal protein S18 | 939.29 | 233.81 | 0.069 | 1853.80 |
| 546291 | RPS27 | Ribosomal protein S27 (metallopanstimulin 1) | 725.59 | 382.56 | 0.172 | 55.70 |
| 546339 | C11orf58 | Chromosome 11 open reading frame 58 | 580.69 | 190.75 | 0.138 | 99.65 |
| 546356 | RPL13A | Ribosomal protein L13a | 1352.43 | 84.32 | 0.000 | 3663.74 |
| 546394 | CCDC72 | Coiled-coil domain containing 72 | 244.28 | 200.01 | 0.241 | 175.77 |
| 547759 | SSBP3 | Single stranded DNA binding protein 3 | 124.35 | 57.76 | 0.310 | 76.79 |
| 549178 | C9orf86 | Chromosome 9 open reading frame 86 | 219.13 | 114.79 | 0.138 | 106.75 |
| 552590 | HTF9C | HpaII tiny fragments locus 9C | 107.24 | 77.34 | 0.276 | 37.92 |
| 553496 | PGM3 | Phosphoglucomutase 3 | 103.08 | 61.39 | 0.379 | 48.42 |
| 553512 | MBOAT5 | Membrane bound O-acyltransferase domain containing 5 | 124.81 | 75.10 | 0.310 | 81.43 |
| 554767 | NUP88 | Nucleoporin 88 kDa | 120.01 | 86.75 | 0.345 | 41.31 |
| 554776 | SREBF1 | Sterol regulatory element binding transcription factor 1 | 171.91 | 88.02 | 0.276 | 65.79 |
| 554894 | WDR54 | WD repeat domain 54 | 114.62 | 72.99 | 0.345 | 48.56 |
| 554896 | C7orf50 | Chromosome 7 open reading frame 50 | 193.18 | 101.69 | 0.207 | 156.46 |
| 555194 | FAM36A | Family with sequence similarity 36, member A | 120.40 | 52.67 | 0.276 | 115.74 |
| 555866 | C1QBP | Complement component 1. q subcomponent binding protein | 312.33 | 77.95 | 0.138 | 179.94 |
| 555873 | HNRPAB | Heterogeneous nuclear ribonucleoprotein A/B | 316.21 | 89.74 | 0.034 | 87.52 |
| 555875 | IDH3A | Isocitrate dehydrogenase 3 (NAD+) alpha | 143.01 | 87.51 | 0.345 | 43.03 |
| 555889 | PSMC2 | Proteasome (prosome, macropain) 26S subunit. ATPase, 2 | 219.37 | 69.24 | 0.172 | 67.04 |
| 555890 | RBBP4 | Retinoblastoma binding protein 4 | 204.72 | 80.47 | 0.172 | 148.13 |
| 555911 | RBM8A | RNA binding motif protein 8A | 125.26 | 75.03 | 0.172 | 110.86 |
| 555969 | RIC8A | Resistance to inhibitors of cholinesterase 8 homolog A (*C. elegans*) | 261.31 | 93.56 | 0.172 | 42.50 |
| 555971 | TMBIM1 | Transmembrane BAX inhibitor motif containing | 219.28 | 114.17 | 0.207 | 100.55 |
| 555973 | MRPS25 | Mitochondrial ribosomal protein S25 | 152.15 | 62.00 | 0.207 | 47.22 |
| 555994 | LONP2 | Ion peptidase 2. peroxisomal | 135.95 | 87.69 | 0.379 | 37.87 |
| 556267 | FBXL10 | F-box and leucine-rich repeat protein 10 | 81.84 | 65.86 | 0.379 | 39.65 |
| 556461 | NDUFV2 | NADH dehydrogenase (ubiquinone) flavoprotein 2. 24 kDa | 146.86 | 108.59 | 0.207 | 99.23 |
| 556795 | PAICS | Phosphoribosylaminoimidazole carboxylase. phosphoribosylaminoimidazole succinocarboxamide synthetase | 253.76 | 89.34 | 0.138 | 122.76 |
| 557550 | NPM1 | Nucleophosmin (nucleolar phosphoprotein B23, numatrin) | 1675.95 | 168.64 | 0.000 | 707.78 |
| 558296 | ACP1 | Acid phosphatase 1, soluble | 123.31 | 58.79 | 0.172 | 76.31 |
| 558313 | COX6A1 | Cytochrome c oxidase subunit VIa polypeptide 1 | 170.58 | 93.53 | 0.241 | 268.12 |
| 558322 | EEF1B2 | Eukaryotic translation elongation factor 1 beta 2 | 450.71 | 94.79 | 0.034 | 725.93 |
| 558325 | EIF5 | Eukaryotic translation initiation factor 5 | 232.38 | 85.09 | 0.172 | 121.20 |
| 558328 | FKBP5 | FK506 binding protein 5 | 117.84 | 59.52 | 0.310 | 88.77 |
| 558330 | FTL | Ferritin, light polypeptide | 2521.41 | 158.72 | 0.069 | 1268.35 |
| 558338 | HSPE1 | Heat shock 10 kDa protein 1 (chaperonin 10) | 270.37 | 133.18 | 0.207 | 259.73 |
| 558345 | IK | IK cytokine, down-regulator of HLA II | 252.13 | 99.25 | 0.138 | 52.12 |
| 558354 | RPSA | Ribosomal protein SA | 1322.76 | 86.38 | 0.034 | 2215.71 |
| 558360 | NDUFB4 | NADH dehydrogenase (ubiquinone) 1 beta subcomplex, 4, 15 kDa | 211.99 | 145.77 | 0.345 | 213.80 |
| 558361 | NME2 | Non-metastatic cells 2, protein (NM23B) expressed in | 300.76 | 113.65 | 0.276 | 377.22 |
| 558362 | NUMA1 | Nuclear mitotic apparatus protein 1 | 186.63 | 72.04 | 0.207 | 70.26 |
| 558376 | RAC1 | Ras-related C3 botulinum toxin substrate 1 (rho family, small GTP binding protein Rac1) | 310.27 | 151.23 | 0.000 | 423.24 |
| 558381 | SNORA65 | Small nucleolar RNA, H/ACA box 65 | 182.13 | 140.06 | 0.172 | 167.44 |
| 558382 | RPL15 | Ribosomal protein L15 | 675.76 | 128.40 | 0.000 | 247.73 |
| 558383 | RPL18A | Ribosomal protein L18a | 705.56 | 175.27 | 0.034 | 1510.30 |
| 558384 | RPL19 | Ribosomal protein L19 | 526.89 | 137.15 | 0.034 | 913.52 |
| 558385 | RPL23A | Ribosomal protein L23a | 699.13 | 138.42 | 0.069 | 591.06 |

TABLE 2-continued

A list of 2087 candidate endogenous reference genes

| | | | | | | | |
|---|---|---|---|---|---|---|---|
| 558386 | RPL34 | Ribosomal protein L34 | | 697.35 | 378.17 | 0.069 | 994.94 |
| 558388 | RPS3A | Ribosomal protein S3A | | 2474.40 | 122.86 | 0.034 | 1599.66 |
| 558389 | RPS8 | Ribosomal protein S8 | | 962.64 | 129.92 | 0.000 | 1884.53 |
| 558390 | RPS24 | Ribosomal protein S24 | | 612.43 | 101.36 | 0.034 | 1096.04 |
| 558391 | RPS26 | Ribosomal protein S26 | | 165.48 | 119.11 | 0.276 | 1253.30 |
| 558396 | SCD | Stearoyl-CoA desaturase (delta-9-desaturase) | | 914.63 | 104.45 | 0.069 | 153.06 |
| 558424 | CSDA | Cold shock domain protein A | | 226.19 | 107.82 | 0.103 | 153.84 |
| 558426 | EIF3S5 | Eukaryotic translation initiation factor 3. subunit 5 epsilon, 47 kDa | | 303.80 | 92.52 | 0.172 | 111.38 |
| 558429 | BUD31 | BUD31 homolog (S. cerevisiae) | | 144.18 | 63.32 | 0.172 | 74.41 |
| 558431 | RPL14 | Ribosomal protein L14 | | 572.84 | 76.90 | 0.069 | 374.90 |
| 558442 | PDCD6IP | Programmed cell death 6 interacting protein | | 197.37 | 92.14 | 0.241 | 62.39 |
| 558448 | TXNL2 | Thioredoxin-like 2 | | 190.19 | 99.31 | 0.276 | 111.05 |
| 558453 | ATP5L | ATP synthase. H+ transporting, mitochondrial F0 complex, subunit g | | 303.51 | 169.99 | 0.172 | 614.08 |
| 558454 | NUDC | Nuclear distribution gene C homolog (A. nidulans) | | 366.87 | 118.17 | 0.207 | 97.57 |
| 558458 | COPS8 | COP9 constitutive photomorphogenic homolog subunit 8 (Arabidopsis) | | 143.44 | 86.61 | 0.207 | 41.97 |
| 558473 | C18orf10 | Chromosome 18 open reading frame 10 | | 143.75 | 80.47 | 0.172 | 66.89 |
| 558499 | CD320 | CD320 molecule | | 188.81 | 75.95 | 0.379 | 45.84 |
| 558511 | PARL | Presenilin associated, rhomboid-like | | 126.27 | 91.30 | 0.276 | 60.47 |
| 558521 | C2orf33 | Chromosome 2 open reading frame 33 | | 133.19 | 79.12 | 0.241 | 84.37 |
| 558591 | ORMDL1 | ORM1-like 1 (S. cerevisiae) | | 156.16 | 85.13 | 0.345 | 92.26 |
| 558825 | PDE4DIP | Phosphodiesterase 4D interacting protein (myomegalin) | | 192.79 | 111.41 | 0.241 | 95.41 |
| 558995 | C1orf151 | Chromosome 1 open reading frame 151 | | 718.64 | 244.03 | 0.103 | 115.01 |
| 567260 | CD2BP2 | CD2 antigen (cytoplasmic tail) binding protein 2 | | 161.65 | 79.42 | 0.207 | 55.10 |
| 567263 | C1orf43 | Chromosome 1 open reading frame 43 | | 337.41 | 80.70 | 0.172 | 106.63 |
| 567267 | ATP2C1 | ATPase. Ca++ transporting. type 2C. member 1 | | 95.02 | 60.83 | 0.345 | 74.61 |
| 567279 | SAP30BP | SAP30 binding protein | | 178.67 | 103.35 | 0.207 | 55.83 |

| UniGene cluster | SHORT SAGE | | LONG SAGE | | | Affymetrix | | Genomic Variants on Human Genome Assembly Build 36 | | |
|---|---|---|---|---|---|---|---|---|---|---|
| | CV | 0's P | Mean | CV | 0's P | Mean | CV | Variation | Cytogen | Locus ID |
| 120 | 77.57 | 0.000 | 182.28 | 77.83 | 0.000 | 536.31 | 44.78 | CopyNumber | 1q25.1 | 177 |
| 142 | 78.94 | 0.036 | 83.00 | 75.28 | 0.000 | | | CopyNumber | 16p11.2 | 2900 |
| 202 | 113.47 | 0.000 | 199.28 | 96.07 | 0.111 | 419.21 | 51.49 | | | |
| 429 | 82.18 | 0.000 | 551.21 | 81.48 | 0.000 | 865.18 | 43.60 | | | |
| 695 | 90.92 | 0.000 | 118.87 | 85.62 | 0.111 | 1052.98 | 100.96 | CopyNumber | 21q22.3 | 3455 |
| 808 | 66.96 | 0.000 | 135.76 | 77.44 | 0.222 | 210.67 | 38.17 | | | |
| 861 | 107.22 | 0.000 | 36.11 | 50.87 | 0.222 | 127.15 | 87.08 | CopyNumber | 16p11.2 | 2903 |
| 1063 | 67.18 | 0.036 | 100.31 | 75.40 | 0.222 | 194.60 | 33.14 | | | |
| 1103 | 111.80 | 0.036 | 125.52 | 97.41 | 0.111 | 106.24 | 57.23 | | | |
| 2430 | 80.01 | 0.071 | 47.30 | 88.89 | 0.222 | 218.15 | 32.90 | | | |
| 2533 | 77.46 | 0.071 | 74.01 | 77.57 | 0.111 | 354.31 | 47.43 | | | |
| 2795 | 95.03 | 0.000 | 259.59 | 82.14 | 0.111 | 2250.38 | 43.77 | | | |
| 2853 | 63.43 | 0.036 | 186.93 | 60.34 | 0.111 | 926.32 | 22.95 | | | |
| 3100 | 76.40 | 0.000 | 61.24 | 67.08 | 0.222 | 517.42 | 29.81 | | | |
| 3254 | 78.32 | 0.036 | 113.88 | 73.94 | 0.111 | 211.49 | 31.45 | Inversion | 11p15.5 | 2202 |
| 3353 | 56.37 | 0.071 | 216.42 | 70.65 | 0.000 | 881.36 | 27.96 | | | |
| 3416 | 131.08 | 0.036 | 68.67 | 112.87 | 0.222 | 360.44 | 151.18 | CopyNumber | 9p22.1 | 1912 |
| 3439 | 80.75 | 0.036 | 89.54 | 93.24 | 0.111 | 191.34 | 38.33 | | | |
| 3530 | 72.15 | 0.036 | 108.31 | 56.32 | 0.000 | 136.00 | 30.88 | | | |
| 3989 | 108.38 | 0.036 | 134.74 | 83.01 | 0.111 | 427.22 | 43.37 | | | |
| 4055 | 135.83 | 0.000 | 441.94 | 118.93 | 0.111 | 64.49 | 38.32 | | | |
| 4742 | 119.15 | 0.036 | 39.71 | 65.93 | 0.222 | 275.64 | 44.77 | CopyNumber | 8q24.3 | 1879 |
| 4747 | 73.50 | 0.071 | 71.07 | 73.04 | 0.111 | 307.46 | 47.47 | | | |
| 4766 | 86.86 | 0.036 | 72.60 | 84.36 | 0.222 | 262.05 | 27.51 | | | |
| 4859 | 103.29 | 0.071 | 110.40 | 111.52 | 0.000 | 299.38 | 40.44 | | | |
| 4997 | 62.12 | 0.000 | 50.72 | 94.59 | 0.111 | 264.44 | 22.10 | | | |
| 4998 | 63.22 | 0.036 | 28.78 | 51.61 | 0.222 | 229.36 | 56.84 | | | |
| 5062 | 101.42 | 0.000 | 111.82 | 81.88 | 0.111 | 800.47 | 52.13 | CopyNumber | 15q24.3 | 2811 |
| 5086 | 72.25 | 0.036 | 53.42 | 73.36 | 0.222 | 135.70 | 28.77 | | | |
| 5120 | 71.64 | 0.000 | 204.68 | 69.54 | 0.111 | 1158.59 | 29.63 | | | |
| 5158 | 67.54 | 0.000 | 138.55 | 60.73 | 0.111 | 383.95 | 36.39 | | | |
| 5245 | 74.90 | 0.000 | 80.69 | 73.69 | 0.000 | 219.54 | 21.60 | | | |
| 5258 | 84.40 | 0.071 | 133.74 | 77.92 | 0.111 | 589.76 | 55.05 | | | |
| 5268 | 78.70 | 0.000 | 46.25 | 73.83 | 0.111 | 113.40 | 37.54 | | | |
| 5298 | 59.08 | 0.000 | 58.54 | 49.70 | 0.111 | 296.11 | 31.82 | | | |
| 5308 | 83.81 | 0.000 | 479.50 | 73.38 | 0.000 | 2422.20 | 38.02 | | | |
| 5324 | 64.23 | 0.000 | 62.22 | 66.74 | 0.111 | 694.81 | 25.69 | | | |
| 5345 | 86.81 | 0.071 | 61.41 | 84.79 | 0.111 | 73.49 | 30.51 | CopyNumber | 2q37.3 | 515 |
| 5662 | 87.26 | 0.000 | 651.22 | 57.10 | 0.000 | 2861.36 | 36.28 | | | |
| 5710 | 67.53 | 0.071 | 34.13 | 80.74 | 0.111 | 452.86 | 45.78 | | | |
| 5719 | 94.26 | 0.000 | 65.99 | 56.36 | 0.000 | 55.53 | 45.18 | CopyNumber | 12p13.31 | 2368 |
| 5912 | 65.61 | 0.000 | 30.20 | 60.87 | 0.111 | 430.78 | 30.03 | | | |
| 5947 | 68.42 | 0.036 | 34.91 | 59.37 | 0.222 | 368.59 | 33.28 | | | |
| 6396 | 72.90 | 0.036 | 94.01 | 39.56 | 0.222 | 869.88 | 31.02 | | | |

TABLE 2-continued

A list of 2087 candidate endogenous reference genes

| | | | | | | | | | | |
|---|---|---|---|---|---|---|---|---|---|---|
| 6454 | 77.38 | 0.000 | 290.31 | 91.04 | 0.000 | 504.85 | 40.25 | CopyNumber | 19p13.12 | 3223 |
| 6459 | 121.97 | 0.036 | 88.34 | 85.38 | 0.111 | 157.79 | 41.08 | CopyNumber | 8q24.3 | 1880 |
| 6551 | 102.10 | 0.000 | 99.28 | 83.28 | 0.000 | 515.56 | 45.37 | | | |
| 6891 | 68.55 | 0.000 | 79.36 | 95.32 | 0.000 | 437.26 | 34.58 | | | |
| 7101 | 85.77 | 0.071 | 81.04 | 84.26 | 0.000 | 183.19 | 27.20 | | | |
| 7236 | 91.55 | 0.000 | 89.02 | 123.50 | 0.111 | 150.63 | 53.39 | CopyNumber | 19q13.33 | 3277 |
| 7476 | 85.55 | 0.000 | 91.48 | 67.53 | 0.000 | 1250.83 | 39.30 | | | |
| 7527 | 92.63 | 0.036 | 52.36 | 54.01 | 0.222 | 97.43 | 36.93 | | | |
| 7744 | 85.28 | 0.000 | 77.42 | 71.13 | 0.000 | 415.46 | 37.27 | CopyNumber | 11q13.1-11q13.2 | 2278 |
| 7753 | 136.12 | 0.000 | 138.00 | 85.95 | 0.111 | 100.65 | 48.84 | CopyNumber | 7q32.1 | 1639 |
| 7768 | 65.21 | 0.000 | 63.80 | 65.95 | 0.111 | 269.17 | 27.39 | CopyNumber | 11q13.1 | 2276 |
| 7862 | 74.15 | 0.036 | 84.67 | 63.85 | 0.111 | | | | | |
| 7910 | 72.05 | 0.036 | 78.63 | 65.90 | 0.111 | 153.70 | 42.23 | | | |
| 7917 | 78.00 | 0.000 | 135.78 | 112.82 | 0.111 | 661.73 | 52.63 | CopyNumber | 3p22.1 | 572 |
| 8102 | 83.01 | 0.000 | 1410.01 | 75.01 | 0.000 | 4250.06 | 30.72 | | | |
| 8372 | 108.88 | 0.000 | 146.74 | 79.82 | 0.111 | 788.19 | 32.34 | | | |
| 8737 | 68.38 | 0.036 | 88.71 | 85.75 | 0.111 | 253.06 | 44.11 | | | |
| 8752 | 57.76 | 0.071 | 52.10 | 62.17 | 0.222 | 102.13 | 32.76 | CopyNumber | 12q13.2 | 2429 |
| 8765 | 64.21 | 0.000 | 53.71 | 59.12 | 0.000 | 228.43 | 30.56 | | | |
| 8859 | 111.07 | 0.036 | 53.33 | 94.17 | 0.222 | 234.96 | 73.37 | | | |
| 8867 | 137.92 | 0.000 | 273.81 | 95.23 | 0.111 | 547.98 | 79.93 | | | |
| 9003 | 69.05 | 0.000 | 66.15 | 65.61 | 0.000 | 148.11 | 36.69 | | | |
| 9015 | 65.95 | 0.000 | 180.11 | 68.32 | 0.000 | | | | | |
| 9043 | 67.83 | 0.000 | 38.48 | 97.33 | 0.111 | 162.00 | 25.78 | | | |
| 9234 | 79.49 | 0.071 | 68.18 | 62.80 | 0.111 | 434.76 | 37.42 | | | |
| 9235 | 92.25 | 0.000 | 67.77 | 88.26 | 0.222 | 256.46 | 58.39 | | | |
| 9527 | 84.48 | 0.036 | 51.11 | 48.09 | 0.222 | 538.70 | 28.49 | | | |
| 9534 | 72.74 | 0.000 | 86.28 | 73.16 | 0.222 | 626.14 | 29.63 | | | |
| 9573 | 92.63 | 0.036 | 31.79 | 54.71 | 0.222 | 778.41 | 33.32 | | | |
| 9589 | 61.30 | 0.036 | 71.77 | 49.75 | 0.111 | 919.32 | 26.81 | | | |
| 9788 | 88.77 | 0.071 | 127.59 | 72.78 | 0.000 | 377.13 | 38.24 | | | |
| 9825 | 66.79 | 0.000 | 56.23 | 48.85 | 0.111 | 365.07 | 28.07 | | | |
| 9857 | 122.60 | 0.000 | 232.82 | 151.99 | 0.000 | 463.40 | 157.98 | | | |
| 10326 | 73.58 | 0.000 | 197.00 | 75.36 | 0.000 | 369.97 | 68.55 | | | |
| 10842 | 94.54 | 0.000 | 239.28 | 115.19 | 0.222 | 718.72 | 44.58 | | | |
| 10848 | 67.53 | 0.071 | 31.76 | 66.74 | 0.111 | 104.71 | 37.33 | CopyNumber | 10q11.21 | 2093 |
| 11125 | 68.78 | 0.071 | 93.47 | 59.46 | 0.000 | 817.21 | 27.49 | | | |
| 11184 | 59.84 | 0.036 | 115.93 | 46.13 | 0.000 | 292.68 | 27.77 | CopyNumber | 9p13.3 | 1937 |
| 11223 | 88.67 | 0.071 | 78.63 | 87.24 | 0.222 | 57.89 | 55.15 | | | |
| 11355 | 104.32 | 0.036 | 66.99 | 75.00 | 0.222 | 62.56 | 35.20 | | | |
| 11463 | 61.89 | 0.036 | 113.19 | 84.50 | 0.111 | 429.95 | 40.75 | | | |
| 12013 | 64.76 | 0.036 | 45.75 | 69.36 | 0.222 | 99.02 | 32.35 | | | |
| 12084 | 81.01 | 0.000 | 364.40 | 89.06 | 0.000 | 623.07 | 39.39 | CopyNumber | 16p11.2 | 2900 |
| 12102 | 67.05 | 0.071 | 114.17 | 52.22 | 0.111 | 518.73 | 22.82 | CopyNumber | 6q21 | 1407 |
| 12107 | 72.91 | 0.036 | 50.80 | 59.67 | 0.111 | 329.36 | 29.47 | | | |
| 12109 | 61.69 | 0.036 | 46.73 | 59.25 | 0.111 | 118.79 | 29.00 | CopyNumber | 2q11.2 | 378 |
| 12144 | 73.94 | 0.071 | 41.87 | 82.28 | 0.222 | 162.21 | 31.04 | | | |
| 12152 | 79.55 | 0.036 | 58.29 | 64.64 | 0.222 | 30.47 | 58.95 | | | |
| 12272 | 64.89 | 0.071 | 48.28 | 64.28 | 0.111 | 236.82 | 29.21 | | | |
| 12341 | 71.85 | 0.000 | 80.90 | 63.60 | 0.222 | 646.53 | 35.91 | | | |
| 12457 | 60.75 | 0.036 | 41.32 | 44.32 | 0.222 | 141.28 | 35.86 | | | |
| 12865 | 77.51 | 0.036 | 56.10 | 68.14 | 0.111 | 161.87 | 24.52 | | | |
| 13662 | 73.45 | 0.071 | 42.54 | 82.56 | 0.111 | 286.77 | 29.53 | | | |
| 14317 | 85.06 | 0.000 | 210.81 | 76.29 | 0.111 | 707.56 | 30.56 | CopyNumber | 15q14 | 2760 |
| 14333 | 93.92 | 0.000 | 49.69 | 65.95 | 0.222 | 52.91 | 32.36 | CopyNumber | 1p36.11 | 49 |
| 14745 | 67.71 | 0.036 | 34.86 | 68.85 | 0.222 | 344.17 | 44.46 | | | |
| 14839 | 60.79 | 0.036 | 72.24 | 59.97 | 0.000 | 425.45 | 27.99 | CopyNumber | 11q12.3 | 2269 |
| 14846 | 71.11 | 0.036 | 35.42 | 56.40 | 0.111 | 290.22 | 58.28 | | | |
| 14894 | 82.05 | 0.000 | 60.76 | 70.36 | 0.111 | 126.08 | 28.41 | | | |
| 15277 | 127.86 | 0.000 | 94.06 | 82.10 | 0.111 | 147.72 | 37.89 | CopyNumber | 16p13.3 | 2866 |
| 15591 | 67.01 | 0.000 | 41.12 | 58.74 | 0.111 | 131.70 | 28.53 | CopyNumber | 7q22.1 | 1598 |
| 15738 | 72.04 | 0.000 | 129.69 | 48.46 | 0.111 | 417.14 | 23.56 | | | |
| 16059 | 66.35 | 0.000 | 71.91 | 74.39 | 0.111 | 679.76 | 46.08 | | | |
| 16130 | 62.56 | 0.000 | 43.34 | 61.70 | 0.222 | 18.64 | 94.29 | CopyNumber | 17q25.1 | 3075 |
| 16349 | 59.57 | 0.071 | 31.68 | 64.66 | 0.222 | 148.04 | 24.93 | CopyNumber | 16q23.2 | 2956 |
| 17118 | 62.14 | 0.071 | 46.03 | 69.29 | 0.111 | 213.73 | 40.31 | CopyNumber | 1p34.3 | 58 |
| 17250 | 79.64 | 0.071 | 117.82 | 78.92 | 0.111 | 294.70 | 33.94 | | | |
| 17680 | 73.53 | 0.071 | 48.01 | 54.77 | 0.111 | 516.93 | 33.95 | CopyNumber | 6q24.2 | 1437 |
| 17731 | 70.13 | 0.000 | 29.51 | 60.36 | 0.111 | 520.71 | 54.10 | | | |
| 17883 | 65.60 | 0.000 | 135.33 | 70.28 | 0.000 | 114.89 | 33.02 | | | |
| 18069 | 90.49 | 0.036 | 63.83 | 85.91 | 0.111 | 211.65 | 49.02 | | | |
| 18128 | 74.70 | 0.036 | 28.66 | 43.42 | 0.222 | 141.00 | 37.06 | CopyNumber | 20q11.22 | 3366 |
| 18349 | 74.07 | 0.036 | 49.61 | 83.49 | 0.222 | 300.87 | 45.97 | | | |
| 19673 | 80.92 | 0.071 | 95.67 | 73.57 | 0.222 | 562.71 | 37.51 | CopyNumber | 8q24.3 | 1879 |
| 20013 | 65.84 | 0.000 | 62.25 | 52.78 | 0.000 | 173.94 | 35.93 | CopyNumber | 1p36.11 | 48 |
| 20107 | 96.88 | 0.036 | 39.46 | 139.41 | 0.222 | 175.52 | 41.33 | CopyNumber | 14q32.33 | 2746 |
| 20157 | 77.35 | 0.036 | 59.44 | 87.93 | 0.222 | 376.62 | 32.83 | | | |

TABLE 2-continued

A list of 2087 candidate endogenous reference genes

| | | | | | | | | | |
|---|---|---|---|---|---|---|---|---|---|
| 20521 | 94.01 | 0.000 | 152.96 | 89.93 | 0.111 | 383.24 | 40.81 | CopyNumber | 19q13.33 | 3277 |
| 20529 | 69.78 | 0.071 | 39.76 | 53.17 | 0.222 | 749.10 | 34.18 | CopyNumber | 1p36.32 | 11 |
| 20573 | 67.85 | 0.000 | 81.56 | 153.79 | 0.111 | 23.55 | 41.49 | | | |
| 20716 | 71.00 | 0.036 | 66.00 | 55.65 | 0.222 | 276.11 | 36.03 | CopyNumber | 1q32.1 | 209 |
| 22393 | 64.62 | 0.036 | 63.67 | 82.21 | 0.222 | 228.15 | 33.72 | | | |
| 22543 | 56.69 | 0.036 | 63.96 | 65.55 | 0.222 | 34.14 | 49.75 | | | |
| 22546 | 71.92 | 0.036 | 42.45 | 98.37 | 0.222 | 651.22 | 63.93 | CopyNumber | 11q12.2 | 2266 |
| 22616 | 75.10 | 0.071 | 35.69 | 58.10 | 0.222 | 144.92 | 52.15 | CopyNumber | 17p13.3 | 2978 |
| 23033 | 58.71 | 0.071 | 39.15 | 53.57 | 0.222 | 341.82 | 43.42 | | | |
| 23111 | 77.82 | 0.071 | 52.47 | 83.58 | 0.222 | 105.11 | 33.54 | CopyNumber | 19p13.13 | 3220 |
| 23978 | 66.48 | 0.036 | 58.25 | 63.84 | 0.222 | 128.24 | 28.55 | | | |
| 24301 | 143.33 | 0.036 | 116.94 | 59.98 | 0.111 | 286.08 | 26.26 | CopyNumber | 19p13.3 | 3198 |
| 24379 | 89.22 | 0.000 | 90.75 | 71.03 | 0.000 | 479.98 | 29.85 | | | |
| 24601 | 136.75 | 0.000 | 195.56 | 129.74 | 0.222 | 34.60 | 49.50 | CopyNumber | 22q13.31 | 3508 |
| 24950 | 186.79 | 0.071 | 189.81 | 135.70 | 0.222 | 307.39 | 104.91 | | | |
| 25155 | 120.45 | 0.071 | 52.76 | 77.03 | 0.222 | 204.80 | 58.51 | | | |
| 25450 | 206.58 | 0.036 | 103.43 | 106.19 | 0.222 | 124.80 | 61.30 | | | |
| 25723 | 98.01 | 0.036 | 74.46 | 92.32 | 0.111 | 204.78 | 31.78 | | | |
| 26010 | 107.96 | 0.036 | 71.92 | 87.71 | 0.111 | 127.90 | 44.05 | CopyNumber | 10p15.2-10p15.3 | 2038 |
| 26023 | 71.18 | 0.036 | 27.14 | 63.42 | 0.222 | 32.41 | 34.48 | | | |
| 26136 | 64.61 | 0.000 | 126.52 | 71.60 | 0.000 | 1187.97 | 29.30 | | | |
| 26232 | 90.53 | 0.071 | 26.46 | 93.62 | 0.222 | 122.41 | 30.42 | | | |
| 26403 | 79.12 | 0.036 | 49.19 | 87.28 | 0.222 | 49.29 | 121.55 | | | |
| 26518 | 108.83 | 0.036 | 82.68 | 57.69 | 0.111 | 145.35 | 56.07 | CopyNumber | 11p15.5 | 2200 |
| 27222 | 70.07 | 0.036 | 92.82 | 77.94 | 0.111 | 408.36 | 36.92 | | | |
| 28491 | 110.80 | 0.000 | 366.05 | 99.16 | 0.000 | 1987.13 | 39.05 | | | |
| 28914 | 124.19 | 0.036 | 75.99 | 55.29 | 0.111 | 172.22 | 38.11 | CopyNumber | 16q24.3 | 2971 |
| 29203 | 106.14 | 0.000 | 45.04 | 65.31 | 0.111 | 60.43 | 48.50 | CopyNumber | 16p13.3 | 2866 |
| 29665 | 99.16 | 0.036 | 72.28 | 88.66 | 0.111 | 350.56 | 37.72 | | | |
| 30011 | 81.69 | 0.071 | 81.96 | 82.93 | 0.222 | 133.44 | 28.49 | CopyNumber | 17p13.3-17p13.2 | 2981 |
| 30026 | 86.33 | 0.000 | 93.91 | 62.29 | 0.111 | 123.60 | 30.35 | CopyNumber | 1p36.33 | 0003 |
| 30345 | 88.62 | 0.000 | 124.96 | 92.01 | 0.222 | 262.70 | 34.03 | | | |
| 30954 | 68.95 | 0.000 | 33.38 | 69.19 | 0.222 | 151.11 | 40.16 | | | |
| 31053 | 81.65 | 0.000 | 122.44 | 66.60 | 0.111 | 341.88 | 36.28 | CopyNumber | 19q13.12 | 3250 |
| 31334 | 61.03 | 0.036 | 78.51 | 49.15 | 0.111 | 134.99 | 47.91 | CopyNumber | 20q13.33 | 3420 |
| 31387 | 84.87 | 0.000 | 46.14 | 75.32 | 0.222 | 173.71 | 43.22 | | | |
| 34045 | 74.24 | 0.071 | 45.53 | 64.82 | 0.111 | 117.61 | 48.58 | | | |
| 34576 | 64.28 | 0.036 | 73.10 | 58.20 | 0.000 | 402.96 | 28.27 | CopyNumber | 7p15.2 | 1525 |
| 34906 | 68.64 | 0.071 | 61.99 | 53.16 | 0.111 | 625.46 | 46.98 | | | |
| 35052 | 57.78 | 0.000 | 362.25 | 60.57 | 0.000 | 855.32 | 36.18 | | | |
| 35828 | 62.01 | 0.000 | 45.72 | 60.60 | 0.222 | 108.48 | 23.16 | CopyNumber | 14q32.33 | 2744 |
| 36587 | 71.83 | 0.000 | 30.96 | 65.30 | 0.222 | 179.98 | 30.62 | | | |
| 36927 | 121.45 | 0.000 | 211.50 | 111.53 | 0.222 | 291.25 | 56.92 | | | |
| 37616 | 95.13 | 0.036 | 111.55 | 102.44 | 0.000 | 164.13 | 70.51 | | | |
| 37916 | 76.45 | 0.036 | 73.92 | 86.57 | 0.000 | 160.38 | 37.39 | CopyNumber | 9q34.3 | 2030 |
| 42806 | 98.22 | 0.071 | 67.92 | 66.52 | 0.222 | 113.20 | 27.89 | CopyNumber | 1p36.33 | 0002 |
| 43297 | 62.31 | 0.036 | 167.46 | 70.07 | 0.000 | | | | | |
| 47062 | 81.09 | 0.000 | 51.75 | 59.62 | 0.111 | 279.70 | 38.81 | CopyNumber | 19q13.12 | 3250 |
| 50098 | 97.25 | 0.000 | 197.41 | 66.02 | 0.111 | 889.01 | 34.95 | | | |
| 50398 | 69.00 | 0.071 | 64.21 | 68.46 | 0.111 | 590.61 | 33.23 | CopyNumber | 4p14 | 824 |
| 50425 | 59.02 | 0.000 | 452.95 | 56.90 | 0.000 | 981.84 | 28.48 | | | |
| 53066 | 89.79 | 0.036 | 84.91 | 123.45 | 0.222 | 86.87 | 42.17 | | | |
| 54277 | 70.86 | 0.036 | 96.39 | 65.47 | 0.222 | 198.46 | 29.56 | | | |
| 54457 | 101.21 | 0.000 | 70.72 | 79.45 | 0.111 | 1276.93 | 35.83 | | | |
| 54642 | 66.57 | 0.036 | 50.30 | 60.80 | 0.222 | 504.88 | 34.60 | | | |
| 54649 | 62.12 | 0.000 | 39.30 | 61.93 | 0.222 | 114.82 | 27.65 | | | |
| 55682 | 77.92 | 0.000 | 55.77 | 52.38 | 0.111 | 1742.75 | 35.36 | CopyNumber | 22q12.3 | 3492 |
| 55847 | 133.75 | 0.000 | 127.47 | 77.36 | 0.222 | 1589.77 | 32.09 | CopyNumber | 12p13.31 | 2368 |
| 58488 | 91.55 | 0.000 | 55.35 | 57.10 | 0.222 | 204.60 | 74.27 | | | |
| 58992 | 99.33 | 0.036 | 54.95 | 72.92 | 0.000 | 19.90 | 46.40 | CopyNumber | 19q13.2 | 3258 |
| 59486 | 80.61 | 0.000 | 36.11 | 94.51 | 0.222 | 125.78 | 61.69 | | | |
| 61812 | 62.20 | 0.036 | 81.03 | 52.93 | 0.222 | 163.53 | 35.91 | | | |
| 65234 | 85.90 | 0.000 | 45.56 | 51.74 | 0.111 | 230.78 | 28.28 | | | |
| 65238 | 74.65 | 0.036 | 76.11 | 68.06 | 0.111 | 138.90 | 30.03 | CopyNumber | 16p11.2 | 2904 |
| 66048 | 75.95 | 0.000 | 37.75 | 57.98 | 0.111 | 62.79 | 37.57 | CopyNumber | 19p13.11 | 3229 |
| 66915 | 138.86 | 0.071 | 97.34 | 71.78 | 0.222 | 1098.67 | 81.32 | | | |
| 68714 | 72.45 | 0.000 | 52.63 | 57.22 | 0.222 | 320.40 | 27.38 | | | |
| 69293 | 98.44 | 0.071 | 85.35 | 81.08 | 0.000 | 585.49 | 38.47 | | | |
| 69554 | 69.56 | 0.036 | 55.49 | 73.57 | 0.111 | 83.68 | 28.75 | | | |
| 69855 | 188.78 | 0.000 | 305.44 | 48.54 | 0.000 | 727.35 | 25.99 | | | |
| 71465 | 105.85 | 0.071 | 66.00 | 78.37 | 0.222 | 243.96 | 77.49 | | | |
| 71787 | 77.93 | 0.071 | 83.49 | 81.21 | 0.222 | 200.16 | 37.18 | | | |
| 73527 | 70.51 | 0.071 | 124.08 | 51.87 | 0.111 | 583.61 | 28.44 | | | |
| 73722 | 85.72 | 0.000 | 261.97 | 71.05 | 0.000 | 463.11 | 27.57 | | | |
| 73799 | 65.89 | 0.071 | 58.08 | 66.99 | 0.000 | 377.98 | 28.45 | | | |
| 73965 | 70.12 | 0.000 | 283.48 | 68.03 | 0.000 | 235.15 | 31.88 | | | |

TABLE 2-continued

A list of 2087 candidate endogenous reference genes

| | | | | | | | | | |
|---|---|---|---|---|---|---|---|---|---|
| 74047 | 87.12 | 0.071 | 30.09 | 43.70 | 0.222 | 43.44 | 43.38 | | |
| 74050 | 65.00 | 0.000 | 50.61 | 69.46 | 0.222 | 85.49 | 33.47 | | |
| 74137 | 67.80 | 0.036 | 162.33 | 96.54 | 0.000 | 765.38 | 31.85 | | |
| 74375 | 80.65 | 0.000 | 94.05 | 93.83 | 0.222 | 79.06 | 34.15 | CopyNumber | 1p36.33 | 2 |
| 74405 | 70.95 | 0.000 | 376.04 | 102.24 | 0.000 | 1073.13 | 29.89 | CopyNumber | 2p25.1 | 280 |
| 74471 | 146.61 | 0.000 | 820.91 | 82.84 | 0.222 | 309.99 | 88.83 | | |
| 74563 | 91.47 | 0.000 | 161.30 | 79.91 | 0.000 | 220.82 | 27.96 | | |
| 74564 | 86.90 | 0.071 | 98.67 | 73.67 | 0.222 | 853.95 | 35.62 | | |
| 74576 | 103.63 | 0.036 | 206.54 | 105.86 | 0.111 | 372.42 | 51.84 | | |
| 75056 | 95.92 | 0.036 | 196.13 | 70.63 | 0.000 | 175.01 | 40.98 | | |
| 75061 | 134.90 | 0.000 | 139.52 | 106.48 | 0.222 | 694.54 | 68.77 | | |
| 75066 | 57.57 | 0.071 | 59.08 | 75.04 | 0.222 | 49.39 | 28.04 | | |
| 75087 | 78.42 | 0.000 | 102.46 | 73.16 | 0.111 | 222.76 | 28.01 | CopyNumber | 7q36.1 | 1667 |
| 75117 | 68.05 | 0.000 | 108.92 | 67.92 | 0.222 | 298.96 | 40.82 | | |
| 75133 | 90.78 | 0.036 | 33.87 | 52.50 | 0.222 | | | | |
| 75139 | 77.20 | 0.071 | 32.14 | 56.90 | 0.111 | 265.49 | 32.96 | | |
| 75189 | 71.71 | 0.036 | 88.49 | 96.81 | 0.111 | 273.22 | 47.07 | | |
| 75227 | 98.77 | 0.000 | 103.41 | 83.59 | 0.111 | 330.85 | 41.09 | | |
| 75243 | 86.87 | 0.000 | 163.16 | 69.12 | 0.000 | 306.90 | 30.86 | CopyNumber | 6p21.32 | 1316 |
| 75249 | 79.25 | 0.036 | 72.48 | 58.84 | 0.111 | 451.23 | 40.81 | CopyNumber | 16p12.3 | 2889 |
| 75254 | 85.88 | 0.036 | 35.63 | 92.11 | 0.222 | 167.60 | 35.94 | CopyNumber | 19q13.33 | 3277 |
| 75318 | 107.17 | 0.071 | 47.29 | 77.96 | 0.222 | 245.52 | 63.96 | | |
| 75348 | 83.65 | 0.000 | 90.61 | 53.97 | 0.000 | 742.51 | 27.52 | | |
| 75438 | 135.05 | 0.071 | 104.15 | 222.79 | 0.111 | 241.61 | 96.64 | | |
| 75527 | 75.11 | 0.036 | 50.93 | 81.60 | 0.222 | 188.80 | 30.23 | | |
| 75724 | 72.09 | 0.000 | 117.37 | 63.92 | 0.000 | 284.42 | 34.05 | | |
| 75798 | 66.34 | 0.000 | 46.25 | 98.54 | 0.111 | 132.09 | 26.63 | | |
| 75841 | 67.70 | 0.036 | 111.03 | 66.56 | 0.222 | 697.12 | 38.13 | | |
| 75890 | 63.35 | 0.071 | 55.70 | 53.32 | 0.222 | 192.57 | 34.39 | | |
| 75914 | 75.69 | 0.000 | 149.78 | 60.21 | 0.111 | 998.68 | 31.35 | CopyNumber | 12q24.31 | 2518 |
| 76111 | 74.32 | 0.036 | 91.80 | 91.74 | 0.222 | 349.38 | 32.91 | | |
| 76394 | 97.13 | 0.071 | 85.81 | 54.54 | 0.111 | 723.48 | 75.27 | CopyNumber | 10q26.3 | 2199 |
| 76480 | 72.15 | 0.071 | 42.20 | 50.89 | 0.222 | 107.11 | 31.94 | | |
| 76662 | 75.63 | 0.071 | 39.52 | 102.23 | 0.222 | 371.15 | 30.57 | | |
| 76686 | 89.86 | 0.000 | 260.60 | 79.93 | 0.111 | 786.14 | 45.48 | | |
| 76847 | 66.20 | 0.071 | 156.31 | 84.21 | 0.111 | 534.34 | 30.42 | CopyNumber | 11q12.3 | 2268 |
| 77060 | 84.28 | 0.000 | 108.25 | 74.95 | 0.111 | 304.90 | 32.72 | CopyNumber | 17p13.2 | 2984 |
| 77269 | 77.93 | 0.000 | 395.01 | 92.11 | 0.000 | 212.81 | 53.48 | CopyNumber | 3p21.31 | 586 |
| 77313 | 109.12 | 0.036 | 102.72 | 140.65 | 0.000 | 74.75 | 36.55 | CopyNumber | 16q24.3 | 2973 |
| 77422 | 91.72 | 0.000 | 60.73 | 89.20 | 0.111 | 377.17 | 61.65 | Inversion | Xp11.23 | 3552 |
| 77558 | 84.61 | 0.000 | 101.75 | 71.51 | 0.111 | 662.90 | 46.96 | | |
| 77578 | 77.49 | 0.000 | 102.87 | 121.76 | 0.222 | 171.09 | 31.33 | | |
| 77793 | 72.60 | 0.000 | 34.98 | 96.71 | 0.222 | 170.28 | 52.53 | | |
| 77897 | 69.16 | 0.071 | 111.11 | 71.27 | 0.000 | 112.01 | 24.87 | | |
| 77961 | 169.44 | 0.000 | 823.99 | 124.02 | 0.000 | 4899.68 | 43.03 | CopyNumber | 6p21.33 | 1313 |
| 77978 | 75.97 | 0.000 | 91.06 | 68.25 | 0.111 | 264.14 | 34.17 | | |
| 78466 | 105.76 | 0.000 | 115.24 | 59.35 | 0.111 | 296.95 | 45.96 | | |
| 78601 | 74.95 | 0.036 | 60.03 | 61.28 | 0.000 | 209.16 | 29.30 | | |
| 78771 | 85.53 | 0.000 | 445.96 | 90.90 | 0.000 | 1179.63 | 41.05 | CopyNumber | Xq21.1 | 3567 |
| 78880 | 89.08 | 0.036 | 41.08 | 84.35 | 0.222 | 167.42 | 38.32 | CopyNumber | 19p13.12 | 3225 |
| 78888 | 111.41 | 0.036 | 130.51 | 70.31 | 0.000 | 1459.58 | 43.93 | | |
| 78989 | 75.96 | 0.000 | 94.26 | 93.28 | 0.000 | 363.83 | 37.58 | | |
| 79064 | 65.62 | 0.071 | 37.14 | 60.46 | 0.222 | 93.49 | 36.45 | | |
| 79081 | 93.36 | 0.036 | 167.72 | 99.22 | 0.111 | 499.05 | 34.22 | | |
| 79088 | 81.96 | 0.000 | 99.08 | 109.91 | 0.222 | 156.03 | 53.20 | CopyNumber | 15q24.3 | 2811 |
| 79101 | 141.29 | 0.071 | 153.49 | 137.97 | 0.111 | 444.07 | 49.53 | | |
| 79110 | 86.13 | 0.036 | 372.48 | 77.25 | 0.000 | 913.17 | 31.25 | | |
| 79322 | 74.35 | 0.036 | 132.17 | 60.84 | 0.000 | 691.01 | 34.62 | | |
| 79335 | 73.95 | 0.036 | 64.11 | 77.17 | 0.222 | 67.72 | 31.29 | | |
| 79387 | 62.64 | 0.000 | 149.41 | 65.96 | 0.111 | 377.33 | 28.18 | | |
| 79402 | 69.22 | 0.036 | 42.24 | 54.66 | 0.111 | 237.05 | 27.80 | | |
| 79411 | 67.91 | 0.000 | 66.14 | 69.85 | 0.222 | 231.21 | 28.82 | | |
| 79625 | 136.24 | 0.000 | 189.30 | 141.24 | 0.222 | 1792.59 | 46.21 | CopyNumber | 20q13.33 | 3419 |
| 80545 | 88.80 | 0.000 | 3675.93 | 53.49 | 0.000 | 8897.81 | 33.60 | | |
| 80919 | 76.35 | 0.036 | 67.97 | 78.25 | 0.111 | 313.08 | 32.42 | | |
| 80986 | 120.32 | 0.000 | 219.34 | 96.44 | 0.000 | 231.11 | 44.42 | CopyNumber | 17q21.32 | 3034 |
| 81328 | 217.63 | 0.036 | 729.78 | 176.26 | 0.000 | 845.91 | 66.53 | | |
| 81424 | 60.84 | 0.000 | 178.67 | 63.11 | 0.222 | 343.25 | 25.72 | | |
| 81848 | 71.54 | 0.071 | 108.12 | 78.45 | 0.222 | 261.11 | 47.46 | | |
| 81964 | 75.88 | 0.071 | 37.25 | 88.70 | 0.222 | 173.27 | 38.81 | | |
| 82201 | 64.48 | 0.071 | 52.80 | 63.18 | 0.222 | 227.05 | 31.28 | | |
| 82327 | 80.48 | 0.000 | 34.79 | 79.12 | 0.222 | 199.40 | 38.88 | CopyNumber | 20q11.22 | 3365 |
| 82719 | 66.25 | 0.071 | 23.77 | 44.79 | 0.111 | 85.74 | 30.33 | | |
| 82793 | 128.02 | 0.036 | 83.47 | 68.72 | 0.222 | 611.12 | 45.54 | | |
| 82887 | 77.92 | 0.071 | 29.21 | 62.08 | 0.222 | 470.22 | 22.27 | | |
| 82890 | 66.89 | 0.000 | 89.92 | 89.16 | 0.111 | 541.67 | 28.47 | | |
| 82916 | 94.85 | 0.000 | 244.03 | 94.29 | 0.000 | 218.30 | 42.67 | | |
| 82927 | 105.59 | 0.036 | 43.00 | 75.49 | 0.222 | 123.23 | 36.72 | | |

TABLE 2-continued

A list of 2087 candidate endogenous reference genes

| | | | | | | | | | |
|---|---|---|---|---|---|---|---|---|---|
| 83190 | 182.78 | 0.036 | 211.86 | 121.95 | 0.222 | 263.79 | 128.00 | | |
| 83347 | 69.02 | 0.036 | 71.54 | 56.24 | 0.000 | 154.79 | 25.38 | | |
| 83383 | 84.31 | 0.036 | 68.79 | 80.95 | 0.111 | 617.70 | 83.89 | | |
| 83734 | 69.26 | 0.071 | 53.32 | 60.39 | 0.000 | 140.82 | 29.73 | CopyNumber | 16p11.2 | 2905 |
| 83753 | 88.26 | 0.000 | 302.30 | 80.76 | 0.111 | 314.59 | 48.19 | CopyNumber | 20p13 | 3302 |
| 83765 | 85.58 | 0.071 | 65.48 | 111.40 | 0.222 | 99.10 | 47.99 | CopyNumber | 5q14.1 | 1155 |
| 83916 | 87.67 | 0.000 | 53.16 | 106.27 | 0.222 | 192.48 | 51.98 | | |
| 84359 | 91.88 | 0.000 | 190.01 | 97.99 | 0.111 | 1358.12 | 25.26 | | |
| 84753 | 105.87 | 0.036 | 215.33 | 92.76 | 0.222 | 92.58 | 76.88 | | |
| 85155 | 135.45 | 0.000 | 398.59 | 101.28 | 0.111 | 463.10 | 46.79 | | |
| 85769 | 68.76 | 0.036 | 46.70 | 56.56 | 0.111 | 203.84 | 26.22 | | |
| 85962 | 84.29 | 0.071 | 75.97 | 60.72 | 0.222 | 14.60 | 66.14 | | |
| 86131 | 79.74 | 0.036 | 38.81 | 70.54 | 0.222 | 91.70 | 50.98 | | |
| 87752 | 96.06 | 0.000 | 186.51 | 80.13 | 0.111 | 86.54 | 36.98 | | |
| 89545 | 67.58 | 0.000 | 183.77 | 60.61 | 0.111 | 631.69 | 33.52 | CopyNumber | 1q21.2- | 152 |
| 89643 | 142.36 | 0.000 | 365.70 | 117.06 | 0.111 | 120.47 | 36.69 | | |
| 89649 | 104.25 | 0.000 | 82.36 | 107.95 | 0.111 | 606.74 | 180.62 | | |
| 89781 | 68.82 | 0.000 | 113.28 | 69.11 | 0.111 | 494.30 | 21.89 | CopyNumber | 17q21.31 | 3026 |
| 89864 | 114.71 | 0.071 | 29.48 | 76.43 | 0.222 | 163.77 | 23.54 | CopyNumber | 6p21.32 | 1314 |
| 90061 | 83.92 | 0.036 | 91.42 | 74.05 | 0.222 | 651.40 | 42.91 | | |
| 90093 | 92.05 | 0.036 | 105.16 | 101.89 | 0.222 | 155.51 | 38.77 | | |
| 90107 | 77.30 | 0.000 | 83.77 | 71.73 | 0.111 | 271.86 | 37.65 | CopyNumber | 20q13.33 | 3417 |
| 90443 | 101.63 | 0.000 | 70.31 | 56.02 | 0.222 | 263.10 | 39.12 | CopyNumber | 11q13.2 | 2278 |
| 91142 | 77.58 | 0.000 | 202.64 | 43.73 | 0.000 | 163.39 | 35.82 | | |
| 91531 | 96.12 | 0.071 | 80.15 | 95.45 | 0.111 | 637.99 | 34.78 | | |
| 93659 | 83.46 | 0.000 | 155.28 | 76.20 | 0.111 | 167.42 | 46.25 | | |
| 93832 | 74.43 | 0.000 | 74.64 | 79.56 | 0.222 | 186.80 | 32.78 | | |
| 95577 | 87.03 | 0.071 | 71.04 | 85.81 | 0.222 | 371.35 | 99.75 | | |
| 96530 | 62.70 | 0.000 | 32.79 | 68.25 | 0.222 | 65.51 | 38.27 | CopyNumber | 17q22 | 3042 |
| 96852 | 64.09 | 0.071 | 35.77 | 59.97 | 0.111 | 461.69 | 19.35 | | |
| 96996 | 71.81 | 0.000 | 189.55 | 52.96 | 0.000 | 218.21 | 29.32 | | |
| 97616 | 65.77 | 0.036 | 108.39 | 65.74 | 0.222 | 102.19 | 51.76 | CopyNumber | 19p13.3 | 3206 |
| 97887 | 68.13 | 0.000 | 92.61 | 67.37 | 0.222 | 239.81 | 49.52 | CopyNumber | 11p13 | 2237 |
| 98751 | 70.96 | 0.036 | 59.19 | 66.83 | 0.222 | 66.72 | 38.38 | | |
| 98791 | 67.83 | 0.036 | 28.93 | 101.87 | 0.222 | 224.90 | 22.28 | CopyNumber | 2q11.2 | 379 |
| 102696 | 79.18 | 0.000 | 92.68 | 80.38 | 0.111 | 211.23 | 39.36 | | |
| 102798 | 87.39 | 0.000 | 110.04 | 53.06 | 0.111 | 793.97 | 25.38 | | |
| 103561 | 85.04 | 0.036 | 55.08 | 51.00 | 0.111 | 262.35 | 26.56 | CopyNumber | 12q24.31 | 2517 |
| 103834 | 80.57 | 0.036 | 64.54 | 76.68 | 0.222 | 293.02 | 59.69 | | |
| 104839 | 100.99 | 0.000 | 225.26 | 136.95 | 0.222 | 87.68 | 65.32 | | |
| 105547 | 81.74 | 0.000 | 160.68 | 82.23 | 0.111 | 143.20 | 86.05 | CopyNumber | 9q34.3 | 2030 |
| 106185 | 89.36 | 0.036 | 64.50 | 91.88 | 0.000 | 183.56 | 43.28 | | |
| 106876 | 63.88 | 0.000 | 56.12 | 75.64 | 0.222 | 138.98 | 35.36 | | |
| 106909 | 79.27 | 0.036 | 39.60 | 58.15 | 0.222 | 516.81 | 27.82 | | |
| 107003 | 124.40 | 0.000 | 813.78 | 84.52 | 0.000 | 197.77 | 54.64 | | |
| 107101 | 89.68 | 0.000 | 175.98 | 78.98 | 0.111 | 268.93 | 27.15 | CopyNumber | 1p36.33 | 4 |
| 107387 | 70.31 | 0.000 | 76.67 | 74.85 | 0.000 | 253.94 | 39.88 | | |
| 107393 | 83.93 | 0.036 | 59.30 | 71.63 | 0.222 | 267.59 | 45.01 | | |
| 108029 | 93.33 | 0.000 | 169.75 | 68.54 | 0.000 | 579.34 | 50.79 | | |
| 108080 | 130.54 | 0.000 | 212.70 | 124.15 | 0.111 | 825.21 | 73.65 | | |
| 108371 | 71.05 | 0.036 | 43.89 | 82.98 | 0.222 | 479.16 | 32.37 | | |
| 108408 | 68.23 | 0.036 | 119.79 | 74.72 | 0.111 | 307.87 | 34.75 | | |
| 108957 | 105.42 | 0.000 | 125.72 | 97.21 | 0.000 | 1244.98 | 34.19 | | |
| 108969 | 69.16 | 0.000 | 54.94 | 59.23 | 0.111 | 484.04 | 31.51 | | |
| 109051 | 126.66 | 0.036 | 115.04 | 127.27 | 0.222 | 405.39 | 56.02 | | |
| 109052 | 93.26 | 0.000 | 149.09 | 47.63 | 0.111 | 1050.08 | 33.47 | CopyNumber | 14q32.33 | 2746 |
| 109672 | 98.84 | 0.036 | 29.04 | 57.79 | 0.111 | 108.91 | 98.07 | | |
| 109798 | 88.57 | 0.036 | 97.36 | 91.62 | 0.111 | 559.23 | 64.63 | | |
| 110695 | 89.57 | 0.000 | 421.58 | 103.23 | 0.000 | 476.37 | 28.95 | | |
| 110849 | 75.22 | 0.000 | 67.73 | 71.02 | 0.000 | 181.15 | 45.21 | | |
| 111286 | 105.86 | 0.071 | 18.21 | 107.86 | 0.222 | 110.28 | 32.60 | | |
| 111577 | 146.37 | 0.071 | 118.94 | 80.20 | 0.111 | 415.46 | 141.25 | | |
| 111801 | 62.24 | 0.036 | 45.24 | 48.41 | 0.111 | 283.10 | 26.11 | CopyNumber | 7q22.1 | 1600 |
| 112058 | 86.73 | 0.000 | 80.73 | 66.67 | 0.111 | 82.86 | 34.43 | | |
| 112318 | 59.33 | 0.036 | 328.41 | 54.43 | 0.000 | | | CopyNumber | 7p15.3 | 1519 |
| 112955 | 83.18 | 0.000 | 68.65 | 74.54 | 0.222 | 175.05 | 32.35 | | |
| 114033 | 66.61 | 0.071 | 46.31 | 51.12 | 0.111 | 208.35 | 29.63 | | |
| 114286 | 105.50 | 0.000 | 160.45 | 104.16 | 0.111 | 138.02 | 46.31 | | |
| 114412 | 69.57 | 0.000 | 89.73 | 60.94 | 0.000 | 565.48 | 23.70 | | |
| 115474 | 68.64 | 0.000 | 26.75 | 40.02 | 0.222 | 38.04 | 51.64 | | |
| 115792 | 86.72 | 0.000 | 64.83 | 84.38 | 0.111 | 84.30 | 30.92 | CopyNumber | 3p21.31 | 574 |
| 116448 | 76.33 | 0.071 | 42.71 | 91.17 | 0.111 | 92.28 | 52.71 | | |
| 117176 | 57.12 | 0.000 | 213.98 | 51.77 | 0.000 | 546.64 | 24.11 | | |
| 117715 | 73.13 | 0.036 | 39.78 | 89.12 | 0.222 | 139.79 | 48.24 | CopyNumber | 11p15.4 | 2212 |
| 118110 | 135.94 | 0.000 | 197.86 | 123.23 | 0.111 | 289.38 | 139.96 | | |
| 118400 | 143.18 | 0.036 | 396.12 | 82.68 | 0.222 | 45.89 | 81.52 | CopyNumber | 7p22.1 | 1487 |
| 118463 | 114.64 | 0.036 | 277.75 | 88.48 | 0.000 | 489.97 | 35.21 | CopyNumber | 11p15.5 | 2200 |
| 118638 | 91.73 | 0.000 | 150.66 | 112.93 | 0.111 | 502.98 | 55.85 | | |

TABLE 2-continued

A list of 2087 candidate endogenous reference genes

| | | | | | | | | | |
|---|---|---|---|---|---|---|---|---|---|
| 118722 | 70.58 | 0.071 | 36.51 | 53.51 | 0.222 | 115.71 | 60.62 | | |
| 118964 | 81.48 | 0.071 | 54.63 | 51.42 | 0.111 | 180.13 | 35.29 | | |
| 118983 | 116.33 | 0.000 | 216.74 | 115.85 | 0.000 | 112.11 | 59.33 | | |
| 119177 | 54.58 | 0.000 | 89.84 | 57.06 | 0.222 | 287.10 | 32.29 | CopyNumber | 12q13.12 | 2421 |
| 119192 | 136.52 | 0.071 | 366.01 | 79.98 | 0.111 | 746.04 | 45.80 | | |
| 119251 | 77.27 | 0.000 | 105.57 | 82.18 | 0.000 | 510.26 | 60.79 | | |
| 119591 | 132.87 | 0.000 | 85.25 | 60.89 | 0.111 | 277.18 | 26.93 | CopyNumber | 19q13.32 | 3268 |
| 119598 | 65.34 | 0.000 | 1828.88 | 55.92 | 0.000 | 5605.82 | 37.33 | | |
| 120323 | 72.42 | 0.000 | 82.14 | 75.76 | 0.222 | 139.72 | 33.20 | | |
| 121088 | 71.71 | 0.036 | 49.78 | 72.44 | 0.111 | 167.42 | 38.93 | CopyNumber | 6p22.3 | 1297 |
| 121549 | 59.29 | 0.036 | 72.38 | 43.55 | 0.111 | 348.76 | 34.62 | | |
| 122363 | 70.90 | 0.071 | 47.10 | 52.74 | 0.222 | 69.77 | 30.93 | | |
| 122523 | 74.89 | 0.000 | 118.63 | 57.28 | 0.000 | 262.80 | 35.66 | | |
| 124126 | 115.07 | 0.000 | 66.49 | 67.09 | 0.111 | 404.01 | 47.98 | CopyNumber | 7q22.1 | 1597 |
| 124147 | 80.00 | 0.036 | 49.60 | 67.28 | 0.111 | 88.88 | 40.69 | | |
| 124246 | 73.44 | 0.000 | 67.23 | 50.90 | 0.222 | 78.00 | 25.49 | | |
| 124366 | 64.80 | 0.036 | 31.83 | 72.36 | 0.222 | 296.88 | 27.96 | CopyNumber | 3q13.12 | 644 |
| 125113 | 208.71 | 0.000 | 207.39 | 70.50 | 0.000 | 130.39 | 26.17 | | |
| 125867 | 149.28 | 0.071 | 249.31 | 163.63 | 0.000 | 127.51 | 42.41 | | |
| 125898 | 68.47 | 0.000 | 463.77 | 95.22 | 0.000 | 3114.95 | 38.76 | | |
| 126497 | 92.86 | 0.071 | 174.55 | 58.17 | 0.000 | 240.18 | 42.08 | | |
| 126774 | 85.40 | 0.071 | 39.13 | 64.55 | 0.222 | 142.39 | 51.09 | | |
| 126938 | 74.59 | 0.036 | 93.26 | 77.82 | 0.111 | 106.86 | 32.06 | CopyNumber | 19q13.32 | 3269 |
| 127092 | 112.32 | 0.071 | 30.80 | 75.39 | 0.222 | 57.16 | 37.84 | CopyNumber | 16q22.3 | 2939 |
| 127249 | 54.54 | 0.000 | 80.21 | 58.63 | 0.111 | 216.47 | 28.77 | CopyNumber | 17q21.32 | 3034 |
| 127386 | 80.59 | 0.000 | 307.40 | 63.02 | 0.111 | | | | |
| 127764 | 63.23 | 0.036 | 156.09 | 58.22 | 0.000 | | | | |
| 128065 | 98.69 | 0.071 | 111.69 | 94.46 | 0.222 | 59.95 | 51.61 | | |
| 128199 | 77.43 | 0.000 | 73.49 | 95.92 | 0.222 | 302.61 | 35.57 | | |
| 128548 | 78.55 | 0.000 | 160.67 | 43.75 | 0.111 | 510.95 | 31.27 | CopyNumber | 4p16.1 | 773 |
| 129634 | 74.38 | 0.071 | 38.63 | 51.13 | 0.222 | 58.68 | 27.28 | | |
| 129673 | 76.37 | 0.000 | 374.81 | 65.02 | 0.111 | 2050.10 | 29.97 | | |
| 130031 | 141.77 | 0.036 | 61.66 | 100.82 | 0.111 | 124.88 | 40.58 | | |
| 130098 | 68.07 | 0.036 | 21.50 | 58.55 | 0.222 | 72.44 | 30.73 | | |
| 130293 | 74.37 | 0.036 | 143.21 | 63.05 | 0.111 | 394.94 | 46.49 | | |
| 130413 | 62.69 | 0.036 | 35.34 | 73.66 | 0.111 | 763.95 | 36.55 | | |
| 131226 | 77.45 | 0.036 | 40.35 | 61.36 | 0.222 | 211.50 | 44.83 | | |
| 132497 | 62.00 | 0.000 | 89.82 | 78.68 | 0.000 | 67.63 | 44.78 | CopyNumber | 1p34.1 | 66 |
| 132513 | 64.29 | 0.036 | 33.27 | 58.33 | 0.222 | 474.25 | 37.94 | CopyNumber | 11p11.2 | 2252 |
| 133892 | 129.65 | 0.036 | 246.87 | 96.64 | 0.111 | 1107.22 | 68.63 | | |
| 134074 | 100.43 | 0.071 | 26.96 | 119.73 | 0.222 | 90.07 | 25.91 | | |
| 134688 | 70.25 | 0.071 | 68.24 | 53.74 | 0.000 | 72.44 | 28.26 | | |
| 135406 | 65.02 | 0.071 | 70.87 | 53.64 | 0.111 | 258.58 | 31.26 | | |
| 136905 | 88.95 | 0.071 | 63.87 | 56.85 | 0.111 | 420.31 | 25.48 | | |
| 136947 | 61.39 | 0.000 | 83.24 | 64.45 | 0.111 | 164.27 | 33.47 | | |
| 137510 | 78.32 | 0.071 | 33.03 | 97.57 | 0.222 | 338.93 | 38.22 | CopyNumber | 12q24.31 | 2520 |
| 138860 | 75.60 | 0.000 | 63.39 | 84.41 | 0.222 | 104.45 | 29.18 | | |
| 139896 | 65.18 | 0.000 | 67.60 | 55.36 | 0.111 | 240.43 | 26.38 | | |
| 140452 | 115.93 | 0.000 | 61.69 | 109.34 | 0.222 | 149.10 | 37.19 | | |
| 142442 | 65.85 | 0.000 | 96.04 | 76.63 | 0.222 | 900.30 | 25.31 | | |
| 143187 | 74.48 | 0.000 | 61.96 | 104.03 | 0.111 | 114.98 | 39.16 | | |
| 143766 | 70.65 | 0.036 | 56.38 | 78.56 | 0.222 | 131.85 | 31.29 | | |
| 143873 | 123.17 | 0.000 | 265.13 | 64.14 | 0.111 | 1812.20 | 70.31 | | |
| 144058 | 67.40 | 0.071 | 30.59 | 57.17 | 0.222 | 91.15 | 33.46 | | |
| 144468 | 77.62 | 0.000 | 72.08 | 68.21 | 0.000 | 369.59 | 42.51 | CopyNumber | 11p15.5 | 2200 |
| 144835 | 59.90 | 0.000 | 1239.80 | 47.18 | 0.000 | 4424.16 | 35.78 | CopyNumber | 11q12.3 | 2268 |
| 144868 | 61.94 | 0.036 | 46.48 | 65.44 | 0.222 | | | | |
| 144941 | 99.27 | 0.036 | 30.70 | 62.58 | 0.222 | 27.70 | 47.48 | | |
| 144949 | 89.85 | 0.036 | 51.55 | 71.38 | 0.111 | 139.69 | 32.40 | | |
| 144980 | 66.37 | 0.036 | 31.70 | 83.79 | 0.111 | 78.74 | 45.38 | | |
| 145049 | 79.64 | 0.036 | 44.08 | 75.91 | 0.222 | | | | |
| 145442 | 67.35 | 0.071 | 65.14 | 62.03 | 0.111 | 227.44 | 39.23 | | |
| 145575 | 224.58 | 0.036 | 45.18 | 76.11 | 0.222 | 202.49 | 59.73 | | |
| 146070 | 128.18 | 0.000 | 178.96 | 54.77 | 0.000 | 93.05 | 36.84 | | |
| 146393 | 72.80 | 0.000 | 88.78 | 95.83 | 0.111 | 667.21 | 52.63 | | |
| 146602 | 102.89 | 0.000 | 281.39 | 83.54 | 0.000 | 1415.55 | 49.65 | | |
| 146804 | 74.69 | 0.036 | 67.23 | 67.16 | 0.222 | 54.96 | 64.90 | | |
| 146806 | 65.76 | 0.036 | 76.43 | 55.00 | 0.111 | 156.47 | 27.78 | | |
| 147433 | 173.87 | 0.036 | 100.81 | 101.76 | 0.111 | 185.23 | 55.89 | | |
| 148078 | 68.19 | 0.000 | 44.30 | 49.13 | 0.222 | 259.39 | 36.71 | | |
| 148272 | 78.08 | 0.000 | 40.88 | 58.49 | 0.222 | 282.89 | 43.22 | | |
| 148330 | 68.24 | 0.000 | 195.74 | 61.44 | 0.111 | 882.12 | 30.42 | | |
| 148340 | 57.95 | 0.036 | 129.05 | 74.68 | 0.111 | 97.73 | 64.77 | CopyNumber | 3p14.2 | 601 |
| 148670 | 89.45 | 0.036 | 35.45 | 93.34 | 0.222 | 56.01 | 87.59 | | |
| 149004 | 102.91 | 0.036 | 30.71 | 66.15 | 0.222 | | | CopyNumber | 16q24.2 | 2967 |
| 149957 | 81.12 | 0.071 | 47.00 | 76.13 | 0.222 | 125.85 | 48.66 | | |
| 149983 | 68.84 | 0.071 | 42.84 | 78.77 | 0.222 | 75.44 | 36.59 | CopyNumber | 1p36.22 | 27 |
| 150107 | 116.09 | 0.071 | 20.91 | 61.58 | 0.222 | 573.50 | 21.98 | CopyNumber | 2p22.3 | 302 |

TABLE 2-continued

A list of 2087 candidate endogenous reference genes

| | | | | | | | | | |
|---|---|---|---|---|---|---|---|---|---|
| 150540 | 90.93 | 0.036 | 48.36 | 86.76 | 0.000 | 183.75 | 29.74 | | |
| 150580 | 80.15 | 0.000 | 1108.77 | 70.34 | 0.000 | 3122.23 | 30.91 | CopyNumber | 17q21.2 | 3022 |
| 150837 | 124.23 | 0.036 | 86.20 | 120.91 | 0.222 | 778.59 | 48.51 | | |
| 151134 | 57.73 | 0.071 | 45.75 | 78.70 | 0.222 | 289.38 | 30.06 | | |
| 151220 | 73.17 | 0.036 | 66.67 | 96.14 | 0.222 | 744.16 | 63.01 | CopyNumber | 4q32.3 | 1031 |
| 151413 | 80.50 | 0.000 | 79.73 | 76.85 | 0.000 | 300.73 | 30.47 | | |
| 151787 | 65.45 | 0.036 | 107.49 | 74.56 | 0.111 | 592.77 | 39.14 | | |
| 152536 | 151.78 | 0.036 | 64.94 | 62.87 | 0.111 | 437.32 | 51.09 | | |
| 153177 | 82.65 | 0.000 | 1290.76 | 62.05 | 0.000 | | | | |
| 154023 | 69.11 | 0.071 | 35.70 | 66.65 | 0.111 | 83.15 | 28.46 | CopyNumber | 9q31.1 | 1976 |
| 154073 | 75.96 | 0.036 | 33.22 | 53.61 | 0.222 | 218.58 | 39.39 | | |
| 155165 | 68.65 | 0.036 | 52.72 | 66.13 | 0.111 | 79.58 | 31.11 | | |
| 155218 | 57.46 | 0.000 | 200.28 | 53.39 | 0.000 | 216.50 | 35.53 | | |
| 155396 | 76.82 | 0.071 | 67.48 | 97.34 | 0.222 | 405.26 | 42.07 | | |
| 155829 | 66.32 | 0.000 | 59.97 | 79.36 | 0.000 | 238.12 | 23.08 | | |
| 156171 | 68.16 | 0.000 | 68.13 | 52.36 | 0.222 | 147.78 | 34.78 | | |
| 156367 | 87.67 | 0.000 | 1712.42 | 68.63 | 0.000 | 4735.69 | 38.82 | | |
| 156667 | 92.93 | 0.036 | 26.62 | 69.37 | 0.222 | 239.39 | 35.65 | | |
| 157160 | 92.71 | 0.071 | 89.61 | 69.92 | 0.000 | 100.13 | 36.59 | CopyNumber | 16p13.3 | 2866 |
| 157351 | 66.51 | 0.036 | 91.00 | 77.95 | 0.000 | 484.52 | 37.70 | | |
| 157379 | 88.98 | 0.000 | 245.35 | 78.54 | 0.000 | | | | |
| 157394 | 115.85 | 0.036 | 40.70 | 64.13 | 0.111 | 128.63 | 71.71 | CopyNumber | 16p13.3 | 2866 |
| 159014 | 63.78 | 0.036 | 89.22 | 60.16 | 0.111 | 163.73 | 32.17 | | |
| 159118 | 93.76 | 0.000 | 80.22 | 75.94 | 0.222 | 173.36 | 116.76 | | |
| 159130 | 70.14 | 0.036 | 83.65 | 78.95 | 0.000 | 257.93 | 22.84 | | |
| 159161 | 97.10 | 0.000 | 133.32 | 61.43 | 0.000 | 599.74 | 28.29 | CopyNumber | 17q25.3 | 3087 |
| 159699 | 69.52 | 0.000 | 37.41 | 64.94 | 0.111 | 210.99 | 69.05 | CopyNumber | 12q24.22 | 2509 |
| 159799 | 64.26 | 0.036 | 34.74 | 59.78 | 0.111 | 91.07 | 36.21 | CopyNumber | 12q24.21 | 2506 |
| 160958 | 79.14 | 0.000 | 114.90 | 52.77 | 0.222 | 127.25 | 40.40 | | |
| 161357 | 64.76 | 0.000 | 46.29 | 76.91 | 0.000 | 147.60 | 39.89 | | |
| 162032 | 67.26 | 0.036 | 70.53 | 79.73 | 0.000 | 255.04 | 27.58 | | |
| 162233 | 74.14 | 0.000 | 90.72 | 65.27 | 0.000 | 179.64 | 29.18 | | |
| 162877 | 69.59 | 0.036 | 50.56 | 52.07 | 0.000 | 521.49 | 49.22 | | |
| 163645 | 76.60 | 0.071 | 24.93 | 67.74 | 0.111 | 84.40 | 61.57 | | |
| 163776 | 71.14 | 0.071 | 37.56 | 78.72 | 0.111 | 528.53 | 41.20 | | |
| 163893 | 57.76 | 0.000 | 58.05 | 59.53 | 0.000 | 271.42 | 33.87 | | |
| 165195 | 65.00 | 0.036 | 108.29 | 54.09 | 0.222 | 943.91 | 27.36 | | |
| 166011 | 93.62 | 0.000 | 49.61 | 56.41 | 0.222 | 312.99 | 31.66 | | |
| 166204 | 68.68 | 0.071 | 31.97 | 87.75 | 0.000 | 320.35 | 36.72 | | |
| 166463 | 56.02 | 0.000 | 192.95 | 59.71 | 0.000 | 787.81 | 25.31 | | |
| 166924 | 72.91 | 0.036 | 55.96 | 77.29 | 0.111 | 350.25 | 27.79 | | |
| 166975 | 84.13 | 0.000 | 175.23 | 59.39 | 0.111 | 567.33 | 40.53 | | |
| 167535 | 67.25 | 0.071 | 31.16 | 78.48 | 0.222 | 189.62 | 34.78 | CopyNumber | 14q13.2 | 2665 |
| 168073 | 57.46 | 0.000 | 79.97 | 43.40 | 0.000 | 97.12 | 34.22 | CopyNumber | 20q11.22 | 3365 |
| 168799 | 72.15 | 0.000 | 85.51 | 85.35 | 0.111 | 127.53 | 38.40 | CopyNumber | 14q11.2 | 2643 |
| 169611 | 69.54 | 0.071 | 37.43 | 50.49 | 0.222 | 285.98 | 24.97 | | |
| 169718 | 96.71 | 0.000 | 139.45 | 63.02 | 0.222 | 232.68 | 35.86 | CopyNumber | 19p13.3 | 3198 |
| 170107 | 87.41 | 0.071 | 47.18 | 78.34 | 0.222 | 1036.03 | 59.06 | | |
| 170131 | 67.79 | 0.036 | 50.82 | 86.27 | 0.111 | 99.84 | 47.80 | CopyNumber | 19p13.3 | 3203 |
| 170553 | 58.81 | 0.071 | 60.80 | 61.32 | 0.222 | 725.07 | 33.82 | | |
| 170622 | 78.58 | 0.000 | 2283.14 | 56.69 | 0.000 | 9908.08 | 42.82 | CopyNumber | 11q13.1 | 2276 |
| 171626 | 63.32 | 0.000 | 241.54 | 57.86 | 0.000 | 1649.53 | 25.79 | | |
| 172550 | 105.11 | 0.000 | 212.10 | 66.20 | 0.111 | 549.43 | 25.49 | | |
| 172755 | 131.11 | 0.036 | 69.54 | 193.88 | 0.111 | 31.12 | 77.04 | | |
| 172928 | 223.12 | 0.000 | 3277.02 | 184.20 | 0.222 | 23.83 | 59.75 | | |
| 173024 | 72.45 | 0.000 | 18.77 | 58.78 | 0.222 | 607.15 | 31.58 | | |
| 173162 | 77.43 | 0.071 | 64.12 | 75.11 | 0.111 | 116.53 | 36.61 | | |
| 173381 | 129.69 | 0.036 | 196.90 | 150.06 | 0.222 | 416.10 | 84.50 | | |
| 173464 | 130.72 | 0.000 | 144.94 | 86.56 | 0.000 | 106.78 | 43.86 | | |
| 173611 | 74.38 | 0.036 | 72.63 | 73.41 | 0.222 | 450.20 | 37.71 | | |
| 173705 | 71.42 | 0.036 | 77.12 | 54.80 | 0.111 | 1003.69 | 44.66 | | |
| 173724 | 129.37 | 0.000 | 480.96 | 98.37 | 0.111 | 328.75 | 117.68 | | |
| 174050 | 81.34 | 0.000 | 161.44 | 58.99 | 0.111 | 435.08 | 32.67 | CopyNumber | 9q34.3 | 2030 |
| 174195 | 121.69 | 0.000 | 59.79 | 61.62 | 0.222 | 1541.94 | 54.35 | | |
| 175473 | 178.89 | 0.000 | 74.84 | 74.19 | 0.111 | 39.59 | 55.77 | | |
| 175955 | 78.53 | 0.071 | 82.37 | 63.20 | 0.000 | 407.41 | 30.39 | CopyNumber | 4q13.2 4q13.3-4q13.2 | 868 |
| 177530 | 105.78 | 0.000 | 370.63 | 61.86 | 0.000 | 1399.62 | 34.95 | | |
| 177766 | 110.71 | 0.036 | 85.86 | 98.28 | 0.222 | 258.95 | 47.27 | | |
| 178551 | 80.06 | 0.000 | 709.53 | 80.15 | 0.000 | 4043.69 | 42.24 | | |
| 178728 | 82.99 | 0.000 | 68.39 | 77.86 | 0.222 | 178.39 | 24.90 | | |
| 179986 | 66.32 | 0.000 | 162.17 | 96.06 | 0.000 | 650.73 | 31.17 | CopyNumber | 6p21.33 | 1312 |
| 180141 | 117.29 | 0.036 | 32.50 | 84.00 | 0.222 | 371.27 | 77.91 | | |
| 180312 | 89.37 | 0.036 | 55.94 | 83.19 | 0.222 | 153.55 | 46.39 | | |
| 180414 | 84.33 | 0.000 | 849.88 | 48.98 | 0.000 | 1613.00 | 26.72 | | |
| 180877 | 77.30 | 0.000 | 324.36 | 71.18 | 0.000 | 1202.80 | 34.96 | | |
| 180903 | 87.91 | 0.000 | 76.16 | 118.67 | 0.111 | 44.42 | 26.29 | CopyNumber | 22q13.33 | 3520 |

TABLE 2-continued

A list of 2087 candidate endogenous reference genes

| | | | | | | | | | | |
|---|---|---|---|---|---|---|---|---|---|---|
| 180909 | 80.07 | 0.000 | 371.75 | 106.26 | 0.000 | 1474.92 | 40.32 | | | |
| 180933 | 80.42 | 0.071 | 73.33 | 92.53 | 0.111 | 346.11 | 27.13 | | | |
| 181046 | 71.47 | 0.000 | 52.77 | 69.61 | 0.111 | 76.22 | 39.96 | | | |
| 181112 | 67.48 | 0.000 | 56.45 | 51.99 | 0.111 | 58.24 | 39.41 | CopyNumber | 13q14.2 | 2567 |
| 181163 | 101.97 | 0.036 | 209.51 | 59.97 | 0.000 | 1671.22 | 28.67 | | | |
| 181244 | 84.91 | 0.000 | 615.31 | 92.95 | 0.000 | | | CopyNumber | 6p21.33 | 1311 |
| 181368 | 73.25 | 0.036 | 72.19 | 59.47 | 0.222 | 877.69 | 37.35 | | | |
| 181444 | 77.92 | 0.000 | 93.53 | 65.83 | 0.111 | 428.12 | 41.92 | | | |
| 182255 | 70.26 | 0.000 | 258.19 | 78.53 | 0.000 | 575.25 | 28.65 | | | |
| 182626 | 59.53 | 0.036 | 77.65 | 60.50 | 0.111 | 114.59 | 33.95 | | | |
| 182885 | 72.14 | 0.071 | 79.54 | 72.22 | 0.111 | 658.87 | 31.09 | | | |
| 183684 | 66.42 | 0.000 | 167.12 | 47.95 | 0.000 | 1226.24 | 19.58 | | | |
| 183706 | 87.65 | 0.000 | 71.68 | 63.07 | 0.111 | 129.53 | 32.44 | | | |
| 183800 | 73.34 | 0.000 | 88.07 | 68.82 | 0.111 | 79.80 | 39.64 | CopyNumber | 22q13.2 | 3503 |
| 183850 | 63.02 | 0.071 | 42.45 | 54.66 | 0.222 | 201.07 | 30.38 | | | |
| 183994 | 111.25 | 0.036 | 107.82 | 63.33 | 0.222 | 314.08 | 45.04 | | | |
| 184062 | 80.16 | 0.000 | 108.22 | 79.79 | 0.111 | 885.45 | 50.28 | | | |
| 184211 | 68.32 | 0.071 | 35.11 | 53.79 | 0.222 | 316.88 | 34.51 | | | |
| 184233 | 67.24 | 0.000 | 149.88 | 69.13 | 0.111 | 465.50 | 38.54 | | | |
| 184492 | 63.40 | 0.071 | 46.02 | 72.84 | 0.222 | 397.55 | 26.36 | CopyNumber | 19p13.2 | 3210 |
| 185172 | 91.53 | 0.000 | 246.66 | 86.19 | 0.000 | 344.82 | 34.87 | CopyNumber | 7q22.1 | 1600 |
| 185597 | 59.04 | 0.000 | 83.15 | 71.88 | 0.111 | 139.56 | 35.15 | CopyNumber | 16q24.3 | 2972 |
| 187199 | 115.54 | 0.000 | 303.70 | 76.68 | 0.000 | | | | | |
| 187635 | 101.59 | 0.000 | 380.46 | 78.22 | 0.000 | 28.66 | 51.48 | CopyNumber | 16p12.3 | 2889 |
| 187763 | 66.27 | 0.000 | 76.79 | 54.16 | 0.222 | 500.24 | 26.46 | | | |
| 187866 | 73.60 | 0.000 | 111.79 | 64.50 | 0.111 | 680.00 | 34.53 | | | |
| 187946 | 84.06 | 0.000 | 104.34 | 48.89 | 0.222 | 200.66 | 75.07 | | | |
| 188501 | 67.55 | 0.000 | 55.47 | 53.26 | 0.222 | 45.76 | 34.94 | | | |
| 188614 | 65.47 | 0.071 | 44.10 | 82.41 | 0.222 | 84.46 | 53.64 | CopyNumber | 12p12.3 | 2387 |
| 188879 | 68.81 | 0.071 | 103.91 | 56.06 | 0.111 | 141.32 | 40.35 | | | |
| 188882 | 62.39 | 0.036 | 30.53 | 64.74 | 0.222 | 163.76 | 30.89 | | | |
| 189075 | 84.72 | 0.000 | 48.42 | 71.25 | 0.222 | 232.97 | 38.78 | | | |
| 189119 | 95.87 | 0.000 | 83.56 | 64.37 | 0.222 | 64.39 | 50.46 | | | |
| 189329 | 60.19 | 0.071 | 28.86 | 71.76 | 0.222 | 86.40 | 35.87 | | | |
| 189716 | 84.20 | 0.000 | 79.20 | 72.95 | 0.111 | 798.87 | 31.92 | | | |
| 189772 | 112.18 | 0.071 | 233.62 | 107.40 | 0.222 | 546.84 | 44.02 | | | |
| 190028 | 96.99 | 0.036 | 64.26 | 55.28 | 0.222 | 715.65 | 50.89 | | | |
| 190086 | 108.77 | 0.000 | 238.35 | 55.47 | 0.111 | 312.07 | 29.80 | | | |
| 190334 | 64.40 | 0.000 | 45.95 | 69.08 | 0.222 | 275.10 | 42.89 | | | |
| 190384 | 61.06 | 0.036 | 49.81 | 60.07 | 0.111 | 232.13 | 26.89 | | | |
| 190722 | 69.16 | 0.000 | 105.73 | 67.89 | 0.000 | 144.16 | 53.90 | | | |
| 190904 | 86.92 | 0.036 | 32.05 | 61.63 | 0.222 | 95.24 | 30.61 | CopyNumber | 19q13.32 | 3268 |
| 191186 | 70.71 | 0.071 | 39.12 | 55.01 | 0.222 | 614.82 | 24.31 | | | |
| 191344 | 80.55 | 0.000 | 98.52 | 86.95 | 0.111 | 757.36 | 36.32 | CopyNumber | 7p14.2 | 1530 |
| 191518 | 87.09 | 0.071 | 92.92 | 81.35 | 0.222 | 176.63 | 30.67 | | | |
| 191987 | 71.55 | 0.071 | 50.78 | 45.94 | 0.222 | 307.98 | 24.32 | CopyNumber | 1p36.33 | 2 |
| 192316 | 65.32 | 0.036 | 43.60 | 69.01 | 0.222 | 176.27 | 33.07 | CopyNumber | 1p36.33 | 3 |
| 192374 | 78.84 | 0.000 | 407.58 | 81.92 | 0.000 | 1068.05 | 35.28 | | | |
| 192425 | 76.85 | 0.000 | 311.90 | 64.60 | 0.000 | | | InversionBreakpoint InversionBreakpoint CopyNumber | 16p11.2 | 2900 |
| 193118 | 62.88 | 0.036 | 41.98 | 71.16 | 0.000 | 331.29 | 46.59 | CopyNumber | 10q22.3 | 2141 |
| 193163 | 145.45 | 0.000 | 64.92 | 125.23 | 0.222 | 62.71 | 48.89 | CopyNumber | 2q14.3 | 408 |
| 193491 | 92.35 | 0.000 | 115.38 | 71.01 | 0.111 | 286.47 | 58.62 | CopyNumber | 18p11.21 | 3105 |
| 194329 | 73.07 | 0.000 | 93.43 | 82.64 | 0.000 | 315.47 | 84.07 | | | |
| 194718 | 66.93 | 0.071 | 50.97 | 67.72 | 0.111 | 497.18 | 30.12 | | | |
| 195464 | 98.64 | 0.036 | 248.43 | 76.79 | 0.000 | 442.92 | 71.56 | Inversion | Xq28 | 3630 |
| 195642 | 78.70 | 0.071 | 39.60 | 101.58 | 0.222 | 88.25 | 56.73 | | | |
| 196983 | 83.49 | 0.071 | 33.94 | 63.95 | 0.222 | 186.36 | 59.61 | | | |
| 198281 | 108.54 | 0.000 | 400.81 | 102.64 | 0.111 | 57.29 | 51.53 | | | |
| 199561 | 68.25 | 0.036 | 72.08 | 76.53 | 0.000 | 89.48 | 31.20 | | | |
| 199625 | 89.82 | 0.000 | 222.28 | 87.19 | 0.111 | 383.94 | 32.48 | | | |
| 200063 | 131.93 | 0.071 | 68.93 | 74.04 | 0.111 | 65.10 | 51.46 | | | |
| 200600 | 81.79 | 0.036 | 59.63 | 66.67 | 0.222 | 239.47 | 30.41 | CopyNumber | 1q22 | 160 |
| 200804 | 109.85 | 0.000 | 135.85 | 90.16 | 0.000 | 879.77 | 36.77 | CopyNumber | 8q12.1 | 1762 |
| 201253 | 75.54 | 0.071 | 53.03 | 72.88 | 0.111 | 150.04 | 34.96 | | | |
| 201390 | 61.96 | 0.036 | 64.00 | 58.40 | 0.111 | 410.22 | 35.22 | | | |
| 201712 | 78.85 | 0.036 | 29.07 | 57.59 | 0.222 | 96.84 | 37.35 | CopyNumber | 16q22.3 | 2941 |
| 202011 | 64.61 | 0.000 | 88.75 | 53.56 | 0.111 | 189.04 | 35.21 | | | |
| 202085 | 70.60 | 0.000 | 180.75 | 62.87 | 0.000 | | | | | |
| 202166 | 57.15 | 0.000 | 166.73 | 45.76 | 0.111 | 1023.72 | 33.49 | Inversion CopyNumber | 5q35.3 | 1270 |
| 202179 | 59.85 | 0.000 | 59.18 | 64.11 | 0.222 | 53.16 | 43.92 | CopyNumber | 5q13.2 | 1143 |
| 203099 | 55.11 | 0.036 | 50.48 | 63.52 | 0.222 | 113.15 | 27.96 | | | |
| 203910 | 83.11 | 0.000 | 151.92 | 125.87 | 0.000 | 46.20 | 51.50 | | | |
| 204041 | 74.62 | 0.036 | 106.38 | 86.68 | 0.111 | 254.62 | 59.64 | | | |
| 204773 | 71.71 | 0.000 | 60.94 | 64.50 | 0.000 | 135.31 | 39.98 | | | |
| 205163 | 62.46 | 0.000 | 151.99 | 70.71 | 0.000 | 517.07 | 39.92 | CopyNumber | 3q22.1 | 670 |

TABLE 2-continued

A list of 2087 candidate endogenous reference genes

| ID | V1 | V2 | V3 | V4 | V5 | V6 | V7 | Type | Location | Number |
|---|---|---|---|---|---|---|---|---|---|---|
| 206500 | 81.07 | 0.036 | 62.30 | 49.78 | 0.222 | | | | | |
| 206824 | 89.50 | 0.000 | 195.81 | 83.44 | 0.111 | 2218.86 | 36.90 | | | |
| 208597 | 62.01 | 0.000 | 112.96 | 50.60 | 0.000 | 481.51 | 24.72 | | | |
| 209983 | 132.48 | 0.071 | 257.96 | 130.11 | 0.222 | 101.23 | 38.96 | | | |
| 210469 | 70.29 | 0.036 | 21.05 | 72.93 | 0.222 | 64.90 | 43.40 | | | |
| 210532 | 74.09 | 0.071 | 82.09 | 84.33 | 0.111 | 61.52 | 28.17 | | | |
| 211463 | 73.34 | 0.000 | 101.29 | 69.16 | 0.222 | 98.91 | 38.82 | CopyNumber | 19p13.2 | 3217 |
| 211594 | 102.99 | 0.071 | 73.05 | 66.89 | 0.111 | 104.24 | 46.28 | CopyNumber | 19q13.2 | 3258 |
| 211914 | 107.07 | 0.036 | 59.20 | 53.55 | 0.111 | 128.87 | 42.11 | CopyNumber | 19p13.3 | 3198 |
| 212102 | 78.06 | 0.000 | 138.13 | 60.95 | 0.111 | 393.98 | 37.87 | | | |
| 212395 | 62.26 | 0.071 | 31.35 | 67.76 | 0.222 | 59.26 | 42.89 | | | |
| 213061 | 98.05 | 0.000 | 327.00 | 72.73 | 0.000 | 1227.71 | 41.68 | | | |
| 213470 | 67.83 | 0.000 | 192.87 | 68.35 | 0.111 | 410.41 | 31.28 | | | |
| 213541 | 84.63 | 0.036 | 85.44 | 89.94 | 0.000 | 429.86 | 31.21 | | | |
| 213666 | 61.77 | 0.036 | 27.18 | 63.86 | 0.222 | 107.77 | 28.26 | | | |
| 213724 | 81.67 | 0.071 | 54.83 | 74.71 | 0.111 | 278.03 | 30.19 | | | |
| 216653 | 74.68 | 0.071 | 33.21 | 71.69 | 0.222 | 343.12 | 32.18 | | | |
| 220950 | 71.10 | 0.071 | 83.15 | 93.30 | 0.000 | 1027.22 | 35.80 | | | |
| 221847 | 107.96 | 0.000 | 214.24 | 135.53 | 0.111 | 687.16 | 51.69 | | | |
| 222510 | 93.05 | 0.071 | 88.95 | 63.95 | 0.222 | 113.62 | 30.43 | CopyNumber | 19p13.3 | 3198 |
| 223141 | 99.93 | 0.036 | 131.95 | 62.74 | 0.111 | 1035.61 | 39.53 | | | |
| 224607 | 152.50 | 0.036 | 87.86 | 158.09 | 0.222 | 137.21 | 45.23 | | | |
| 226007 | 164.81 | 0.071 | 47.81 | 52.32 | 0.222 | 40.09 | 36.30 | | | |
| 226117 | 83.46 | 0.000 | 65.79 | 116.54 | 0.111 | 371.84 | 56.86 | CopyNumber | 22q13.1 | 3496 |
| 226755 | 93.25 | 0.000 | 194.51 | 65.63 | 0.111 | 278.34 | 38.95 | | | |
| 227067 | 67.54 | 0.071 | 33.57 | 86.75 | 0.222 | 231.33 | 33.85 | CopyNumber | 1p36.33 | 3 |
| 227253 | 81.31 | 0.036 | 55.73 | 71.93 | 0.111 | 101.17 | 28.59 | | | |
| 227777 | 72.56 | 0.000 | 81.21 | 76.44 | 0.111 | 415.86 | 66.71 | | | |
| 229641 | 64.35 | 0.000 | 118.72 | 79.68 | 0.000 | 809.47 | 34.84 | CopyNumber | 5p13.3 | 1105 |
| 231295 | 68.62 | 0.071 | 21.81 | 62.84 | 0.222 | 87.17 | 37.84 | CopyNumber | 17q24.2 | 3061 |
| 231616 | 83.55 | 0.036 | 105.55 | 56.13 | 0.000 | 385.33 | 37.02 | CopyNumber | 19p13.13-19p13.12 | 3221 |
| 232194 | 64.71 | 0.000 | 51.79 | 57.10 | 0.111 | 405.35 | 23.20 | | | |
| 232543 | 132.95 | 0.036 | 98.19 | 105.59 | 0.222 | 74.17 | 72.02 | | | |
| 233458 | 89.76 | 0.000 | 44.01 | 49.80 | 0.000 | 127.26 | 26.28 | | | |
| 233552 | 59.88 | 0.071 | 23.54 | 97.43 | 0.222 | 130.13 | 32.17 | CopyNumber | 7p14.1 | 1535 |
| 233952 | 90.17 | 0.000 | 319.55 | 67.24 | 0.000 | 101.92 | 36.48 | | | |
| 234521 | 91.19 | 0.071 | 81.43 | 91.57 | 0.222 | 69.82 | 35.53 | | | |
| 236030 | 71.56 | 0.036 | 23.36 | 61.13 | 0.222 | 83.17 | 36.95 | CopyNumber | 12q13.2 | 2429 |
| 237536 | 90.09 | 0.036 | 49.15 | 76.51 | 0.111 | 483.90 | 44.44 | | | |
| 237971 | 91.89 | 0.036 | 78.94 | 95.20 | 0.222 | 246.47 | 64.85 | | | |
| 238839 | 67.07 | 0.000 | 145.01 | 65.51 | 0.000 | 190.91 | 36.76 | | | |
| 240170 | 87.00 | 0.000 | 118.73 | 122.83 | 0.222 | 37.21 | 46.26 | CopyNumber | 12q13.2 | 2429 |
| 241336 | 61.07 | 0.000 | 155.72 | 77.04 | 0.111 | 721.67 | 34.47 | | | |
| 241543 | 76.34 | 0.000 | 45.73 | 60.57 | 0.222 | 203.39 | 33.10 | | | |
| 241558 | 64.15 | 0.000 | 47.89 | 63.03 | 0.222 | 122.71 | 28.63 | | | |
| 241575 | 70.86 | 0.000 | 45.40 | 74.01 | 0.222 | 432.03 | 30.80 | CopyNumber | 16p13.3 | 2866 |
| 241576 | 71.75 | 0.000 | 35.61 | 63.06 | 0.222 | 626.29 | 37.40 | | | |
| 241579 | 107.31 | 0.000 | 207.46 | 85.28 | 0.222 | | | | | |
| 242458 | 57.83 | 0.036 | 73.30 | 49.12 | 0.000 | 415.64 | 29.35 | | | |
| 242947 | 58.36 | 0.000 | 3864.18 | 41.07 | 0.000 | 13.84 | 72.12 | | | |
| 246112 | 67.73 | 0.000 | 136.82 | 57.97 | 0.111 | 1178.68 | 27.77 | CopyNumber | 2q11.2 | 378 |
| 246310 | 76.17 | 0.000 | 145.70 | 64.99 | 0.111 | 618.59 | 39.03 | | | |
| 246413 | 81.25 | 0.036 | 112.38 | 61.72 | 0.111 | 183.60 | 54.30 | | | |
| 246781 | 62.94 | 0.071 | 41.90 | 55.75 | 0.222 | 10.39 | 88.93 | | | |
| 247052 | 67.52 | 0.000 | 567.58 | 47.87 | 0.000 | 1471.14 | 26.19 | CopyNumber | 3p21.31 | 583 |
| 247186 | 64.96 | 0.000 | 37.62 | 80.54 | 0.222 | 77.06 | 31.82 | CopyNumber | 16p11.2 | 2904 |
| 247975 | 105.68 | 0.000 | 438.14 | 91.84 | 0.000 | 104.18 | 46.50 | | | |
| 248267 | 96.06 | 0.036 | 85.59 | 77.62 | 0.000 | 267.18 | 59.58 | | | |
| 248941 | 61.08 | 0.036 | 51.35 | 63.24 | 0.222 | 221.26 | 33.54 | CopyNumber | 5q13.2 | 1143 |
| 249600 | 70.96 | 0.071 | 67.36 | 81.11 | 0.222 | 73.53 | 34.15 | | | |
| 250009 | 61.55 | 0.000 | 59.19 | 55.14 | 0.111 | 418.28 | 26.81 | | | |
| 250429 | 69.07 | 0.071 | 30.41 | 44.58 | 0.222 | 130.29 | 29.98 | | | |
| 250758 | 61.91 | 0.000 | 91.07 | 70.47 | 0.222 | 135.51 | 35.81 | | | |
| 250899 | 79.57 | 0.000 | 193.37 | 90.68 | 0.000 | 526.51 | 34.77 | | | |
| 250905 | 66.32 | 0.000 | 77.23 | 58.42 | 0.111 | 1248.73 | 26.47 | | | |
| 251531 | 101.66 | 0.000 | 119.04 | 61.83 | 0.222 | 359.88 | 30.37 | | | |
| 252457 | 76.40 | 0.000 | 54.99 | 74.23 | 0.000 | 13.56 | 94.81 | CopyNumber | 16q24.2-16q24.3 | 2970 |
| 252713 | 72.27 | 0.071 | 50.47 | 59.99 | 0.111 | 74.87 | 50.43 | | | |
| 252967 | 64.23 | 0.000 | 74.53 | 57.70 | 0.111 | 168.08 | 23.83 | | | |
| 253726 | 58.02 | 0.000 | 89.50 | 50.88 | 0.000 | 451.23 | 27.68 | | | |
| 253903 | 101.02 | 0.071 | 152.14 | 104.18 | 0.222 | 591.87 | 57.57 | | | |
| 254042 | 67.31 | 0.000 | 162.34 | 45.49 | 0.000 | 920.76 | 27.97 | CopyNumber | 6p21.33 | 1313 |
| 255015 | 52.53 | 0.036 | 52.05 | 70.92 | 0.111 | 607.92 | 28.15 | | | |
| 255093 | 61.27 | 0.000 | 87.62 | 65.22 | 0.111 | 184.42 | 34.31 | | | |
| 255932 | 75.20 | 0.071 | 63.07 | 84.50 | 0.111 | 246.82 | 28.40 | | | |
| 255935 | 97.23 | 0.000 | 310.78 | 117.34 | 0.111 | 10.29 | 49.34 | | | |

TABLE 2-continued

A list of 2087 candidate endogenous reference genes

| | | | | | | | | | |
|---|---|---|---|---|---|---|---|---|---|
| 255973 | 77.67 | 0.000 | 121.74 | 58.40 | 0.111 | 88.24 | 45.36 | | |
| 256301 | 143.00 | 0.036 | 131.52 | 125.09 | 0.111 | 193.25 | 117.05 | | |
| 256549 | 73.37 | 0.071 | 66.78 | 109.62 | 0.111 | 72.47 | 43.74 | CopyNumber | 16p13.3 | 2866 |
| 257008 | 94.53 | 0.000 | 239.54 | 60.00 | 0.000 | 206.91 | 69.09 | | |
| 257341 | 80.14 | 0.071 | 32.10 | 94.24 | 0.222 | | | | |
| 257761 | 74.40 | 0.071 | 57.97 | 89.39 | 0.222 | 90.97 | 44.23 | | |
| 258551 | 113.91 | 0.036 | 31.42 | 52.51 | 0.111 | 212.75 | 23.35 | CopyNumber | 2q35 | 496 |
| 258563 | 74.13 | 0.000 | 51.06 | 53.28 | 0.222 | 270.95 | 35.45 | | |
| 258798 | 192.40 | 0.000 | 100.67 | 52.60 | 0.222 | 109.62 | 31.17 | | |
| 259461 | 79.93 | 0.036 | 118.37 | 49.94 | 0.000 | 119.14 | 28.75 | | |
| 260603 | 112.19 | 0.036 | 28.87 | 96.98 | 0.111 | 114.76 | 44.19 | | |
| 262823 | 101.47 | 0.036 | 35.90 | 64.77 | 0.222 | 268.43 | 30.93 | | |
| 265829 | 134.13 | 0.036 | 60.09 | 147.84 | 0.222 | 88.23 | 82.34 | | |
| 268488 | 75.37 | 0.000 | 22.47 | 50.04 | 0.222 | 260.69 | 26.22 | CopyNumber | 1p36.32 | 12 |
| 268530 | 81.96 | 0.036 | 168.88 | 85.78 | 0.000 | 106.18 | 37.76 | | |
| 268742 | 79.56 | 0.000 | 96.43 | 68.28 | 0.111 | 881.42 | 37.73 | | |
| 268849 | 62.43 | 0.000 | 127.97 | 70.40 | 0.222 | 666.34 | 58.26 | CopyNumber | 6p21.2 | 1325 |
| 268939 | 88.77 | 0.000 | 69.60 | 63.46 | 0.111 | 993.14 | 26.39 | | |
| 269528 | 65.55 | 0.000 | 77.77 | 59.98 | 0.111 | 321.03 | 37.48 | | |
| 269577 | 52.27 | 0.036 | 116.39 | 58.52 | 0.000 | 163.78 | 33.49 | CopyNumber | 20p13 | 3304 |
| 269782 | 67.13 | 0.071 | 73.22 | 67.37 | 0.111 | 139.08 | 34.10 | | |
| 269944 | 60.66 | 0.000 | 46.86 | 64.04 | 0.222 | 297.40 | 32.90 | CopyNumber | 11p11.2 | 2254 |
| 270291 | 83.84 | 0.000 | 288.23 | 52.39 | 0.000 | 489.18 | 51.55 | | |
| 270428 | 69.26 | 0.036 | 56.42 | 53.38 | 0.000 | 575.82 | 78.18 | | |
| 270525 | 70.97 | 0.071 | 49.58 | 95.80 | 0.222 | 482.93 | 25.81 | | |
| 270869 | 61.79 | 0.036 | 41.81 | 83.43 | 0.222 | 159.67 | 24.39 | | |
| 271135 | 68.23 | 0.036 | 96.12 | 59.45 | 0.000 | 1364.03 | 36.20 | | |
| 271695 | 74.54 | 0.071 | 51.23 | 58.22 | 0.222 | 431.22 | 39.81 | | |
| 272062 | 90.33 | 0.071 | 134.84 | 67.71 | 0.222 | 403.60 | 48.89 | | |
| 272168 | 70.53 | 0.071 | 24.14 | 85.55 | 0.222 | 235.12 | 31.23 | | |
| 272630 | 60.27 | 0.000 | 49.35 | 72.52 | 0.111 | 70.37 | 33.27 | | |
| 272927 | 66.36 | 0.000 | 55.23 | 67.21 | 0.111 | 132.83 | 49.23 | | |
| 273077 | 75.82 | 0.071 | 65.81 | 74.94 | 0.111 | 284.35 | 38.35 | | |
| 274184 | 70.70 | 0.071 | 73.81 | 63.57 | 0.111 | 79.41 | 33.16 | | |
| 274772 | 65.96 | 0.000 | 78.91 | 69.49 | 0.000 | 341.50 | 37.35 | | |
| 274873 | 81.69 | 0.000 | 64.18 | 62.49 | 0.111 | 401.63 | 28.94 | | |
| 275243 | 132.16 | 0.000 | 386.53 | 100.02 | 0.222 | 2365.31 | 75.71 | | |
| 275775 | 134.20 | 0.071 | 141.95 | 138.41 | 0.222 | 1379.68 | 60.08 | | |
| 275865 | 62.60 | 0.071 | 77.19 | 60.06 | 0.111 | 390.18 | 35.84 | | |
| 276738 | 85.73 | 0.071 | 75.29 | 88.57 | 0.222 | 41.28 | 79.67 | | |
| 277035 | 117.16 | 0.000 | 49.43 | 96.96 | 0.111 | 820.49 | 57.32 | CopyNumber | 3q21.3 | 667 |
| 277517 | 74.29 | 0.000 | 43.19 | 64.65 | 0.222 | 340.59 | 48.75 | | |
| 278186 | 85.24 | 0.071 | 64.92 | 117.05 | 0.111 | 125.86 | 38.10 | | |
| 278362 | 66.62 | 0.000 | 67.90 | 71.94 | 0.000 | 328.98 | 38.55 | | |
| 278426 | 62.04 | 0.000 | 92.55 | 57.10 | 0.111 | 156.41 | 42.46 | CopyNumber | 7q22.1 | 1597 |
| 278429 | 64.98 | 0.036 | 103.18 | 62.08 | 0.111 | 94.29 | 29.86 | | |
| 278500 | 68.19 | 0.036 | 75.86 | 73.54 | 0.222 | 106.63 | 48.00 | | |
| 278569 | 82.25 | 0.000 | 200.20 | 102.95 | 0.222 | 107.25 | 51.38 | | |
| 278573 | 101.10 | 0.000 | 114.44 | 148.80 | 0.111 | 650.32 | 46.92 | | |
| 278721 | 83.27 | 0.036 | 71.10 | 71.24 | 0.222 | 72.60 | 42.44 | | |
| 279061 | 67.08 | 0.036 | 44.30 | 63.18 | 0.222 | 197.52 | 31.29 | CopyNumber | 17p13.3 | 2975 |
| 279245 | 76.47 | 0.000 | 75.15 | 85.55 | 0.111 | 91.87 | 45.55 | | |
| 279257 | 66.80 | 0.036 | 93.74 | 71.44 | 0.111 | 194.76 | 31.27 | | |
| 279413 | 129.76 | 0.036 | 110.16 | 104.82 | 0.111 | 47.09 | 59.50 | | |
| 279529 | 81.69 | 0.036 | 104.37 | 66.22 | 0.222 | 1363.23 | 45.45 | CopyNumber | 5q35.3 | 1268 |
| 279583 | 71.86 | 0.036 | 199.42 | 57.52 | 0.000 | 103.71 | 39.63 | Inversion CopyNumber | 16p12.2-16p12.1 | 2894 |
| 279623 | 77.55 | 0.071 | 41.14 | 84.94 | 0.111 | 251.43 | 82.76 | CopyNumber | 16p13.3 | 2866 |
| 279640 | 65.23 | 0.036 | 40.21 | 83.36 | 0.222 | 301.86 | 23.97 | | |
| 279652 | 91.16 | 0.000 | 56.36 | 73.29 | 0.222 | 122.30 | 52.34 | | |
| 279669 | 82.14 | 0.071 | 83.17 | 76.56 | 0.222 | 90.40 | 49.23 | | |
| 279696 | 83.17 | 0.036 | 102.39 | 93.03 | 0.000 | 431.21 | 44.69 | | |
| 279806 | 69.81 | 0.000 | 647.74 | 79.09 | 0.111 | 1392.91 | 24.99 | | |
| 279836 | 58.12 | 0.000 | 42.38 | 77.37 | 0.222 | 109.90 | 38.28 | CopyNumber | 11p13-11p12 | 2245 |
| 279920 | 78.76 | 0.000 | 209.25 | 54.55 | 0.111 | 1143.94 | 32.04 | | |
| 279929 | 81.28 | 0.000 | 119.27 | 50.43 | 0.111 | 615.57 | 32.57 | | |
| 280202 | 67.43 | 0.036 | 34.06 | 68.28 | 0.111 | | | | |
| 280342 | 64.79 | 0.000 | 190.05 | 68.21 | 0.111 | 507.64 | 35.59 | | |
| 280378 | 78.00 | 0.036 | 59.08 | 52.49 | 0.111 | 324.22 | 34.79 | | |
| 282410 | 75.08 | 0.000 | 346.66 | 83.21 | 0.000 | 863.13 | 37.39 | | |
| 282700 | 59.59 | 0.071 | 89.12 | 64.76 | 0.111 | 474.36 | 29.57 | | |
| 282901 | 61.28 | 0.000 | 161.17 | 55.92 | 0.111 | 586.28 | 30.27 | | |
| 282998 | 87.12 | 0.000 | 109.61 | 89.33 | 0.000 | 203.95 | 38.00 | | |
| 283111 | 77.12 | 0.000 | 54.33 | 58.77 | 0.111 | 148.42 | 37.10 | | |
| 283454 | 55.19 | 0.071 | 33.55 | 62.22 | 0.111 | 72.33 | 42.83 | | |
| 283521 | 77.37 | 0.000 | 76.39 | 64.83 | 0.222 | 21.40 | 67.57 | | |
| 283610 | 59.73 | 0.071 | 45.77 | 73.57 | 0.111 | 113.35 | 30.58 | | |

TABLE 2-continued

A list of 2087 candidate endogenous reference genes

| | | | | | | | | | | |
|---|---|---|---|---|---|---|---|---|---|---|
| 283652 | 77.33 | 0.036 | 55.65 | 73.75 | 0.222 | 173.00 | 38.91 | | | |
| 283739 | 146.71 | 0.071 | 51.69 | 109.60 | 0.222 | 360.93 | 32.32 | | | |
| 284208 | 78.08 | 0.071 | 29.66 | 65.71 | 0.111 | 301.23 | 63.92 | | | |
| 284279 | 69.22 | 0.000 | 39.54 | 69.82 | 0.222 | 123.20 | 36.70 | | | |
| 284286 | 81.75 | 0.036 | 67.66 | 95.49 | 0.222 | 1531.44 | 35.52 | CopyNumber | 7p13 | 1537 |
| 284491 | 136.63 | 0.000 | 305.06 | 99.27 | 0.000 | 226.73 | 38.91 | CopyNumber | 21q22.3 | 3455 |
| 285354 | 59.95 | 0.071 | 60.82 | 74.39 | 0.222 | 168.00 | 27.87 | | | |
| 285976 | 94.65 | 0.000 | 98.07 | 53.23 | 0.111 | 573.85 | 77.02 | | | |
| 286221 | 75.65 | 0.000 | 248.30 | 58.65 | 0.000 | 3463.94 | 35.74 | | | |
| 286226 | 101.42 | 0.036 | 32.24 | 72.06 | 0.222 | 207.01 | 28.47 | | | |
| 288193 | 61.78 | 0.000 | 45.54 | 63.87 | 0.111 | 349.23 | 36.00 | | | |
| 288856 | 87.34 | 0.071 | 197.77 | 57.17 | 0.000 | 1020.14 | 40.67 | | | |
| 288969 | 73.68 | 0.071 | 31.39 | 60.73 | 0.222 | 278.99 | 36.61 | | | |
| 289008 | 59.92 | 0.036 | 63.72 | 61.38 | 0.222 | 271.56 | 30.69 | | | |
| 289092 | 116.11 | 0.036 | 289.77 | 159.61 | 0.111 | 458.68 | 76.94 | CopyNumber | 16q24.1 | 2960 |
| 289123 | 66.03 | 0.000 | 78.85 | 81.68 | 0.000 | 272.21 | 82.53 | CopyNumber | 12q13.3 | 2432 |
| 289271 | 87.86 | 0.000 | 314.40 | 88.75 | 0.000 | 394.29 | 60.90 | CopyNumber | 8q24.3 | 1879 |
| 290243 | 125.85 | 0.000 | 761.77 | 103.49 | 0.000 | 101.29 | 27.98 | | | |
| 290404 | 75.80 | 0.071 | 40.20 | 86.49 | 0.111 | 1710.99 | 28.57 | | | |
| 290758 | 67.69 | 0.000 | 91.13 | 56.76 | 0.222 | 361.48 | 36.00 | CopyNumber | 11q12.2 | 2266 |
| 291587 | 59.78 | 0.000 | 43.57 | 53.60 | 0.111 | 178.10 | 32.56 | | | |
| 292026 | 69.01 | 0.036 | 40.56 | 58.47 | 0.222 | 211.07 | 26.51 | | | |
| 292063 | 62.83 | 0.000 | 145.61 | 55.21 | 0.000 | 49.54 | 46.81 | | | |
| 292078 | 78.84 | 0.036 | 77.92 | 77.84 | 0.111 | 475.13 | 31.13 | | | |
| 292265 | 64.89 | 0.071 | 34.72 | 84.99 | 0.222 | 384.26 | 31.49 | CopyNumber | 10p15.3 | 2033 |
| 292457 | 160.14 | 0.000 | 215.82 | 73.61 | 0.111 | 63.85 | 61.00 | | | |
| 292493 | 70.67 | 0.000 | 424.46 | 81.44 | 0.000 | 831.58 | 26.17 | | | |
| 292524 | 67.18 | 0.071 | 25.82 | 53.79 | 0.222 | 195.08 | 27.33 | | | |
| 292579 | 75.20 | 0.036 | 75.85 | 66.75 | 0.111 | 420.33 | 36.15 | | | |
| 293563 | 104.96 | 0.036 | 137.26 | 82.64 | 0.111 | 165.89 | 47.95 | | | |
| 295917 | 77.96 | 0.036 | 56.00 | 89.69 | 0.222 | 319.57 | 47.66 | | | |
| 297324 | 107.68 | 0.000 | 190.59 | 111.57 | 0.222 | 155.47 | 67.70 | | | |
| 298198 | 79.37 | 0.000 | 97.17 | 92.03 | 0.111 | 293.20 | 59.13 | | | |
| 298280 | 86.67 | 0.000 | 235.59 | 89.33 | 0.111 | 1546.16 | 35.33 | | | |
| 298654 | 101.00 | 0.071 | 136.05 | 94.16 | 0.111 | 181.32 | 68.18 | | | |
| 299002 | 118.98 | 0.036 | 211.61 | 81.78 | 0.000 | 590.01 | 51.94 | CopyNumber | 19q13.2 | 3258 |
| 299055 | 67.41 | 0.071 | 60.49 | 51.37 | 0.000 | 1136.65 | 27.04 | | | |
| 300141 | 82.66 | 0.000 | 880.44 | 79.56 | 0.000 | | | | | |
| 300684 | 86.52 | 0.036 | 19.56 | 66.08 | 0.222 | 55.18 | 33.61 | | | |
| 300772 | 407.50 | 0.000 | 144.07 | 60.22 | 0.111 | 11.36 | 80.27 | | | |
| 300816 | 68.45 | 0.000 | 144.04 | 91.05 | 0.222 | 258.49 | 31.17 | | | |
| 300834 | 53.83 | 0.000 | 46.55 | 59.38 | 0.111 | | | | | |
| 301404 | 84.83 | 0.036 | 127.77 | 69.34 | 0.000 | 48.88 | 37.40 | | | |
| 301412 | 70.03 | 0.000 | 161.71 | 51.02 | 0.000 | 573.46 | 31.44 | | | |
| 302742 | 97.96 | 0.036 | 99.87 | 126.82 | 0.222 | 620.43 | 57.69 | CopyNumber | 21q22.11 | 3448 |
| 302903 | 73.32 | 0.036 | 155.07 | 64.76 | 0.111 | 503.88 | 36.57 | CopyNumber | 16p13.3 | 2866 |
| 303676 | 78.57 | 0.036 | 106.32 | 83.93 | 0.222 | 263.04 | 37.05 | | | |
| 304192 | 89.25 | 0.071 | 87.57 | 78.41 | 0.111 | 1681.62 | 40.81 | | | |
| 304682 | 146.41 | 0.000 | 586.08 | 115.24 | 0.000 | 1233.74 | 48.30 | | | |
| 306123 | 69.15 | 0.071 | 59.10 | 53.26 | 0.222 | 125.75 | 44.20 | | | |
| 306242 | 71.12 | 0.000 | 48.63 | 99.39 | 0.222 | 136.24 | 37.00 | | | |
| 306329 | 62.26 | 0.000 | 60.88 | 78.67 | 0.222 | 316.67 | 32.67 | | | |
| 306425 | 73.63 | 0.000 | 34.17 | 79.05 | 0.000 | 84.65 | 38.45 | CopyNumber | 6q14.1 | 1383 |
| 308122 | 77.12 | 0.036 | 78.26 | 58.86 | 0.111 | 226.98 | 30.91 | CopyNumber | 14q32.12 | 2733 |
| 308340 | 93.90 | 0.071 | 39.81 | 69.75 | 0.222 | 83.71 | 47.24 | | | |
| 308709 | 105.53 | 0.000 | 111.91 | 66.83 | 0.000 | 310.05 | 37.58 | CopyNumber | 15q15.3 | 2771 |
| 309090 | 85.59 | 0.071 | 177.79 | 69.74 | 0.111 | 45.16 | 35.63 | | | |
| 309231 | 80.54 | 0.036 | 63.95 | 73.06 | 0.111 | 580.07 | 23.13 | | | |
| 309641 | 75.27 | 0.000 | 99.07 | 83.98 | 0.000 | 264.53 | 42.66 | | | |
| 309753 | 69.18 | 0.000 | 71.16 | 72.16 | 0.111 | 742.22 | 44.20 | CopyNumber | 7p14.1 | 1534 |
| 309849 | 73.60 | 0.071 | 28.98 | 68.38 | 0.222 | 94.62 | 48.92 | | | |
| 310542 | 92.37 | 0.071 | 77.69 | 87.64 | 0.222 | 156.90 | 38.84 | | | |
| 310645 | 69.28 | 0.036 | 100.90 | 54.85 | 0.000 | 1125.09 | 21.18 | | | |
| 311072 | 86.83 | 0.036 | 27.73 | 57.37 | 0.222 | 367.02 | 38.90 | | | |
| 311346 | 67.53 | 0.036 | 44.51 | 86.22 | 0.111 | 53.25 | 44.95 | CopyNumber | 12p12.1 | 2391 |
| 311609 | 70.74 | 0.000 | 104.20 | 81.30 | 0.000 | 237.18 | 48.06 | CopyNumber | 19p13.12 | 3223 |
| 311640 | 106.83 | 0.000 | 510.33 | 73.34 | 0.000 | 93.77 | 42.99 | | | |
| 312098 | 97.67 | 0.071 | 80.93 | 101.94 | 0.111 | 35.13 | 77.49 | | | |
| 313847 | 55.80 | 0.036 | 26.60 | 71.34 | 0.222 | 299.35 | 40.72 | | | |
| 314263 | 68.60 | 0.071 | 103.11 | 55.03 | 0.000 | 89.94 | 34.68 | CopyNumber | 12q13.3 | 2430 |
| 314359 | 69.38 | 0.000 | 355.31 | 42.03 | 0.000 | 154.82 | 30.01 | | | |
| 315177 | 90.19 | 0.000 | 79.21 | 90.27 | 0.000 | 225.39 | 34.43 | CopyNumber | 3p21.31 | 586 |
| 315230 | 75.35 | 0.000 | 128.92 | 93.04 | 0.222 | 276.19 | 37.74 | | | |
| 319334 | 88.71 | 0.036 | 167.66 | 92.28 | 0.000 | 64.37 | 38.27 | | | |
| 321391 | 64.74 | 0.000 | 42.64 | 64.44 | 0.111 | 435.65 | 30.96 | | | |
| 321541 | 59.35 | 0.036 | 127.00 | 41.41 | 0.111 | 662.88 | 41.93 | CopyNumber | 15q22.31 | 2793 |
| 323363 | 64.47 | 0.000 | 29.43 | 51.70 | 0.222 | | | | | |
| 323489 | 81.42 | 0.036 | 73.56 | 84.83 | 0.222 | 152.22 | 30.03 | | | |

TABLE 2-continued

A list of 2087 candidate endogenous reference genes

| | | | | | | | | | | |
|---|---|---|---|---|---|---|---|---|---|---|
| 324250 | 79.24 | 0.000 | 158.34 | 82.02 | 0.000 | 324.22 | 27.86 | | | |
| 324844 | 83.37 | 0.000 | 138.52 | 92.47 | 0.111 | 368.21 | 49.14 | | | |
| 325650 | 136.52 | 0.000 | 82.13 | 109.38 | 0.222 | 108.42 | 62.31 | | | |
| 326387 | 61.74 | 0.000 | 159.12 | 60.70 | 0.111 | 1355.73 | 29.26 | | | |
| 330384 | 69.44 | 0.000 | 68.69 | 88.89 | 0.222 | 263.52 | 45.28 | | | |
| 331431 | 64.62 | 0.036 | 34.89 | 61.05 | 0.222 | 164.96 | 25.51 | CopyNumber | 4p14 | 825 |
| 333388 | 90.31 | 0.000 | 248.00 | 49.98 | 0.000 | 56.06 | 41.65 | CopyNumber | 8q24.3 | 1878 |
| 333579 | 73.99 | 0.000 | 207.00 | 86.45 | 0.000 | 578.55 | 32.43 | | | |
| 333786 | 82.77 | 0.000 | 297.78 | 97.96 | 0.000 | 88.80 | 27.84 | | | |
| 333823 | 89.78 | 0.036 | 42.96 | 56.87 | 0.222 | 126.65 | 54.02 | | | |
| 334017 | 82.51 | 0.000 | 1496.72 | 84.82 | 0.111 | | | | | |
| 334479 | 72.52 | 0.036 | 61.34 | 57.88 | 0.222 | 224.68 | 33.05 | CopyNumber | 16p13.3 | 2866 |
| 334534 | 94.59 | 0.000 | 64.42 | 72.27 | 0.222 | 230.52 | 56.05 | | | |
| 334587 | 98.49 | 0.036 | 127.44 | 77.96 | 0.222 | 56.82 | 48.84 | | | |
| 334713 | 72.87 | 0.071 | 69.27 | 86.41 | 0.222 | 158.37 | 38.36 | | | |
| 334851 | 102.17 | 0.000 | 101.40 | 41.98 | 0.111 | 553.93 | 45.99 | | | |
| 334868 | 56.26 | 0.071 | 23.15 | 52.67 | 0.222 | 170.24 | 29.57 | | | |
| 335003 | 52.84 | 0.000 | 53.68 | 52.65 | 0.111 | 280.86 | 27.96 | CopyNumber | 16q24.3 | 2972 |
| 335057 | 68.54 | 0.000 | 137.12 | 58.17 | 0.000 | 682.36 | 27.44 | | | |
| 335163 | 75.40 | 0.071 | 45.38 | 129.15 | 0.222 | 69.59 | 99.48 | | | |
| 335918 | 98.06 | 0.071 | 79.89 | 54.30 | 0.222 | 222.21 | 54.25 | CopyNumber | 1q22 | 160 |
| 337295 | 84.21 | 0.036 | 137.57 | 72.92 | 0.111 | 116.16 | 50.84 | CopyNumber | 11q13.1 | 2272 |
| 337766 | 68.01 | 0.000 | 202.91 | 74.78 | 0.000 | 3513.66 | 53.34 | CopyNumber | 12q23.3 | 2494 |
| 339278 | 66.75 | 0.000 | 93.08 | 54.14 | 0.111 | 612.93 | 27.37 | | | |
| 339639 | 71.56 | 0.000 | 59.94 | 63.25 | 0.222 | 530.98 | 32.89 | | | |
| 339697 | 73.00 | 0.000 | 206.27 | 69.44 | 0.111 | 207.55 | 60.06 | | | |
| 343911 | 79.02 | 0.000 | 73.68 | 85.85 | 0.111 | 126.75 | 36.12 | | | |
| 345694 | 57.05 | 0.000 | 44.59 | 53.30 | 0.000 | 118.43 | 29.68 | | | |
| 346868 | 85.04 | 0.071 | 86.46 | 71.11 | 0.222 | 78.76 | 41.86 | | | |
| 348418 | 65.21 | 0.036 | 41.25 | 56.56 | 0.111 | 133.63 | 28.30 | | | |
| 349656 | 69.11 | 0.000 | 122.42 | 91.03 | 0.111 | 65.67 | 33.86 | | | |
| 350194 | 67.50 | 0.071 | 57.18 | 56.35 | 0.222 | 974.29 | 21.31 | | | |
| 350229 | 97.88 | 0.000 | 64.62 | 89.22 | 0.111 | 182.02 | 57.82 | | | |
| 350268 | 84.85 | 0.071 | 121.48 | 94.64 | 0.111 | 854.94 | 33.25 | | | |
| 350364 | 62.80 | 0.071 | 32.70 | 56.87 | 0.222 | 489.36 | 49.85 | | | |
| 350927 | 60.49 | 0.000 | 549.42 | 42.63 | 0.000 | 1242.87 | 45.82 | | | |
| 351099 | 73.49 | 0.071 | 48.32 | 58.61 | 0.111 | 151.95 | 26.94 | | | |
| 351296 | 70.85 | 0.000 | 100.35 | 47.00 | 0.111 | 210.84 | 29.83 | CopyNumber | 11q12.3 | 2268 |
| 351316 | 231.65 | 0.000 | 962.00 | 171.72 | 0.222 | 602.84 | 78.49 | | | |
| 351474 | 98.35 | 0.000 | 56.04 | 104.42 | 0.111 | 65.42 | 73.26 | | | |
| 351680 | 134.97 | 0.036 | 51.32 | 81.83 | 0.222 | 1028.80 | 33.00 | | | |
| 351875 | 195.85 | 0.000 | 285.77 | 81.89 | 0.000 | 1982.14 | 49.61 | | | |
| 352341 | 75.79 | 0.071 | 26.39 | 65.54 | 0.222 | 37.24 | 43.85 | | | |
| 352656 | 71.84 | 0.036 | 58.63 | 44.06 | 0.111 | 875.31 | 43.75 | | | |
| 352768 | 72.88 | 0.036 | 106.19 | 71.31 | 0.111 | 881.32 | 24.35 | CopyNumber | 6q27 | 1479 |
| 354056 | 76.13 | 0.071 | 56.50 | 78.63 | 0.111 | 126.70 | 123.02 | CopyNumber | 7q11.23 | 1572 |
| 355141 | 91.77 | 0.000 | 101.53 | 69.50 | 0.111 | 220.79 | 44.58 | | | |
| 355606 | 60.91 | 0.071 | 76.85 | 66.68 | 0.000 | 574.94 | 34.63 | | | |
| 355643 | 77.96 | 0.036 | 108.17 | 72.63 | 0.111 | 1201.76 | 27.22 | CopyNumber | 16p13.3 | 2866 |
| 355708 | 63.12 | 0.036 | 37.30 | 87.81 | 0.222 | 262.34 | 29.20 | CopyNumber | 2q11.2 | 378 |
| 355750 | 71.27 | 0.000 | 106.84 | 50.91 | 0.000 | 80.87 | 40.21 | | | |
| 355753 | 84.23 | 0.036 | 38.89 | 56.95 | 0.111 | 336.82 | 37.01 | | | |
| 355867 | 93.77 | 0.071 | 48.09 | 62.22 | 0.222 | 280.34 | 54.64 | CopyNumber | 12q13.3 | 2432 |
| 355927 | 64.41 | 0.000 | 147.13 | 64.66 | 0.111 | 941.32 | 36.63 | | | |
| 355934 | 69.80 | 0.036 | 156.14 | 50.78 | 0.000 | 161.58 | 25.13 | | | |
| 355983 | 66.37 | 0.000 | 154.52 | 67.35 | 0.222 | 404.14 | 34.07 | | | |
| 356061 | 67.49 | 0.000 | 116.51 | 74.14 | 0.111 | 218.65 | 28.55 | CopyNumber | 16q24.2 | 2967 |
| 356096 | 70.29 | 0.000 | 168.35 | 68.41 | 0.111 | 168.20 | 43.07 | | | |
| 356190 | 88.54 | 0.000 | 478.54 | 95.96 | 0.000 | 3961.19 | 25.93 | | | |
| 356270 | 65.90 | 0.036 | 46.04 | 72.70 | 0.222 | 257.48 | 42.37 | | | |
| 356285 | 79.82 | 0.000 | 329.64 | 78.06 | 0.000 | 799.76 | 33.14 | | | |
| 356331 | 59.53 | 0.000 | 1683.27 | 56.79 | 0.000 | 5223.43 | 28.46 | | | |
| 356366 | 92.12 | 0.000 | 1928.74 | 63.68 | 0.000 | | | CopyNumber | 16p13.3 | 2866 |
| 356371 | 75.13 | 0.000 | 2350.46 | 66.23 | 0.000 | 112.06 | 33.10 | | | |
| 356377 | 82.23 | 0.000 | 62.50 | 63.16 | 0.222 | 320.21 | 50.05 | | | |
| 356467 | 66.21 | 0.000 | 55.00 | 59.52 | 0.000 | 527.54 | 28.10 | | | |
| 356501 | 153.63 | 0.000 | 51.63 | 63.33 | 0.000 | 250.13 | 58.63 | | | |
| 356502 | 73.27 | 0.000 | 2501.03 | 44.31 | 0.000 | 4303.08 | 32.44 | CopyNumber | 15q23 | 2800 |
| 356549 | 65.60 | 0.000 | 84.68 | 67.51 | 0.222 | 294.91 | 45.11 | | | |
| 356630 | 59.68 | 0.000 | 135.65 | 56.95 | 0.111 | 256.98 | 31.53 | | | |
| 356647 | 75.20 | 0.000 | 113.95 | 64.30 | 0.000 | 982.39 | 31.67 | Inversion | 14q13.1-14q13.2 | 2663 |
| 356654 | 68.00 | 0.036 | 50.52 | 58.00 | 0.111 | 529.64 | 18.33 | | | |
| 356766 | 85.27 | 0.036 | 207.71 | 52.85 | 0.111 | 3532.27 | 54.09 | | | |
| 356769 | 148.76 | 0.071 | 82.19 | 77.74 | 0.111 | 211.91 | 50.28 | | | |
| 356799 | 127.42 | 0.000 | 82.88 | 66.53 | 0.000 | | | | | |
| 357901 | 181.23 | 0.036 | 350.43 | 80.27 | 0.111 | 407.08 | 74.43 | | | |
| 362728 | 62.46 | 0.000 | 117.00 | 40.93 | 0.222 | 292.65 | 31.92 | | | |

TABLE 2-continued

A list of 2087 candidate endogenous reference genes

| | | | | | | | | | |
|---|---|---|---|---|---|---|---|---|---|
| 365116 | 68.53 | 0.036 | 126.74 | 72.33 | 0.222 | 109.68 | 38.27 | | |
| 368084 | 67.93 | 0.036 | 82.52 | 74.16 | 0.111 | 330.85 | 36.03 | | |
| 368149 | 84.73 | 0.000 | 319.23 | 99.32 | 0.000 | 306.87 | 38.36 | | |
| 368157 | 132.67 | 0.000 | 60.76 | 64.42 | 0.222 | 96.04 | 37.48 | | |
| 368240 | 63.21 | 0.036 | 41.47 | 63.19 | 0.222 | 282.82 | 29.11 | | |
| 368264 | 104.35 | 0.036 | 82.07 | 152.01 | 0.000 | 93.79 | 33.59 | | |
| 368376 | 63.69 | 0.000 | 60.30 | 75.16 | 0.111 | 475.42 | 40.92 | | |
| 368402 | 86.05 | 0.036 | 31.92 | 91.55 | 0.111 | 104.92 | 68.11 | CopyNumber 8q24.3 | 1876 |
| 368404 | 74.03 | 0.036 | 46.42 | 53.59 | 0.000 | 79.74 | 27.69 | | |
| 368525 | 121.26 | 0.000 | 89.35 | 75.68 | 0.222 | 699.89 | 47.37 | | |
| 368598 | 79.84 | 0.036 | 50.09 | 69.21 | 0.222 | 212.95 | 33.37 | CopyNumber 2q32.1 | 464 |
| 368934 | 97.54 | 0.000 | 420.24 | 80.76 | 0.000 | 2026.16 | 62.15 | | |
| 368985 | 64.59 | 0.000 | 54.64 | 54.70 | 0.222 | 245.08 | 30.39 | | |
| 369017 | 64.56 | 0.000 | 69.11 | 41.17 | 0.222 | 181.79 | 39.53 | | |
| 369052 | 64.31 | 0.000 | 70.30 | 47.70 | 0.000 | 455.50 | 36.14 | | |
| 369068 | 62.84 | 0.000 | 90.19 | 99.10 | 0.111 | 210.93 | 35.73 | | |
| 369125 | 86.12 | 0.036 | 66.79 | 75.85 | 0.222 | | | CopyNumber 2q24.2 | 437 |
| 369285 | 183.68 | 0.000 | 62.35 | 137.25 | 0.222 | 34.54 | 60.02 | | |
| 369356 | 80.32 | 0.071 | 113.07 | 56.67 | 0.111 | 217.18 | 43.38 | | |
| 369606 | 78.57 | 0.071 | 63.17 | 66.71 | 0.111 | 145.32 | 32.96 | | |
| 369607 | 63.47 | 0.036 | 49.42 | 69.10 | 0.111 | 289.22 | 36.24 | CopyNumber 4p16.3 | 758 |
| 369614 | 68.46 | 0.071 | 43.68 | 55.15 | 0.222 | 348.84 | 31.68 | | |
| 369615 | 89.80 | 0.071 | 29.44 | 70.80 | 0.222 | 118.05 | 30.52 | | |
| 369761 | 72.58 | 0.036 | 199.77 | 81.21 | 0.000 | 1028.59 | 25.79 | | |
| 369785 | 70.47 | 0.000 | 99.64 | 68.29 | 0.000 | 519.82 | 35.06 | | |
| 369920 | 77.09 | 0.000 | 168.51 | 77.20 | 0.111 | 505.36 | 31.36 | | |
| 370024 | 81.89 | 0.000 | 128.78 | 60.25 | 0.000 | 422.20 | 27.11 | | |
| 370247 | 75.77 | 0.000 | 233.67 | 70.23 | 0.000 | 40.96 | 41.82 | CopyNumber 11q24.3 | 2355 |
| 370292 | 77.26 | 0.036 | 36.54 | 69.28 | 0.000 | 327.17 | 36.76 | CopyNumber 10q26.2 | 2190 |
| 370312 | 65.22 | 0.036 | 69.14 | 59.74 | 0.222 | 173.14 | 30.85 | | |
| 370408 | 81.05 | 0.000 | 47.84 | 69.75 | 0.222 | 458.21 | 44.61 | CopyNumber 22q11.21 | 3466 |
| 370581 | 86.13 | 0.000 | 191.83 | 64.65 | 0.111 | 579.49 | 33.71 | CopyNumber 1p34.2 | 60 |
| 370770 | 84.48 | 0.036 | 95.64 | 93.45 | 0.111 | 452.54 | 31.23 | CopyNumber 2p15 | 345 |
| 370771 | 118.09 | 0.036 | 242.66 | 151.31 | 0.222 | 251.27 | 55.14 | | |
| 370895 | 82.56 | 0.000 | 100.06 | 76.14 | 0.111 | 881.82 | 34.34 | | |
| 370927 | 121.90 | 0.036 | 52.90 | 64.05 | 0.222 | 432.84 | 47.49 | | |
| 370937 | 87.18 | 0.071 | 124.70 | 85.67 | 0.111 | 561.13 | 45.91 | | |
| 371001 | 69.51 | 0.000 | 170.33 | 68.79 | 0.111 | 454.07 | 35.94 | | |
| 371416 | 78.55 | 0.036 | 36.50 | 64.63 | 0.111 | 96.75 | 35.90 | CopyNumber 19p13.2 | 3217 |
| 371563 | 63.43 | 0.036 | 59.64 | 75.25 | 0.111 | 202.76 | 25.54 | | |
| 371788 | 59.70 | 0.000 | 54.31 | 56.93 | 0.222 | 206.21 | 29.90 | | |
| 371889 | 68.61 | 0.000 | 325.06 | 67.81 | 0.000 | 936.64 | 56.60 | | |
| 372003 | 61.79 | 0.000 | 80.84 | 79.74 | 0.111 | 89.46 | 30.69 | | |
| 372050 | 66.34 | 0.071 | 46.09 | 73.62 | 0.222 | 82.63 | 32.40 | | |
| 372286 | 64.63 | 0.036 | 30.00 | 59.49 | 0.222 | 354.14 | 23.10 | | |
| 372331 | 89.80 | 0.036 | 81.60 | 144.08 | 0.222 | 232.33 | 49.08 | | |
| 372541 | 65.94 | 0.071 | 66.46 | 82.62 | 0.111 | 186.66 | 25.95 | | |
| 372616 | 72.02 | 0.036 | 35.25 | 60.41 | 0.222 | 143.19 | 33.51 | | |
| 372914 | 126.22 | 0.000 | 100.73 | 126.29 | 0.111 | 231.60 | 56.38 | | |
| 373550 | 88.97 | 0.036 | 184.03 | 68.60 | 0.222 | 209.76 | 48.79 | | |
| 373741 | 79.81 | 0.000 | 77.80 | 98.88 | 0.000 | 412.67 | 38.36 | | |
| 373763 | 63.54 | 0.036 | 195.53 | 52.32 | 0.111 | | | | |
| 373952 | 94.13 | 0.036 | 30.34 | 82.86 | 0.111 | 96.20 | 32.08 | CopyNumber 17p13.2 | 2984 |
| 373959 | 63.44 | 0.000 | 33.58 | 71.55 | 0.000 | 183.05 | 41.76 | | |
| 374043 | 66.27 | 0.036 | 34.15 | 82.28 | 0.222 | 106.28 | 22.55 | | |
| 374257 | 90.84 | 0.071 | 57.56 | 72.95 | 0.222 | 65.71 | 68.99 | | |
| 374378 | 119.35 | 0.036 | 125.53 | 97.64 | 0.111 | 225.89 | 60.82 | | |
| 374477 | 56.99 | 0.000 | 105.78 | 48.32 | 0.000 | 246.92 | 24.70 | | |
| 374503 | 59.32 | 0.000 | 271.15 | 58.47 | 0.000 | 2139.38 | 28.45 | | |
| 374588 | 75.34 | 0.000 | 683.86 | 58.24 | 0.000 | 413.28 | 42.63 | | |
| 374596 | 85.39 | 0.000 | 2551.73 | 61.31 | 0.000 | 5206.59 | 33.30 | | |
| 374650 | 126.18 | 0.036 | 88.32 | 93.01 | 0.222 | 2238.80 | 53.03 | | |
| 374973 | 72.70 | 0.071 | 33.02 | 75.69 | 0.222 | 110.84 | 45.58 | | |
| 375001 | 70.26 | 0.000 | 87.30 | 74.38 | 0.222 | 100.50 | 40.21 | | |
| 375108 | 143.73 | 0.071 | 764.58 | 129.71 | 0.222 | 128.99 | 45.16 | | |
| 375217 | 66.70 | 0.000 | 45.51 | 78.12 | 0.222 | 38.58 | 33.48 | | |
| 376046 | 131.46 | 0.071 | 67.73 | 85.63 | 0.222 | 324.83 | 59.30 | | |
| 376933 | 85.54 | 0.000 | 188.71 | 94.17 | 0.111 | 932.24 | 43.14 | | |
| 377155 | 84.44 | 0.000 | 52.03 | 67.04 | 0.000 | 165.50 | 32.72 | | |
| 378103 | 84.12 | 0.036 | 640.07 | 72.81 | 0.000 | 2299.39 | 45.40 | CopyNumber 19q13.43 | 3293 |
| 378532 | 74.21 | 0.071 | 19.77 | 57.36 | 0.222 | 143.45 | 34.11 | | |
| 378808 | 80.58 | 0.071 | 42.68 | 76.86 | 0.222 | 1023.41 | 32.72 | | |
| 380403 | 77.18 | 0.071 | 39.70 | 97.70 | 0.111 | 152.35 | 50.89 | | |
| 380774 | 69.78 | 0.036 | 367.07 | 72.51 | 0.000 | 704.94 | 28.60 | | |
| 380953 | 120.40 | 0.000 | 1164.30 | 50.87 | 0.000 | 4148.67 | 36.69 | CopyNumber 17q25.1 | 3072 |
| 380973 | 66.60 | 0.000 | 541.31 | 51.30 | 0.000 | 636.85 | 33.23 | | |
| 381008 | 113.07 | 0.000 | 775.01 | 80.40 | 0.000 | 541.08 | 39.56 | | |
| 381058 | 58.41 | 0.036 | 40.33 | 63.46 | 0.222 | 25.40 | 47.69 | | |

TABLE 2-continued

A list of 2087 candidate endogenous reference genes

| | | | | | | | | | |
|---|---|---|---|---|---|---|---|---|---|
| 381072 | 76.95 | 0.000 | 77.98 | 75.38 | 0.111 | 163.52 | 63.87 | | |
| 381123 | 73.37 | 0.000 | 1876.45 | 45.25 | 0.000 | 8803.79 | 35.35 | | |
| 381126 | 143.53 | 0.000 | 523.32 | 77.49 | 0.000 | 40.73 | 27.35 | CopyNumber | 5q33.1 | 1236 |
| 381189 | 74.68 | 0.036 | 232.19 | 94.40 | 0.000 | 495.84 | 37.72 | | |
| 381219 | 98.54 | 0.000 | 704.33 | 65.39 | 0.000 | 1933.04 | 37.91 | | |
| 381256 | 99.47 | 0.036 | 83.41 | 96.68 | 0.111 | 46.96 | 62.16 | | |
| 382044 | 92.25 | 0.036 | 85.09 | 76.07 | 0.111 | 98.39 | 41.13 | | |
| 382168 | 85.81 | 0.071 | 40.65 | 65.81 | 0.222 | 47.88 | 50.87 | CopyNumber | 20q13.12-20q13.13 | 3395 |
| 385913 | 75.07 | 0.071 | 85.26 | 93.35 | 0.222 | 200.81 | 51.44 | | |
| 385986 | 67.61 | 0.036 | 72.40 | 68.58 | 0.000 | 238.36 | 27.33 | | |
| 386434 | 72.97 | 0.036 | 52.83 | 73.51 | 0.111 | 344.41 | 26.93 | | |
| 386465 | 67.39 | 0.071 | 32.55 | 77.62 | 0.111 | 144.09 | 43.35 | | |
| 386939 | 79.30 | 0.036 | 38.64 | 50.55 | 0.111 | 171.14 | 24.98 | | |
| 387208 | 63.45 | 0.000 | 727.99 | 60.47 | 0.000 | 2811.53 | 37.85 | | |
| 387804 | 85.40 | 0.036 | 481.25 | 60.76 | 0.000 | 2686.84 | 38.70 | | |
| 388034 | 67.46 | 0.071 | 46.51 | 81.22 | 0.222 | 140.62 | 25.58 | | |
| 388654 | 81.47 | 0.000 | 93.30 | 67.09 | 0.111 | 637.15 | 55.44 | CopyNumber | 9q32 | 1992 |
| 388664 | 53.99 | 0.000 | 1460.59 | 41.29 | 0.000 | 6835.36 | 34.82 | | |
| 388739 | 68.80 | 0.036 | 122.75 | 82.72 | 0.111 | 520.74 | 24.62 | | |
| 388927 | 71.40 | 0.071 | 139.68 | 66.05 | 0.111 | 356.99 | 30.26 | | |
| 388956 | 85.77 | 0.036 | 71.01 | 94.85 | 0.111 | | | | |
| 389037 | 84.61 | 0.036 | 47.66 | 65.23 | 0.222 | 91.25 | 34.83 | | |
| 389107 | 94.66 | 0.036 | 263.90 | 108.16 | 0.000 | 892.91 | 48.86 | CopyNumber | 16p13.3 | 2866 |
| 389171 | 82.45 | 0.036 | 44.74 | 103.84 | 0.111 | 192.72 | 33.61 | | |
| 389649 | 125.20 | 0.036 | 163.93 | 82.73 | 0.000 | 425.65 | 32.06 | CopyNumber | 17q25.3 | 3084 |
| 389734 | 78.85 | 0.071 | 38.68 | 121.32 | 0.111 | 289.67 | 51.68 | | |
| 389996 | 180.39 | 0.000 | 327.19 | 82.08 | 0.000 | 1922.00 | 29.42 | | |
| 390667 | 74.42 | 0.000 | 105.64 | 80.72 | 0.111 | 468.47 | 48.33 | | |
| 393201 | 67.22 | 0.071 | 96.98 | 68.05 | 0.111 | 509.48 | 35.05 | | |
| 395482 | 65.92 | 0.036 | 44.74 | 59.27 | 0.111 | 102.70 | 40.91 | CopyNumber | 8q24.3 | 1874 |
| 396644 | 69.48 | 0.036 | 133.73 | 60.82 | 0.111 | 1142.75 | 35.09 | | |
| 396740 | 68.39 | 0.036 | 43.05 | 64.23 | 0.111 | 445.56 | 26.13 | | |
| 396783 | 118.29 | 0.036 | 110.63 | 82.09 | 0.111 | 261.57 | 76.08 | | |
| 397609 | 254.69 | 0.000 | 633.23 | 56.50 | 0.000 | 13138.69 | 29.06 | | |
| 399800 | 66.18 | 0.036 | 44.45 | 64.79 | 0.111 | 75.35 | 36.85 | | |
| 400295 | 72.44 | 0.000 | 2244.41 | 48.14 | 0.000 | 13951.77 | 33.35 | | |
| 401509 | 85.63 | 0.036 | 115.39 | 64.94 | 0.000 | 118.05 | 44.04 | | |
| 401903 | 90.23 | 0.000 | 453.74 | 70.31 | 0.000 | 114.88 | 45.33 | | |
| 401929 | 68.45 | 0.000 | 2446.06 | 47.57 | 0.000 | 4419.77 | 40.15 | Inversion | Xq28 | 3631 |
| 403917 | 63.27 | 0.071 | 80.15 | 43.62 | 0.222 | 142.49 | 52.88 | | |
| 404056 | 68.09 | 0.036 | 52.37 | 46.66 | 0.000 | 187.40 | 29.97 | | |
| 404321 | 116.89 | 0.000 | 104.40 | 74.14 | 0.111 | 419.99 | 34.26 | | |
| 405144 | 69.11 | 0.000 | 415.47 | 73.52 | 0.000 | 396.95 | 31.07 | | |
| 405410 | 76.64 | 0.071 | 78.70 | 71.34 | 0.000 | 433.35 | 42.84 | | |
| 405514 | 69.02 | 0.071 | 38.09 | 82.50 | 0.111 | 418.51 | 26.82 | CopyNumber | 17q21.32-17q21.31 | 3030 |
| 405590 | 81.80 | 0.036 | 169.04 | 77.14 | 0.000 | 245.79 | 24.62 | | |
| 405880 | 78.38 | 0.000 | 92.99 | 92.66 | 0.000 | 940.03 | 50.82 | | |
| 405942 | 83.39 | 0.071 | 57.96 | 72.26 | 0.000 | 158.43 | 35.77 | | |
| 406062 | 84.43 | 0.036 | 131.48 | 52.80 | 0.222 | 1502.27 | 27.41 | | |
| 406068 | 75.82 | 0.036 | 114.88 | 92.45 | 0.111 | 127.41 | 44.39 | | |
| 406096 | 82.28 | 0.036 | 155.28 | 110.89 | 0.222 | 111.15 | 33.70 | | |
| 406277 | 63.86 | 0.036 | 80.15 | 58.28 | 0.111 | 262.74 | 27.77 | | |
| 406300 | 110.40 | 0.000 | 1789.62 | 51.80 | 0.000 | 3379.42 | 39.25 | | |
| 406423 | 82.14 | 0.036 | 108.09 | 55.19 | 0.222 | 227.08 | 30.58 | | |
| 406510 | 99.80 | 0.000 | 362.39 | 97.60 | 0.000 | 1484.49 | 47.35 | | |
| 406520 | 68.92 | 0.000 | 79.16 | 46.52 | 0.000 | 552.71 | 43.50 | CopyNumber | 7q22.1 | 1598 |
| 406534 | 76.53 | 0.036 | 84.44 | 74.61 | 0.111 | 81.66 | 48.02 | CopyNumber | 19p13.3 | 3204 |
| 406590 | 80.43 | 0.000 | 116.59 | 54.77 | 0.111 | 3669.45 | 26.79 | | |
| 406620 | 105.57 | 0.000 | 937.84 | 74.78 | 0.000 | | | CopyNumber | 6p21.31 | 1319 |
| 406683 | 397.62 | 0.036 | 101.26 | 87.65 | 0.111 | 4567.96 | 36.31 | CopyNumber | 19p13.3 | 3198 |
| 406799 | 62.82 | 0.036 | 34.19 | 47.08 | 0.222 | 624.11 | 32.91 | | |
| 406840 | 63.67 | 0.071 | 35.33 | 63.00 | 0.222 | 417.25 | 27.92 | | |
| 407368 | 85.75 | 0.000 | 208.80 | 51.34 | 0.000 | 189.03 | 26.77 | | |
| 407580 | 55.41 | 0.071 | 40.52 | 91.55 | 0.111 | 136.75 | 49.37 | | |
| 407995 | 102.74 | 0.000 | 792.47 | 129.50 | 0.000 | 1327.53 | 53.18 | | |
| 408018 | 73.73 | 0.000 | 1638.52 | 53.51 | 0.000 | 1595.26 | 49.48 | | |
| 408073 | 101.78 | 0.000 | 1040.65 | 78.37 | 0.000 | 5022.25 | 35.22 | | |
| 408236 | 178.08 | 0.036 | 191.09 | 140.73 | 0.111 | 166.92 | 28.73 | | |
| 408257 | 73.75 | 0.000 | 176.37 | 73.95 | 0.000 | 346.00 | 33.39 | | |
| 408293 | 79.96 | 0.071 | 55.21 | 76.68 | 0.222 | | | | |
| 408324 | 79.03 | 0.071 | 70.97 | 91.67 | 0.222 | 261.14 | 38.52 | | |
| 408428 | 57.10 | 0.000 | 54.54 | 56.13 | 0.111 | | | | |
| 408581 | 168.89 | 0.000 | 47.66 | 93.70 | 0.111 | 22.32 | 70.59 | CopyNumber | 10p11.23 | 2079 |
| 408909 | 55.91 | 0.000 | 107.48 | 55.68 | 0.000 | 462.90 | 38.03 | CopyNumber | 5p13.3 | 1105 |
| 409140 | 68.36 | 0.000 | 146.00 | 65.13 | 0.111 | 1015.79 | 34.02 | | |
| 409223 | 88.98 | 0.000 | 109.75 | 63.00 | 0.111 | 1498.41 | 63.96 | | |

TABLE 2-continued

A list of 2087 candidate endogenous reference genes

| | | | | | | | | | |
|---|---|---|---|---|---|---|---|---|---|
| 409230 | 77.08 | 0.000 | 45.77 | 60.03 | 0.222 | 358.93 | 29.50 | CopyNumber | 6p21.32 | 1314 |
| 409834 | 82.56 | 0.000 | 145.39 | 69.35 | 0.000 | 1395.23 | 31.06 | CopyNumber | 9q34.3 | 2030 |
| 410197 | 63.50 | 0.071 | 28.39 | 50.29 | 0.111 | 193.36 | 31.09 | | | |
| 410596 | 66.47 | 0.071 | 34.69 | 51.96 | 0.111 | 972.56 | 29.87 | | | |
| 410817 | 89.11 | 0.000 | 967.12 | 38.98 | 0.000 | 4919.57 | 40.81 | CopyNumber | 16q24.3 | 2972 |
| 411480 | 73.79 | 0.000 | 66.40 | 53.89 | 0.222 | 180.20 | 28.59 | CopyNumber | 2p13.1 | 356 |
| 411641 | 133.02 | 0.000 | 73.09 | 72.11 | 0.111 | 141.55 | 88.01 | | | |
| 411847 | 71.19 | 0.036 | 79.52 | 59.04 | 0.000 | 277.48 | 39.90 | | | |
| 412103 | 67.52 | 0.036 | 35.32 | 74.96 | 0.111 | 239.50 | 42.79 | CopyNumber | 13q12.11 | 2541 |
| 412117 | 79.30 | 0.036 | 72.03 | 73.91 | 0.111 | 106.69 | 32.88 | | | |
| 412196 | 75.22 | 0.071 | 30.98 | 71.64 | 0.222 | 199.00 | 43.49 | | | |
| 412433 | 63.22 | 0.036 | 78.22 | 90.02 | 0.111 | 272.65 | 29.98 | CopyNumber | 11q13.1-<br>11q13.2 | 2278 |
| 412468 | 119.89 | 0.036 | 65.27 | 91.38 | 0.111 | 141.12 | 32.72 | | | |
| 412842 | 70.86 | 0.071 | 69.10 | 79.95 | 0.111 | 232.58 | 28.04 | | | |
| 413036 | 70.20 | 0.071 | 69.74 | 59.75 | 0.111 | 243.79 | 34.29 | | | |
| 413482 | 80.49 | 0.036 | 49.57 | 57.15 | 0.111 | 337.81 | 43.89 | | | |
| 414579 | 80.14 | 0.071 | 71.27 | 55.92 | 0.222 | | | | | |
| 415342 | 79.01 | 0.000 | 111.61 | 77.60 | 0.222 | 459.69 | 25.69 | | | |
| 416049 | 68.55 | 0.036 | 43.93 | 72.18 | 0.222 | 197.48 | 40.51 | | | |
| 416436 | 70.64 | 0.000 | 58.84 | 53.49 | 0.000 | 108.37 | 40.38 | InversionBreakpoint<br>CopyNumber<br>CopyNumber | 7q11.23-<br>7q11.22 | 1569 |
| 417004 | 136.17 | 0.000 | 201.17 | 72.90 | 0.222 | 521.74 | 63.64 | | | |
| 417029 | 74.72 | 0.036 | 99.27 | 71.29 | 0.000 | 200.46 | 37.83 | | | |
| 418123 | 202.05 | 0.036 | 138.03 | 241.75 | 0.222 | 319.38 | 64.64 | CopyNumber | 9q21.33-<br>9q22.1 | 1960 |
| 418175 | 85.40 | 0.000 | 67.13 | 69.58 | 0.111 | 354.32 | 39.90 | CopyNumber | 8q24.3 | 1880 |
| 418233 | 101.45 | 0.000 | 117.46 | 123.53 | 0.000 | 280.39 | 36.32 | | | |
| 418450 | 105.88 | 0.000 | 56.80 | 81.39 | 0.222 | 159.74 | 29.02 | | | |
| 418533 | 61.17 | 0.036 | 73.40 | 66.43 | 0.222 | 340.85 | 38.60 | | | |
| 418668 | 90.41 | 0.000 | 162.79 | 95.51 | 0.111 | 100.95 | 36.86 | CopyNumber | 19p13.3 | 3198 |
| 419640 | 82.10 | 0.071 | 72.52 | 61.17 | 0.111 | 1390.88 | 23.87 | | | |
| 420269 | 205.21 | 0.036 | 412.78 | 162.70 | 0.222 | 70.62 | 57.13 | | | |
| 420272 | 65.09 | 0.000 | 101.26 | 85.37 | 0.000 | 239.55 | 31.21 | | | |
| 421257 | 83.68 | 0.000 | 1327.95 | 45.08 | 0.000 | 5761.57 | 31.60 | | | |
| 421509 | 88.01 | 0.036 | 110.18 | 89.29 | 0.000 | 938.99 | 34.34 | | | |
| 422113 | 70.57 | 0.036 | 55.85 | 49.24 | 0.111 | 252.93 | 58.42 | CopyNumber | 10q26.3 | 2199 |
| 423935 | 65.96 | 0.000 | 87.90 | 52.75 | 0.222 | 148.10 | 43.63 | CopyNumber | 6p21.32 | 1314 |
| 423968 | 79.75 | 0.000 | 113.92 | 73.70 | 0.111 | 461.34 | 31.00 | CopyNumber | 7q22.1 | 1600 |
| 424126 | 98.54 | 0.000 | 300.03 | 49.27 | 0.000 | 154.40 | 28.34 | CopyNumber | 15q15.3 | 2771 |
| 424908 | 81.21 | 0.000 | 64.53 | 78.90 | 0.111 | 265.87 | 44.69 | | | |
| 425777 | 80.47 | 0.036 | 77.84 | 85.16 | 0.111 | 366.93 | 47.98 | CopyNumber | 11q12.1 | 2261 |
| 426296 | 64.88 | 0.071 | 75.24 | 62.36 | 0.111 | 1457.22 | 32.65 | | | |
| 426359 | 87.85 | 0.000 | 111.22 | 63.93 | 0.222 | 458.50 | 41.77 | | | |
| 429052 | 92.93 | 0.000 | 242.82 | 57.76 | 0.222 | 1214.90 | 32.34 | | | |
| 429353 | 79.94 | 0.036 | 65.42 | 71.89 | 0.111 | 343.74 | 43.42 | | | |
| 429581 | 114.95 | 0.000 | 135.56 | 64.30 | 0.222 | 1000.39 | 35.21 | | | |
| 429819 | 89.35 | 0.000 | 44.35 | 56.24 | 0.111 | 112.40 | 29.86 | | | |
| 429839 | 70.25 | 0.036 | 59.72 | 96.19 | 0.000 | 526.01 | 27.93 | CopyNumber | 1p32.3 | 71 |
| 430425 | 77.22 | 0.000 | 63.83 | 73.92 | 0.000 | 645.48 | 26.65 | CopyNumber | 1p36.33 | 3 |
| 430551 | 76.02 | 0.000 | 71.02 | 65.06 | 0.000 | 221.97 | 39.09 | | | |
| 430606 | 54.49 | 0.000 | 144.68 | 41.23 | 0.111 | 503.23 | 31.70 | | | |
| 430657 | 80.31 | 0.071 | 49.61 | 85.30 | 0.222 | 278.49 | 29.31 | | | |
| 430733 | 68.85 | 0.036 | 62.86 | 88.39 | 0.111 | 19.58 | 102.83 | | | |
| 431101 | 80.78 | 0.036 | 82.46 | 93.00 | 0.111 | 302.22 | 42.11 | | | |
| 431367 | 68.42 | 0.071 | 40.76 | 57.01 | 0.222 | 317.45 | 23.88 | | | |
| 431498 | 58.31 | 0.000 | 50.68 | 71.27 | 0.111 | 215.07 | 31.63 | | | |
| 431550 | 68.11 | 0.000 | 104.26 | 94.29 | 0.222 | 36.35 | 49.04 | CopyNumber | 2q11.2 | 384 |
| 431668 | 67.73 | 0.000 | 220.78 | 53.03 | 0.111 | 783.69 | 38.20 | | | |
| 431850 | 72.50 | 0.036 | 34.04 | 80.31 | 0.111 | 12.95 | 42.74 | CopyNumber | 22q11.22-<br>22q11.21 | 3472 |
| 431861 | 75.28 | 0.036 | 122.14 | 101.94 | 0.222 | 73.76 | 32.92 | | | |
| 431926 | 135.79 | 0.071 | 84.76 | 110.75 | 0.222 | 190.15 | 30.68 | | | |
| 432121 | 83.85 | 0.000 | 184.40 | 74.24 | 0.111 | 42.79 | 41.58 | CopyNumber | 19p13.13 | 3220 |
| 432438 | 80.60 | 0.071 | 52.75 | 89.48 | 0.111 | 211.51 | 33.45 | | | |
| 432491 | 76.58 | 0.036 | 40.08 | 63.63 | 0.222 | 127.64 | 31.44 | | | |
| 432690 | 65.69 | 0.000 | 31.94 | 67.02 | 0.222 | 611.10 | 28.10 | | | |
| 432760 | 97.72 | 0.000 | 118.99 | 66.08 | 0.111 | 276.03 | 25.41 | | | |
| 432898 | 79.34 | 0.000 | 1010.53 | 58.63 | 0.000 | 4901.72 | 34.25 | | | |
| 432976 | 72.23 | 0.000 | 73.94 | 60.54 | 0.222 | 75.50 | 28.05 | | | |
| 433154 | 96.48 | 0.071 | 34.89 | 56.17 | 0.222 | 376.16 | 26.85 | | | |
| 433201 | 91.66 | 0.036 | 152.71 | 94.95 | 0.111 | 576.21 | 55.18 | | | |
| 433222 | 103.15 | 0.036 | 189.47 | 72.45 | 0.000 | 1186.75 | 51.60 | | | |
| 433291 | 85.16 | 0.071 | 76.18 | 72.63 | 0.111 | 114.48 | 38.12 | | | |
| 433307 | 77.86 | 0.071 | 96.78 | 92.13 | 0.000 | 114.79 | 35.45 | | | |
| 433343 | 65.49 | 0.000 | 184.42 | 53.88 | 0.000 | 291.09 | 38.55 | CopyNumber | 16p13.3 | 2866 |
| 433345 | 120.01 | 0.000 | 213.51 | 71.24 | 0.000 | 862.00 | 56.26 | | | |

TABLE 2-continued

A list of 2087 candidate endogenous reference genes

| | | | | | | | | | |
|---|---|---|---|---|---|---|---|---|---|
| 433419 | 60.89 | 0.000 | 500.10 | 50.66 | 0.000 | 1779.46 | 34.78 | | |
| 433512 | 84.34 | 0.071 | 85.96 | 81.88 | 0.222 | 1236.34 | 38.08 | | |
| 433529 | 170.20 | 0.036 | 2199.40 | 54.31 | 0.000 | 14172.61 | 40.90 | CopyNumber | 19q13.33 | 3277 |
| 433540 | 69.15 | 0.000 | 64.51 | 73.27 | 0.000 | 211.95 | 23.86 | | |
| 433573 | 63.03 | 0.000 | 57.01 | 59.43 | 0.111 | 123.88 | 31.69 | CopyNumber | 11q13.1 | 2276 |
| 433615 | 92.22 | 0.000 | 388.92 | 80.94 | 0.111 | 1034.66 | 46.90 | CopyNumber | 9q34.3 | 2030 |
| 433701 | 71.70 | 0.000 | 2139.00 | 50.10 | 0.000 | 7744.18 | 32.81 | | |
| 433722 | 74.06 | 0.036 | 27.81 | 59.03 | 0.222 | 141.76 | 60.11 | CopyNumber | 8p21.3 | 1710 |
| 433732 | 90.12 | 0.071 | 85.09 | 83.28 | 0.111 | 103.47 | 51.61 | | |
| 433750 | 73.70 | 0.000 | 60.65 | 76.09 | 0.222 | 80.25 | 36.40 | CopyNumber | 3q27.1 | 733 |
| 433759 | 58.35 | 0.000 | 139.75 | 61.48 | 0.111 | 411.26 | 35.14 | | |
| 433795 | 85.23 | 0.036 | 87.81 | 51.85 | 0.111 | 404.06 | 43.69 | | |
| 433863 | 66.30 | 0.000 | 430.25 | 65.24 | 0.000 | 1139.88 | 60.50 | | |
| 433901 | 72.42 | 0.000 | 618.72 | 88.72 | 0.000 | 1212.52 | 34.44 | | |
| 433951 | 77.15 | 0.000 | 631.83 | 67.81 | 0.111 | 627.74 | 38.31 | CopyNumber | 19p13.3 | 3198 |
| 434102 | 72.84 | 0.000 | 538.05 | 84.61 | 0.000 | 2487.38 | 32.06 | | |
| 434207 | 74.97 | 0.071 | 49.39 | 68.58 | 0.222 | 97.26 | 42.61 | CopyNumber | 20p11.23 | 3342 |
| 434219 | 137.02 | 0.036 | 51.48 | 60.93 | 0.222 | 80.88 | 28.08 | | |
| 434401 | 76.58 | 0.000 | 58.22 | 90.45 | 0.222 | 245.63 | 25.67 | | |
| 434937 | 79.45 | 0.000 | 143.66 | 68.38 | 0.111 | 736.59 | 35.97 | | |
| 434953 | 126.26 | 0.000 | 167.82 | 113.49 | 0.111 | 50.78 | 49.08 | | |
| 434980 | 73.22 | 0.000 | 373.57 | 81.91 | 0.111 | 63.94 | 46.60 | | |
| 435044 | 119.14 | 0.036 | 65.58 | 58.30 | 0.222 | 171.64 | 27.03 | CopyNumber | 22q13.31 | 3512 |
| 435064 | 53.57 | 0.071 | 27.55 | 70.25 | 0.222 | 213.71 | 32.00 | | |
| 435120 | 91.12 | 0.036 | 52.68 | 89.10 | 0.222 | 111.38 | 57.81 | | |
| 435136 | 83.96 | 0.000 | 172.33 | 62.24 | 0.000 | 53.09 | 51.23 | | |
| 435166 | 68.02 | 0.071 | 73.27 | 65.77 | 0.111 | 310.78 | 56.86 | | |
| 435231 | 128.11 | 0.071 | 40.03 | 61.55 | 0.000 | 85.70 | 26.38 | CopyNumber | 5p13.3 | 1105 |
| 435255 | 62.36 | 0.071 | 56.26 | 62.36 | 0.222 | 90.51 | 30.90 | | |
| 435326 | 74.42 | 0.071 | 49.09 | 59.90 | 0.222 | 78.17 | 52.63 | CopyNumber | 3q26.33 | 731 |
| 435512 | 77.87 | 0.000 | 34.15 | 50.88 | 0.222 | 190.85 | 63.23 | | |
| 435535 | 73.62 | 0.071 | 34.83 | 91.49 | 0.000 | 260.08 | 66.53 | | |
| 435610 | 69.17 | 0.000 | 86.37 | 78.22 | 0.111 | 404.43 | 20.92 | | |
| 435741 | 64.08 | 0.000 | 87.01 | 63.94 | 0.000 | 98.47 | 35.51 | CopyNumber | 16q23.2 | 2956 |
| 435759 | 74.67 | 0.071 | 52.90 | 67.87 | 0.222 | 332.76 | 29.01 | CopyNumber | 2q37.3 | 516 |
| 435771 | 67.86 | 0.036 | 56.30 | 74.26 | 0.111 | 90.36 | 28.25 | | |
| 435841 | 72.67 | 0.071 | 23.60 | 100.76 | 0.222 | 161.24 | 24.64 | | |
| 435850 | 84.40 | 0.036 | 105.96 | 99.27 | 0.111 | 267.53 | 47.21 | CopyNumber | 8q11.23 | 1756 |
| 435933 | 58.96 | 0.036 | 57.82 | 69.98 | 0.111 | 211.82 | 30.44 | | |
| 435948 | 62.53 | 0.036 | 29.62 | 71.91 | 0.222 | 149.70 | 30.57 | | |
| 435952 | 57.02 | 0.036 | 28.36 | 84.91 | 0.111 | 104.05 | 37.95 | | |
| 435974 | 78.61 | 0.071 | 68.25 | 91.00 | 0.222 | 218.66 | 65.62 | | |
| 436035 | 91.16 | 0.000 | 187.52 | 75.63 | 0.000 | 3174.68 | 46.99 | | |
| 436093 | 78.08 | 0.000 | 76.39 | 64.46 | 0.111 | 136.65 | 33.53 | | |
| 436204 | 64.95 | 0.036 | 29.22 | 78.13 | 0.222 | 250.23 | 22.99 | | |
| 436298 | 167.91 | 0.036 | 265.70 | 177.92 | 0.222 | 42.37 | 74.64 | | |
| 436405 | 77.90 | 0.036 | 27.67 | 56.95 | 0.222 | 313.71 | 26.76 | | |
| 436437 | 94.20 | 0.036 | 77.60 | 93.12 | 0.222 | 918.38 | 80.58 | | |
| 436446 | 66.68 | 0.000 | 99.63 | 53.06 | 0.111 | 309.25 | 35.80 | | |
| 436500 | 72.80 | 0.036 | 60.68 | 75.22 | 0.222 | 472.17 | 25.55 | CopyNumber | 7p13 | 1537 |
| 436568 | 131.69 | 0.000 | 1219.01 | 117.62 | 0.111 | 50.53 | 68.91 | | |
| 436578 | 90.18 | 0.000 | 113.73 | 79.39 | 0.000 | 140.58 | 43.95 | | |
| 436657 | 178.41 | 0.000 | 500.52 | 138.23 | 0.111 | 15.83 | 89.67 | | |
| 436687 | 75.22 | 0.000 | 611.23 | 84.03 | 0.000 | 638.97 | 31.31 | | |
| 436803 | 73.05 | 0.000 | 85.70 | 97.89 | 0.111 | 316.09 | 35.27 | | |
| 437056 | 103.58 | 0.036 | 43.41 | 77.96 | 0.222 | 163.82 | 26.89 | | |
| 437060 | 74.69 | 0.000 | 167.53 | 67.12 | 0.000 | 1114.79 | 54.47 | | |
| 437110 | 118.34 | 0.000 | 457.69 | 74.53 | 0.111 | | | | |
| 437178 | 108.35 | 0.000 | 118.41 | 93.36 | 0.000 | 491.49 | 49.15 | | |
| 437256 | 85.27 | 0.071 | 27.23 | 74.49 | 0.222 | 133.85 | 34.04 | | |
| 437277 | 113.92 | 0.036 | 112.16 | 68.25 | 0.222 | 562.98 | 51.58 | CopyNumber | 5q35.3 | 1271 |
| 437367 | 80.84 | 0.036 | 76.15 | 76.20 | 0.111 | 240.02 | 54.01 | | |
| 437388 | 92.45 | 0.071 | 42.31 | 57.64 | 0.222 | 238.37 | 40.11 | | |
| 437403 | 73.99 | 0.036 | 83.00 | 65.86 | 0.000 | 913.95 | 48.77 | | |
| 437594 | 63.31 | 0.000 | 2995.32 | 44.60 | 0.000 | 3402.65 | 43.18 | CopyNumber | 11p15.5 | 2200 |
| 437638 | 230.82 | 0.000 | 332.76 | 161.65 | 0.000 | 726.60 | 84.34 | | |
| 437779 | 79.94 | 0.000 | 162.25 | 59.57 | 0.000 | 1026.73 | 29.41 | | |
| 437831 | 69.32 | 0.071 | 42.55 | 70.99 | 0.222 | 349.70 | 25.46 | | |
| 438072 | 75.82 | 0.071 | 37.78 | 63.33 | 0.111 | 226.25 | 39.89 | | |
| 438219 | 66.65 | 0.071 | 41.29 | 63.30 | 0.222 | 161.95 | 25.67 | | |
| 438429 | 82.19 | 0.000 | 2234.04 | 58.24 | 0.000 | 4443.85 | 41.78 | | |
| 438678 | 95.46 | 0.000 | 66.45 | 74.83 | 0.111 | 417.69 | 43.11 | CopyNumber | 11p15.5 | 2200 |
| 438720 | 110.88 | 0.036 | 245.01 | 102.14 | 0.111 | 150.74 | 57.91 | CopyNumber | 7q22.1 | 1598 |
| 438970 | 65.73 | 0.036 | 35.85 | 46.43 | 0.111 | 1820.04 | 33.55 | | |
| 438974 | 65.29 | 0.036 | 44.97 | 79.81 | 0.111 | | | CopyNumber | 7q22.1 | 1603 |
| 439480 | 63.35 | 0.036 | 57.48 | 70.79 | 0.111 | 236.05 | 33.28 | | |
| 439481 | 387.86 | 0.000 | 88.09 | 67.88 | 0.222 | 169.24 | 40.86 | CopyNumber | 17q22 | 3047 |
| 439548 | 61.68 | 0.071 | 37.93 | 64.75 | 0.222 | 1054.07 | 45.16 | | |

TABLE 2-continued

A list of 2087 candidate endogenous reference genes

| | | | | | | | | | | |
|---|---|---|---|---|---|---|---|---|---|---|
| 439552 | 95.86 | 0.071 | 229.49 | 79.88 | 0.111 | 6558.96 | 35.24 | | | |
| 439815 | 64.93 | 0.036 | 157.75 | 73.89 | 0.000 | 568.16 | 45.34 | | | |
| 440382 | 63.06 | 0.000 | 67.84 | 45.41 | 0.111 | 163.60 | 26.30 | | | |
| 440544 | 76.58 | 0.000 | 183.45 | 74.43 | 0.111 | 120.48 | 60.51 | CopyNumber | 1p36.11 | 46 |
| 440599 | 545.85 | 0.000 | 639.75 | 338.15 | 0.000 | 377.40 | 37.66 | | | |
| 440604 | 69.40 | 0.000 | 120.21 | 77.49 | 0.222 | 219.86 | 29.08 | CopyNumber | 16q22.3 | 2941 |
| 440899 | 108.09 | 0.036 | 90.62 | 83.07 | 0.111 | 375.62 | 48.63 | | | |
| 440932 | 67.69 | 0.000 | 103.15 | 59.03 | 0.111 | 1062.06 | 42.62 | CopyNumber | 17q25.2 | 3077 |
| 440960 | 72.81 | 0.071 | 47.81 | 52.64 | 0.111 | 258.65 | 30.69 | CopyNumber | 19p13.13 | 3220 |
| 440961 | 70.30 | 0.000 | 77.69 | 104.24 | 0.000 | 450.65 | 39.28 | | | |
| 441072 | 127.50 | 0.000 | 185.74 | 85.71 | 0.000 | 731.13 | 33.84 | CopyNumber | 11p15.5 | 2200 |
| 441550 | 76.06 | 0.036 | 56.52 | 72.10 | 0.222 | 236.69 | 37.99 | | | |
| 442344 | 88.49 | 0.071 | 72.66 | 94.29 | 0.000 | 207.03 | 63.14 | CopyNumber | 13q33.3-13q34 | 2880 |
| 442798 | 54.05 | 0.036 | 54.26 | 57.73 | 0.222 | 231.34 | 26.39 | | | |
| 443134 | 85.46 | 0.036 | 64.44 | 87.35 | 0.222 | 198.90 | 27.17 | | | |
| 443379 | 72.92 | 0.071 | 67.86 | 68.96 | 0.111 | 224.78 | 38.54 | | | |
| 443837 | 77.55 | 0.071 | 46.32 | 62.18 | 0.222 | 174.43 | 34.43 | CopyNumber | 17q21.32 | 3031 |
| 443914 | 58.76 | 0.000 | 247.64 | 46.39 | 0.000 | 1457.78 | 49.68 | | | |
| 444279 | 61.65 | 0.000 | 80.72 | 51.79 | 0.111 | 746.56 | 26.60 | | | |
| 444356 | 57.17 | 0.036 | 92.25 | 70.76 | 0.222 | 182.95 | 39.12 | CopyNumber | 17q25.1 | 3073 |
| 444468 | 78.70 | 0.000 | 67.26 | 84.13 | 0.111 | 310.40 | 27.53 | | | |
| 444472 | 73.19 | 0.071 | 54.83 | 62.43 | 0.111 | 195.91 | 35.50 | | | |
| 444569 | 110.59 | 0.000 | 189.12 | 138.53 | 0.000 | 519.72 | 46.05 | | | |
| 444673 | 71.14 | 0.036 | 92.42 | 75.43 | 0.111 | 67.52 | 34.65 | | | |
| 444724 | 59.51 | 0.036 | 21.27 | 56.05 | 0.222 | 81.02 | 40.08 | | | |
| 444818 | 72.48 | 0.071 | 40.54 | 62.78 | 0.111 | 209.04 | 23.65 | | | |
| 444931 | 61.84 | 0.071 | 30.56 | 69.88 | 0.222 | 113.86 | 30.06 | | | |
| 444969 | 72.90 | 0.071 | 59.68 | 83.21 | 0.000 | 136.35 | 35.35 | | | |
| 444986 | 81.88 | 0.071 | 31.66 | 59.27 | 0.222 | 182.02 | 33.14 | | | |
| 445081 | 108.71 | 0.036 | 70.28 | 132.55 | 0.222 | 544.37 | 97.79 | | | |
| 445351 | 153.11 | 0.000 | 1533.86 | 144.30 | 0.111 | 39.15 | 60.06 | CopyNumber | 22q13.1 | 3496 |
| 445394 | 61.72 | 0.000 | 60.05 | 68.24 | 0.000 | 1169.19 | 31.54 | | | |
| 445498 | 69.47 | 0.071 | 37.53 | 51.18 | 0.111 | 126.46 | 22.30 | CopyNumber | 14q24.3 | 2709 |
| 445511 | 100.89 | 0.071 | 43.28 | 70.81 | 0.222 | 220.12 | 43.86 | | | |
| 445570 | 85.23 | 0.000 | 287.35 | 53.42 | 0.000 | 2381.68 | 28.41 | | | |
| 445803 | 90.03 | 0.000 | 123.83 | 68.80 | 0.111 | 1202.42 | 33.85 | | | |
| 445893 | 61.34 | 0.036 | 158.23 | 69.47 | 0.000 | 147.47 | 27.99 | | | |
| 445977 | 66.19 | 0.036 | 69.10 | 64.20 | 0.111 | 644.29 | 43.60 | | | |
| 446017 | 76.51 | 0.036 | 155.50 | 54.07 | 0.000 | 397.35 | 48.34 | | | |
| 446091 | 71.17 | 0.036 | 85.02 | 65.59 | 0.111 | 941.23 | 28.02 | CopyNumber | 6q25.3 | 1460 |
| 446123 | 64.84 | 0.000 | 57.10 | 56.16 | 0.222 | 166.18 | 39.16 | | | |
| 446149 | 93.31 | 0.000 | 369.45 | 112.87 | 0.000 | 1387.86 | 59.45 | CopyNumber | 12p12.1 | 2390 |
| 446260 | 71.29 | 0.000 | 126.46 | 62.05 | 0.111 | 720.78 | 37.72 | | | |
| 446336 | 118.95 | 0.000 | 56.90 | 54.31 | 0.111 | 182.90 | 31.05 | | | |
| 446345 | 75.64 | 0.000 | 2881.93 | 51.03 | 0.000 | | | | | |
| 446414 | 79.62 | 0.036 | 56.65 | 96.50 | 0.111 | 83.57 | 42.55 | Inversion | 3q13.12 | 646 |
| 446427 | 55.94 | 0.000 | 444.92 | 41.01 | 0.000 | 1860.94 | 22.07 | CopyNumber | 19p13.3 | 3199 |
| 446445 | 117.64 | 0.000 | 85.11 | 64.37 | 0.111 | 220.61 | 30.91 | | | |
| 446450 | 91.72 | 0.000 | 785.60 | 75.69 | 0.000 | 1838.91 | 35.62 | | | |
| 446574 | 101.45 | 0.000 | 1048.70 | 47.73 | 0.111 | 4295.62 | 48.23 | | | |
| 446588 | 74.06 | 0.000 | 514.97 | 50.47 | 0.000 | 10114.50 | 28.56 | | | |
| 446623 | 59.32 | 0.000 | 440.12 | 53.84 | 0.000 | 280.15 | 39.09 | | | |
| 446628 | 69.18 | 0.000 | 1715.03 | 60.31 | 0.000 | 4069.97 | 36.87 | | | |
| 446641 | 74.66 | 0.000 | 70.78 | 78.14 | 0.000 | 226.36 | 28.05 | | | |
| 446852 | 65.91 | 0.036 | 169.80 | 67.64 | 0.000 | 1472.64 | 39.26 | CopyNumber | 22q13.1 | 3486 |
| 447477 | 59.67 | 0.036 | 112.12 | 53.27 | 0.222 | | | | | |
| 447492 | 70.38 | 0.000 | 576.32 | 85.45 | 0.111 | 128.97 | 28.68 | | | |
| 447547 | 68.05 | 0.036 | 63.65 | 59.13 | 0.222 | | | | | |
| 448226 | 91.01 | 0.000 | 1605.76 | 74.12 | 0.000 | 1888.46 | 41.47 | | | |
| 448588 | 89.27 | 0.000 | 289.59 | 98.53 | 0.222 | 1421.10 | 61.15 | | | |
| 448646 | 106.73 | 0.000 | 2172.80 | 57.81 | 0.000 | | | | | |
| 448879 | 104.70 | 0.071 | 169.47 | 88.62 | 0.000 | | | | | |
| 449114 | 62.43 | 0.000 | 277.65 | 67.95 | 0.111 | 25.47 | 56.84 | | | |
| 449171 | 78.63 | 0.000 | 672.79 | 37.65 | 0.000 | | | CopyNumber | 9q21.32 | 1957 |
| 454534 | 72.76 | 0.036 | 51.63 | 64.52 | 0.222 | 87.97 | 34.37 | CopyNumber | 19q13.12 | 3247 |
| 454699 | 69.32 | 0.071 | 522.93 | 101.80 | 0.000 | | | | | |
| 456507 | 68.08 | 0.036 | 50.47 | 65.93 | 0.222 | 358.16 | 38.22 | | | |
| 456557 | 65.44 | 0.036 | 88.99 | 75.61 | 0.222 | 120.23 | 30.51 | CopyNumber | 1p34.1 | 66 |
| 458320 | 67.14 | 0.071 | 31.00 | 50.77 | 0.222 | 136.02 | 27.81 | | | |
| 458358 | 94.79 | 0.071 | 58.21 | 86.21 | 0.222 | 256.39 | 41.07 | | | |
| 458414 | 135.42 | 0.036 | 193.99 | 95.48 | 0.222 | 1264.21 | 74.29 | | | |
| 458458 | 96.04 | 0.000 | 151.41 | 91.30 | 0.000 | | | | | |
| 458747 | 58.82 | 0.036 | 95.42 | 71.07 | 0.222 | 98.53 | 30.78 | | | |
| 459106 | 67.41 | 0.036 | 30.94 | 43.03 | 0.222 | 350.68 | 35.89 | | | |
| 459149 | 77.24 | 0.071 | 63.96 | 81.98 | 0.222 | 208.67 | 32.53 | | | |
| 459174 | 64.84 | 0.071 | 65.88 | 81.46 | 0.111 | 430.22 | 38.61 | | | |
| 459211 | 74.24 | 0.071 | 63.93 | 96.88 | 0.111 | 121.40 | 39.40 | CopyNumber | 15q25.3 | 2828 |

TABLE 2-continued

A list of 2087 candidate endogenous reference genes

| | | | | | | | | | |
|---|---|---|---|---|---|---|---|---|---|
| 459596 | 97.43 | 0.036 | 59.17 | 70.19 | 0.111 | 97.92 | 30.16 | CopyNumber | 16p13.3 | 2866 |
| 459649 | 98.22 | 0.071 | 74.77 | 93.41 | 0.111 | 141.86 | 39.47 | CopyNumber | 16p13.3 | 2866 |
| 459927 | 87.23 | 0.000 | 2248.86 | 63.06 | 0.000 | 1030.19 | 45.59 | CopyNumber | 2q37.1 | 507 |
| 459940 | 87.15 | 0.000 | 129.67 | 70.79 | 0.222 | 677.27 | 59.84 | | | |
| 460238 | 100.06 | 0.000 | 31.15 | 69.28 | 0.000 | 250.78 | 29.94 | | | |
| 460317 | 72.75 | 0.036 | 35.75 | 55.10 | 0.222 | 115.06 | 30.41 | | | |
| 460336 | 67.69 | 0.071 | 40.70 | 46.75 | 0.000 | 45.79 | 44.88 | | | |
| 460468 | 64.03 | 0.036 | 56.42 | 63.75 | 0.111 | 230.88 | 23.36 | CopyNumber | 16p11.2 | 2900 |
| 460499 | 92.61 | 0.071 | 48.97 | 54.21 | 0.000 | 37.47 | 53.32 | CopyNumber | 16p11.2 | 2900 |
| 460574 | 83.01 | 0.071 | 78.45 | 91.21 | 0.111 | 746.92 | 27.83 | | | |
| 460923 | 71.51 | 0.036 | 28.17 | 61.28 | 0.222 | 152.22 | 22.68 | CopyNumber | 16q21 | 2926 |
| 460929 | 96.28 | 0.071 | 141.87 | 83.05 | 0.111 | 370.86 | 56.55 | CopyNumber | 16q21 | 2926 |
| 460978 | 73.44 | 0.036 | 49.25 | 81.01 | 0.222 | 250.20 | 31.68 | | | |
| 461047 | 103.47 | 0.071 | 67.54 | 106.04 | 0.111 | 70.12 | 87.63 | | | |
| 461131 | 122.98 | 0.036 | 127.62 | 157.34 | 0.222 | 76.67 | 41.61 | | | |
| 461361 | 78.50 | 0.036 | 30.76 | 40.03 | 0.222 | 174.78 | 41.86 | CopyNumber | 16q23.1 | 2944 |
| 461379 | 83.32 | 0.000 | 96.52 | 91.91 | 0.111 | 641.27 | 33.25 | | | |
| 461722 | 71.51 | 0.000 | 48.48 | 53.92 | 0.111 | 186.99 | 29.54 | CopyNumber | 16q24.3 | 2971 |
| 461777 | 79.87 | 0.000 | 81.52 | 105.93 | 0.111 | | | | | |
| 461896 | 75.47 | 0.000 | 126.02 | 74.34 | 0.000 | 134.80 | 28.05 | | | |
| 461925 | 71.77 | 0.000 | 103.12 | 73.82 | 0.222 | 147.49 | 38.95 | | | |
| 462035 | 62.46 | 0.000 | 66.85 | 67.94 | 0.111 | 216.51 | 26.40 | CopyNumber | 17p13.2 | 2983 |
| 462086 | 56.55 | 0.036 | 58.35 | 72.87 | 0.111 | 140.21 | 27.82 | Inversion | 17p11.2 | 2999 |
| 462306 | 151.24 | 0.036 | 384.89 | 136.76 | 0.111 | 93.89 | 42.37 | | | |
| 462316 | 52.50 | 0.036 | 45.98 | 51.91 | 0.000 | 305.99 | 31.78 | | | |
| 462492 | 75.74 | 0.000 | 101.26 | 70.86 | 0.222 | 889.15 | 34.30 | | | |
| 462550 | 77.59 | 0.036 | 37.84 | 47.17 | 0.111 | 481.28 | 40.17 | | | |
| 462956 | 121.13 | 0.071 | 41.50 | 83.60 | 0.111 | 272.89 | 75.13 | | | |
| 462998 | 165.03 | 0.000 | 412.00 | 132.76 | 0.222 | 318.32 | 32.43 | | | |
| 463010 | 74.65 | 0.036 | 48.26 | 79.91 | 0.000 | 297.90 | 46.77 | CopyNumber | 17q21.2 | 3021 |
| 463035 | 84.60 | 0.036 | 88.96 | 78.41 | 0.222 | 29.55 | 123.40 | | | |
| 463041 | 60.04 | 0.000 | 61.76 | 105.33 | 0.111 | 85.41 | 37.40 | CopyNumber | 1p36.23 | 24 |
| 463059 | 99.58 | 0.000 | 97.24 | 64.76 | 0.000 | 708.36 | 33.04 | | | |
| 463295 | 128.90 | 0.000 | 22.01 | 67.66 | 0.222 | 89.26 | 24.02 | CopyNumber | 17q21.32-17q21.31 | 3030 |
| 463506 | 144.88 | 0.036 | 69.53 | 99.95 | 0.000 | 311.25 | 41.57 | CopyNumber | 17q22 | 3044 |
| 463702 | 182.82 | 0.071 | 17.71 | 63.68 | 0.222 | 71.51 | 32.11 | | | |
| 463797 | 86.43 | 0.071 | 35.50 | 77.38 | 0.222 | 60.88 | 56.60 | | | |
| 464071 | 87.71 | 0.000 | 221.39 | 89.76 | 0.000 | 219.07 | 81.15 | CopyNumber | 1p36.22 | 27 |
| 464137 | 80.94 | 0.036 | 49.33 | 90.69 | 0.000 | 60.37 | 44.17 | | | |
| 464210 | 106.68 | 0.000 | 141.21 | 95.75 | 0.111 | 537.14 | 49.17 | | | |
| 464336 | 99.04 | 0.000 | 283.74 | 88.39 | 0.000 | 2084.95 | 55.71 | CopyNumber | 17q25.3 | 3087 |
| 464438 | 107.95 | 0.036 | 166.40 | 112.66 | 0.000 | 98.95 | 38.69 | | | |
| 464472 | 95.86 | 0.000 | 207.88 | 42.93 | 0.000 | 1126.38 | 32.54 | | | |
| 464595 | 58.98 | 0.000 | 59.05 | 58.88 | 0.111 | 215.87 | 47.07 | CopyNumber | 18p11.22 | 3100 |
| 464652 | 61.77 | 0.036 | 54.95 | 54.53 | 0.222 | 517.28 | 24.42 | | | |
| 464912 | 70.39 | 0.000 | 76.41 | 70.71 | 0.111 | 213.12 | 37.13 | | | |
| 465224 | 72.99 | 0.036 | 75.36 | 57.77 | 0.222 | 700.57 | 30.47 | | | |
| 465374 | 103.77 | 0.071 | 157.39 | 115.14 | 0.000 | 330.15 | 48.22 | | | |
| 465498 | 68.69 | 0.000 | 88.16 | 71.12 | 0.111 | 400.88 | 28.38 | | | |
| 465529 | 122.89 | 0.036 | 107.98 | 78.16 | 0.111 | 288.27 | 45.92 | CopyNumber | 19p13.3 | 3198 |
| 465543 | 63.89 | 0.071 | 84.61 | 58.95 | 0.111 | 64.19 | 57.71 | | | |
| 465627 | 70.89 | 0.000 | 133.95 | 67.91 | 0.000 | 301.85 | 37.18 | CopyNumber | 19p13.3 | 3205 |
| 465645 | 77.44 | 0.000 | 75.74 | 54.65 | 0.000 | 386.74 | 35.78 | | | |
| 465808 | 66.58 | 0.000 | 143.70 | 66.22 | 0.111 | 434.39 | 30.19 | | | |
| 465849 | 69.39 | 0.000 | 91.55 | 80.10 | 0.111 | 44.47 | 66.21 | | | |
| 465924 | 84.07 | 0.036 | 50.18 | 61.81 | 0.222 | 165.00 | 42.35 | CopyNumber | 1p36.13 | 35 |
| 466044 | 72.79 | 0.036 | 84.23 | 68.24 | 0.111 | 73.78 | 52.32 | CopyNumber | 19p13.12 | 3223 |
| 466088 | 111.92 | 0.000 | 181.29 | 71.15 | 0.111 | 179.65 | 56.72 | | | |
| 466148 | 84.06 | 0.000 | 97.34 | 76.06 | 0.111 | 203.63 | 72.98 | | | |
| 466471 | 105.82 | 0.000 | 168.18 | 142.62 | 0.000 | 626.83 | 50.67 | | | |
| 466693 | 102.86 | 0.000 | 67.60 | 126.08 | 0.222 | 176.70 | 34.39 | | | |
| 466766 | 118.35 | 0.036 | 34.50 | 83.74 | 0.222 | 45.08 | 45.77 | | | |
| 466775 | 79.83 | 0.036 | 68.63 | 60.69 | 0.222 | 244.72 | 28.23 | CopyNumber | 19q13.2 | 3260 |
| 467084 | 54.59 | 0.036 | 34.59 | 66.69 | 0.222 | 99.92 | 38.09 | CopyNumber | 1p36.12 | 37 |
| 467097 | 76.10 | 0.036 | 128.68 | 86.64 | 0.111 | 397.83 | 35.85 | CopyNumber | 19q13.33 | 3276 |
| 467192 | 73.99 | 0.000 | 138.33 | 71.24 | 0.111 | 315.89 | 28.78 | | | |
| 467279 | 53.14 | 0.000 | 77.66 | 63.14 | 0.111 | 125.33 | 61.82 | CopyNumber | 19q13.42 | 3287 |
| 467284 | 110.65 | 0.036 | 1280.99 | 75.58 | 0.000 | | | CopyNumber | 19q13.42 | 3287 |
| 467408 | 63.16 | 0.000 | 325.76 | 90.96 | 0.111 | 393.32 | 76.72 | | | |
| 467637 | 49.68 | 0.000 | 192.26 | 43.69 | 0.111 | 218.92 | 31.71 | CopyNumber | 1p36.12 | 39 |
| 467696 | 92.22 | 0.000 | 54.70 | 92.68 | 0.111 | 81.56 | 46.18 | | | |
| 467701 | 84.27 | 0.036 | 80.50 | 96.79 | 0.222 | 611.36 | 76.96 | | | |
| 467807 | 67.35 | 0.000 | 271.07 | 62.85 | 0.000 | 1249.38 | 26.16 | | | |
| 467824 | 65.40 | 0.036 | 37.46 | 47.95 | 0.222 | 425.41 | 25.22 | | | |
| 467960 | 55.30 | 0.071 | 78.25 | 53.53 | 0.222 | 1591.91 | 35.68 | | | |
| 468018 | 78.99 | 0.000 | 181.90 | 57.84 | 0.111 | 221.20 | 50.86 | | | |
| 468415 | 66.24 | 0.071 | 77.48 | 62.56 | 0.111 | 149.98 | 25.30 | CopyNumber | 2p21 | 325 |

TABLE 2-continued

A list of 2087 candidate endogenous reference genes

| | | | | | | | | | | |
|---|---|---|---|---|---|---|---|---|---|---|
| 468442 | 60.35 | 0.000 | 431.37 | 47.50 | 0.000 | 3361.97 | 24.79 | | | |
| 468760 | 79.05 | 0.036 | 31.54 | 72.64 | 0.111 | 405.11 | 28.06 | | | |
| 469022 | 70.82 | 0.071 | 71.82 | 59.11 | 0.111 | 223.87 | 28.02 | | | |
| 469171 | 71.16 | 0.071 | 32.92 | 79.80 | 0.222 | 196.57 | 24.11 | | | |
| 469331 | 87.59 | 0.000 | 191.43 | 51.78 | 0.111 | 1314.48 | 35.64 | CopyNumber | 2q11.2 | 378 |
| 469820 | 71.71 | 0.000 | 38.70 | 85.72 | 0.222 | 246.69 | 30.95 | CopyNumber | 2q14.2 | 402 |
| 469863 | 57.98 | 0.000 | 457.07 | 59.63 | 0.000 | | | | | |
| 469925 | 77.87 | 0.000 | 361.73 | 80.70 | 0.000 | 456.73 | 35.81 | CopyNumber | 2q14.3-2q21.1 | 410 |
| 469970 | 76.12 | 0.000 | 60.03 | 58.11 | 0.000 | 250.41 | 21.69 | | | |
| 470091 | 62.78 | 0.000 | 636.64 | 72.45 | 0.000 | | | | | |
| 470233 | 104.74 | 0.071 | 31.04 | 74.54 | 0.111 | 227.42 | 28.85 | | | |
| 470417 | 65.73 | 0.000 | 36.16 | 73.00 | 0.222 | 240.63 | 29.90 | CopyNumber | 1p35.2-1p35.1 | 53 |
| 470477 | 78.56 | 0.000 | 176.13 | 76.36 | 0.000 | 704.61 | 35.82 | CopyNumber | 1p35.2-1p35.1 | 53 |
| 470577 | 112.63 | 0.000 | 64.25 | 63.02 | 0.000 | | | | | |
| 470588 | 62.13 | 0.000 | 49.83 | 47.08 | 0.222 | 38.39 | 32.85 | | | |
| 470943 | 79.99 | 0.036 | 73.35 | 126.49 | 0.222 | 655.85 | 58.91 | | | |
| 471011 | 67.05 | 0.071 | 67.25 | 53.93 | 0.222 | 121.32 | 42.55 | | | |
| 471104 | 89.45 | 0.000 | 149.19 | 59.04 | 0.111 | 602.32 | 48.56 | | | |
| 471207 | 63.61 | 0.071 | 49.29 | 54.88 | 0.222 | 136.91 | 52.19 | | | |
| 471441 | 78.02 | 0.000 | 176.65 | 89.29 | 0.111 | 498.87 | 39.72 | | | |
| 471461 | 73.53 | 0.071 | 32.43 | 58.01 | 0.222 | 196.76 | 59.72 | | | |
| 471593 | 53.91 | 0.071 | 36.64 | 49.61 | 0.222 | 288.93 | 31.86 | | | |
| 471768 | 90.76 | 0.071 | 70.68 | 83.24 | 0.111 | 111.27 | 42.60 | CopyNumber | 1p34.3 | 57 |
| 471818 | 63.33 | 0.071 | 35.69 | 55.32 | 0.111 | 1268.99 | 34.78 | | | |
| 471851 | 70.38 | 0.000 | 115.85 | 67.87 | 0.111 | 499.38 | 30.04 | | | |
| 471873 | 109.74 | 0.071 | 97.75 | 113.82 | 0.111 | 48.62 | 53.92 | | | |
| 471933 | 63.18 | 0.000 | 202.14 | 53.09 | 0.000 | 624.43 | 29.36 | | | |
| 471975 | 70.45 | 0.071 | 36.48 | 73.24 | 0.222 | 242.80 | 24.13 | CopyNumber | 20p13 | 3306 |
| 472010 | 105.00 | 0.000 | 67.84 | 111.58 | 0.222 | 155.71 | 45.29 | | | |
| 472024 | 64.21 | 0.036 | 69.70 | 48.63 | 0.111 | 1913.94 | 28.06 | | | |
| 472031 | 59.04 | 0.000 | 211.67 | 50.43 | 0.111 | | | CopyNumber | 4q24 | 915 |
| 472038 | 67.26 | 0.071 | 32.17 | 50.19 | 0.111 | 123.01 | 32.36 | | | |
| 472056 | 68.89 | 0.036 | 112.97 | 60.49 | 0.111 | | | | | |
| 472119 | 66.76 | 0.071 | 31.86 | 112.28 | 0.222 | 139.92 | 34.83 | | | |
| 472185 | 78.25 | 0.000 | 242.12 | 90.19 | 0.000 | 1069.96 | 32.56 | | | |
| 472213 | 95.80 | 0.071 | 41.74 | 48.04 | 0.111 | 48.90 | 42.31 | | | |
| 472330 | 96.95 | 0.036 | 69.76 | 90.01 | 0.111 | 465.49 | 45.06 | | | |
| 472475 | 69.13 | 0.000 | 78.28 | 70.30 | 0.000 | 139.49 | 37.18 | | | |
| 472535 | 99.64 | 0.071 | 77.90 | 44.78 | 0.222 | 199.94 | 32.50 | CopyNumber | 1p36.33 | 2 |
| 472558 | 74.34 | 0.000 | 132.04 | 58.70 | 0.000 | 639.31 | 31.64 | | | |
| 472651 | 79.84 | 0.000 | 36.65 | 74.11 | 0.222 | 314.39 | 34.69 | | | |
| 472737 | 61.99 | 0.071 | 43.99 | 48.64 | 0.222 | 363.10 | 33.74 | CopyNumber | 20q12 | 3378 |
| 473296 | 84.70 | 0.000 | 63.19 | 58.70 | 0.222 | 168.83 | 41.41 | CopyNumber | 20q13.33 | 3420 |
| 473583 | 60.46 | 0.000 | 514.27 | 77.95 | 0.000 | 1676.15 | 36.77 | | | |
| 473648 | 73.17 | 0.036 | 64.60 | 71.35 | 0.222 | 102.03 | 32.42 | | | |
| 473721 | 128.82 | 0.000 | 134.23 | 123.75 | 0.111 | 33.23 | 53.19 | | | |
| 473761 | 72.57 | 0.000 | 132.69 | 52.87 | 0.111 | 657.85 | 38.65 | | | |
| 473788 | 64.69 | 0.000 | 111.64 | 71.83 | 0.222 | 157.28 | 26.24 | | | |
| 474005 | 61.86 | 0.000 | 75.34 | 61.40 | 0.111 | 478.66 | 79.39 | | | |
| 474010 | 78.81 | 0.000 | 59.76 | 58.87 | 0.222 | 891.19 | 36.45 | | | |
| 474053 | 147.51 | 0.000 | 499.17 | 168.59 | 0.222 | 29.70 | 60.90 | | | |
| 474083 | 72.19 | 0.036 | 75.46 | 78.10 | 0.111 | 114.78 | 33.60 | | | |
| 474213 | 79.94 | 0.000 | 36.27 | 50.63 | 0.222 | 196.39 | 29.08 | | | |
| 474584 | 80.62 | 0.071 | 112.70 | 73.66 | 0.000 | 162.31 | 31.89 | | | |
| 474643 | 74.60 | 0.000 | 58.12 | 75.67 | 0.222 | 795.97 | 39.57 | CopyNumber | 22q12.3 | 3485 |
| 474751 | 97.07 | 0.000 | 78.94 | 84.91 | 0.222 | 372.66 | 35.97 | CopyNumber | 22q12.3 | 3492 |
| 474833 | 89.25 | 0.036 | 58.59 | 72.73 | 0.111 | 237.54 | 48.09 | | | |
| 474914 | 69.41 | 0.036 | 62.09 | 108.62 | 0.111 | 72.32 | 40.96 | | | |
| 474938 | 60.89 | 0.036 | 23.46 | 63.42 | 0.222 | 59.35 | 36.45 | | | |
| 474949 | 73.51 | 0.036 | 92.75 | 72.43 | 0.111 | 309.31 | 39.95 | | | |
| 474982 | 85.98 | 0.000 | 78.19 | 80.45 | 0.111 | 320.54 | 79.01 | CopyNumber | 22q13.2 | 3503 |
| 475125 | 207.12 | 0.000 | 64.68 | 86.52 | 0.222 | 119.70 | 27.01 | | | |
| 475319 | 67.49 | 0.036 | 43.01 | 77.46 | 0.222 | 62.08 | 33.32 | | | |
| 475382 | 139.32 | 0.036 | 33.09 | 54.60 | 0.222 | 133.66 | 23.64 | | | |
| 475392 | 65.47 | 0.036 | 34.18 | 68.93 | 0.222 | 258.78 | 29.27 | | | |
| 475663 | 63.62 | 0.000 | 53.92 | 65.40 | 0.111 | 432.72 | 25.21 | | | |
| 475733 | 81.21 | 0.036 | 146.31 | 89.30 | 0.222 | 173.94 | 39.02 | | | |
| 475812 | 68.94 | 0.071 | 52.89 | 70.48 | 0.222 | 1013.17 | 36.02 | | | |
| 476018 | 69.79 | 0.000 | 149.54 | 73.93 | 0.000 | 200.35 | 60.22 | | | |
| 476033 | 64.70 | 0.000 | 34.53 | 60.01 | 0.111 | 864.12 | 31.66 | CopyNumber | 1p32.3 | 71 |
| 476179 | 79.60 | 0.000 | 59.30 | 85.57 | 0.111 | 194.12 | 38.59 | CopyNumber | 3p21.31 | 580 |
| 476221 | 67.55 | 0.000 | 66.80 | 51.17 | 0.222 | 603.05 | 35.35 | | | |
| 476231 | 80.66 | 0.000 | 113.22 | 65.22 | 0.111 | 228.30 | 24.27 | | | |
| 476308 | 72.23 | 0.000 | 22.50 | 50.59 | 0.222 | 178.95 | 107.93 | CopyNumber | 3p21.1 | 590 |
| 476365 | 67.35 | 0.036 | 87.65 | 77.78 | 0.111 | 406.18 | 49.02 | CopyNumber | 1p32.3 | 73 |
| 476448 | 82.54 | 0.036 | 26.09 | 48.03 | 0.111 | 273.21 | 70.63 | | | |

TABLE 2-continued

A list of 2087 candidate endogenous reference genes

| | | | | | | | | | |
|---|---|---|---|---|---|---|---|---|---|
| 476706 | 89.82 | 0.000 | 112.58 | 110.62 | 0.222 | 81.22 | 37.20 | | |
| 476930 | 58.53 | 0.000 | 66.80 | 47.34 | 0.111 | 174.86 | 28.52 | | |
| 477157 | 67.07 | 0.000 | 152.23 | 52.84 | 0.111 | | | | |
| 477789 | 79.84 | 0.000 | 117.57 | 72.54 | 0.222 | 721.27 | 53.90 | | |
| 477892 | 78.36 | 0.036 | 57.25 | 57.97 | 0.222 | 310.08 | 37.49 | | |
| 478000 | 64.58 | 0.071 | 50.48 | 78.17 | 0.111 | 341.67 | 50.94 | CopyNumber | 3q25.2 | 695 |
| 478044 | 91.75 | 0.000 | 243.91 | 67.91 | 0.000 | | | | |
| 478553 | 71.73 | 0.000 | 280.28 | 57.47 | 0.000 | 1815.88 | 27.23 | CopyNumber | 3q27.3 | 735 |
| 479208 | 70.67 | 0.036 | 49.83 | 85.49 | 0.222 | 273.64 | 45.06 | CopyNumber | 4p15.33-4p15.32 | 780 |
| 479264 | 90.31 | 0.036 | 53.68 | 100.71 | 0.222 | 408.08 | 53.78 | CopyNumber | 4p15.32 | 782 |
| 479634 | 68.03 | 0.036 | 41.66 | 53.90 | 0.000 | 172.97 | 40.28 | CopyNumber | 4p13 | 831 |
| 479693 | 56.38 | 0.000 | 130.06 | 53.34 | 0.111 | 284.38 | 38.70 | | |
| 479728 | 83.62 | 0.000 | 3178.15 | 102.50 | 0.000 | 4934.56 | 42.86 | CopyNumber | 12p13.31 | 2368 |
| 479747 | 70.99 | 0.036 | 64.38 | 45.15 | 0.222 | 7.50 | 52.67 | Inversion CopyNumber | 16q23.1 | 2943 |
| 479814 | 68.90 | 0.071 | 58.18 | 86.26 | 0.111 | 282.68 | 26.04 | | |
| 480073 | 71.32 | 0.036 | 300.48 | 64.32 | 0.000 | 630.71 | 24.05 | | |
| 480311 | 89.15 | 0.036 | 59.40 | 90.37 | 0.222 | 67.76 | 39.38 | | |
| 480465 | 68.49 | 0.036 | 34.96 | 55.94 | 0.111 | 256.72 | 29.28 | | |
| 480653 | 90.52 | 0.000 | 190.63 | 63.63 | 0.222 | 682.67 | 41.50 | | |
| 481571 | 70.58 | 0.000 | 535.04 | 63.11 | 0.000 | 1077.46 | 44.16 | | |
| 481720 | 79.80 | 0.036 | 93.11 | 81.12 | 0.222 | 200.72 | 60.41 | | |
| 481898 | 73.18 | 0.000 | 50.50 | 72.53 | 0.111 | 147.39 | 32.08 | CopyNumber | 1p22.2 | 109 |
| 482144 | 85.86 | 0.000 | 471.96 | 66.50 | 0.000 | | | | |
| 482363 | 60.86 | 0.000 | 36.22 | 51.54 | 0.222 | 233.09 | 31.51 | | |
| 482526 | 63.94 | 0.000 | 168.03 | 60.84 | 0.000 | 627.83 | 38.92 | | |
| 482868 | 62.26 | 0.000 | 47.36 | 57.55 | 0.111 | 85.83 | 30.54 | | |
| 483036 | 86.03 | 0.071 | 34.06 | 72.88 | 0.222 | 186.72 | 49.93 | | |
| 483067 | 195.81 | 0.000 | 113.05 | 119.75 | 0.222 | 107.96 | 48.75 | | |
| 483295 | 77.80 | 0.000 | 53.80 | 57.74 | 0.222 | 1552.44 | 38.85 | CopyNumber | 5q31.1 | 1221 |
| 483408 | 59.58 | 0.000 | 101.17 | 58.25 | 0.222 | 332.91 | 23.51 | | |
| 483454 | 95.38 | 0.000 | 276.29 | 56.43 | 0.222 | 240.02 | 66.66 | | |
| 483486 | 70.29 | 0.071 | 53.21 | 62.00 | 0.111 | 273.51 | 21.50 | | |
| 484138 | 135.13 | 0.071 | 55.94 | 56.87 | 0.222 | 135.74 | 33.03 | CopyNumber | 5q35.1 | 1257 |
| 484188 | 89.14 | 0.071 | 98.14 | 90.97 | 0.111 | 1025.85 | 27.84 | CopyNumber | 5q35.2 | 1260 |
| 484242 | 68.78 | 0.000 | 36.97 | 64.48 | 0.222 | 152.49 | 26.36 | | |
| 484288 | 72.10 | 0.000 | 44.27 | 51.35 | 0.222 | 205.62 | 31.99 | | |
| 484363 | 74.19 | 0.000 | 128.94 | 71.40 | 0.000 | 135.92 | 30.55 | | |
| 484551 | 83.81 | 0.071 | 35.00 | 75.65 | 0.111 | | | | |
| 484813 | 92.28 | 0.071 | 140.15 | 85.01 | 0.222 | 357.48 | 42.75 | | |
| 485155 | 104.91 | 0.000 | 1053.71 | 62.95 | 0.000 | 233.33 | 38.86 | | |
| 485195 | 72.46 | 0.036 | 32.33 | 115.62 | 0.222 | 98.61 | 44.74 | | |
| 485246 | 89.00 | 0.036 | 63.99 | 82.34 | 0.222 | 305.16 | 41.61 | | |
| 485262 | 65.94 | 0.000 | 121.08 | 68.51 | 0.111 | 1132.47 | 23.10 | | |
| 485365 | 89.21 | 0.036 | 50.62 | 83.69 | 0.222 | 24.30 | 39.23 | | |
| 485616 | 118.44 | 0.036 | 54.62 | 126.87 | 0.222 | 202.89 | 41.15 | | |
| 486542 | 66.70 | 0.036 | 40.95 | 55.22 | 0.111 | 532.52 | 25.97 | | |
| 487027 | 102.66 | 0.036 | 172.51 | 92.92 | 0.000 | 456.54 | 51.77 | | |
| 487054 | 83.58 | 0.000 | 196.99 | 81.02 | 0.111 | 96.63 | 33.00 | CopyNumber | 6q25.3 | 1460 |
| 487635 | 90.09 | 0.036 | 87.13 | 86.36 | 0.111 | 418.48 | 59.45 | | |
| 487774 | 69.59 | 0.000 | 441.11 | 76.24 | 0.000 | 858.14 | 28.90 | | |
| 488171 | 78.74 | 0.000 | 1889.50 | 43.31 | 0.000 | 205.88 | 23.98 | | |
| 488181 | 66.18 | 0.000 | 72.82 | 72.57 | 0.111 | 150.84 | 51.09 | | |
| 488307 | 118.69 | 0.000 | 40.98 | 83.43 | 0.222 | 116.63 | 31.66 | | |
| 488478 | 63.31 | 0.000 | 60.31 | 56.88 | 0.222 | 531.39 | 27.89 | CopyNumber | 7q11.21-7q11.22 | 1563 |
| 488671 | 63.52 | 0.000 | 66.99 | 86.38 | 0.222 | 146.22 | 35.88 | CopyNumber | 7q11.23-7q11.22 | 1569 |
| 489207 | 229.58 | 0.036 | 95.96 | 93.07 | 0.000 | 100.25 | 84.19 | CopyNumber | 7q21.3 | 1596 |
| 489284 | 174.12 | 0.000 | 270.09 | 108.06 | 0.111 | 502.47 | 67.41 | CopyNumber | 7q22.1 | 1597 |
| 489287 | 72.56 | 0.000 | 89.22 | 87.25 | 0.111 | 137.90 | 40.47 | CopyNumber | 7q22.1 | 1597 |
| 489336 | 73.40 | 0.036 | 29.14 | 50.97 | 0.222 | 434.70 | 40.35 | | |
| 489615 | 157.53 | 0.000 | 87.65 | 120.96 | 0.111 | 238.13 | 62.54 | | |
| 490203 | 94.98 | 0.000 | 149.77 | 111.35 | 0.222 | 71.14 | 35.48 | | |
| 490394 | 80.08 | 0.036 | 124.86 | 65.68 | 0.000 | 343.69 | 34.12 | | |
| 490415 | 84.59 | 0.000 | 165.38 | 70.44 | 0.111 | 321.85 | 40.17 | | |
| 490745 | 67.85 | 0.000 | 174.03 | 73.05 | 0.111 | 107.47 | 33.33 | | |
| 490795 | 84.72 | 0.036 | 61.57 | 91.56 | 0.222 | 366.95 | 44.62 | | |
| 490874 | 71.64 | 0.071 | 51.50 | 59.92 | 0.222 | 199.27 | 40.49 | CopyNumber | 1q22 | 160 |
| 491336 | 79.86 | 0.071 | 26.67 | 61.36 | 0.222 | 59.45 | 31.69 | | |
| 491359 | 117.62 | 0.000 | 444.58 | 141.63 | 0.000 | 144.60 | 37.95 | | |
| 491440 | 84.00 | 0.000 | 127.99 | 68.91 | 0.111 | 584.73 | 41.60 | | |
| 491494 | 76.88 | 0.000 | 179.06 | 70.15 | 0.111 | 578.57 | 38.69 | | |
| 491597 | 68.90 | 0.071 | 78.66 | 71.01 | 0.111 | 47.73 | 29.91 | | |
| 491695 | 61.10 | 0.036 | 47.66 | 66.95 | 0.111 | 115.13 | 36.13 | CopyNumber | 8q11.21 | 1744 |
| 491745 | 79.23 | 0.036 | 91.43 | 97.21 | 0.222 | 517.81 | 34.02 | CopyNumber | 8q11.23 | 1756 |
| 491988 | 80.07 | 0.036 | 148.34 | 53.25 | 0.000 | 761.27 | 37.05 | | |

TABLE 2-continued

A list of 2087 candidate endogenous reference genes

| | | | | | | | | | |
|---|---|---|---|---|---|---|---|---|---|
| 492236 | 58.47 | 0.071 | 53.23 | 50.26 | 0.111 | 378.81 | 31.38 | | |
| 492314 | 134.13 | 0.000 | 280.47 | 119.64 | 0.111 | 867.01 | 82.56 | | |
| 492445 | 79.94 | 0.071 | 34.07 | 68.47 | 0.222 | 235.18 | 33.32 | | |
| 492599 | 63.87 | 0.000 | 104.23 | 64.07 | 0.222 | 1025.28 | 42.75 | | |
| 492805 | 98.49 | 0.071 | 45.41 | 54.06 | 0.222 | 714.35 | 33.62 | | |
| 493362 | 78.53 | 0.036 | 36.00 | 66.40 | 0.111 | 1207.36 | 49.22 | | |
| 493750 | 62.06 | 0.036 | 19.06 | 55.52 | 0.222 | 369.95 | 32.38 | | |
| 494173 | 148.42 | 0.000 | 295.60 | 110.96 | 0.111 | 876.15 | 113.53 | | |
| 494419 | 79.67 | 0.000 | 84.24 | 54.97 | 0.222 | 1836.27 | 27.61 | | |
| 494457 | 75.88 | 0.000 | 131.41 | 71.03 | 0.111 | 140.35 | 49.81 | | |
| 494604 | 77.33 | 0.000 | 102.64 | 45.34 | 0.000 | 1093.70 | 32.75 | | |
| 494614 | 67.07 | 0.071 | 131.49 | 59.76 | 0.111 | 271.73 | 34.09 | | |
| 494691 | 100.32 | 0.000 | 1473.17 | 85.74 | 0.000 | 1356.61 | 41.82 | CopyNumber | 17p13.2 | 2984 |
| 494700 | 111.44 | 0.036 | 45.03 | 71.95 | 0.222 | 142.65 | 50.45 | CopyNumber | 9q31.1 | 1982 |
| 494985 | 58.47 | 0.000 | 23.54 | 51.61 | 0.111 | 69.32 | 28.36 | | |
| 495039 | 77.88 | 0.000 | 53.22 | 87.48 | 0.111 | 241.85 | 32.88 | | |
| 495349 | 51.38 | 0.000 | 73.03 | 68.57 | 0.000 | 128.78 | 41.86 | | |
| 495471 | 132.48 | 0.000 | 61.04 | 104.84 | 0.222 | 111.31 | 28.11 | CopyNumber | 9q34.3 | 2030 |
| 495605 | 103.21 | 0.000 | 259.83 | 98.52 | 0.000 | 1069.64 | 37.36 | CopyNumber | Xp22.33 | 3522 |
| 495851 | 103.41 | 0.036 | 155.32 | 96.68 | 0.000 | 133.50 | 48.69 | | |
| 495960 | 75.83 | 0.071 | 89.70 | 72.01 | 0.222 | 23.52 | 45.21 | | |
| 496068 | 80.35 | 0.036 | 68.03 | 85.57 | 0.222 | 133.18 | 34.99 | | |
| 496098 | 67.73 | 0.036 | 47.15 | 59.31 | 0.222 | 174.56 | 31.62 | | |
| 496271 | 89.89 | 0.071 | 67.91 | 73.61 | 0.222 | | | | |
| 496487 | 88.77 | 0.000 | 227.53 | 59.84 | 0.111 | 1039.79 | 27.70 | | |
| 496646 | 74.01 | 0.071 | 51.96 | 94.43 | 0.222 | 242.03 | 33.02 | | |
| 496684 | 91.16 | 0.000 | 90.84 | 89.82 | 0.111 | 116.47 | 51.77 | CopyNumber | Xq24 | 3603 |
| 497183 | 76.76 | 0.036 | 93.97 | 66.65 | 0.111 | 259.92 | 53.23 | | |
| 497599 | 111.15 | 0.036 | 134.22 | 94.08 | 0.111 | 192.73 | 115.77 | | |
| 497692 | 81.57 | 0.036 | 38.61 | 69.57 | 0.222 | 88.50 | 26.06 | CopyNumber | 1q32.3 | 223 |
| 497893 | 70.25 | 0.036 | 80.49 | 54.75 | 0.222 | 85.47 | 38.00 | CopyNumber | 1q42.12 | 234 |
| 498239 | 85.83 | 0.071 | 42.11 | 68.85 | 0.222 | 313.30 | 70.17 | | |
| 498313 | 73.37 | 0.071 | 61.83 | 57.22 | 0.222 | 166.23 | 33.54 | | |
| 498317 | 97.53 | 0.000 | 34.96 | 52.65 | 0.222 | 241.17 | 32.40 | | |
| 498455 | 60.99 | 0.071 | 41.69 | 52.75 | 0.222 | 159.22 | 29.80 | | |
| 498548 | 65.53 | 0.036 | 83.74 | 56.09 | 0.111 | 544.75 | 28.88 | | |
| 498727 | 212.50 | 0.000 | 375.51 | 152.25 | 0.111 | 393.92 | 82.64 | | |
| 499145 | 63.76 | 0.036 | 90.25 | 49.65 | 0.000 | 362.61 | 30.38 | CopyNumber | 10p12.1 | 2075 |
| 499158 | 77.10 | 0.036 | 36.41 | 89.25 | 0.111 | 487.66 | 24.83 | CopyNumber | 22q13.1 | 3496 |
| 499594 | 68.79 | 0.000 | 38.30 | 61.11 | 0.000 | 43.26 | 67.66 | CopyNumber | 10q11.23 | 2097 |
| 499833 | 65.54 | 0.036 | 31.78 | 67.31 | 0.111 | 65.25 | 48.78 | | |
| 499891 | 64.27 | 0.036 | 90.85 | 48.08 | 0.000 | 119.21 | 32.55 | | |
| 499925 | 99.08 | 0.071 | 47.23 | 93.94 | 0.111 | 425.42 | 26.54 | | |
| 499960 | 53.38 | 0.036 | 75.36 | 58.96 | 0.111 | 230.51 | 30.46 | | |
| 500067 | 91.39 | 0.000 | 42.67 | 83.69 | 0.222 | 85.13 | 38.67 | | |
| 500101 | 91.91 | 0.000 | 122.55 | 71.82 | 0.222 | 523.98 | 46.28 | | |
| 500375 | 72.57 | 0.000 | 42.54 | 60.50 | 0.111 | 173.31 | 57.99 | | |
| 500409 | 90.31 | 0.000 | 97.98 | 79.16 | 0.222 | 111.85 | 38.24 | CopyNumber | 10q23.2 | 2151 |
| 500546 | 80.29 | 0.071 | 32.37 | 73.60 | 0.222 | 114.50 | 26.14 | | |
| 500674 | 61.65 | 0.036 | 100.83 | 54.64 | 0.111 | 101.84 | 40.78 | | |
| 500775 | 56.77 | 0.000 | 154.32 | 52.88 | 0.111 | 358.69 | 18.38 | | |
| 500842 | 76.32 | 0.000 | 109.14 | 53.92 | 0.000 | 70.07 | 32.85 | | |
| 500874 | 92.56 | 0.000 | 190.37 | 116.30 | 0.000 | 302.13 | 30.53 | | |
| 501012 | 80.92 | 0.036 | 59.53 | 67.35 | 0.222 | 56.69 | 51.38 | | |
| 501023 | 76.62 | 0.036 | 34.17 | 71.76 | 0.222 | 359.89 | 46.05 | | |
| 501203 | 60.32 | 0.036. | 58.65 | 70.61 | 0.000 | 203.01 | 29.78 | | |
| 501293 | 159.72 | 0.000 | 331.94 | 61.09 | 0.111 | 257.95 | 64.96 | | |
| 501309 | 91.32 | 0.000 | 179.56 | 76.44 | 0.000 | 74.58 | 38.37 | CopyNumber | 19p13.3 | 3198 |
| 501353 | 76.11 | 0.000 | 85.50 | 67.94 | 0.111 | 165.38 | 38.49 | CopyNumber | 19p13.3 | 3199 |
| 501376 | 74.39 | 0.000 | 46.23 | 52.90 | 0.222 | 117.83 | 30.84 | CopyNumber | 10q26.2 | 2190 |
| 501420 | 72.23 | 0.071 | 51.43 | 76.62 | 0.222 | 8.49 | 69.55 | | |
| 501629 | 193.96 | 0.071 | 304.65 | 100.03 | 0.000 | 1073.10 | 56.96 | | |
| 501684 | 67.20 | 0.071 | 72.15 | 58.11 | 0.111 | 182.45 | 25.59 | CopyNumber | 11p15.4 | 2203 |
| 501735 | 80.80 | 0.036 | 48.77 | 90.13 | 0.222 | 66.88 | 36.29 | CopyNumber | 11p15.4 | 2205 |
| 501853 | 66.72 | 0.036 | 45.46 | 83.18 | 0.111 | 258.40 | 27.75 | CopyNumber | 11p15.4 | 2212 |
| 501924 | 70.20 | 0.036 | 22.66 | 58.29 | 0.111 | | | CopyNumber | 11p15.3 | 2216 |
| 501991 | 74.39 | 0.071 | 51.32 | 69.18 | 0.222 | 239.62 | 40.48 | | |
| 502302 | 104.67 | 0.036 | 65.09 | 114.45 | 0.111 | 58.12 | 61.81 | | |
| 502328 | 105.65 | 0.036 | 192.87 | 102.65 | 0.000 | 277.01 | 57.86 | CopyNumber | 11p13 | 2243 |
| 502461 | 88.29 | 0.000 | 63.08 | 66.07 | 0.222 | 92.47 | 41.06 | | |
| 502528 | 68.66 | 0.000 | 135.26 | 95.87 | 0.111 | 414.87 | 34.37 | CopyNumber | 11p11.2 | 2254 |
| 502630 | 86.54 | 0.000 | 188.95 | 62.55 | 0.111 | 974.26 | 31.28 | | |
| 502659 | 83.71 | 0.000 | 137.92 | 78.61 | 0.000 | 418.65 | 40.34 | CopyNumber | 1p13.2-1p13.1 | 141 |
| 502705 | 75.99 | 0.000 | 63.68 | 62.88 | 0.222 | 200.89 | 34.78 | | |
| 502745 | 116.28 | 0.000 | 165.50 | 152.75 | 0.111 | 33.94 | 90.81 | | |
| 502769 | 70.29 | 0.000 | 127.45 | 65.13 | 0.000 | 146.88 | 43.18 | CopyNumber | 11q12.3 | 2269 |
| 502773 | 85.33 | 0.000 | 36.02 | 52.79 | 0.222 | 382.36 | 89.13 | | |

TABLE 2-continued

A list of 2087 candidate endogenous reference genes

| | | | | | | | | | |
|---|---|---|---|---|---|---|---|---|---|
| 502823 | 89.25 | 0.000 | 97.58 | 72.37 | 0.000 | 1483.75 | 48.37 | | |
| 502829 | 49.99 | 0.000 | 140.90 | 56.82 | 0.000 | 377.34 | 29.68 | CopyNumber | 11q13.1 | 2274 |
| 502836 | 80.42 | 0.000 | 108.10 | 81.32 | 0.222 | 186.99 | 39.86 | | |
| 502842 | 98.83 | 0.071 | 91.38 | 63.44 | 0.111 | 262.91 | 27.81 | | |
| 502872 | 160.73 | 0.000 | 168.69 | 130.10 | 0.111 | 162.72 | 27.57 | | |
| 502876 | 121.94 | 0.036 | 240.25 | 126.64 | 0.111 | 1110.19 | 63.79 | | |
| 503093 | 105.81 | 0.000 | 272.03 | 101.56 | 0.000 | 1003.83 | 41.56 | | |
| 503222 | 70.44 | 0.000 | 78.57 | 60.15 | 0.111 | 436.02 | 32.33 | | |
| 503251 | 75.49 | 0.036 | 52.37 | 80.76 | 0.000 | 269.32 | 30.88 | CopyNumber | 11q13.4 | 2286 |
| 503597 | 72.02 | 0.036 | 44.54 | 65.19 | 0.222 | 993.22 | 28.63 | | |
| 503709 | 80.48 | 0.036 | 56.09 | 56.61 | 0.000 | 359.18 | 41.09 | | |
| 503716 | 74.54 | 0.036 | 67.10 | 57.41 | 0.111 | 401.83 | 39.72 | CopyNumber | 11q22.3 | 2327 |
| 503787 | 62.10 | 0.036 | 88.32 | 64.96 | 0.222 | 94.48 | 36.57 | | |
| 504237 | 84.57 | 0.071 | 67.58 | 73.38 | 0.111 | 96.18 | 41.40 | | |
| 504517 | 74.64 | 0.000 | 2607.18 | 71.46 | 0.000 | | | | |
| 504613 | 89.25 | 0.000 | 223.84 | 85.33 | 0.111 | 62.36 | 60.07 | | |
| 504620 | 86.81 | 0.000 | 160.25 | 104.00 | 0.111 | 1302.64 | 32.11 | | |
| 504687 | 187.11 | 0.000 | 417.49 | 95.88 | 0.222 | 784.44 | 114.26 | | |
| 504828 | 60.20 | 0.036 | 35.05 | 61.58 | 0.222 | 272.03 | 32.15 | | |
| 504895 | 88.83 | 0.000 | 185.08 | 83.41 | 0.000 | 509.46 | 28.54 | | |
| 505033 | 85.57 | 0.071 | 37.32 | 52.34 | 0.000 | 231.87 | 47.13 | | |
| 505059 | 69.53 | 0.000 | 146.67 | 85.08 | 0.000 | 401.54 | 42.58 | | |
| 505625 | 85.89 | 0.036 | 105.74 | 98.40 | 0.111 | 141.17 | 35.31 | | |
| 505652 | 54.99 | 0.000 | 128.09 | 56.80 | 0.000 | 337.62 | 27.67 | | |
| 505676 | 67.86 | 0.036 | 90.76 | 76.70 | 0.222 | 152.86 | 29.88 | | |
| 505705 | 81.22 | 0.000 | 811.93 | 36.92 | 0.000 | 2225.97 | 26.97 | CopyNumber | 12q13.2 | 2429 |
| 505806 | 90.69 | 0.036 | 62.89 | 118.65 | 0.222 | 193.34 | 42.44 | | |
| 505824 | 125.62 | 0.071 | 46.25 | 72.86 | 0.111 | 171.87 | 30.26 | CopyNumber | 22q13.31 | 3505 |
| 506215 | 79.99 | 0.000 | 94.43 | 66.41 | 0.000 | 157.71 | 28.13 | | |
| 506325 | 83.72 | 0.071 | 84.67 | 58.55 | 0.111 | 347.25 | 61.58 | | |
| 506759 | 118.14 | 0.036 | 94.62 | 70.61 | 0.111 | 37.81 | 36.31 | | |
| 506861 | 78.06 | 0.000 | 95.81 | 90.86 | 0.000 | 79.06 | 33.92 | | |
| 507074 | 74.70 | 0.000 | 83.96 | 62.86 | 0.222 | 432.06 | 61.29 | | |
| 507162 | 98.40 | 0.000 | 29.80 | 68.25 | 0.111 | 92.08 | 59.64 | | |
| 507584 | 68.17 | 0.000 | 150.24 | 63.80 | 0.000 | 369.22 | 38.69 | | |
| 507680 | 54.78 | 0.036 | 49.68 | 77.53 | 0.222 | 203.53 | 42.58 | | |
| 507910 | 69.11 | 0.000 | 69.36 | 64.58 | 0.111 | 88.32 | 41.59 | | |
| 507916 | 97.27 | 0.036 | 192.99 | 102.63 | 0.000 | 52.82 | 43.91 | | |
| 508010 | 93.45 | 0.036 | 32.99 | 90.85 | 0.222 | 166.37 | 35.28 | | |
| 508644 | 68.43 | 0.036 | 49.21 | 55.85 | 0.222 | 110.99 | 40.54 | | |
| 509163 | 93.24 | 0.036 | 35.34 | 54.15 | 0.222 | 375.23 | 41.32 | | |
| 509226 | 88.83 | 0.000 | 236.57 | 70.64 | 0.000 | 179.58 | 33.62 | | |
| 509264 | 71.38 | 0.000 | 82.07 | 77.38 | 0.000 | 427.67 | 35.66 | | |
| 509414 | 89.01 | 0.036 | 72.77 | 69.54 | 0.000 | 512.55 | 27.88 | | |
| 509622 | 105.94 | 0.036 | 112.54 | 148.47 | 0.000 | 237.96 | 45.40 | | |
| 509736 | 72.67 | 0.000 | 720.87 | 60.73 | 0.111 | 4674.01 | 38.38 | | |
| 509791 | 66.04 | 0.036 | 289.40 | 66.68 | 0.000 | 2482.97 | 38.50 | | |
| 509909 | 66.97 | 0.036 | 31.58 | 63.60 | 0.222 | 102.28 | 29.40 | | |
| 510087 | 96.58 | 0.036 | 144.88 | 56.65 | 0.000 | | | | |
| 510328 | 60.49 | 0.000 | 87.51 | 60.32 | 0.111 | 344.12 | 27.98 | | |
| 510402 | 70.87 | 0.071 | 74.30 | 67.71 | 0.222 | 332.17 | 39.17 | | |
| 511067 | 63.37 | 0.071 | 30.52 | 92.27 | 0.222 | 178.77 | 26.75 | | |
| 511138 | 72.01 | 0.071 | 51.32 | 77.97 | 0.111 | 386.10 | 50.09 | CopyNumber | 15q15.1 | 2768 |
| 511149 | 73.09 | 0.071 | 47.43 | 61.92 | 0.222 | 219.59 | 40.88 | | |
| 511425 | 66.07 | 0.000 | 306.59 | 64.17 | 0.000 | 766.85 | 32.72 | | |
| 511504 | 156.60 | 0.036 | 118.98 | 198.75 | 0.222 | 93.53 | 41.90 | | |
| 511862 | 113.15 | 0.036 | 78.27 | 91.67 | 0.111 | | | | |
| 511952 | 83.56 | 0.036 | 45.39 | 80.23 | 0.222 | 280.77 | 42.92 | | |
| 512005 | 86.15 | 0.000 | 177.05 | 97.71 | 0.000 | | | | |
| 512465 | 60.22 | 0.000 | 101.69 | 51.11 | 0.000 | 1328.32 | 37.34 | | |
| 512525 | 140.21 | 0.000 | 564.24 | 59.56 | 0.111 | | | CopyNumber | 15q25.2 | 2822 |
| 512607 | 74.76 | 0.000 | 66.75 | 86.55 | 0.111 | 188.34 | 40.78 | | |
| 512640 | 95.97 | 0.036 | 87.26 | 49.87 | 0.000 | 353.07 | 25.39 | | |
| 512661 | 114.56 | 0.036 | 78.95 | 73.16 | 0.111 | 225.56 | 27.09 | | |
| 512676 | 89.69 | 0.036 | 472.46 | 56.90 | 0.000 | 3826.23 | 33.98 | | |
| 512693 | 65.72 | 0.071 | 32.21 | 61.74 | 0.222 | 243.81 | 32.66 | CopyNumber | 14q11.2 | 2641 |
| 512756 | 68.12 | 0.071 | 36.00 | 87.05 | 0.222 | 82.76 | 24.22 | CopyNumber | 22q11.21 | 3469 |
| 512815 | 57.32 | 0.000 | 72.82 | 58.05 | 0.222 | 349.78 | 23.00 | CopyNumber | 19p13.3 | 3199 |
| 512857 | 98.39 | 0.000 | 389.64 | 108.93 | 0.000 | 236.30 | 44.67 | CopyNumber | 11p15.5 | 2200 |
| 512867 | 145.32 | 0.000 | 57.53 | 59.42 | 0.111 | 756.60 | 42.54 | | |
| 512908 | 81.46 | 0.000 | 139.12 | 83.26 | 0.000 | 529.32 | 26.51 | | |
| 513043 | 79.47 | 0.036 | 65.23 | 53.50 | 0.222 | 200.34 | 26.92 | | |
| 513055 | 71.45 | 0.000 | 46.53 | 69.38 | 0.111 | 428.66 | 34.03 | | |
| 513057 | 72.89 | 0.000 | 108.87 | 84.74 | 0.000 | 172.47 | 40.79 | | |
| 513058 | 89.89 | 0.000 | 89.17 | 120.69 | 0.111 | 251.55 | 55.04 | | |
| 513071 | 80.98 | 0.036 | 61.02 | 85.52 | 0.111 | 416.01 | 37.15 | | |
| 513083 | 90.78 | 0.000 | 747.03 | 87.03 | 0.000 | 13273.59 | 32.07 | | |
| 513141 | 104.92 | 0.000 | 106.35 | 102.92 | 0.222 | 68.76 | 57.99 | CopyNumber | 15q26.1 | 2836 |

TABLE 2-continued

A list of 2087 candidate endogenous reference genes

| | | | | | | | | | |
|---|---|---|---|---|---|---|---|---|---|
| 513145 | 72.65 | 0.000 | 82.48 | 62.05 | 0.111 | 690.46 | 36.42 | CopyNumber | 15q26.1 | 2836 |
| 513153 | 127.64 | 0.036 | 57.82 | 56.98 | 0.000 | 112.68 | 79.81 | | | |
| 513230 | 68.82 | 0.036 | 88.04 | 62.79 | 0.111 | 102.18 | 30.45 | CopyNumber | 16p13.3 | 2866 |
| 513242 | 76.58 | 0.036 | 70.14 | 78.60 | 0.000 | 134.47 | 29.60 | CopyNumber | 16p13.3 | 2866 |
| 513261 | 83.40 | 0.036 | 100.06 | 63.05 | 0.000 | 66.99 | 49.34 | CopyNumber | 16p13.3 | 2866 |
| 513266 | 88.47 | 0.000 | 43.44 | 51.74 | 0.222 | 420.41 | 37.37 | CopyNumber | 16p13.3 | 2866 |
| 513470 | 74.31 | 0.071 | 23.98 | 100.87 | 0.222 | 126.44 | 34.12 | CopyNumber | 16p11.2 | 2900 |
| 513488 | 126.33 | 0.071 | 80.83 | 109.04 | 0.111 | 135.41 | 35.18 | | | |
| 513490 | 141.10 | 0.000 | 600.22 | 108.89 | 0.000 | 1936.06 | 50.21 | CopyNumber | 16p11.2 | 2903 |
| 513520 | 74.53 | 0.036 | 51.84 | 63.38 | 0.222 | 107.26 | 38.88 | | | |
| 513522 | 86.72 | 0.000 | 262.60 | 56.68 | 0.000 | 109.64 | 38.78 | | | |
| 513631 | 66.09 | 0.036 | 43.26 | 73.49 | 0.222 | 231.71 | 24.36 | | | |
| 513856 | 69.11 | 0.000 | 58.26 | 78.43 | 0.111 | 50.56 | 33.92 | | | |
| 513984 | 103.20 | 0.036 | 56.92 | 80.13 | 0.111 | 110.00 | 28.54 | Inversion | 17p11.2 | 2999 |
| 514012 | 104.20 | 0.000 | 68.14 | 88.15 | 0.222 | 111.02 | 33.44 | | | |
| 514036 | 78.04 | 0.071 | 40.32 | 72.95 | 0.111 | 150.39 | 21.29 | | | |
| 514038 | 71.06 | 0.071 | 98.33 | 73.54 | 0.222 | 282.81 | 33.39 | | | |
| 514174 | 127.42 | 0.036 | 218.64 | 117.36 | 0.111 | 423.86 | 101.58 | | | |
| 514196 | 72.49 | 0.000 | 707.66 | 61.15 | 0.000 | 8554.76 | 27.60 | CopyNumber | 17q21.31 | 3024 |
| 514211 | 139.51 | 0.036 | 50.70 | 81.92 | 0.222 | 182.87 | 97.71 | | | |
| 514216 | 73.83 | 0.000 | 115.83 | 85.67 | 0.111 | 792.84 | 46.18 | | | |
| 514220 | 104.37 | 0.000 | 175.85 | 118.04 | 0.222 | 722.34 | 44.39 | | | |
| 514297 | 72.66 | 0.036 | 77.55 | 75.65 | 0.222 | 353.72 | 26.50 | CopyNumber | 17q21.32 | 3034 |
| 514303 | 86.25 | 0.000 | 174.64 | 95.39 | 0.222 | 134.97 | 51.53 | CopyNumber | 17q21.33 | 3035 |
| 514435 | 68.14 | 0.036 | 40.72 | 84.74 | 0.222 | 147.89 | 37.81 | CopyNumber | 16q22.1 | 2937 |
| 514489 | 80.99 | 0.071 | 44.98 | 74.04 | 0.000 | 217.12 | 36.85 | | | |
| 514535 | 115.82 | 0.036 | 81.79 | 89.33 | 0.222 | 806.22 | 54.38 | | | |
| 514581 | 87.86 | 0.000 | 2385.84 | 64.09 | 0.000 | 12015.94 | 27.98 | CopyNumber | 17q25.3 | 3086 |
| 514590 | 79.57 | 0.000 | 82.16 | 60.88 | 0.111 | 270.30 | 30.55 | | | |
| 514819 | 63.43 | 0.000 | 91.91 | 57.33 | 0.111 | 146.77 | 39.49 | CopyNumber | 17q12 | 3015 |
| 514870 | 75.67 | 0.036 | 116.52 | 66.41 | 0.111 | 1076.27 | 31.74 | | | |
| 514920 | 70.87 | 0.036 | 42.93 | 92.05 | 0.222 | 305.87 | 26.30 | CopyNumber | 17q21.32 | 3034 |
| 514934 | 64.83 | 0.000 | 93.36 | 57.74 | 0.222 | 489.19 | 36.29 | CopyNumber | 1p13.2-1p13.1 | 141 |
| 515003 | 90.52 | 0.000 | 73.12 | 71.02 | 0.111 | 244.41 | 34.43 | CopyNumber | 19p13.3 | 3198 |
| 515005 | 84.23 | 0.036 | 84.14 | 115.67 | 0.111 | 111.71 | 28.21 | CopyNumber | 19p13.3 | 3198 |
| 515018 | 81.16 | 0.036 | 38.38 | 92.19 | 0.222 | 975.69 | 36.28 | CopyNumber | 17q24.1 | 3057 |
| 515053 | 79.56 | 0.036 | 327.53 | 82.45 | 0.000 | 130.71 | 37.38 | CopyNumber | 19p13.3 | 3201 |
| 515070 | 61.50 | 0.000 | 1309.96 | 51.55 | 0.000 | 2287.41 | 36.04 | | | |
| 515092 | 92.89 | 0.071 | 63.55 | 123.14 | 0.222 | 142.44 | 34.66 | | | |
| 515155 | 77.95 | 0.000 | 107.39 | 48.32 | 0.222 | 1314.81 | 29.66 | | | |
| 515162 | 99.70 | 0.000 | 174.56 | 65.50 | 0.111 | 738.50 | 33.21 | CopyNumber | 19p13.13 | 3220 |
| 515164 | 83.59 | 0.000 | 81.45 | 86.75 | 0.222 | 111.33 | 38.03 | | | |
| 515210 | 159.79 | 0.000 | 500.13 | 127.33 | 0.111 | 405.99 | 51.27 | | | |
| 515255 | 77.20 | 0.000 | 150.61 | 99.16 | 0.000 | 275.62 | 55.00 | | | |
| 515266 | 74.02 | 0.036 | 54.18 | 59.54 | 0.222 | 129.69 | 29.52 | | | |
| 515271 | 69.78 | 0.071 | 36.74 | 77.34 | 0.111 | 130.40 | 32.76 | | | |
| 515329 | 66.72 | 0.000 | 534.24 | 65.17 | 0.000 | 3426.69 | 32.80 | CopyNumber | 1p36.31 | 17 |
| 515371 | 70.79 | 0.000 | 343.10 | 48.33 | 0.111 | 1005.23 | 29.71 | | | |
| 515406 | 149.32 | 0.000 | 65.79 | 61.04 | 0.222 | 287.02 | 37.67 | CopyNumber | 19q13.2 | 3259 |
| 515417 | 66.12 | 0.000 | 107.98 | 54.42 | 0.000 | 153.02 | 44.34 | CopyNumber | 19q13.2 | 3260 |
| 515432 | 97.88 | 0.036 | 44.58 | 59.07 | 0.111 | 404.46 | 33.77 | | | |
| 515472 | 85.54 | 0.000 | 277.80 | 71.92 | 0.000 | 1110.26 | 42.17 | | | |
| 515475 | 68.85 | 0.071 | 36.35 | 61.24 | 0.222 | 28.67 | 48.11 | | | |
| 515487 | 274.74 | 0.000 | 142.33 | 104.31 | 0.111 | 173.36 | 32.28 | | | |
| 515494 | 119.52 | 0.071 | 146.78 | 92.71 | 0.111 | 112.41 | 47.69 | CopyNumber | 19q13.32 | 3268 |
| 515500 | 76.81 | 0.000 | 102.79 | 91.08 | 0.222 | | | | | |
| 515515 | 49.82 | 0.000 | 182.19 | 48.37 | 0.000 | 152.89 | 38.45 | CopyNumber | 19q13.32 | 3273 |
| 515517 | 88.12 | 0.000 | 299.84 | 58.12 | 0.000 | 7157.08 | 36.30 | | | |
| 515524 | 71.77 | 0.000 | 80.95 | 66.53 | 0.111 | 391.51 | 35.24 | CopyNumber | 19q13.33 | 3275 |
| 515540 | 75.18 | 0.000 | 189.06 | 82.37 | 0.111 | 165.22 | 50.26 | CopyNumber | 19q13.33 | 3278 |
| 515550 | 69.11 | 0.000 | 172.43 | 76.53 | 0.111 | 561.99 | 34.69 | | | |
| 515598 | 74.86 | 0.071 | 38.40 | 66.79 | 0.111 | 138.35 | 27.47 | | | |
| 515607 | 65.02 | 0.036 | 55.58 | 56.62 | 0.111 | 158.32 | 52.15 | CopyNumber | 19q13.42 | 3288 |
| 515642 | 65.18 | 0.000 | 99.65 | 61.65 | 0.000 | 197.53 | 45.80 | | | |
| 515785 | 105.76 | 0.036 | 219.93 | 101.68 | 0.000 | 214.35 | 62.17 | | | |
| 515846 | 76.72 | 0.036 | 69.80 | 136.41 | 0.222 | 151.33 | 51.40 | CopyNumber | 19q13.33 | 3276 |
| 515848 | 79.47 | 0.000 | 50.31 | 62.08 | 0.111 | 672.95 | 55.07 | | | |
| 515890 | 80.81 | 0.036 | 100.90 | 82.45 | 0.111 | 935.79 | 30.21 | CopyNumber | 2p23.2-2p23.1 | 300 |
| 516075 | 80.99 | 0.036 | 54.66 | 76.57 | 0.222 | 157.18 | 35.84 | | | |
| 516077 | 82.82 | 0.071 | 56.97 | 75.78 | 0.000 | 146.37 | 36.19 | | | |
| 516087 | 72.96 | 0.071 | 33.52 | 80.94 | 0.222 | 302.28 | 19.82 | | | |
| 516111 | 89.42 | 0.000 | 51.66 | 89.35 | 0.222 | 183.74 | 28.09 | CopyNumber | 2p13.1 | 356 |
| 516114 | 76.16 | 0.071 | 48.69 | 52.22 | 0.111 | 215.69 | 73.89 | CopyNumber | 2p13.1 | 356 |
| 516157 | 71.75 | 0.000 | 187.71 | 78.16 | 0.000 | 146.38 | 36.40 | | | |
| 516450 | 82.86 | 0.000 | 54.05 | 65.03 | 0.222 | 129.56 | 29.36 | CopyNumber | 2q14.3-2q21.1 | 410 |

TABLE 2-continued

A list of 2087 candidate endogenous reference genes

| | | | | | | | | | |
|---|---|---|---|---|---|---|---|---|---|
| 516522 | 78.65 | 0.000 | 43.56 | 73.85 | 0.222 | 158.20 | 39.84 | | |
| 516539 | 64.18 | 0.000 | 157.83 | 64.03 | 0.111 | 335.66 | 28.98 | | |
| 516587 | 75.09 | 0.036 | 89.91 | 71.91 | 0.111 | 266.02 | 25.33 | | |
| 516633 | 70.34 | 0.036 | 119.71 | 62.46 | 0.111 | 38.49 | 36.65 | CopyNumber | 2q32.1 | 456 |
| 516711 | 87.42 | 0.000 | 50.69 | 95.23 | 0.222 | 148.16 | 36.16 | | |
| 516790 | 76.19 | 0.071 | 46.62 | 74.67 | 0.222 | 107.23 | 36.95 | | |
| 516807 | 71.31 | 0.000 | 60.83 | 83.48 | 0.222 | 86.90 | 29.56 | CopyNumber | 2q37.3 | 516 |
| 516826 | 108.19 | 0.071 | 35.66 | 84.03 | 0.111 | 151.54 | 92.04 | | |
| 516855 | 76.73 | 0.000 | 81.22 | 90.29 | 0.111 | 67.23 | 34.92 | | |
| 517080 | 76.28 | 0.071 | 23.53 | 51.42 | 0.222 | 79.83 | 30.97 | | |
| 517106 | 158.42 | 0.036 | 155.61 | 98.37 | 0.222 | 1027.69 | 57.60 | | |
| 517134 | 72.40 | 0.000 | 77.76 | 62.28 | 0.111 | 210.01 | 25.80 | | |
| 517145 | 114.98 | 0.036 | 448.32 | 88.56 | 0.000 | 135.06 | 29.88 | | |
| 517168 | 83.39 | 0.000 | 616.48 | 87.90 | 0.000 | 607.75 | 49.57 | | |
| 517216 | 119.03 | 0.000 | 135.47 | 130.41 | 0.222 | 76.10 | 46.15 | | |
| 517232 | 73.76 | 0.071 | 32.93 | 49.49 | 0.111 | 125.67 | 43.67 | | |
| 517240 | 62.59 | 0.036 | 68.91 | 63.03 | 0.111 | 546.02 | 33.01 | | |
| 517262 | 56.95 | 0.036 | 106.71 | 47.20 | 0.000 | 453.65 | 25.51 | | |
| 517293 | 86.33 | 0.000 | 196.11 | 66.38 | 0.111 | 1344.41 | 51.31 | | |
| 517338 | 80.24 | 0.000 | 77.61 | 75.20 | 0.111 | 340.46 | 41.14 | | |
| 517342 | 163.80 | 0.071 | 33.97 | 52.74 | 0.222 | 152.42 | 25.59 | | |
| 517356 | 140.28 | 0.000 | 114.91 | 84.11 | 0.222 | 170.23 | 74.30 | | |
| 517357 | 55.86 | 0.000 | 28.35 | 52.86 | 0.111 | 107.26 | 33.50 | CopyNumber | 22q11.21 | 3463 |
| 517421 | 80.19 | 0.000 | 44.23 | 77.66 | 0.222 | 119.57 | 29.20 | CopyNumber | 22q11.21 | 3467 |
| 517438 | 78.06 | 0.036 | 26.64 | 70.20 | 0.222 | 67.48 | 48.02 | | |
| 517517 | 71.96 | 0.036 | 47.98 | 48.58 | 0.222 | 59.52 | 37.67 | | |
| 517543 | 68.12 | 0.036 | 74.51 | 88.10 | 0.111 | 83.91 | 46.35 | | |
| 517582 | 97.38 | 0.071 | 65.71 | 77.50 | 0.222 | 104.81 | 77.46 | | |
| 517622 | 74.85 | 0.000 | 74.01 | 87.22 | 0.222 | 166.60 | 36.65 | | |
| 517641 | 62.07 | 0.036 | 22.98 | 61.04 | 0.222 | 296.00 | 30.89 | | |
| 517666 | 82.83 | 0.036 | 80.25 | 64.44 | 0.222 | 667.96 | 39.27 | CopyNumber | 22q13.2 | 3504 |
| 517731 | 91.26 | 0.000 | 65.22 | 73.35 | 0.000 | 220.84 | 43.41 | | |
| 517768 | 117.43 | 0.036 | 25.76 | 80.17 | 0.222 | 508.84 | 63.13 | | |
| 517792 | 64.90 | 0.000 | 96.83 | 54.04 | 0.000 | 859.89 | 24.77 | | |
| 517817 | 69.75 | 0.071 | 33.30 | 51.38 | 0.111 | 305.79 | 29.77 | | |
| 517827 | 70.35 | 0.000 | 131.04 | 69.12 | 0.000 | 671.35 | 29.32 | | |
| 517888 | 77.52 | 0.036 | 95.09 | 58.38 | 0.222 | 103.41 | 36.07 | | |
| 517948 | 68.83 | 0.036 | 63.83 | 84.82 | 0.222 | 141.09 | 23.16 | CopyNumber | 3p21.31 | 580 |
| 517949 | 71.07 | 0.036 | 123.55 | 64.91 | 0.222 | 203.81 | 34.54 | | |
| 517969 | 81.54 | 0.036 | 84.63 | 88.21 | 0.222 | 142.60 | 39.43 | | |
| 517981 | 78.80 | 0.000 | 22.98 | 50.79 | 0.222 | 103.97 | 29.66 | CopyNumber | 3p21.31 | 586 |
| 518060 | 65.51 | 0.036 | 134.03 | 74.66 | 0.000 | 392.29 | 40.39 | | |
| 518123 | 62.29 | 0.036 | 95.99 | 66.38 | 0.111 | 474.82 | 27.22 | | |
| 518236 | 84.23 | 0.036 | 80.10 | 61.00 | 0.000 | 319.95 | 36.04 | | |
| 518244 | 55.08 | 0.000 | 111.32 | 61.11 | 0.000 | 314.23 | 33.48 | CopyNumber | 3q21.3 | 668 |
| 518249 | 60.78 | 0.000 | 175.57 | 66.17 | 0.111 | 786.47 | 28.84 | | |
| 518250 | 62.86 | 0.036 | 67.52 | 62.70 | 0.111 | 145.96 | 34.99 | | |
| 518265 | 54.39 | 0.000 | 141.98 | 43.28 | 0.000 | 341.22 | 32.71 | | |
| 518326 | 63.93 | 0.036 | 210.14 | 56.18 | 0.000 | 903.16 | 40.84 | | |
| 518346 | 76.42 | 0.000 | 96.28 | 40.13 | 0.111 | 1384.11 | 39.61 | CopyNumber | 3q25.31 | 703 |
| 518374 | 194.16 | 0.000 | 83.91 | 105.38 | 0.111 | 228.30 | 73.20 | CopyNumber | 1q25.2-1q25.3 | 186 |
| 518424 | 65.39 | 0.000 | 65.91 | 71.07 | 0.111 | 472.78 | 36.48 | | |
| 518460 | 86.56 | 0.000 | 144.56 | 61.00 | 0.111 | 474.56 | 36.78 | CopyNumber | 3q27.1 | 733 |
| 518464 | 78.82 | 0.000 | 131.96 | 60.97 | 0.222 | 341.49 | 43.16 | CopyNumber | 3q27.1 | 733 |
| 518525 | 108.66 | 0.000 | 559.19 | 97.79 | 0.000 | 1176.03 | 58.17 | | |
| 518551 | 87.47 | 0.000 | 989.61 | 83.61 | 0.000 | | | | |
| 518608 | 66.98 | 0.036 | 53.34 | 50.94 | 0.222 | 233.50 | 33.35 | | |
| 518609 | 135.38 | 0.000 | 166.56 | 130.43 | 0.111 | 588.35 | 32.89 | | |
| 518750 | 94.60 | 0.000 | 288.21 | 79.65 | 0.000 | 1360.79 | 25.92 | | |
| 518805 | 142.88 | 0.000 | 1068.25 | 127.25 | 0.000 | 249.62 | 81.08 | | |
| 518827 | 57.74 | 0.000 | 355.52 | 56.22 | 0.111 | 84.24 | 38.17 | | |
| 519276 | 93.94 | 0.000 | 113.47 | 81.01 | 0.000 | 230.33 | 36.58 | CopyNumber | 1q32.1 | 213 |
| 519304 | 60.54 | 0.036 | 36.33 | 87.42 | 0.222 | 114.84 | 33.78 | | |
| 519336 | 66.53 | 0.071 | 34.53 | 74.90 | 0.222 | 314.36 | 37.07 | CopyNumber | 5q12.3 | 1140 |
| 519347 | 68.95 | 0.071 | 34.71 | 73.49 | 0.222 | 207.52 | 27.55 | | |
| 519520 | 70.03 | 0.000 | 741.35 | 73.96 | 0.000 | | | | |
| 519523 | 81.66 | 0.000 | 55.73 | 84.24 | 0.222 | 3.52 | 261.11 | | |
| 519557 | 79.60 | 0.000 | 93.24 | 91.88 | 0.111 | 2662.06 | 27.88 | | |
| 519718 | 67.90 | 0.036 | 45.99 | 67.49 | 0.000 | 115.89 | 35.44 | | |
| 519756 | 92.45 | 0.071 | 40.69 | 113.09 | 0.222 | 132.53 | 29.71 | CopyNumber | 5q35.1 | 1258 |
| 519818 | 97.23 | 0.000 | 59.90 | 67.91 | 0.111 | 188.05 | 33.00 | CopyNumber | 5q35.3 | 1273 |
| 519909 | 101.05 | 0.000 | 244.91 | 76.44 | 0.222 | 117.68 | 50.36 | | |
| 519930 | 69.33 | 0.036 | 121.92 | 56.23 | 0.111 | 110.92 | 29.41 | | |
| 520026 | 87.98 | 0.000 | 108.58 | 87.98 | 0.222 | 62.19 | 41.41 | | |
| 520028 | 222.76 | 0.000 | 1404.48 | 164.02 | 0.000 | 1040.72 | 63.83 | | |
| 520037 | 63.50 | 0.071 | 45.72 | 74.52 | 0.222 | 158.73 | 56.07 | | |
| 520070 | 64.71 | 0.000 | 185.65 | 53.29 | 0.111 | 672.92 | 34.49 | | |

TABLE 2-continued

A list of 2087 candidate endogenous reference genes

| | | | | | | | | | |
|---|---|---|---|---|---|---|---|---|---|
| 520140 | 84.60 | 0.036 | 75.11 | 85.11 | 0.111 | 74.72 | 42.98 | | |
| 520189 | 97.80 | 0.036 | 77.42 | 57.29 | 0.222 | 38.86 | 41.39 | | |
| 520205 | 70.26 | 0.000 | 81.96 | 68.26 | 0.222 | 596.12 | 27.17 | | |
| 520210 | 74.37 | 0.000 | 122.94 | 70.34 | 0.222 | 538.81 | 39.96 | | |
| 520287 | 65.65 | 0.071 | 131.99 | 67.30 | 0.111 | 252.76 | 37.55 | | |
| 520313 | 83.70 | 0.036 | 103.31 | 73.66 | 0.000 | 842.14 | 32.44 | | |
| 520383 | 69.15 | 0.036 | 54.79 | 74.80 | 0.222 | 51.28 | 37.61 | | |
| 520421 | 121.20 | 0.071 | 155.06 | 87.58 | 0.111 | 2195.13 | 80.88 | | |
| 520459 | 84.53 | 0.000 | 159.85 | 66.78 | 0.111 | 399.69 | 40.23 | InversionBreakpoint CopyNumber | 7q11.23 | 1572 |
| 520623 | 81.68 | 0.036 | 27.31 | 61.61 | 0.222 | 248.55 | 33.13 | | |
| 520640 | 91.02 | 0.000 | 1961.29 | 60.59 | 0.111 | 5036.63 | 31.42 | CopyNumber | 7p22.1 | 1487 |
| 520740 | 85.41 | 0.000 | 97.72 | 112.58 | 0.111 | 187.18 | 70.60 | | |
| 520794 | 70.80 | 0.036 | 49.78 | 44.95 | 0.111 | 40.24 | 56.59 | CopyNumber | 7p13 | 1537 |
| 520898 | 110.99 | 0.000 | 400.82 | 102.01 | 0.000 | 21.23 | 57.80 | | |
| 520943 | 59.21 | 0.000 | 305.60 | 62.29 | 0.000 | 662.42 | 26.48 | | |
| 520967 | 70.34 | 0.000 | 252.42 | 65.79 | 0.000 | 120.89 | 29.85 | CopyNumber | 7q11.23 | 1572 |
| 520973 | 130.49 | 0.000 | 298.97 | 145.41 | 0.111 | 1152.33 | 82.08 | CopyNumber | 7q11.23 | 1572 |
| 520974 | 80.79 | 0.036 | 179.20 | 74.93 | 0.111 | 1930.00 | 33.13 | CopyNumber | 7q11.23 | 1572 |
| 521064 | 70.08 | 0.071 | 60.61 | 80.98 | 0.111 | 558.65 | 43.97 | | |
| 521151 | 85.62 | 0.036 | 47.47 | 134.19 | 0.222 | 127.30 | 30.14 | | |
| 521289 | 65.97 | 0.036 | 64.57 | 62.31 | 0.222 | 236.18 | 49.64 | | |
| 521487 | 69.54 | 0.000 | 276.67 | 67.15 | 0.000 | 538.96 | 41.02 | | |
| 521640 | 133.20 | 0.000 | 85.15 | 63.55 | 0.111 | 298.27 | 31.34 | | |
| 521809 | 69.55 | 0.000 | 72.24 | 94.32 | 0.000 | 125.31 | 30.12 | CopyNumber | 9q34.3 | 2030 |
| 521903 | 143.71 | 0.000 | 176.08 | 67.76 | 0.000 | 27.38 | 72.01 | | |
| 521924 | 82.37 | 0.036 | 59.55 | 73.11 | 0.111 | 401.23 | 45.90 | | |
| 521969 | 86.81 | 0.000 | 55.63 | 96.01 | 0.000 | 400.95 | 33.05 | | |
| 521973 | 80.96 | 0.036 | 39.93 | 90.53 | 0.111 | 142.18 | 54.69 | | |
| 522074 | 162.66 | 0.071 | 183.70 | 145.60 | 0.000 | 75.36 | 43.60 | | |
| 522110 | 63.85 | 0.071 | 29.44 | 57.72 | 0.222 | 152.37 | 38.21 | | |
| 522114 | 58.16 | 0.000 | 93.47 | 54.91 | 0.000 | 909.36 | 30.72 | | |
| 522310 | 102.19 | 0.036 | 111.23 | 114.70 | 0.111 | 227.49 | 72.44 | | |
| 522373 | 177.96 | 0.000 | 134.50 | 163.88 | 0.111 | 1015.67 | 83.01 | | |
| 522394 | 84.47 | 0.000 | 695.64 | 96.96 | 0.000 | 892.36 | 34.63 | | |
| 522463 | 71.14 | 0.000 | 4621.60 | 78.17 | 0.000 | | | | |
| 522507 | 66.02 | 0.036 | 114.54 | 64.14 | 0.000 | 369.13 | 29.46 | CopyNumber | 9q34.3 | 2030 |
| 522584 | 80.07 | 0.000 | 1864.38 | 65.53 | 0.000 | 2817.95 | 42.35 | | |
| 522590 | 65.85 | 0.000 | 87.04 | 74.78 | 0.111 | 155.78 | 39.35 | | |
| 522632 | 157.61 | 0.000 | 149.26 | 117.91 | 0.111 | 1399.30 | 82.97 | | |
| 522665 | 99.28 | 0.071 | 78.39 | 77.48 | 0.111 | 169.43 | 65.16 | | |
| 522675 | 68.02 | 0.071 | 35.39 | 56.96 | 0.222 | 89.16 | 49.55 | | |
| 522752 | 63.85 | 0.036 | 65.13 | 87.37 | 0.111 | 226.13 | 30.00 | | |
| 522817 | 92.87 | 0.000 | 243.72 | 76.57 | 0.000 | 446.45 | 43.91 | | |
| 522819 | 75.66 | 0.000 | 128.02 | 77.03 | 0.000 | 442.54 | 53.56 | | |
| 522823 | 65.96 | 0.000 | 55.52 | 55.51 | 0.111 | 80.40 | 39.08 | Inversion | Xq28 | 3631 |
| 522932 | 74.41 | 0.071 | 62.12 | 87.31 | 0.222 | 932.94 | 35.74 | CopyNumber | 10q11.23 | 2097 |
| 522995 | 72.57 | 0.000 | 92.76 | 85.46 | 0.222 | 155.41 | 29.78 | | |
| 523004 | 91.74 | 0.000 | 1093.46 | 104.71 | 0.000 | 1020.96 | 39.57 | | |
| 523012 | 151.59 | 0.036 | 108.27 | 101.71 | 0.111 | 460.74 | 105.86 | | |
| 523054 | 58.03 | 0.000 | 85.81 | 56.99 | 0.111 | 215.84 | 28.86 | CopyNumber | 1p36.11 | 48 |
| 523131 | 64.37 | 0.036 | 54.95 | 87.13 | 0.000 | 176.91 | 27.06 | | |
| 523145 | 77.65 | 0.000 | 77.46 | 74.44 | 0.000 | 713.08 | 34.57 | | |
| 523215 | 72.87 | 0.000 | 87.19 | 71.68 | 0.111 | 515.77 | 29.73 | CopyNumber | 10q24.31 | 2164 |
| 523238 | 72.68 | 0.000 | 120.04 | 66.25 | 0.222 | 77.37 | 32.28 | | |
| 523262 | 70.08 | 0.036 | 131.35 | 69.97 | 0.000 | 1073.88 | 31.10 | | |
| 523299 | 84.00 | 0.071 | 94.08 | 72.86 | 0.222 | 94.93 | 27.98 | | |
| 523302 | 73.40 | 0.036 | 52.80 | 58.41 | 0.111 | 39.16 | 33.68 | | |
| 523560 | 81.28 | 0.000 | 971.82 | 62.39 | 0.000 | | 34.93 | | |
| 523680 | 83.52 | 0.000 | 107.04 | 96.51 | 0.111 | 160.42 | 34.93 | | |
| 523789 | 160.56 | 0.000 | 399.15 | 138.88 | 0.000 | 126.46 | 81.17 | | |
| 523829 | 93.80 | 0.036 | 62.35 | 75.95 | 0.111 | 128.33 | 63.45 | | |
| 523836 | 118.62 | 0.000 | 551.15 | 91.25 | 0.000 | 692.25 | 64.89 | CopyNumber | 11q13.1-11q13.2 | 2278 |
| 523852 | 122.32 | 0.000 | 140.78 | 82.29 | 0.222 | 223.69 | 123.19 | CopyNumber | 11q13.2-11q13.3 | 2280 |
| 523875 | 85.23 | 0.036 | 67.45 | 82.01 | 0.222 | 138.28 | 32.54 | | |
| 524009 | 72.05 | 0.071 | 48.51 | 71.53 | 0.222 | 181.41 | 38.91 | | |
| 524081 | 79.74 | 0.036 | 25.40 | 66.56 | 0.222 | 131.07 | 30.87 | | |
| 524084 | 71.59 | 0.000 | 52.46 | 63.40 | 0.222 | 310.09 | 30.43 | | |
| 524161 | 56.55 | 0.071 | 58.04 | 46.88 | 0.000 | 158.34 | 33.48 | CopyNumber | 10p13 | 2062 |
| 524171 | 65.02 | 0.036 | 39.20 | 45.15 | 0.222 | | | | |
| 524183 | 99.77 | 0.036 | 250.38 | 82.32 | 0.111 | 259.10 | 66.52 | CopyNumber | 12p13.33 | 2363 |
| 524195 | 77.48 | 0.036 | 45.90 | 110.88 | 0.222 | 329.67 | 54.17 | | |
| 524214 | 65.06 | 0.000 | 93.97 | 80.62 | 0.111 | 429.42 | 38.04 | | |
| 524219 | 102.77 | 0.000 | 1283.75 | 138.72 | 0.000 | 1413.03 | 41.62 | | |
| 524271 | 101.04 | 0.000 | 72.07 | 117.41 | 0.111 | 303.87 | 28.52 | | |
| 524367 | 97.52 | 0.000 | 23.68 | 69.12 | 0.222 | 212.52 | 34.89 | | |

TABLE 2-continued

A list of 2087 candidate endogenous reference genes

| | | | | | | | | | | |
|---|---|---|---|---|---|---|---|---|---|---|
| 524395 | 160.71 | 0.071 | 629.43 | 152.46 | 0.111 | 691.04 | 113.98 | | | |
| 524464 | 63.84 | 0.000 | 249.77 | 51.93 | 0.111 | 800.60 | 36.87 | | | |
| 524502 | 63.30 | 0.036 | 38.16 | 53.21 | 0.222 | 35.02 | 67.39 | CopyNumber | 12q13.2 | 2429 |
| 524530 | 62.04 | 0.071 | 58.64 | 69.36 | 0.222 | 119.54 | 33.29 | | | |
| 524590 | 62.24 | 0.071 | 32.90 | 59.64 | 0.222 | 168.27 | 24.98 | CopyNumber | 12q21.1 | 2454 |
| 524599 | 101.39 | 0.036 | 171.63 | 88.17 | 0.111 | 877.45 | 45.68 | | | |
| 524690 | 157.16 | 0.071 | 37.45 | 91.05 | 0.222 | 129.11 | 25.70 | CopyNumber | 1p34.2 | 60 |
| 524788 | 66.86 | 0.071 | 46.71 | 77.38 | 0.222 | 152.65 | 26.13 | | | |
| 524809 | 81.00 | 0.071 | 32.60 | 68.39 | 0.222 | 71.44 | 35.75 | | | |
| 524899 | 64.26 | 0.000 | 95.67 | 74.61 | 0.222 | 638.70 | 30.17 | | | |
| 524920 | 66.48 | 0.000 | 61.67 | 67.69 | 0.111 | 789.95 | 26.29 | | | |
| 524969 | 65.49 | 0.000 | 50.51 | 61.47 | 0.222 | 159.56 | 35.37 | | | |
| 525134 | 62.67 | 0.036 | 52.40 | 77.61 | 0.222 | 157.75 | 32.67 | | | |
| 525163 | 68.79 | 0.036 | 118.15 | 66.40 | 0.000 | 209.09 | 38.04 | | | |
| 525232 | 89.47 | 0.036 | 78.60 | 84.11 | 0.000 | 536.96 | 31.58 | | | |
| 525238 | 93.87 | 0.000 | 59.16 | 67.35 | 0.111 | 602.44 | 37.66 | | | |
| 525330 | 77.23 | 0.000 | 183.06 | 61.77 | 0.000 | 381.49 | 40.05 | | | |
| 525391 | 59.57 | 0.036 | 42.13 | 65.68 | 0.222 | 156.20 | 32.83 | CopyNumber | 1p32.3 | 74 |
| 525527 | 71.43 | 0.071 | 100.14 | 58.46 | 0.111 | 184.06 | 29.23 | CopyNumber | 1p36.33-1p36.32 | 4 |
| 525626 | 70.54 | 0.036 | 28.27 | 80.56 | 0.222 | 93.85 | 33.60 | CopyNumber | 14q32.33 | 2747 |
| 525899 | 90.18 | 0.000 | 114.54 | 61.10 | 0.222 | 197.83 | 28.39 | | | |
| 526464 | 68.99 | 0.036 | 26.13 | 58.80 | 0.222 | 142.58 | 30.88 | CopyNumber | 15q24.1 | 2808 |
| 526521 | 96.01 | 0.000 | 250.88 | 101.74 | 0.000 | 147.15 | 33.86 | | | |
| 527105 | 68.10 | 0.000 | 371.42 | 53.26 | 0.000 | 445.41 | 26.61 | | | |
| 527193 | 66.74 | 0.000 | 1409.75 | 60.87 | 0.000 | 54.69 | 37.93 | | | |
| 527348 | 68.02 | 0.071 | 31.17 | 107.14 | 0.111 | 156.88 | 41.93 | | | |
| 527412 | 112.08 | 0.036 | 111.78 | 104.84 | 0.222 | 954.00 | 37.46 | | | |
| 527861 | 75.05 | 0.000 | 174.55 | 93.72 | 0.000 | 778.13 | 44.76 | | | |
| 527862 | 77.71 | 0.000 | 121.83 | 69.64 | 0.222 | | | CopyNumber | 16p13.3 | 2866 |
| 527980 | 93.19 | 0.000 | 140.08 | 80.91 | 0.111 | 72.21 | 28.28 | CopyNumber | 15q21.1 | 2774 |
| 528050 | 86.07 | 0.071 | 39.50 | 93.86 | 0.222 | 153.01 | 24.84 | | | |
| 528222 | 71.25 | 0.000 | 56.92 | 67.43 | 0.222 | 297.99 | 38.18 | | | |
| 528300 | 70.72 | 0.071 | 37.21 | 64.60 | 0.111 | 143.10 | 32.16 | CopyNumber | 10p15.2-10p15.3 | 2038 |
| 528305 | 69.32 | 0.000 | 323.87 | 54.84 | 0.000 | 1767.97 | 27.06 | | | |
| 528572 | 107.18 | 0.036 | 40.58 | 69.71 | 0.222 | 121.35 | 39.94 | CopyNumber | 8p21.3 | 1710 |
| 528668 | 82.67 | 0.000 | 640.96 | 72.93 | 0.000 | | | | | |
| 528780 | 78.91 | 0.036 | 95.64 | 74.72 | 0.111 | 545.27 | 28.60 | | | |
| 528803 | 63.96 | 0.000 | 69.19 | 61.88 | 0.222 | 637.49 | 39.09 | Inversion | 16p12.2-16p12.1 | 2894 |
| 529059 | 86.70 | 0.000 | 155.84 | 79.33 | 0.000 | 436.61 | 43.10 | CopyNumber | 19p13.2 | 3216 |
| 529132 | 101.86 | 0.000 | 206.58 | 89.23 | 0.000 | 607.67 | 37.45 | | | |
| 529244 | 79.26 | 0.036 | 48.81 | 59.97 | 0.222 | 299.18 | 31.69 | CopyNumber | 2q12.2 | 387 |
| 529280 | 59.84 | 0.036 | 42.59 | 87.27 | 0.222 | 122.27 | 29.28 | | | |
| 529303 | 118.67 | 0.000 | 324.14 | 115.14 | 0.111 | 857.43 | 38.03 | | | |
| 529369 | 89.29 | 0.000 | 25.26 | 76.50 | 0.111 | 9.01 | 69.95 | | | |
| 529400 | 76.13 | 0.000 | 40.63 | 114.07 | 0.111 | 32.05 | 45.08 | | | |
| 529420 | 107.73 | 0.000 | 106.80 | 48.77 | 0.000 | 56.41 | 37.58 | | | |
| 529591 | 68.74 | 0.000 | 78.81 | 61.99 | 0.111 | 467.29 | 39.56 | | | |
| 529618 | 87.09 | 0.036 | 82.62 | 91.59 | 0.111 | 36.01 | 56.84 | CopyNumber Inversion CopyNumber | 3q29 | 753 |
| 529631 | 74.72 | 0.000 | 620.31 | 56.60 | 0.000 | 176.79 | 30.79 | CopyNumber | 3q29 | 755 |
| 529782 | 58.53 | 0.000 | 130.67 | 66.49 | 0.000 | 146.41 | 27.77 | | | |
| 529798 | 75.07 | 0.000 | 328.92 | 49.58 | 0.000 | 1755.52 | 30.60 | | | |
| 529862 | 62.81 | 0.000 | 117.16 | 56.20 | 0.222 | | | | | |
| 529890 | 63.76 | 0.000 | 331.32 | 41.79 | 0.000 | 3988.58 | 27.20 | CopyNumber | 5q35.3 | 1270 |
| 529892 | 108.94 | 0.036 | 139.13 | 107.43 | 0.222 | | | CopyNumber | 5q35.3 | 1271 |
| 529957 | 57.49 | 0.036 | 71.45 | 52.24 | 0.000 | 242.41 | 35.55 | | | |
| 530096 | 68.28 | 0.000 | 137.92 | 57.16 | 0.111 | 422.18 | 29.43 | | | |
| 530118 | 65.41 | 0.000 | 57.21 | 50.39 | 0.111 | 386.79 | 22.90 | | | |
| 530291 | 94.65 | 0.000 | 62.14 | 78.23 | 0.000 | 77.23 | 37.30 | | | |
| 530314 | 113.91 | 0.000 | 72.35 | 69.84 | 0.111 | 135.51 | 32.51 | CopyNumber | 9q34.3 | 2030 |
| 530331 | 79.95 | 0.071 | 96.65 | 72.31 | 0.111 | 393.16 | 48.43 | | | |
| 530381 | 84.23 | 0.000 | 44.92 | 94.49 | 0.111 | 740.81 | 47.85 | | | |
| 530412 | 108.42 | 0.000 | 884.31 | 121.35 | 0.000 | 755.69 | 25.73 | | | |
| 530436 | 68.51 | 0.036 | 39.15 | 65.12 | 0.000 | 89.36 | 36.15 | | | |
| 530479 | 68.09 | 0.071 | 50.16 | 67.87 | 0.222 | 130.74 | 30.76 | | | |
| 530687 | 76.35 | 0.000 | 123.16 | 101.20 | 0.111 | 388.74 | 29.72 | CopyNumber | 11p15.5 | 2200 |
| 530734 | 78.25 | 0.036 | 43.82 | 67.00 | 0.222 | 203.80 | 36.73 | | | |
| 530753 | 64.89 | 0.000 | 122.19 | 58.43 | 0.111 | 1049.37 | 27.21 | | | |
| 530823 | 71.49 | 0.036 | 34.72 | 46.24 | 0.111 | 219.78 | 24.63 | | | |
| 530862 | 76.97 | 0.071 | 24.06 | 57.79 | 0.111 | 216.03 | 27.91 | CopyNumber | 12q13.12 | 2421 |
| 531081 | 144.33 | 0.000 | 188.82 | 111.97 | 0.111 | 1778.83 | 73.47 | | | |
| 531089 | 64.92 | 0.000 | 58.25 | 72.81 | 0.222 | 240.62 | 40.78 | | | |
| 531176 | 69.91 | 0.036 | 192.02 | 57.22 | 0.111 | 407.01 | 25.65 | | | |
| 531330 | 73.90 | 0.000 | 113.07 | 68.46 | 0.111 | 834.17 | 46.89 | CopyNumber | 9p24.3 | 1883 |

TABLE 2-continued

A list of 2087 candidate endogenous reference genes

| | | | | | | | | | |
|---|---|---|---|---|---|---|---|---|---|
| 531614 | 75.55 | 0.071 | 84.93 | 89.38 | 0.111 | 260.94 | 66.65 | | |
| 531752 | 65.88 | 0.071 | 46.35 | 66.00 | 0.000 | 53.66 | 35.52 | | |
| 531856 | 113.19 | 0.000 | 567.60 | 102.77 | 0.000 | 10.32 | 101.76 | | |
| 531876 | 75.41 | 0.036 | 87.48 | 59.71 | 0.222 | 539.73 | 29.29 | | |
| 531879 | 73.81 | 0.071 | 33.40 | 53.04 | 0.111 | 88.51 | 36.03 | | |
| 532359 | 71.75 | 0.000 | 899.39 | 67.01 | 0.000 | 3112.89 | 40.25 | | |
| 532399 | 60.44 | 0.071 | 53.30 | 56.19 | 0.111 | 556.41 | 25.27 | | |
| 532755 | 59.70 | 0.071 | 35.53 | 57.88 | 0.222 | 174.78 | 35.47 | | |
| 532790 | 82.55 | 0.000 | 83.21 | 52.24 | 0.222 | 153.66 | 31.53 | | |
| 532793 | 105.70 | 0.036 | 160.69 | 81.87 | 0.111 | 299.76 | 37.08 | CopyNumber | 17q21.32 | 3031 |
| 532803 | 110.79 | 0.000 | 194.85 | 85.55 | 0.111 | 251.26 | 89.23 | | |
| 532826 | 124.52 | 0.036 | 436.04 | 83.52 | 0.000 | 55.92 | 39.14 | | |
| 532853 | 75.00 | 0.000 | 86.71 | 66.43 | 0.111 | 104.95 | 47.87 | | |
| 533030 | 90.84 | 0.036 | 91.99 | 90.93 | 0.111 | 235.53 | 30.97 | CopyNumber | 22q13.1 | 3496 |
| 533059 | 100.23 | 0.000 | 432.63 | 104.06 | 0.111 | 952.40 | 34.46 | CopyNumber | 6p21.33 | 1312 |
| 533122 | 60.64 | 0.071 | 124.04 | 67.72 | 0.000 | 610.09 | 26.23 | | |
| 533136 | 71.52 | 0.000 | 67.48 | 58.25 | 0.111 | 202.24 | 47.72 | CopyNumber | 4p16.2 | 761 |
| 533192 | 67.13 | 0.036 | 119.13 | 68.06 | 0.000 | 390.25 | 37.80 | | |
| 533222 | 60.55 | 0.071 | 36.87 | 44.13 | 0.111 | 164.72 | 28.30 | CopyNumber | 5q12.1 | 1137 |
| 533245 | 65.70 | 0.036 | 46.71 | 63.31 | 0.111 | 179.53 | 24.31 | CopyNumber | 5q31.1 | 1222 |
| 533282 | 56.67 | 0.000 | 183.69 | 77.18 | 0.000 | 1100.81 | 25.29 | | |
| 533308 | 68.45 | 0.036 | 48.77 | 64.22 | 0.222 | 202.26 | 24.39 | | |
| 533317 | 143.97 | 0.000 | 745.87 | 104.93 | 0.111 | 2393.96 | 70.88 | | |
| 533437 | 71.07 | 0.036 | 132.40 | 64.32 | 0.222 | | | | |
| 533440 | 143.68 | 0.036 | 45.51 | 61.68 | 0.222 | 235.54 | 58.67 | | |
| 533474 | 59.55 | 0.036 | 53.89 | 75.77 | 0.111 | 128.82 | 31.21 | | |
| 533479 | 69.59 | 0.036 | 96.22 | 76.98 | 0.111 | 86.44 | 31.09 | | |
| 533526 | 71.06 | 0.000 | 49.86 | 57.89 | 0.111 | 218.93 | 31.26 | | |
| 533624 | 70.85 | 0.000 | 959.57 | 58.54 | 0.000 | 1867.45 | 27.19 | | |
| 533712 | 65.23 | 0.036 | 55.59 | 73.88 | | 259.05 | | | |
| 533722 | 65.50 | 0.000 | 204.31 | 50.13 | 0.000 | 1297.83 | 21.87 | | |
| 533771 | 93.54 | 0.000 | 50.24 | 77.32 | 0.222 | 1094.17 | 25.43 | CopyNumber | 16p13.3 | 2866 |
| 533782 | 221.65 | 0.036 | 544.77 | 104.33 | 0.222 | 29.71 | 50.29 | | |
| 533977 | 109.58 | 0.071 | 160.18 | 105.13 | 0.111 | 1758.85 | 51.28 | CopyNumber | 1q21.1 | 147 |
| 533985 | 197.67 | 0.036 | 55.92 | 64.84 | 0.111 | 188.23 | 31.85 | | |
| 533986 | 68.64 | 0.036 | 24.58 | 130.07 | 0.222 | 179.95 | 28.58 | | |
| 534125 | 142.62 | 0.000 | 832.59 | 105.81 | 0.111 | 4813.26 | 38.31 | CopyNumber | 6p21.33 | 1313 |
| 534168 | 75.97 | 0.036 | 323.99 | 55.72 | 0.000 | 1011.41 | 45.93 | CopyNumber | Xq24 | 3602 |
| 534212 | 77.33 | 0.000 | 43.32 | 66.35 | 0.222 | 99.62 | 33.06 | CopyNumber | 1q21.1 | 147 |
| 534255 | 96.87 | 0.000 | 2910.69 | 103.61 | 0.000 | 4736.90 | 32.54 | CopyNumber | 15q21.1 | 2773 |
| 534307 | 90.48 | 0.036 | 47.43 | 99.71 | | | | | |
| 534314 | 85.64 | 0.000 | 902.22 | 82.80 | 0.000 | 123.06 | 45.02 | | |
| 534326 | 91.25 | 0.000 | 113.47 | 96.69 | 0.111 | 398.89 | 46.54 | | |
| 534338 | 66.09 | 0.036 | 78.26 | 71.00 | 0.222 | 158.13 | 58.47 | CopyNumber | 16p11.2 | 2903 |
| 534346 | 77.56 | 0.000 | 650.12 | 74.11 | 0.000 | | | | |
| 534350 | 71.06 | 0.071 | 29.73 | 56.39 | 0.222 | 141.64 | 41.82 | | |
| 534453 | 90.65 | 0.000 | 296.51 | 95.48 | 0.000 | 624.74 | 38.70 | | |
| 534454 | 130.28 | 0.000 | 192.47 | 72.01 | 0.000 | 88.66 | 32.89 | CopyNumber | 17q25.3 | 3087 |
| 534457 | 62.64 | 0.071 | 61.53 | 74.61 | 0.000 | 730.32 | 25.54 | | |
| 534473 | 63.86 | 0.071 | 93.62 | 63.87 | 0.222 | 453.91 | 46.23 | | |
| 534483 | 56.84 | 0.071 | 41.04 | 62.68 | 0.222 | 271.95 | 33.02 | | |
| 536275 | 69.43 | 0.071 | 36.99 | 76.62 | 0.222 | 305.46 | 30.60 | | |
| 541269 | 79.15 | 0.000 | 244.71 | 86.94 | 0.000 | | | | |
| 546248 | 137.05 | 0.036 | 819.47 | 122.30 | 0.000 | 277.158 | 66.77 | | |
| 546250 | 75.46 | 0.000 | 135.33 | 72.35 | 0.000 | 457.00 | 31.62 | | |
| 546253 | 79.22 | 0.036 | 154.37 | 88.05 | 0.222 | 80.29 | 33.55 | | |
| 546261 | 89.83 | 0.036 | 496.55 | 65.24 | 0.000 | 6040.82 | 27.54 | | |
| 546269 | 75.45 | 0.000 | 1517.81 | 42.29 | 0.000 | 14429.75 | 31.95 | | |
| 546271 | 65.78 | 0.000 | 386.41 | 50.39 | 0.000 | 1283.29 | 34.90 | | |
| 546286 | 89.05 | 0.000 | 1172.72 | 54.31 | 0.000 | 4362.29 | 39.28 | | |
| 546289 | 108.77 | 0.000 | 1051.06 | 67.54 | 0.000 | 4831.90 | 38.49 | | |
| 546290 | 94.06 | 0.000 | 2012.36 | 62.38 | 0.000 | 6697.93 | 38.63 | | |
| 546291 | 84.07 | 0.000 | 142.03 | 61.95 | 0.000 | 5073.35 | 34.62 | CopyNumber | 12p13.33-12p13.32 | 2364 |
| 546339 | 64.42 | 0.000 | 67.76 | 55.24 | 0.111 | 535.27 | 24.30 | | |
| 546356 | 59.11 | 0.000 | 4388.69 | 51.21 | 0.000 | 6301.04 | 40.02 | CopyNumber | 19q13.33 | 3277 |
| 546394 | 111.80 | 0.000 | 185.13 | 58.61 | 0.000 | | | | |
| 547759 | 63.46 | 0.071 | 48.56 | 84.67 | 0.000 | | | | |
| 549178 | 82.90 | 0.000 | 82.93 | 55.18 | 0.111 | | | CopyNumber | 9q34.3 | 2030 |
| 552590 | 70.08 | 0.036 | 25.28 | 65.81 | 0.222 | | | CopyNumber | 22q11.21 | 3466 |
| 553496 | 72.62 | 0.071 | 41.08 | 79.89 | 0.222 | 43.50 | 72.79 | | |
| 553512 | 113.45 | 0.000 | 44.13 | 95.01 | 0.111 | | | | |
| 554767 | 64.47 | 0.071 | 35.90 | 65.85 | 0.222 | | | | |
| 554776 | 84.70 | 0.071 | 46.58 | 100.28 | 0.222 | | | Inversion | 17p11.2 | 2999 |
| 554894 | 87.26 | 0.071 | 45.88 | 73.07 | 0.222 | | | CopyNumber | 2p13.1 | 356 |
| 554896 | 89.43 | 0.000 | 112.49 | 60.07 | 0.000 | 291.19 | 31.70 | CopyNumber | 7p22.3 | 1481 |
| 555194 | 75.14 | 0.036 | 108.54 | 77.43 | 0.222 | | | | |
| 555866 | 100.49 | 0.000 | 206.53 | 89.92 | 0.000 | 185.01 | 47.68 | | |

TABLE 2-continued

A list of 2087 candidate endogenous reference genes

| | | | | | | | | | | |
|---|---|---|---|---|---|---|---|---|---|---|
| 555873 | 116.51 | 0.000 | 174.85 | 100.43 | 0.111 | | | | | |
| 555875 | 78.46 | 0.036 | 17.73 | 91.10 | 0.222 | | | | | |
| 555889 | 61.77 | 0.036 | 59.41 | 70.56 | 0.222 | | | | | |
| 555890 | 64.41 | 0.000 | 151.98 | 72.68 | 0.111 | | | CopyNumber | 1p35.1 | 54 |
| 555911 | 83.61 | 0.000 | 120.74 | 64.55 | 0.000 | 182.74 | 32.39 | CopyNumber | 1q21.1 | 147 |
| 555969 | 85.57 | 0.036 | 27.90 | 60.28 | 0.222 | 187.95 | 28.62 | | | |
| 555971 | 102.99 | 0.071 | 43.43 | 70.29 | 0.000 | | | | | |
| 555973 | 61.02 | 0.071 | 25.39 | 54.32 | 0.222 | 365.86 | 37.66 | CopyNumber | 3p24.3 | 538 |
| 555994 | 67.15 | 0.071 | 17.47 | 70.28 | 0.222 | 113.88 | 43.85 | CopyNumber | 16q12.1 | 2912 |
| 556267 | 68.11 | 0.036 | 37.29 | 76.22 | 0.222 | | | | | |
| 556461 | 109.80 | 0.000 | 89.26 | 94.15 | 0.111 | | | | | |
| 556795 | 113.17 | 0.071 | 222.20 | 105.92 | 0.111 | | | | | |
| 557550 | 90.20 | 0.000 | 781.42 | 91.24 | 0.000 | 2030.99 | 30.63 | | | |
| 558296 | 65.84 | 0.000 | 71.76 | 64.47 | 0.222 | 293.40 | 20.63 | CopyNumber | 2p25.3 | 261 |
| 558313 | 83.46 | 0.000 | 103.84 | 61.28 | 0.111 | | | | | |
| 558322 | 81.02 | 0.000 | 781.10 | 60.08 | 0.000 | | | | | |
| 558325 | 58.04 | 0.071 | 105.00 | 59.17 | 0.000 | | | | | |
| 558328 | 175.31 | 0.071 | 41.72 | 74.68 | 0.222 | 724.52 | 77.69 | CopyNumber | 6p21.31 | 1321 |
| 558330 | 119.70 | 0.000 | 1306.25 | 81.82 | 0.000 | | | CopyNumber | 19q13.33 | 3275 |
| 558338 | 94.69 | 0.000 | 392.75 | 84.14 | 0.111 | | | | | |
| 558345 | 68.96 | 0.036 | 47.70 | 48.55 | 0.222 | | | | | |
| 558354 | 85.28 | 0.000 | 3392.33 | 80.75 | 0.000 | | | | | |
| 558360 | 85.52 | 0.000 | 198.33 | 51.08 | 0.111 | | | | | |
| 558361 | 86.68 | 0.000 | 276.67 | 71.79 | 0.111 | | | | | |
| 558362 | 74.08 | 0.036 | 45.59 | 64.87 | 0.222 | 229.35 | 49.45 | | | |
| 558376 | 55.75 | 0.000 | 528.10 | 45.88 | 0.000 | | | | | |
| 558381 | 127.10 | 0.000 | 52.20 | 90.63 | 0.000 | | | | | |
| 558382 | 62.95 | 0.036 | 245.75 | 66.13 | 0.111 | | | | | |
| 558383 | 92.57 | 0.000 | 850.60 | 69.48 | 0.111 | | | | | |
| 558384 | 70.50 | 0.000 | 972.23 | 66.45 | 0.000 | | | CopyNumber | 17q12 | 3020 |
| 558385 | 76.67 | 0.000 | 522.14 | 55.82 | 0.111 | | | | | |
| 558386 | 70.79 | 0.000 | 1008.37 | 63.71 | 0.000 | | | | | |
| 558388 | 76.32 | 0.000 | 1561.96 | 59.50 | 0.000 | | | | | |
| 558389 | 86.31 | 0.000 | 2526.25 | 46.00 | 0.000 | | | | | |
| 558390 | 76.07 | 0.000 | 653.91 | 60.77 | 0.000 | | | | | |
| 558391 | 71.38 | 0.000 | 1018.49 | 62.26 | 0.000 | | | | | |
| 558396 | 101.60 | 0.071 | 177.30 | 89.88 | 0.222 | 187.47 | 100.01 | | | |
| 558424 | 92.40 | 0.000 | 144.32 | 74.76 | 0.000 | | | | | |
| 558426 | 67.09 | 0.036 | 90.90 | 62.22 | 0.111 | | | | | |
| 558429 | 78.14 | 0.036 | 73.01 | 72.78 | 0.111 | | | CopyNumber | 7q22.1 | 1597 |
| 558431 | 100.68 | 0.000 | 155.33 | 60.37 | 0.000 | | | | | |
| 558442 | 63.18 | 0.000 | 51.45 | 69.20 | 0.000 | | | | | |
| 558448 | 67.59 | 0.000 | 46.04 | 58.56 | 0.111 | | | | | |
| 558453 | 82.84 | 0.000 | 530.26 | 57.92 | 0.000 | | | | | |
| 558454 | 75.98 | 0.000 | 112.20 | 87.34 | 0.111 | | | CopyNumber | 1p36.11 | 49 |
| 558458 | 67.67 | 0.071 | 35.79 | 63.61 | 0.111 | | | | | |
| 558473 | 70.64 | 0.000 | 40.37 | 55.42 | 0.222 | 104.21 | 36.46 | CopyNumber | 18q12.2 | 3132 |
| 558499 | 78.66 | 0.071 | 43.18 | 52.43 | 0.222 | 69.81 | 63.34 | CopyNumber | 19p13.2 | 3210 |
| 558511 | 54.61 | 0.000 | 46.40 | 50.18 | 0.222 | | | | | |
| 558521 | 78.28 | 0.000 | 61.92 | 65.33 | 0.111 | | | | | |
| 558591 | 68.02 | 0.071 | 85.80 | 56.76 | 0.111 | 687.61 | 32.03 | | | |
| 558825 | 107.55 | 0.000 | 42.12 | 72.58 | 0.000 | | | CopyNumber | 1q21.1 | 147 |
| 558995 | 53.36 | 0.000 | 186.71 | 64.24 | 0.111 | | | | | |
| 567260 | 63.25 | 0.036 | 44.20 | 70.83 | 0.222 | 14.03 | 385.13 | CopyNumber | 16p11.2 | 2903 |
| 567263 | 62.05 | 0.000 | 93.74 | 61.88 | 0.222 | 27.38 | 49.92 | | | |
| 567267 | 57.55 | 0.036 | 44.12 | 65.62 | 0.000 | 26.18 | 56.35 | | | |
| 567279 | 65.02 | 0.036 | 43.97 | 59.48 | 0.111 | | | CopyNumber | 17q25.1 | 3074 |

Mean: mean gene expression level,
CV: coefficient of variation,
0's P: 0's proportion Example 3: Identification of ERG Among the candidate ERGs, reference genes were further identified according to the following process.

First, CVs were calculated for each UniGene cluster in the datasets including EST, ShortSAGE, LongSAGE and microarray (Affymetrix HG-U133, CA), and genes were preferentially ranked in ascending order of CV. Out of the 400 genes (approx. 20% of the candidate ERG) which were preferentially ranked in ascending order of CV from each dataset, 13 ERGs were found to be common to all four datasets (Table 3). The 13 ERGs were identified as Accession No. Hs 500775(ZNF207), Accession No. Hs 446427 (OAZ1), Accession No. Hs 530118(LUC7L2), Accession No. Hs 208597(CTBP1), Accession No. Hs 440382 (TRIM27), Accession No. Hs 444279(GPBP1), Accession No. Hs 250009(ARL8B), Accession No. Hs 9589 (UBQLN1), Accession No. Hs 253726(PAPOLA), Accession No. Hs 146806(CUL1), Accession No. Hs 533222 (DIMT1L), Accession No. Hs 494985(FBXW2) and Accession No. Hs 242458 (SPG21).

The gene ontology thereof was determined from a Gene Ontology site (http://www.geneontology.org/).

Most of the identified genes (ZNF207, OAZ1, CTBP1, PAPOLA, and FBXW2) were involved in basic cellular physiological processes, particularly in cellular metabolic processes. TRIM27 and CUL1 are genes responsible for cell proliferation. OAZ1 showed the lowest CV in both Short-SAGE and LongSAGE. CTBP1 and ZNF207 were the most stable genes in CGAP and Microarray, respectively. OAZ1, which is involved in polyamine biosynthesis, showed the highest expression across all four datasets, with relatively low CV in all datasets except for the EST dataset.

EXPERIMENTAL EXAMPLE 4: Correlation Analysis of Reference Gene Between Datasets Pearson and Spearman's rank correlation analyses were performed on the ERGs identified according to the present invention in a manner similar to that of Experimental Example 2 to compare the four datasets in terms of gene expression and CV.

Significant correlations between expression values were observed within some of the datasets, whereas no significant correlations of CV between any of the datasets were observed.

Although the Spearman correlation between EST-Microarray (0.374, P=0.206) and ShortSAGE-Microarray (0.511, P=0.076) was not significant, the gene expression of the 13 ERGs showed a significant Pearson correlation (p<0.001). No significant correlation in CV was found between the datasets (P>0.05). With the respective transcripts thereof found in all tissues in both ShortSAGE and LongSAGE, CDC142 and MYL6 were most stably expressed among the ERGs. HBP1 and PSMC1 showed the lowest CV in EST and Microarray.

Experimental Example 5: Comparison Between Novel Reference Gene and Traditional Reference Gene in Gene Expression Datasets The 13 endogenous reference genes identified according to the present invention were compared with 13 traditional reference genes (Table 4) in terms of gene expression level and CV.

As a result, the six traditional endogenous reference genes, RPLP0, ACTB, PPIA, GAPD, PGK1 and B2M, showed high expression levels, while the other genes, GUSB, HPRT1, TBP, TFRC, ALAS1, H6PD and HMBS, exhibited relatively low expression levels, in all four datasets (FIG. 6). These results are in line with those of the previous report, in which potential endogenous expression genes were analyzed for mRNA level using qRT-PCR (Radonic A et al., Biochem Biophys Res Commun, 313(4), 856-862, 2004). The expression levels of the endogenous reference genes identified according to the present invention were similar to or slightly higher than those of the low-abundance group of the traditional endogenous reference genes.

In addition, all of the endogenous reference genes identified according to the present invention, except for a few, showed lower CV values than traditional reference genes (FIG. 7). In other words, the endogenous reference genes of the present invention are generally low in expression variation across a wide range of tissues, indicating that the identified reference genes according to the present invention are more stably expressed than traditional endogenous reference genes.

TABLE 3

ERGs identified from four datasets

| UniGene cluster | Symbol | Gene Title | EST Mean | EST CV | EST 0's P | SHORT SAGE Mean | SHORT SAGE CV | SHORT SAGE 0's P | LONG SAGE Mean | LONG SAGE CV | LONG SAGE 0's P |
|---|---|---|---|---|---|---|---|---|---|---|---|
| Hs446427 | GAZ1 | Ornithine decarboxylate antizyme 1 | 673.68 | 62.71 | 0.069 | 576.38 | 55.94 | 0 | 444.92 | 41.01 | 0 |
| Hs9589 | UBQLNI | Ubiquilin 1 | 111.34 | 60.19 | 0.31 | 75.93 | 61.3 | 0.036 | 71.77 | 49.75 | 0.111 |
| Hs444279 | GPBP1 | GC-rich promoter binding protein 1 | 132.95 | 56.92 | 0.241 | 63.11 | 61.65 | 0 | 80.72 | 51.79 | 0.111 |
| Hs208597 | CTBP1 | C-terminal binding protein 1 | 136.74 | 48.53 | 0.138 | 213.99 | 62.01 | 0 | 112.96 | 50.6 | 0 |
| Hs253726 | PAPOLA | Poly(A) polymerase alpha | 216.15 | 65.36 | 0.172 | 118.24 | 58.02 | 0 | 89.5 | 50.88 | 0 |
| Hs250009 | ARL8B | ADP ribosylation factor-like 8B | 132.27 | 55.79 | 0.379 | 134.21 | 61.55 | 0 | 59.19 | 55.14 | 0.111 |
| Hs241455 | SPG21 | Spastic paraplegia 21 (autosomal receive, Mast syndrome) | 120.35 | 59.44 | 0.31 | 76.41 | 57.83 | 0.036 | 73.3 | 49.12 | 0 |
| Hs530118 | LUC7L2 | LUC7-like 2 (S. cerevisiae) | 132.76 | 59.55 | 0.172 | 74.65 | 65.41 | 0 | 57.21 | 50.39 | 0.111 |
| Hs500775 | ZNF207 | Zinc finger protein 207 | 233.29 | 62.27 | 0.034 | 165.68 | 56.77 | 0 | 154.32 | 52.88 | 0.111 |
| Hs533222 | DIMT1L | DIM1 dimethyladenosine (transferase 1-like S. cerevisiae) | 129.17 | 69.14 | 0.379 | 42.41 | 60.55 | 0.071 | 36.87 | 44.13 | 0.111 |
| Hs440382 | TRIM27 | Tripartite motif containing 27 | 155.33 | 68.54 | 0.172 | 80.66 | 63.06 | 0 | 67.84 | 45.41 | 0.111 |
| Hs146806 | CUL1 | Culin 1 | 120.27 | 57.5 | 0.207 | 69.33 | 65.76 | 0.036 | 76.43 | 55 | 0.111 |
| Hs494985 | FBXW2 | F-box and WD-40 domain protein 2 | 97.45 | 68.65 | 0.379 | 40.27 | 58.47 | 0 | 23.54 | 51.61 | 0.111 |

| UniGene cluster | Affymetrix Mean | Affymetrix CV | Gene Ontology Biological Process | Molecular Function |
|---|---|---|---|---|
| Hs446427 | 1860.9 | 22.07 | Polyamine biosynthesis | Ornithine decarboxylase inhibitor activity |
| Hs9589 | 919.32 | 26.81 | | Kinase binding |
| Hs444279 | 746.56 | 26.6 | | |
| Hs208597 | 481.51 | 24.72 | Negative regulation of cell proliferation; Protein phosphorylation; Viral genome replication | Protein C-terminus binding Transcription factor binding |

TABLE 3-continued

| | | | | | |
|---|---|---|---|---|---|
| | Hs253726 | 451.23 | 27.68 | mRNA polyadenylation | RNA binding |
| | Hs250009 | 418.28 | 26.81 | Chromosome segregation | α-tubulin binding β-tubulin binding; GDP binding; GTP binding; GTPase activity |
| | Hs241455 | 415.64 | 29.35 | Antigen receptor-mediated signaling pathway | CD4 receptor binding |
| | Hs530118 | 386.79 | 22.9 | | |
| | Hs500775 | 358.69 | 18.38 | Regulation of transcription, DNA-dependent | Transcription factor activity; Zinc ion binding |
| | Hs533222 | 164.72 | 28.3 | | |
| | Hs440382 | 163.6 | 26.3 | Cell proliferation; Spermatogenesis | Metal ion binding, Transmembrane receptor protein tyrosine kinase activity |
| | Hs146806 | 156.47 | 27.78 | Cell cycle arrest; G1/S transition of mitotic cell cycle; Induction of apoptosis by intracellular signals; Negative regulation of cell proliferation | Protein binding |
| | Hs494985 | 69.32 | 28.36 | Proteolysis | Protein binding ubiquitin conjugating enzyme activity; ubiquitin-protein ligase activity |

Mean: Mean gene expression level,
CV: Coefficient of variation,
0's P: 0's proportion

TABLE 4

Traditional ERGs used in present invention

| UniGene cluster | Symbol | Gene Title | EST Mean | EST CV | EST 0's P | SHORT SAGE Mean | SHORT SAGE CV | SHORT SAGE 0's P |
|---|---|---|---|---|---|---|---|---|
| Hs.448226 | RPIP0 | Riboclinical protein, large, P0 | 3,809.2 | 75.92 | 0 | 1,108.65 | 91.01 | 0 |
| Hs.520640 | ACTB | β-actin | 4,381.34 | 95.98 | 0.034 | 1,348.49 | 91.02 | 0 |
| Hs.356331 | PPIA | Peptidylprolyl-isomerase A (cyclophilin A) | 1,225.7 | 78.02 | 0.034 | 1,646.83 | 59.53 | 0 |
| Hs.479728 | GAPDH | Glyceraldehyde-3-phosphate dehydrogenase | 7,330.22 | 80.18 | 0 | 3,167.05 | 83.62 | 0 |
| Hs.78771 | PGK1 | Phosphoglycerate kinase 1 | 681.19 | 86.72 | 0.034 | 423.67 | 85.52 | 0 |
| Hs.534255 | B2M | β-2-nucroglobulin | 1,303.98 | 172.16 | 0 | 2,594.12 | 96.87 | 0 |
| Hs.255230 | GUSB | β-Glucurcoidase | 116.77 | 89.37 | 0.414 | 40.98 | 67.81 | 0.107 |
| Hs.412707 | HPRT1 | Hypoxanthine phosphoriborytransferase 1 | 103.48 | 63.18 | 0.345 | 32.51 | 63.51 | 0.107 |
| Hs.1100 | TBP | TATA box binding protein | 71.45 | 47.77 | 0.448 | 31.94 | 62.8 | 0.286 |
| Hs.529618 | TFRC | Transferrin recepter (p90, CD71) | 212.76 | 85.52 | 0.241 | 89.51 | 87.09 | 0.036 |
| Hs.82609 | HMB8 | Hydroxymethylbilane synthase | 176.26 | 105.68 | 0.172 | 32.51 | 76.51 | 0.214 |
| Hs.463511 | H6PD | Hexose-6-phosphate dehydrogenase (glucose-1-dehydrogenase) | 101.9 | 86.9 | 0.483 | 44.65 | 70.8 | 0.071 |
| Hs.476308 | ALAS1 | δ-Aminolevulinate synthase 1 | 132.82 | 82.5 | 0.345 | 50.43 | 72.23 | 0 |

| UniGene cluster | LONG SAGE Mean | LONG SAGE CV | LONG SAGE 0's P | Affymetrix Mean | Affymetrix CV |
|---|---|---|---|---|---|
| Hs.448226 | 1,605.76 | 74.12 | 0 | 1,888.46 | 41.47 |
| Hs.520640 | 1,961.29 | 60.59 | 0.111 | 5,036.63 | 31.42 |
| Hs.356331 | 1,683.27 | 56.79 | 0 | 5,223.43 | 28.46 |
| Hs.479728 | 3,178.15 | 102.5 | 0 | 4,934.56 | 42.86 |
| Hs.78771 | 445.96 | 90.9 | 0 | 1,179.63 | 41.05 |
| Hs.534255 | 2,910.69 | 103.61 | 0 | 4,736.9 | 32.54 |
| Hs.255230 | 11.42 | 89.36 | 0.556 | 360.37 | 49.14 |
| Hs.412707 | 33.29 | 49.07 | 0.222 | 233.36 | 40.85 |

TABLE 4-continued

Traditional ERGs used in present invention

| | | | | | |
|---|---|---|---|---|---|
| Hs.1100 | 17.58 | 69.22 | 0.444 | 25.44 | 73.23 |
| Hs.529618 | 82.62 | 91.59 | 0.111 | 36.01 | 56.84 |
| Hs.82609 | 28.04 | 42.5 | 0.444 | 119.08 | 33.63 |
| Hs.463511 | 25.33 | 101.45 | 0.222 | 25.04 | 28.85 |
| Hs.476308 | 22.6 | 50.59 | 0.202 | 178.95 | 107.93 |

Mean: Mean gene expression level,
CV: Coefficient of variation,
0's P: 0's proportion Experimental Example 6: Gene Copy Number Variations of ERGs The 13 ERGs identified according to the present invention were examined for gene copy number variation with reference to the Database of Genomic Variants (http://projects.tcag.ca/variation/). Only OAZ1 and DIMT1L, among the 13 genes of the present invention, were found in chromosome regions known to exhibit gene copy number variation (Table 5). In contrast, many (ACTB, GAPDH, PGK1, B2M, TBP, TFRC, ALAS1) of the traditional reference genes were located at such genomic loci (Table 5). These results suggest that almost all of the identified reference genes of the present invention, except for the two genes, can be used as guide genes for the measurement of gene amplification because they might be highly unlikely to show variation in gene copy number.

Experimental Example 7: Validation of Reference Gene

<7-1> Validation of Expression Level of ERG by Quantitative RT-PCR (qRT-PCR)

For use in validating the expression stability of the ERGs identified from the datasets, a total of 108 human samples, including 26 frozen human tissues, 60 formalin-fixed, paraffin embedded (FFPE) human tissues, and 22 human cancer cell lines were obtained (Table 6). The 60 FFPE tissues were composed of 10 breast cancer tissues, 8 normal stomach tissues, 9 stomach cancer tissues, 10 normal ovary tissues, 4 ovarian dropsy tissues, 9 borderline ovarian tumors, and ovarian cancer tissues. Total RNA was isolated from these tissues and cell lines. For frozen human tissues and human cancer cell line samples, RNA which met the requirements of A260/280≥1.80 and rRNA (28S/18S)≥1.0 was used in qRT-PCR. cDNA was synthesized from the RNA using a standard technique and then diluted in distilled water (1:3 cDNA:DW) before qRT-PCR. PCR primers are summarized, together with the Universal Probe Library (UPL) thereof, in Table 7, below.

For use in this qRT-PCR, traditional ERGs were selected on the basis of the use frequency in previous reports and commercially available kits and the CV calculated from the database of the present invention. The 8 ERGs (B2M, ACTB, GAPDH, HMBS, PPIA, HPRT1, TBP and H6PD) that are most widely used can be found in commercially available kits such as Taqman human endogenous control plate (Applied Biosystems) and HKG selection kit (Roche Applied Science, Ohl F et, al., J Mol Med 83:1014-24, 2005; Roche Applied Science Technical Note No. LC 15/2005; Applied Biosystems, 2001). Each gene was measured at 530 nm using an FAM-conjugate UPL probe (Roche Applied Science) or a custom-made specific probe (TIB MOLBIOL GmbH, Germany). All PCR was performed in a Lightcycler 2.0 (Roche Applied Science, USA) using standard protocols.

PCR efficiency for each gene was measured using a cDNA serial dilution (Pfaffl M W et al., Nucleic Acids Res 29: e45, 2001) of the stomach cancer cell line MKN74 and calculated with Lightcycler software 4.0 (Roche Applied Science, USA). It was found to fall within a range from 90 to 100% (Table 8).

Also, PCR efficiency for each probe in tissue samples was estimated using a LinRegPCR program (Ramakers C et al., Neurosci Lett 339:62-6, 2003). A Cp value is an average of three measurements for each gene. The same genes from different tissue samples were measured under the same PCR conditions so as to minimize experimental variation. Because it was not measured in any of 4 samples, normal lung, liver, breast and kidney tissues, the Cp value of H6PD was omitted from subsequent calculations. For each experiment that was conducted in triplicate, the Cp values were found to have a CV less than 5%.

Expression levels of 20 genes, except for H6PD, across 48 samples, including frozen human tissues and cancer cell lines, are depicted in FIG. 8. The 13 novel ERGs of the present invention were expressed in all 48 samples. 7 traditional ERGs showed a wide expression range (Cp: 13.52~29.39) whereas H6PD was not found in some tissues. The 13 ERGs ranged in Cp from 18.90 to 28.79 (FIG. 9). Traditional ERGs can be classified into a high-expression group (median <20 cycles) and a low-expression group (median >23 cycles). B2M, PPIA, GAPDH and ACTB are included in the high-expression group and HPRT1, TBP, and HMBS are found in the low-expression group. All of the novel ERGs of the present invention, except for OAZ1, show expression levels between those of the high-expression group and the low-expression group of the traditional ERGs. ZNF2007 had the highest expression level among the ERGs, followed by UBQLN1 and CUL1. OAZ1 had the lowest expression level.

TABLE 5

Gene copy number variations of traditional ERG and novel ERG

| | Novel candidate ERGs | | | | | Traditional ERGs | | | |
|---|---|---|---|---|---|---|---|---|---|
| Gene Symbol | Genomic location* | Genomic Variation** | | | Gene symbol | Genomic location* | Genomic Variation** | | |
| | | Variation type | Locus ID | References | | | Variation type | Locus ID | References |
| ZNF207 | 17q11.2 | | | | RPLP0 | 12q24.23 | | | |
| OAZ1 | 19p13.3 | Copy number | 3199 | Wong et al (2007) | ACTB | 7p22.1 | Copy number | 1487 | Wong et al (2007) |
| LUC7L2 | 7q34 | | | | PPIA | 7p13 | | | |
| CTBP1 | 4p16.3 | | | | GAPDH | 12p13.31 | Copy number | 2368 | Redon et al (2006) |
| TRIM27 | 6p22.1 | | | | PGK1 | Xq21.1 | Copy number | 3567 | Iafrate et al (2004) |
| GPBP1 | 5q11.2 | | | | B2M | 15q21.1 | Copy number | 2773 | Redon et al (2006) |
| UBQLN1 | 9q21.33 | | | | GUSB | 7q11.21 | | | |
| ARL8B | 3p26.1 | | | | HPRT1 | Xq26.2 | | | |
| PAPOLA | 14q32.2 | | | | TBP | 6q27 | Copy number | 1479 | Redon et al (2006) |
| CUL1 | 7q36.1 | | | | TFRC | 3q29 | Copy number | 753 | Iafrate et al (2004) |
| DIMT1L | 5q12.1 | Copy number | 1137 | Redon et al (2006) | | | Copy number | | Redon et al (2006) |
| FBXW2 | 9q33.2 | | | | HMBS | 11q23.3 | | | |
| SPG21 | 15q22.31 | | | | H6PD | 1p36.22 | | | |
| | | | | | ALAS1 | 3p21.2 | Copy number | 590 | Wong et al (2007) |

*Genomic location was searched from Ensembl (http://www.ensembl.org/index:html)
**Genomic variations were searched in the Database of Genomic Variants (http://projects.tcag/ca/variation/, Human Genomic Assembly Build 36 (hg18)).

<7-2> Validation of ERG Using Expression Stability Based on qRT-PCR Data

Gene expression stability was analyzed using geNorm v3.4 software (Vandesompele J et al., Genome Biol 3:RESEARCH0034, 2002) and NormFinder software (Andersen C L et al., Cancer Res 64:5245-50, 2004). For geNorm and NormFinder analysis, Cp values were converted into relative expression levels in consideration of the PCR efficiencies of genes shown in Table 8 (GeNorm software manual, update on Sep. 6, 2004. //medgen.ugnet.be/~jvdesomp/genorm/). Relative expression was calculated according to the following Mathematical Formula 4.

$$\text{Relative Expression} = (1+E)^{\Delta Cp} \quad \text{<Mathematical Formula 4>}$$

$\Delta Cp$ = Minimum Cp – Sample Cp;
Minimum Cp = lowest Cp value; and
E = PCR Efficiency Correlation between the gene expression stability calculated with the geNorm or NormFinder program (M by geNorm, S by NormFinder) and the CV calculated in each dataset was analyzed with R analysis software (//www.R-project.org).

All of the genes were found to have M values (<0.9) lower than the default limit, 1.5, of geNorm, with high expression stability, as analyzed using the geNorm program (Table 9). Lower M values for mean expression stability mean more stable expression. GPBP1 and CUL1 were observed to show the most stable expression. Among the genes analyzed, B2M is the lowest stable expression gene, with the highest M value of 0.888, followed by ACTB (M=0.843), HMBS (M=0.815) and GAPDH (M=0.793) in descending order of expression instability.

When using the NormFinder program, TBP and PAPOLA were ranked as the top two in terms of expression stability (Table 9). Consistent with the geNorm result, B2M, ACTB, GAPDH, HMBS and HPRT1 were found to be less stable in expression level than the novel ERGs of the present invention. Both programs demonstrated that most of the novel ERGs identified according to the present invention show more stable expression levels than do traditional ERGs. Further, when analyzed for gene expression stability using a LinRegPCR program on the basis of the relative expression calculated with PCR efficiency, most novel ERGs were found to maintain higher expression stability than traditional ERGs.

There is no significant correlation between the M values calculated with geNorm and the CV values in Microarray and LongSAGE (p>0.05), whereas significance was found in correlation between M values and CV values in EST (Pearson correlation coefficient: 0.676, p=0.001) and ShortSAGE (Pearson correlation coefficient: 0.659, p=0.00$^2$). Likewise, as for the Stability values (S), calculated with NormFinder, significant correlation was found in EST, ShortSAGE and LongSAGE, but not in microarray. Both the M and the S values showed higher agreement with CV in EST and ShortSAGE than in Affymetrix (Table 10).

Furthermore, the 13 novel ERGs were analyzed for expression in 60 FFPE samples using qRT-PCR in order to examine the possibility of applying them to the tissues in which high RNA degradation occurs. All of the genes, except for DIMTIL, were found to be expressed in all 60 samples. Cp was observed to range from 18.85 to 33.02 for traditional ERGs and from 23.33 to 31.38 for the novel ERGs (FIG. 9). Because of the lack of amplification in 5 samples, DIMTIL was omitted from subsequent stability analyses. Despite difference in the type of samples used in the experiments, almost all genes, except for several genes, were observed to be expressed in a pattern similar to that observed in the previous 48 samples. These results indicate that the novel ERGs of the present invention can be applied to gene expression in FFPE samples. geNorm and NormFinder analyses demonstrate that most of the novel ERGs are more stably expressed with lower Cp values in FFPE samples, as well as in the 48 samples, than are traditional ERGs (Table 9).

TABLE 6

Human tissues and cancer cell lines used in Real time-PCR

| No. | Tissue or cell lines | Type | Normal (N)/ Tumor (T) | Diagnosis | Remarks |
|---|---|---|---|---|---|
| 1 | Adrenal gland | frozen tissue | N | Normal | |

TABLE 6-continued

Human tissues and cancer cell lines used in Real time-PCR

| No. | Tissue or cell lines | Type | Normal (N)/Tumor (T) | Diagnosis | Remarks |
|---|---|---|---|---|---|
| 2 | Brain | frozen tissue | N | Normal | |
| 3 | Breast | frozen tissue | N | Normal | |
| 4 | Colon | frozen tissue | N | Normal | Normal tissue adjacent to signet ring cell carcinoma, ascending colon |
| 5 | Esophagus | frozen tissue | N | Normal | |
| 6 | Kidney | frozen tissue | N | Normal | |
| 7 | Liver | frozen tissue | N | Normal | |
| 8 | Lung | frozen tissue | N | Normal | |
| 9 | Omentum | frozen tissue | N | Normal | |
| 10 | Ovary | frozen tissue | N | Normal | |
| 11 | Placenta | frozen tissue | N | Normal | |
| 12 | Placenta | frozen tissue | N | Normal | Immature placenta with focal intervillous calcification, normal two umbilical arteries and one vein, and no-evidence of chorioamnionitis |
| 13 | Rectum | frozen tissue | N | Normal | |
| 14 | Salivary gland | frozen tissue | N | Normal | |
| 15 | Thyroid gland | frozen tissue | N | Normal | |
| 16 | Tonsil | frozen tissue | N | Normal | |
| 17 | Uterus | frozen tissue | N | Normal | |
| 18 | Vein | frozen tissue | N | Normal | |
| 19 | Vulva | frozen tissue | N | Normal | |
| 20 | Brain | frozen tissue | T | Glioblastoma multiforme | |
| 21 | Breast | frozen tissue | T | Invasive ductal carcinoma, uppe rcentral | |
| 22 | Transverse colon | frozen tissue | T | Ulcerofungating carcinoma transverse colon, Mucinous adenocarcinoma | |
| 23 | Lung | frozen tissue | T | Pleomorphic carcinoma | |
| 24 | Ovary | frozen tissue | T | Transitional cell carcinoma, bilateral ovaries | |
| 25 | Rectum | frozen tissue | T | Adenocarcinoma, moderately differentiated with mucin production | |
| 26 | Stomach | frozen tissue | T | Advanced gastric carcinoma, Tubular adenocarcinoma, M/D | |
| 27 | HL-60 | cell lines | T | Leukemia | Blood |
| 28 | MDA-MB-231 | cell lines | T | Breast cancer | Breast |
| 29 | C33A | cell lines | T | Cervical cancer | Cervix |
| 30 | HeLa | cell lines | T | Cervical cancer | Lung |
| 31 | HCC-44 | cell lines | T | Lung cancer | |
| 32 | A549 | cell lines | T | Lung cancer | |
| 33 | Caov3 | cell lines | T | Ovarian cancer | Ovary |
| 34 | OV-90 | cell lines | T | Ovarian cancer | |
| 35 | OVCAR3 | cell lines | T | Ovarian cancer | |
| 36 | SK-OV3 | cell lines | T | Ovarian cancer | |
| 37 | SNU119 | cell lines | T | Ovarian cancer | |
| 38 | SW626 | cell lines | T | Ovarian cancer | |
| 39 | AGS | cell lines | T | Gastric cancer | Stomach |
| 40 | Kato III | cell lines | T | Gastric cancer | |
| 41 | MKN1 | cell lines | T | Gastric cancer | |
| 42 | MKN74 | cell lines | T | Gastric cancer | |
| 43 | NCI-N87 | cell lines | T | Gastric cancer | |
| 44 | SNU5 | cell lines | T | Gastric cancer | |
| 45 | SNU16 | cell lines | T | Gastric cancer | |
| 46 | SNU484 | cell lines | T | Gastric cancer | |
| 47 | SNU601 | cell lines | T | Gastric cancer | |
| 48 | SNU638 | cell lines | T | Gastric cancer | |

*: Normal tissue adjacent to signet ring cell carcinoma, ascending colon; and
**: immature placenta with focal intervillous calcifications, normal two umbilical arteries and one vein, and no evidence of chorioamnionitis.

TABLE 7

Primers and Taqman Probes for Real-Time PCR

| Gene Names | UPL No. | Sense Primers | Anti-Sense Primers | Product (bp) |
|---|---|---|---|---|
| GAPDH | 60 | SEQ ID NO. 1: agccacatgctcagaca | SEQ ID NO. 2: gccaatacgaccaaatcc | 66 |
| ACTB | 64 | SEQ ID NO. 3: ccaaccgcgagaagatga | SEQ ID NO. 4: ccagaggcgtacagggatag | 97 |
| B2M | 42 | SEQ ID NO. 5: ttctggcctggaggctatc | SEQ ID NO. 6: tcaggaaatttgactttccattc | 86 |
| PPIA | # | SEQ ID NO. 7: catctgcactgccaagactgag | SEQ ID NO. 8: tgcaatccagctaggcatg | 326 |

TABLE 7-continued

Primers and Taqman Probes for Real-Time PCR

| Gene Names | UPL No. | Sense Primers (SEQ ID) | Anti-Sense Primers (SEQ ID) | Product (bp) |
|---|---|---|---|---|
| HPRT1 | 73 | SEQ ID NO. 9: tgaccttgatttattttgcatacc | SEQ ID NO. 10: cgagcaagacgttcagtcct | 102 |
| HBMS | 26 | SEQ ID NO. 11: tgtggtgggaaccagctc | SEQ ID NO. 12: tgttgaggtttccccgaat | 92 |
| TBP | 3 | SEQ ID NO. 13: gctggcccatagtgatcttt | SEQ ID NO. 14: cttcacacgccaagaaacagt | 60 |
| H6PD | 89 | SEQ ID NO. 15: tggagatcatcatgaaagagacc | SEQ ID NO. 16: gcgaatgacaccgtactcct | 74 |
| ZNF207 | 27 | SEQ ID NO. 17: ctgtttcctagcacagcacaa | SEQ ID NO. 18: ggtttgaaatctgtaccaacagg | 65 |
| OAZ1 | 74 | SEQ ID NO. 19: caccatgccgctcctaag | SEQ ID NO. 20: gagggagaccctggaactct | 67 |
| LUC7L2 | 85 | SEQ ID NO. 21: cgatcacacagcaagaatcc | SEQ ID NO. 22: agatcgatgtctgcgatgc | 60 |
| CTBP1 | 77 | SEQ ID NO. 23: actgcgtgaccctgcact | SEQ ID NO. 24: gccccttgtctcatctgc | 86 |
| TRIM27 | 7 | SEQ ID NO. 25: caggcacgagctgaactct | SEQ ID NO. 26: agctgctcaaactcccaaac | 71 |
| GPBP1 | 4 | SEQ ID NO. 27: tcacttgaggcagaacacaga | SEQ ID NO. 28: agcacatgtttcatcattttcac | 75 |
| UBQLN1 | 73 | SEQ ID NO. 29: gaatcctgaccttgctgcac | SEQ ID NO. 30: ttgggagctgttgtctcattt | 92 |
| ARL8B | 82 | SEQ ID NO. 31: aagcatgtgggagcggtat | SEQ ID NO. 32: cgatctgcagcatctatcatgt | 66 |
| PAPOLA | 78 | SEQ ID NO. 33: gctacgaagaccagtccattg | SEQ ID NO. 34: tgttggtcacagatgctgct | 91 |
| CUL1 | 65 | SEQ ID NO. 35: gcgaggtcctcactcagc | SEQ ID NO. 36: ttctttctcaattagaatgtcaatgc | 86 |
| DIMT1L | 77 | SEQ ID NO. 37: tccagtgttgtaaggatagaacctaag | SEQ ID NO. 38: Ccttactagaccatcccattcct | 75 |
| FBXW2 | 3 | SEQ ID NO. 39: cggctctgcagacttcact | SEQ ID NO. 40: ttgcacttctgcaaaactacct | 111 |
| SPG21 | 21 | SEQ ID NO. 41: gatgtcttttccggcagat | SEQ ID NO. 42: cgagatggtcccaataaactg | 88 |

TABLE 8

PCR Efficiency of Genes

| Gene Name | UPL Probe Nos. | PCR Efficiency (Diluted)* | PCR Efficiency (LinRegPCR)** |
|---|---|---|---|
| GAPDH | 60 | 1.899 | 1.735 ± 0.048(137) |
| ACTB | 64 | 2.038 | 1.491 ± 0.034(137) |
| B2M | 42 | 1.868 | 1.717 ± 0.068(140) |
| PPIA | # | 1.877 | 1.773 ± 0.058(142) |
| HPRT1 | 73 | 1.800 | 1.771 ± 0.024(143) |
| HMBS | 26 | 1.954 | 1.431 ± 0.031(143) |
| TBP | 3 | 1.826 | 1.447 ± 0.038(142) |
| H6PD | 89 | 1.874 | 1.832 ± 0.026(64) |
| ZNF207 | 27 | 1.869 | 1.648 ± 0.018(142) |
| OAZ1 | 74 | 2.068 | 1.498 ± 0.059(142) |
| LUC7L2 | 85 | 1.829 | 1.709 ± 0.047(143) |
| CTBP1 | 77 | 2.064 | 1.651 ± 0.055(141) |
| TRIM27 | 7 | 1.908 | 1.693 ± 0.034(143) |
| GPBP1 | 4 | 1.844 | 1.715 ± 0.031(141) |
| UBQLN1 | 73 | 1.864 | 1.723 ± 0.027(143) |
| ARL8B | 82 | 1.838 | 1.499 ± 0.074(139) |
| PAPOLA | 78 | 1.830 | 1.509 ± 0.032(141) |
| CUL1 | 65 | 1.810 | 1.695 ± 0.027(139) |
| DIMT1L | 77 | 1.906 | 1.655 ± 0.037(141) |

TABLE 8-continued

PCR Efficiency of Genes

| Gene Name | UPL Probe Nos. | PCR Efficiency (Diluted)* | PCR Efficiency (LinRegPCR)** |
|---|---|---|---|
| FBXW2 | 3 | 1.891 | 1.638 ± 0.02(142) |
| SPG21 | 21 | 1.826 | 1.636 ± 0.021(142) |

*PCR Efficiency; calculated with Roche Lightcycler software 4.0 using serial diluted cDNA of MKN 74 stomach cancer cell line;
**PCR Efficiency; calculated with LinRegPCR(Ramakers et. al., Neurosci Lett 339(1): 62-66, 2003); and,
: F-ttcttgctggtcttgccatTcctgga-p;
T: TAMRA-labeled;
F: FAM-labeled;
P: phosphate.

TABLE 9

Expression Stability of Novel and Traditional ERGs Calculated by geNorm and NormFinder based on Real-Time PCR Data

| 48 Samples | | | | 60 FFPE Samples* | | | |
|---|---|---|---|---|---|---|---|
| GeNorm | | NormFinder | | GeNorm | | NormFinder | |
| Genes | M | Genes | S | Genes | M | Genes | S |
| GPBP1 | 0.496 | TBP | 0.276 | GPBP1 | 0.409 | ARL8B | 0.233 |
| CUL1 | | PAPOLA | 0.280 | PAPOLA | | LUC7L2 | 0.235 |
| PAPOLA | 0.536 | CUL1 | 0.287 | ARL8B | 0.437 | OAZ1 | 0.247 |
| TBP | 0.548 | LUC7L2 | 0.290 | CTBP1 | 0.454 | CTBP1 | 0.251 |
| LUC7L2 | 0.565 | CTBP1 | 0.312 | LUC7L2 | 0.483 | UBQLN1 | 0.273 |
| TRIM27 | 0.585 | GPBP1 | 0.317 | SPG21 | 0.509 | SPG21 | 0.280 |
| FBXW2 | 0.597 | TRIM27 | 0.317 | FBXW2 | 0.528 | FBXW2 | 0.286 |
| CTBP1 | 0.608 | FBXW2 | 0.329 | OAZ1 | 0.545 | PAPOLA | 0.290 |
| UBQLN1 | 0.623 | DIMT1L | 0.364 | UBQLN1 | 0.555 | TRIM27 | 0.327 |
| DIMT1L | 0.637 | PPIA | 0.383 | TRIM27 | 0.567 | GPBP1 | 0.345 |
| PPIA | 0.661 | UBQLN | 10.398 | TBP | 0.580 | HPRT1 | 0.368 |
| OAZ1 | 0.682 | OAZ1 | 0.438 | CUL1 | 0.593 | CUL1 | 0.383 |
| ZNF207 | 0.709 | ARL8B | 0.494 | HPRT1 | 0.609 | TBP | 0.402 |
| ARL8B | 0.731 | SPG21 | 0.502 | ZNF207 | 0.625 | HMBS | 0.407 |
| SPG21 | 0.749 | ZNF207 | 0.502 | HMBS | 0.641 | ZNF207 | 0.440 |
| HPRT1 | 0.770 | HPRT1 | 0.516 | GAPDH | 0.668 | PPIA | 0.461 |
| GAPDH | 0.793 | HMBS | 0.587 | PPIA | 0.692 | GAPDH | 0.527 |
| HMBS | 0.815 | GAPDH | 0.591 | B2M | 0.715 | B2M | 0.530 |
| ACTB | 0.843 | ACTB | 0.618 | ACTB | 0.737 | ACTB | 0.541 |
| B2M | 0.888 | B2M | 0.815 | | | | |

*DIMT1L was excluded from the analysis.
M: mean expression stability calculated with geNorm program;
S: Stability calculated with NormFinder program.

TABLE 11

List of 567 Samples Including 13 Tissues in HG-U133 Array

| Tissues | Categories | Morphology | Nos. of Samples | |
|---|---|---|---|---|
| Brain | Benign | Meningioma | 7 | 23 |
| | Malignant | Glioblastoma Multiforme | 7 | |
| | | Oligodendroglioma | 6 | |
| | | Medulloblastoma | 3 | |
| Breast | Normal | Normal Tissue | 18 | 74 |
| | Malignant | Infiltrating Duct Carcinoma | 36 | |
| | | Infiltrating Duct and Lobular Carcinoma | 7 | |
| | | Infiltrating Lobular Carcinoma | 13 | |

TABLE 10

Correlation between CV in each dataset and expression stability calculated with geNorm and NormFinder

| | EST-M | EST-S | Short SAGE-M | Short SAGE-S | Long SAGE-M | Long SAGE-S | Affy-M | Affy-S | M-S |
|---|---|---|---|---|---|---|---|---|---|
| Pearson | 0.676 | 0.792 | 0.659 | 0.75 | 0.427 | 0.561 | 0.039 | 0.017 | 0.953 |
| P value | 0.001 | <0.001 | 0.002 | <0.001 | 0.061 | 0.01 | 0.869 | 0.944 | <0.001 |
| Spearman | 0.589 | 0.605 | 0.277 | 0.268 | 0.092 | 0.105 | 0.424 | 0.357 | 0.955 |
| P value | 0.006 | 0.005 | 0.237 | 0.254 | 0.701 | 0.661 | 0.063 | 0.123 | <0.001 |
| Pearson | 0.623 | 0.626 | 0.656 | 0.737 | 0.481 | 0.672 | 0.243 | 0.335 | 0.852 |
| P value | 0.004 | 0.004 | 0.002 | <0.001 | 0.037 | 0.002 | 0.317 | 0.161 | <0.001 |
| Spearman | 0.653 | 0.596 | 0.515 | 0.502 | 0.374 | 0.567 | 0.521 | 0.583 | 0.841 |
| P value | 0.002 | 0.008 | 0.024 | 0.03 | 0.115 | 0.013 | 0.022 | 0.009 | <0.001 |

M: Mean expression stability calculated with geNorm;
S: Stability calculated with NormFinder

TABLE 11-continued

List of 567 Samples Including 13 Tissues in HG-U133 Array

| Tissues | Categories | Morphology | Nos. of Samples | |
|---|---|---|---|---|
| Colon | Normal | Normal Tissue | 22 | 62 |
| | Malignant | Adenocarcinoma | 33 | |
| | | Mucinous Adenocarcinoma | 7 | |
| Esophagus | Normal | Normal Tissue | 11 | 17 |
| | Malignant | Adenocarcinoma | 6 | |
| Kidney | Normal | Normal Tissue | 26 | 51 |
| | Benign | Oncocytoma | 5 | |
| | Malignant | Clear Cell Adenocarcinoma | 6 | |
| | | Renal Cell Carcinoma | 14 | |
| Liver | Normal | Normal Tissue | 10 | 29 |
| | Malignant | Hepatocellular Carcinoma | 19 | |
| Lung | Normal | Normal Tissue | 26 | 58 |
| | Malignant | Adenocarcinoma | 15 | |
| | | Squamous Cell Carcinoma | 17 | |
| Lymph Node | Normal | Normal Tissue | 4 | 23 |
| | Malignant | Hodgkin's Disease | 4 | |
| | | Malignant Lymphoma | 15 | |
| Ovary | Normal | Normal Tissue | 10 | 50 |
| | Malignant | Adenocarcinoma | 5 | |
| | | Clear Cell Adenocarcinoma | 6 | |
| | | Mucinous Cystadenocarcinoma | 5 | |
| | | Serous Cystadenocarcinoma | 6 | |
| | | Papillary Serous Adenocarcinoma | 18 | |
| Pancreas | Normal | Normal Tissue | 13 | 41 |
| | Malignant | Adenocarcinoma | 28 | |
| Prostate | Normal | Normal Tissue | 14 | 41 |
| | Malignant | Adenocarcinoma | 27 | |
| Rectum | Normal | Normal Tissue | 17 | 38 |
| | Malignant | Adenocarcinoma | 21 | |
| Stomach | Normal | Normal Tissue | 17 | 60 |
| | Malignant | Adenocarcinoma | 37 | |
| | | Signet Ring Cell Carcinoma | 6 | |
| Total | | | 567 | |

This application contains references to amino acid sequences and/or nucleic acid sequences which have been submitted herewith as the sequence listing text file. The aforementioned sequence listing is hereby incorporated by reference in its entirety pursuant to 37 C.F.R. § 61.52(e).

The invention claimed is:

1. A method for quantifying an expression level of a target gene in a formalin-fixed, paraffin embedded (FFPE) tissue sample of human breast cancer tissues, comprising:
   1) synthesizing cDNA from RNA of a subject;
   2) performing real time PCR to amplify the target gene and endogenous reference gene OAZ1 using a pair of primers and/or probes with the cDNA serving as a template; and
   3) normalizing an expression level of the target gene to that of the endogenous reference gene OAZ1 of step 2).

2. The method according to claim 1, wherein the endogenous reference gene is amplified by a pair of primers and/or probes.

* * * * *

SEQUENCE LISTING

```
<160> NUMBER OF SEQ ID NOS: 42

<210> SEQ ID NO 1
<211> LENGTH: 18
<212> TYPE: DNA
<213> ORGANISM: Artificial Sequence
<220> FEATURE:
<223> OTHER INFORMATION: GAPDH F

<400> SEQUENCE: 1
agccacatcg ctcagaca                                                 18

<210> SEQ ID NO 2
<211> LENGTH: 19
<212> TYPE: DNA
<213> ORGANISM: Artificial Sequence
<220> FEATURE:
<223> OTHER INFORMATION: GAPDH R

<400> SEQUENCE: 2
gcccaatacg accaaatcc                                                19

<210> SEQ ID NO 3
<211> LENGTH: 18
<212> TYPE: DNA
<213> ORGANISM: Artificial Sequence
<220> FEATURE:
<223> OTHER INFORMATION: ACTB F

<400> SEQUENCE: 3
ccaaccgcga gaagatga                                                 18

<210> SEQ ID NO 4
<211> LENGTH: 20
<212> TYPE: DNA
<213> ORGANISM: Artificial Sequence
<220> FEATURE:
<223> OTHER INFORMATION: ACTB R

<400> SEQUENCE: 4
```
ccagaggcgt acagggatag                                           20

<210> SEQ ID NO 5
<211> LENGTH: 19
<212> TYPE: DNA
<213> ORGANISM: Artificial Sequence
<220> FEATURE:
<223> OTHER INFORMATION: B2M F

<400> SEQUENCE: 5
ttctggcctg gaggctatc                                            19

<210> SEQ ID NO 6
<211> LENGTH: 23
<212> TYPE: DNA
<213> ORGANISM: Artificial Sequence
<220> FEATURE:
<223> OTHER INFORMATION: B2M R

<400> SEQUENCE: 6
tcaggaaatt tgactttcca ttc                                       23

<210> SEQ ID NO 7
<211> LENGTH: 22
<212> TYPE: DNA
<213> ORGANISM: Artificial Sequence
<220> FEATURE:
<223> OTHER INFORMATION: PPIA F

<400> SEQUENCE: 7
catctgcact gccaagactg ag                                        22

<210> SEQ ID NO 8
<211> LENGTH: 19
<212> TYPE: DNA
<213> ORGANISM: Artificial Sequence
<220> FEATURE:
<223> OTHER INFORMATION: PPIA R

<400> SEQUENCE: 8
tgcaatccag ctaggcatg                                            19

<210> SEQ ID NO 9
<211> LENGTH: 24
<212> TYPE: DNA
<213> ORGANISM: Artificial Sequence
<220> FEATURE:
<223> OTHER INFORMATION: HPRT1 F

<400> SEQUENCE: 9
tgaccttgat ttattttgca tacc                                      24

<210> SEQ ID NO 10
<211> LENGTH: 20
<212> TYPE: DNA
<213> ORGANISM: Artificial Sequence
<220> FEATURE:
<223> OTHER INFORMATION: HPRT1 R

<400> SEQUENCE: 10
cgagcaagac gttcagtcct                                           20

<210> SEQ ID NO 11
<211> LENGTH: 18
<212> TYPE: DNA
<213> ORGANISM: Artificial Sequence

```
<220> FEATURE:
<223> OTHER INFORMATION: HMBS F

<400> SEQUENCE: 11
tgtggtggga accagctc                                                  18

<210> SEQ ID NO 12
<211> LENGTH: 19
<212> TYPE: DNA
<213> ORGANISM: Artificial Sequence
<220> FEATURE:
<223> OTHER INFORMATION: HMBS R

<400> SEQUENCE: 12
tgttgaggtt tccccgaat                                                 19

<210> SEQ ID NO 13
<211> LENGTH: 20
<212> TYPE: DNA
<213> ORGANISM: Artificial Sequence
<220> FEATURE:
<223> OTHER INFORMATION: TBP F

<400> SEQUENCE: 13
gctggcccat agtgatcttt                                                20

<210> SEQ ID NO 14
<211> LENGTH: 21
<212> TYPE: DNA
<213> ORGANISM: Artificial Sequence
<220> FEATURE:
<223> OTHER INFORMATION: TBP R

<400> SEQUENCE: 14
cttcacacgc caagaaacag t                                              21

<210> SEQ ID NO 15
<211> LENGTH: 23
<212> TYPE: DNA
<213> ORGANISM: Artificial Sequence
<220> FEATURE:
<223> OTHER INFORMATION: H6PD F

<400> SEQUENCE: 15
tggagatcat catgaaagag acc                                            23

<210> SEQ ID NO 16
<211> LENGTH: 20
<212> TYPE: DNA
<213> ORGANISM: Artificial Sequence
<220> FEATURE:
<223> OTHER INFORMATION: H6PD R

<400> SEQUENCE: 16
gcgaatgaca ccgtactcct                                                20

<210> SEQ ID NO 17
<211> LENGTH: 21
<212> TYPE: DNA
<213> ORGANISM: Artificial Sequence
<220> FEATURE:
<223> OTHER INFORMATION: ZNF207 F

<400> SEQUENCE: 17
ctgtttccta gcacagcaca a                                              21
```

```
<210> SEQ ID NO 18
<211> LENGTH: 23
<212> TYPE: DNA
<213> ORGANISM: Artificial Sequence
<220> FEATURE:
<223> OTHER INFORMATION: ZNF207 R

<400> SEQUENCE: 18
ggtttgaaat ctgtaccaac agg                                   23

<210> SEQ ID NO 19
<211> LENGTH: 18
<212> TYPE: DNA
<213> ORGANISM: Artificial Sequence
<220> FEATURE:
<223> OTHER INFORMATION: OAZ1 F

<400> SEQUENCE: 19
caccatgccg ctcctaag                                         18

<210> SEQ ID NO 20
<211> LENGTH: 20
<212> TYPE: DNA
<213> ORGANISM: Artificial Sequence
<220> FEATURE:
<223> OTHER INFORMATION: OAZ1 R

<400> SEQUENCE: 20
gagggagacc ctggaactct                                       20

<210> SEQ ID NO 21
<211> LENGTH: 20
<212> TYPE: DNA
<213> ORGANISM: Artificial Sequence
<220> FEATURE:
<223> OTHER INFORMATION: LUC7L2 F

<400> SEQUENCE: 21
cgatcacaca gcaagaatcc                                       20

<210> SEQ ID NO 22
<211> LENGTH: 19
<212> TYPE: DNA
<213> ORGANISM: Artificial Sequence
<220> FEATURE:
<223> OTHER INFORMATION: LUC7L2 R

<400> SEQUENCE: 22
agatcgatgt ctgcgatgc                                        19

<210> SEQ ID NO 23
<211> LENGTH: 18
<212> TYPE: DNA
<213> ORGANISM: Artificial Sequence
<220> FEATURE:
<223> OTHER INFORMATION: CTBP1 F

<400> SEQUENCE: 23
actgcgtgac cctgcact                                         18

<210> SEQ ID NO 24
<211> LENGTH: 18
<212> TYPE: DNA
<213> ORGANISM: Artificial Sequence
<220> FEATURE:
<223> OTHER INFORMATION: CTBP1 R
```

```
<400> SEQUENCE: 24
gccccttgtc tcatctgc                                                18

<210> SEQ ID NO 25
<211> LENGTH: 19
<212> TYPE: DNA
<213> ORGANISM: Artificial Sequence
<220> FEATURE:
<223> OTHER INFORMATION: TRIM27 F

<400> SEQUENCE: 25
caggcacgag ctgaactct                                               19

<210> SEQ ID NO 26
<211> LENGTH: 20
<212> TYPE: DNA
<213> ORGANISM: Artificial Sequence
<220> FEATURE:
<223> OTHER INFORMATION: TRIM27 R

<400> SEQUENCE: 26
agctgctcaa actcccaaac                                              20

<210> SEQ ID NO 27
<211> LENGTH: 21
<212> TYPE: DNA
<213> ORGANISM: Artificial Sequence
<220> FEATURE:
<223> OTHER INFORMATION: GPBP1 F

<400> SEQUENCE: 27
tcacttgagg cagaacacag a                                            21

<210> SEQ ID NO 28
<211> LENGTH: 23
<212> TYPE: DNA
<213> ORGANISM: Artificial Sequence
<220> FEATURE:
<223> OTHER INFORMATION: GPBP1 R

<400> SEQUENCE: 28
agcacatgtt tcatcatttt cac                                          23

<210> SEQ ID NO 29
<211> LENGTH: 20
<212> TYPE: DNA
<213> ORGANISM: Artificial Sequence
<220> FEATURE:
<223> OTHER INFORMATION: UBQLN1 F

<400> SEQUENCE: 29
gaatcctgac cttgctgcac                                              20

<210> SEQ ID NO 30
<211> LENGTH: 21
<212> TYPE: DNA
<213> ORGANISM: Artificial Sequence
<220> FEATURE:
<223> OTHER INFORMATION: UBQLN1 R

<400> SEQUENCE: 30
ttgggagctg ttgtctcatt t                                            21

<210> SEQ ID NO 31
```

```
<210> SEQ ID NO 31
<211> LENGTH: 19
<212> TYPE: DNA
<213> ORGANISM: Artificial Sequence
<220> FEATURE:
<223> OTHER INFORMATION: ARL8B F

<400> SEQUENCE: 31
aagcatgtgg gagcggtat                                              19

<210> SEQ ID NO 32
<211> LENGTH: 22
<212> TYPE: DNA
<213> ORGANISM: Artificial Sequence
<220> FEATURE:
<223> OTHER INFORMATION: ARL8B R

<400> SEQUENCE: 32
cgatctgcag catctatcat gt                                          22

<210> SEQ ID NO 33
<211> LENGTH: 21
<212> TYPE: DNA
<213> ORGANISM: Artificial Sequence
<220> FEATURE:
<223> OTHER INFORMATION: PAPOLA F

<400> SEQUENCE: 33
gctacgaaga ccagtccatt g                                           21

<210> SEQ ID NO 34
<211> LENGTH: 20
<212> TYPE: DNA
<213> ORGANISM: Artificial Sequence
<220> FEATURE:
<223> OTHER INFORMATION: PAPOLA R

<400> SEQUENCE: 34
tgttggtcac agatgctgct                                             20

<210> SEQ ID NO 35
<211> LENGTH: 18
<212> TYPE: DNA
<213> ORGANISM: Artificial Sequence
<220> FEATURE:
<223> OTHER INFORMATION: CUL1 F

<400> SEQUENCE: 35
gcgaggtcct cactcagc                                               18

<210> SEQ ID NO 36
<211> LENGTH: 26
<212> TYPE: DNA
<213> ORGANISM: Artificial Sequence
<220> FEATURE:
<223> OTHER INFORMATION: CUL1 R

<400> SEQUENCE: 36
ttctttctca attagaatgt caatgc                                      26

<210> SEQ ID NO 37
<211> LENGTH: 27
<212> TYPE: DNA
<213> ORGANISM: Artificial Sequence
<220> FEATURE:
<223> OTHER INFORMATION: DIMT1L F

<400> SEQUENCE: 37
```

```
tccagtgttg taaggataga acctaag                                              27

<210> SEQ ID NO 38
<211> LENGTH: 23
<212> TYPE: DNA
<213> ORGANISM: Artificial Sequence
<220> FEATURE:
<223> OTHER INFORMATION: DIMT1L R

<400> SEQUENCE: 38
ccttactaga ccatcccatt cct                                                  23

<210> SEQ ID NO 39
<211> LENGTH: 19
<212> TYPE: DNA
<213> ORGANISM: Artificial Sequence
<220> FEATURE:
<223> OTHER INFORMATION: FBXW2 F

<400> SEQUENCE: 39
cggctctgca gacttcact                                                       19

<210> SEQ ID NO 40
<211> LENGTH: 22
<212> TYPE: DNA
<213> ORGANISM: Artificial Sequence
<220> FEATURE:
<223> OTHER INFORMATION: FBXW2 R

<400> SEQUENCE: 40
ttgcacttct gcaaaactac ct                                                   22

<210> SEQ ID NO 41
<211> LENGTH: 20
<212> TYPE: DNA
<213> ORGANISM: Artificial Sequence
<220> FEATURE:
<223> OTHER INFORMATION: SPG21 F

<400> SEQUENCE: 41
gatgtctttt tccggcagat                                                      20

<210> SEQ ID NO 42
<211> LENGTH: 21
<212> TYPE: DNA
<213> ORGANISM: Artificial Sequence
<220> FEATURE:
<223> OTHER INFORMATION: SPG21 R

<400> SEQUENCE: 42
cgagatggtc ccaataaact g                                                    21
```